(12) United States Patent
Fensome et al.

(10) Patent No.: US 11,197,867 B2
(45) Date of Patent: *Dec. 14, 2021

(54) AMINOPYRIMIDINYL COMPOUNDS

(71) Applicant: Pfizer Inc., New York, NY (US)

(72) Inventors: Andrew Fensome, Harvard, MA (US);
Ariamala Gopalsamy, Lexington, MA (US); Brian S. Gerstenberger, Cambridge, MA (US); Ivan Viktorovich Efremov, Chestnut Hill, MA (US); Zhao-Kui Wan, Lexington, MA (US); Betsy Pierce, East Lyme, CT (US); Jean-Baptiste Telliez, Lexington, MA (US); John I. Trujillo, Ledyard, CT (US); Liying Zhang, Malden, MA (US); Li Xing, Lexington, MA (US); Eddine Saiah, Brookline, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,027

(22) Filed: Jul. 2, 2020

(65) Prior Publication Data

US 2020/0330477 A1    Oct. 22, 2020

Related U.S. Application Data

(60) Continuation of application No. 16/580,667, filed on Sep. 24, 2019, now Pat. No. 10,980,815, which is a
(Continued)

(51) Int. Cl.
*A61K 31/506* (2006.01)
*A61K 31/55* (2006.01)
(Continued)

(52) U.S. Cl.
CPC ............ *A61K 31/55* (2013.01); *A61K 31/506* (2013.01); *A61K 45/06* (2013.01); *C07D 401/14* (2013.01);
(Continued)

(58) Field of Classification Search
CPC .................................................... A61K 31/506
See application file for complete search history.

(56) References Cited

U.S. PATENT DOCUMENTS 5,434,303 A  7/1995 Böhm et al.
7,381,833 B2  6/2008 Sato et al.
(Continued)

FOREIGN PATENT DOCUMENTS

CN     102574857 A    7/2012
WO   2007/042299 A1  4/2007
(Continued)

OTHER PUBLICATIONS

Chekkara et al, "Molecular Docking Studies of Phenylaminopyrimidine and Pyrazolylaminopyrimidine Derivatives as Janus Kinase 2 (JAK2) Inhibitors", International Journal of Pharmacy and Pharmaceutical Sciences 6(2):225-230 (2014).
(Continued)

*Primary Examiner* — Brian E McDowell
(74) *Attorney, Agent, or Firm* — A. David Joran

(57) ABSTRACT

A compound compound having the structure:

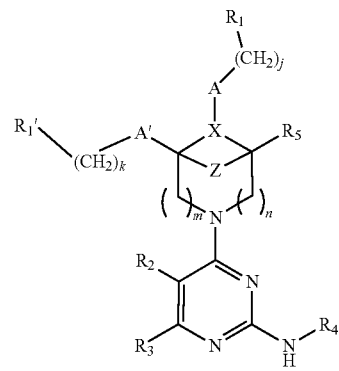

or a pharmaceutically acceptable salt thereof, wherein X is N or CR, where R is hydrogen, deuterium, $C_1$-$C_4$ alkyl, $C_1$-$C_4$ alkoxy, $C_3$-$C_6$ cycloalkyl, aryl, heteroaryl, aryl($C_1$-$C_6$ alkyl), CN, amino, alkylamino, dialkylamino, $CF_3$, or hydroxyl; A is selected from the group consisting of a bond, C=O, —$SO_2$—, —(C=O)$NR_0$—, and —($CR_aR_b$)$_q$—, where $R_0$ is H or $C_1$-$C_4$ alkyl, and $R_a$ and $R_b$ are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, etc.; A' is selected from the group consisting of a bond, C=O, —$SO_2$—, —(C=O)$NR_0$'—, —$NR_0$'(C=O)—, and —($CR_a$'$R_b$')$_q$—, where $R_0$' is H or $C_1$-$C_4$ alkyl, and $R_a$' and $R_b$' are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, heteroaryl($C_1$-$C_6$ alkyl), and heterocyclic ($C_1$-$C_6$ alkyl); Z is —($CH_2$)$_h$— or a bond, where one or more methylene units are optionally substituted by one or more $C_1$-$C_3$ alkyl, CN, OH, methoxy, or halo, and where said alkyl may be substituted by one or more fluorine atoms; $R_1$ and $R_1$' are independently selected from the group consisting of hydrogen, deuterium, $C_1$-$C_4$ alkyl, $C_3$-$C_6$ cycloalkyl, aryl, heteroaryl, aryl($C_1$-$C_6$ alkyl), CN, etc., wherein said alkyl, aryl, cycloalkyl, heterocyclic, or heteroaryl is further optionally substituted with one or more substituents selected from the group consisting of $C_1$-$C_6$ alkyl, halo, CN, $C_1$-$C_4$ alkylamino, $C_3$-$C_6$ cycloalkyl, etc.; $R_2$ is selected from the group consisting of hydrogen, deuterium, $C_1$-$C_6$ alkyl, $C_3$-$C_6$ cycloalkyl, halo, and cyano, where said alkyl may be substituted by one or more fluorine atoms; $R_3$ is selected from the group consisting of hydrogen, deuterium, and amino; $R_4$ is monocyclic or bicyclic aryl or monocyclic or bicyclic heteroaryl wherein said aryl or heteroaryl is optionally substituted with one or more substituents selected from the
(Continued)

group consisting of $C_1$-$C_6$ alkyl, heterocycloalkyl, halo, $C_3$-$C_6$ cycloalkyl, etc., where said alkyl, cycloalkyl, alkoxy, or heterocycloalkyl may be substituted by one or more $C_1$-$C_6$ alkyl, halo, CN, OH, alkoxy, amino, —$CO_2H$, —(CO)$NH_2$, —(CO)NH($C_1$-$C_6$ alkyl), or —(CO)N($C_1$-$C_6$ alkyl)$_2$, and where said alkyl may be further substituted by one or more fluorine atoms; $R_5$ is independently selected from the group consisting of hydrogen, $C_1$-$C_6$ alkyl, $C_1$-$C_6$ alkoxy, and hydroxyl; h is 1, 2 or 3; j and k are independently 0, 1, 2, or 3; m and n are independently 0, 1 or 2; and, q is 0, 1 or 2. Also provided are methods of treatment as Janus Kinase inhibitors and pharmaceutical compositions containing the compounds of the invention and combinations with other therapeutic agents.

9 Claims, No Drawings

Related U.S. Application Data division of application No. 15/585,626, filed on May 3, 2017, now Pat. No. 10,463,675, which is a continuation of application No. 14/829,753, filed on Aug. 19, 2015, now Pat. No. 9,663,526.

(60) Provisional application No. 62/039,969, filed on Aug. 21, 2014.

(51) Int. Cl.
  A61K 45/06     (2006.01)
  C07D 401/14    (2006.01)
  C07D 403/14    (2006.01)
  C07D 405/14    (2006.01)
  C07D 487/08    (2006.01)
  C07D 519/00    (2006.01)

(52) U.S. Cl.
  CPC ......... *C07D 403/14* (2013.01); *C07D 405/14* (2013.01); *C07D 487/08* (2013.01); *C07D 519/00* (2013.01)

(56) References Cited

U.S. PATENT DOCUMENTS

| 7,803,822 B2 | 9/2010 | Kubo et al. |
| 2016/0052930 A1 | 2/2016 | Fensome et al. |

FOREIGN PATENT DOCUMENTS

| WO | 2007/072163 A2 | 6/2007 |
| WO | 2007/084557 A2 | 7/2007 |
| WO | 2008/119792 A1 | 10/2008 |
| WO | 2009/005675 A1 | 1/2009 |
| WO | 2010/006938 A1 | 1/2010 |
| WO | 2010/075273 A1 | 7/2010 |
| WO | 2011/003418 A1 | 1/2011 |
| WO | 2011/106114 A1 | 9/2011 |
| WO | 2012/022681 A2 | 2/2012 |
| WO | 2013/043964 A1 | 3/2013 |
| WO | 2016/026937 A1 | 2/2016 |

OTHER PUBLICATIONS

Grundström et al., "Cyclopropane analogues to acetylenic oxotremorine antagonists", Aca Pharm. Sueica 9(5):491-498 (1972).
Kisseleva et al, "Signaling through the JAK/STAT pathway, recent advances and future challenges", Gene 285:1-24 (2002).
Laroche et al, "Titanium-mediated synthesis of bicyclic cyclopropylamines from unsaturated nitriles", Tetrahedron Letters 44(12):2485-2487 (2003).
Liang et al, "Lead Optimization of a 4-Aminopyridine Benzamide Scaffold To Identify Potent, Selective, and Orally Bioavailable TYK2 Inhibitors", Journal of Medicinal Chemistry 56:4521-4536 (2013).
Liang et al., "Therapeutic potential of tyrosine kinase 2 in autoimmunity", Expert Opin. Ther. Targets 18(5):571-580 (2014).
Murray, "The JAK-STAT Signaling Pathway: Input and Output Integration", The Journal of Immunology 178:2623-2629 (2007).
Neubauer et al., "Jak2 Deficiency Defines an Essential Developmental Checkpoint in Definitive Hematopoiesis", Cell 93:397-409 (1998).
O'Shea et al., "Cytokine Signaling in 2002: New Surprises in the Jak/Stat Pathway", Cell 109:S121-S131 (2002).
Parganas et al., "Jak2 Is Essential for Signaling through a Variety of Cytokine Receptors", Cell 93:385-395 (1998).
PCT International Search Report and Written Opinion for PCT/IB2015/056021 dated Oct. 28, 2015.
Tseng et al., "The synthesis of Daidzein Derivatives", The Journal of National Taiwan Normal University 30:537-545 (1985).
Yamaoka et al., "The Janus kinases (Jaks)", Genome Biology 5:253 (2004).

AMINOPYRIMIDINYL COMPOUNDS

This application is a continuation of Ser. No. 16/580,667, filed Sep. 24, 2019, which is a division of Ser. No. 15/585,626, filed May 3, 2017, which was a continuation of the prior co-pending application Ser. No. 14/829,753, filed Aug. 19, 2015, which claimed the benefit under 35 U.S.C. §119(e) of Serial No. 62/039,969, filed Aug. 21, 2014.

FIELD OF THE INVENTION

The present invention provides pharmaceutically active amino pyrimidinyl compounds and analogues. Such compounds are useful for inhibiting Janus Kinase (JAK). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, cell function, survival, apoptosis, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., Gene, 2002, 285, 1; Yamaoka et al. *Genome Biology* 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the interferon (IFN) family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes: TYK2 and JAK1 in particular. TYK2 is a JAK kinase family member, and is important in the signaling of the type I interferons (IFNa, INFb) IL-6, IL-10, IL-12 and IL-23 (Liang, Y. et al., Expert Opinion on Therapeutic Targets, 18, 5, 571-580 (2014)). As such, TYK2 signals with other members of the JAK kinase family in the following combinations: TYK2/JAK1, TYK2/JAK2, TYK2/JAK1/JAK2. TYK2 has been shown to be important in the differentiation and function of multiple cell types important in inflammatory disease and autoimmune disease including natural killer cells, B cells, and T helper cell types. Aberrant TYK2 expression is associated with multiple autoimmune or inflammatory conditions. JAK1 is a member of the Janus family of protein kinases composed of JAK1, JAK2, JAK3 and TYK2. JAK1 is expressed to various levels in all tissues. Many cytokine receptors signal through pairs of JAK kinases in the following combinations: JAK1/JAK2, JAK1/JAK3, JAK1/TYK2, JAK2/TYK2 or JAK2/JAK2. JAK1 is the most broadly paired JAK kinase in this context and is required for signaling by γ-common (IL-2Rγ) cytokine receptors, IL-6 receptor family, Type I, II and III receptor families and IL-10 receptor family. Animal studies have shown that JAK1 is required for the development, function and homeostasis of the immune system. Modulation of immune activity through inhibition of JAK1 kinase activity can prove useful in the treatment of various immune disorders (Murray, P. J., *J. Immunol.*, 178, 2623-2629 (2007); Kisseleva, T., et al., Gene, 285, 1-24 (2002); O'Shea, J. J., et al., *Cell,* 109 (suppl.). S121-S131 (2002)) while avoiding JAK2 dependent erythropoietin (EPO) and thrombopoietin (TPO) signaling (Neubauer H., et al., *Cell,* 93(3), 397-409 (1998); Parganas E., et al., *Cell,* 93(3), 385-95 (1998)).

SUMMARY OF THE INVENTION

The present invention provides a compound of formula I having the structure:

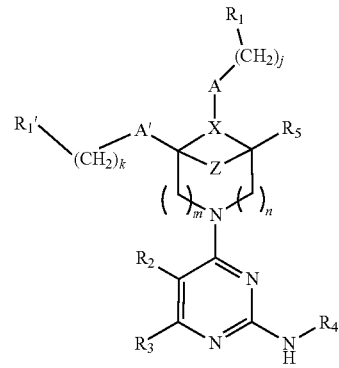

or a pharmaceutically acceptable salt thereof, wherein X is N or CR, where R is hydrogen, deuterium, $C_1$-$C_4$ alkyl, $C_1$-$C_4$ alkoxy, $C_3$-$C_6$ cycloalkyl, aryl, heteroaryl, aryl($C_1$-$C_6$ alkyl), CN, amino, alkylamino, dialkylamino, $CF_3$, or hydroxyl;

A is selected from the group consisting of a bond, C=O, —$SO_2$—, —(C=O)$NR_0$—, and —($CR_aR_b)_q$—, where $R_0$ is H or $C_1$-$C_4$ alkyl, and $R_a$ and $R_b$ are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, heteroaryl ($C_1$-$C_6$ alkyl), and heterocyclic($C_1$-$C_6$ alkyl);

A' is selected from the group consisting of a bond, C=O, —$SO_2$—, —(C=O)$NR_0$', —$NR_0$'(C=O)—, and —($CR_a'R_b')_q$—, where $R_0$' is H or $C_1$-$C_4$ alkyl, and $R_a$' and $R_b$' are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, heteroaryl($C_1$-$C_6$ alkyl), and heterocyclic ($C_1$-$C_6$ alkyl);

Z is —$(CH_2)_n$— or a bond, where one or more methylene units are optionally substituted by one or more $C_1$-$C_3$ alkyl, CN, OH, methoxy, or halo, and where said alkyl may be substituted by one or more fluorine atoms;

$R_1$ and $R_1'$ are independently selected from the group consisting of hydrogen, deuterium, $C_1$-$C_4$ alkyl, $C_3$-$C_6$ cycloalkyl, aryl, heteroaryl, aryl($C_1$-$C_6$ alkyl), CN, amino, alkylamino, dialkylamino, fluoroalkyl, alkoxy, heteroaryl ($C_1$-$C_6$ alkyl), heterocyclic and heterocyclic($C_1$-$C_6$ alkyl), wherein said alkyl, aryl, cycloalkyl, heterocyclic, or heteroaryl is further optionally substituted with one or more substituents selected from the group consisting of $C_1$-$C_6$ alkyl, halo, CN, hydroxy, methoxy, amino, $C_1$-$C_4$ alkyl amino, di($C_1$-$C_4$ alkyl)amino, $CF_3$, —$SO_2$—($C_1$-$C_6$ alkyl), and $C_3$-$C_6$ cycloalkyl;

$R_2$ is selected from the group consisting of hydrogen, deuterium, $C_1$-$C_6$ alkyl, $C_3$-$C_6$ cycloalkyl, halo, and cyano, where said alkyl may be substituted by one or more fluorine atoms;

$R_3$ is selected from the group consisting of hydrogen, deuterium, and amino;

$R_4$ is monocyclic or bicyclic aryl or monocyclic or bicyclic heteroaryl wherein said aryl or heteroaryl is optionally substituted with one or more substituents selected from the group consisting of $C_1$-$C_6$ alkyl, heterocycloalkyl, halo, CN, hydroxy, —$CO_2H$, $C_1$-$C_6$ alkoxy, amino, —N($C_1$-$C_6$ alkyl) (CO)($C_1$-$C_6$ alkyl), —NH(CO)($C_1$-$C_6$ alkyl), —(CO)$NH_2$, —(CO)NH($C_1$-$C_6$ alkyl), —(CO)N($C_1$-$C_6$ alkyl)$_2$, —($C_1$-$C_6$ alkyl)amino, —N($C_1$-$C_6$ alkyl)$_2$, —$SO_2$—($C_1$-$C_6$ alkyl), —(SO)$NH_2$, and $C_3$-$C_6$ cycloalkyl, where said alkyl, cycloalkyl, alkoxy, or heterocycloalkyl may be substituted by one or more $C_1$-$C_6$ alkyl, halo, CN, OH, alkoxy, amino, —$CO_2H$, —(CO)$NH_2$, —(CO)NH($C_1$-$C_6$ alkyl), or —(CO)N($C_1$-$C_6$ alkyl)$_2$, and where said alkyl may be further substituted by one or more fluorine atoms;

$R_5$ is independently selected from the group consisting of hydrogen, $C_1$-$C_6$ alkyl, $C_1$-$C_6$ alkoxy, and hydroxyl;

h is 1, 2 or 3; j and k are independently 0, 1, 2, or 3; m and n are independently 0, 1 or 2; and, q is 0, 1 or 2.

In other aspects, the present invention also provides:

pharmaceutical compositions which comprise a pharmaceutically acceptable carrier and a compound of formula I; methods for treating conditions or disorders including myositis, vasculitis, pemphigus, Crohn's disease, lupus, nephritis, psoriasis, multiple sclerosis, major depression disorder, allergy, asthma, Sjogren's disease, dry eye syndrome, transplant rejection, cancer, inflammatory bowel disease, septic shock, cardiopulmonary dysfunction, vitiligo, alopecia, acute respiratory disease, ankylosing spondylitis, autoimmune hepatitis, primary sclerosing cholangitis, primary biliary cirrhosis, Alzheimer's disease, or cachexia by administering to a subject in need a therapeutically effective amount of a compound of formula I or a pharmaceutically acceptable salt thereof;

methods for treating conditions or disorders including atopic dermatitis, eczema, psoriasis, scleroderma, lupus, pruritus, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of formula I, or a pharmaceutically acceptable salt thereof; and, methods for the preparation of compounds of the present invention.

The present invention will be further understood from the following description given by way of example only. The present invention is directed to a class of amino pyrimidine derivatives. In particular, the present invention is directed to amino pyrimidine compounds useful as inhibitors of JAK, and particularly TYK2 and JAK1. While the present invention is not so limited, an appreciation of various aspects of the invention will be gained through the following discussion and the examples.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH group. The term "heterocyclic" refers to a saturated or partially saturated (i.e., non aromatic) heterocycle which contains five to ten ring atoms where one or more, preferably, one, two or three ring atoms, are heteratom(s) selected from N, O and S, the remaining being carbon, and which may be attached via a ring nitrogen atom or a ring carbon atom. Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon containing six to ten ring carbon atoms which may be attached via one of the ring carbon atoms. Equally, when substituted, the substituent may be located on a ring carbon atom. Specific examples include, but are not limited to, phenyl, toluyl, xylyl, trimethylphenyl, and naphthyl. Examples of aryl substituents include, but are not limited to, alkyl, hydroxyl, halo, nitrile, alkoxy, trifluoromethyl, carboxamido, $SO_2Me$, benzyl, and substituted benzyl.

The term "heteroaryl" refers to a monovalent aromatic monocyclic or bicyclic heterocycle of five to ten ring atoms where one or more, preferably, one, two or three ring atoms, are heteratom(s) selected from N, O, and S, the remaining being carbon, and which may be attached via a ring carbon atom or a ring nitrogen atom with an appropriate valency. Equally, when substituted, the substituent may be located on a ring carbon atom or a ring nitrogen atom with an appropriate valency. Specific examples include, but are not limited to, thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_nH_{2n-1}$. Examples include, but are not limited to, cyclopropyl, cyclobutyl, cyclopentyl, cyclohexyl, and cycloheptyl. Unless otherwise specified, a cycloalkyl group comprises from 3 to 8 carbon atoms.

The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of cancer, cardiovascular disease, or pain and inflammation and the frequency of incidence over treatment of each agent by itself, while avoiding adverse side effects typically associated with alternative therapies.

"Pharmaceutically acceptable" means suitable for use in mammals, companion animals or livestock animals.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are TYK2 and JAK1 modulators useful for the treatment of diseases and conditions associated with dysregulation of TYK2 and JAK1. The present invention further provides pharmaceutical compositions comprising such JAK enzyme modulators as well as methods of treating and/or preventing such diseases and conditions. Accordingly, the present invention provides a compound of formula I having the structure:

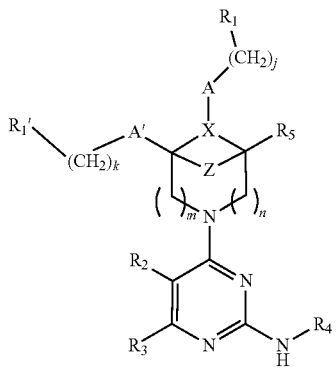

or a pharmaceutically acceptable salt thereof, wherein X is N or CR, where R is hydrogen, deuterium, $C_1$-$C_4$ alkyl, $C_1$-$C_4$ alkoxy, $C_3$-$C_6$ cycloalkyl, aryl, heteroaryl, aryl($C_1$-$C_6$ alkyl), CN, amino, alkylamino, dialkylamino, $CF_3$, or hydroxyl;

A is selected from the group consisting of a bond, C=O, —$SO_2$—, —(C=O)$NR_0$—, and —($CR_aR_b)_q$—, where $R_0$ is H or $C_1$-$C_4$ alkyl, and $R_a$ and $R_b$ are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, heteroaryl($C_1$-$C_6$ alkyl), and heterocyclic($C_1$-$C_6$ alkyl);

A' is selected from the group consisting of a bond, C=O, —$SO_2$—, —(C=O)$NR_0$'—, —$NR_0$'(C=O)—, and —($CR_a'R_b')_q$—, where $R_0$' is H or $C_1$-$C_4$ alkyl, and $R_a$' and $R_b$' are independently hydrogen, deuterium, $C_1$-$C_6$ alkyl, $C_3$-$C_6$ cycloalkyl, aryl, aryl($C_1$-$C_6$ alkyl), heteroaryl, ($C_1$-$C_6$ alkyl)heteroaryl, heteroaryl($C_1$-$C_6$ alkyl), and heterocyclic($C_1$-$C_6$ alkyl);

Z is —$(CH_2)_h$— or a bond, where one or more methylene units are optionally substituted by one or more $C_1$-$C_3$ alkyl, CN, OH, methoxy, or halo, and where said alkyl may be substituted by one or more fluorine atoms;

$R_1$ and $R_1$' are independently selected from the group consisting of hydrogen, deuterium, $C_1$-$C_4$ alkyl, $C_3$-$C_6$ cycloalkyl, aryl, heteroaryl, aryl($C_1$-$C_6$ alkyl), CN, amino, alkylamino, dialkylamino, fluoroalkyl, alkoxy, heteroaryl($C_1$-$C_6$ alkyl), and heterocyclic($C_1$-$C_6$ alkyl), wherein said alkyl, aryl, cycloalkyl, heterocyclic, or heteroaryl is further optionally substituted with one or more substituents selected from the group consisting of $C_1$-$C_6$ alkyl, halo, CN, hydroxy, methoxy, amino, $C_1$-$C_4$ alkyl amino, di($C_1$-$C_4$ alkyl)amino, $CF_3$, —$SO_2$—($C_1$-$C_6$ alkyl), and $C_3$-$C_6$cycloalkyl;

$R_2$ is selected from the group consisting of hydrogen, deuterium, $C_1$-$C_6$ alkyl, $C_3$-$C_6$cycloalkyl, halo, and cyano, where said alkyl may be substituted by one or more fluorine atoms;

$R_3$ is selected from the group consisting of hydrogen, deuterium, and amino;

$R_4$ is monocyclic or bicyclic aryl or monocyclic or bicyclic heteroaryl wherein said aryl or heteroaryl is optionally substituted with one or more substituents selected from the group consisting of $C_1$-$C_6$ alkyl, heterocycloalkyl, halo, CN, hydroxy, —$CO_2H$, $C_1$-$C_6$ alkoxy, amino, —N($C_1$-$C_6$ alkyl)(CO)($C_1$-$C_6$ alkyl), —NH(CO)($C_1$-$C_6$ alkyl), —(CO)$NH_2$, —(CO)NH($C_1$-$C_6$ alkyl), —(CO)N($C_1$-$C_6$ alkyl)$_2$, —($C_1$-$C_6$ alkyl)amino, —N($C_1$-$C_6$ alkyl)$_2$, —$SO_2$—($C_1$-$C_6$ alkyl), —(SO)$NH_2$, and $C_3$-$C_6$ cycloalkyl, where said alkyl, cycloalkyl, alkoxy, or heterocycloalkyl may be substituted by one or more $C_1$-$C_6$ alkyl, halo, CN, OH, alkoxy, amino, —$CO_2H$, —(CO)$NH_2$, —(CO)NH($C_1$-$C_6$ alkyl), or —(CO)N($C_1$-$C_6$ alkyl)$_2$, and where said alkyl may be further substituted by one or more fluorine atoms;

$R_5$ is independently selected from the group consisting of hydrogen, $C_1$-$C_6$ alkyl, $C_1$-$C_6$ alkoxy, and hydroxyl;

h is 1, 2 or 3; j and k are independently 0, 1, 2, or 3; m and n are independently 0, 1 or 2; and, q is 0, 1 or 2.

The invention also provides a compound having the structure:

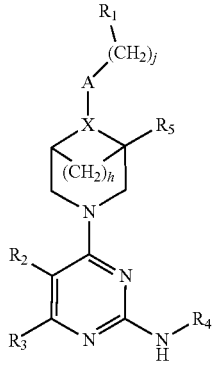

or a pharmaceutically acceptable salt thereof, wherein

X is N;

A is selected from the group consisting of a bond, C=O, —SO$_2$—, —(C=O)NR$_0$—, and —(CR$_a$R$_b$)$_q$—, where R$_0$ is H or C$_1$-C$_4$ alkyl, and R$_a$ and R$_b$ are independently hydrogen, deuterium, C$_1$-C$_6$ alkyl, C$_3$-C$_6$ cycloalkyl, aryl, aryl(C$_1$-C$_6$ alkyl), heteroaryl, (C$_1$-C$_6$ alkyl)heteroaryl, heteroaryl (C$_1$-C$_6$ alkyl), and heterocyclic(C$_1$-C$_6$ alkyl);

R$_1$ is selected from the group consisting of hydrogen, deuterium, C$_1$-C$_4$ alkyl, C$_3$-C$_6$ cycloalkyl, aryl, heteroaryl, aryl(C$_1$-C$_6$ alkyl), CN, amino, alkylamino, dialkylamino, fluoroalkyl, alkoxy, heteroaryl(C$_1$-C$_6$ alkyl), and heterocyclic(C$_1$-C$_6$ alkyl), wherein said alkyl, aryl, cycloalkyl, heterocyclic, or heteroaryl is further optionally substituted with one or more substituents selected from the group consisting of C$_1$-C$_6$ alkyl, halo, CN, hydroxy, methoxy, amino, C$_1$-C$_4$ alkyl amino, di(C$_1$-C$_4$ alkyl)amino, CF$_3$, —SO$_2$—(C$_1$-C$_6$ alkyl), and C$_3$-C$_6$ cycloalkyl;

R$_2$ is selected from the group consisting of hydrogen, deuterium, C$_1$-C$_6$ alkyl, C$_3$-C$_6$ cycloalkyl, halo, and cyano, where said alkyl may be substituted by one or more fluorine atoms;

R$_3$ is selected from the group consisting of hydrogen and deuterium;

R$_4$ is monocyclic or bicyclic aryl or monocyclic or bicyclic heteroaryl wherein said aryl or heteroaryl is optionally substituted with one or more substituents selected from the group consisting of C$_1$-C$_6$ alkyl, heterocycloalkyl, halo, CN, hydroxy, —CO$_2$H, C$_1$-C$_6$ alkoxy, amino, —N(C$_1$-C$_6$ alkyl)(CO)(C$_1$-C$_6$ alkyl), —NH(CO)(C$_1$-C$_6$ alkyl), —(CO)NH$_2$, —(CO)NH(C$_1$-C$_6$ alkyl), —(CO)N(C$_1$-C$_6$ alkyl)$_2$, —(C$_1$-C$_6$ alkyl)amino, —N(C$_1$-C$_6$ alkyl)$_2$, —SO$_2$—(C$_1$-C$_6$ alkyl), —(SO)NH$_2$, and C$_3$-C$_6$ cycloalkyl, where said alkyl, cycloalkyl, alkoxy, or heterocycloalkyl may be substituted by one or more C$_1$-C$_6$ alkyl, halo, CN, OH, alkoxy, amino, —CO$_2$H, —(CO)NH$_2$, —(CO)NH(C$_1$-C$_6$ alkyl), or —(CO)N(C$_1$-C$_6$ alkyl)$_2$, and where said alkyl may be further substituted by one or more fluorine atoms;

h is 1, j is 1, 2, or 3; and, q is 0, 1 or 2.

The invention further provides a compound having the structure:

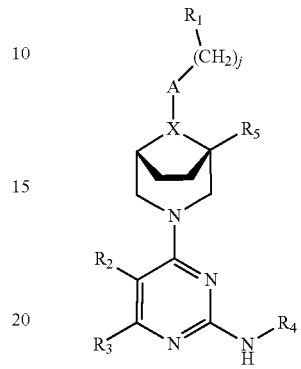

or a pharmaceutically acceptable salt thereof, wherein

X is N;

A is selected from the group consisting of a bond, C=O, —SO$_2$—, —(C=O)NR$_0$—, and —(CR$_a$R$_b$)$_q$—, where R$_0$ is H or C$_1$-C$_4$ alkyl, and R$_a$ and R$_b$ are independently hydrogen, deuterium, C$_1$-C$_6$ alkyl, C$_3$-C$_6$ cycloalkyl, aryl, aryl(C$_1$-C$_6$ alkyl), heteroaryl, (C$_1$-C$_6$ alkyl)heteroaryl, heteroaryl (C$_1$-C$_6$ alkyl), and heterocyclic(C$_1$-C$_6$ alkyl);

R$_1$ is selected from the group consisting of hydrogen, deuterium, C$_1$-C$_4$ alkyl, C$_3$-C$_6$ cycloalkyl, aryl, heteroaryl, aryl(C$_1$-C$_6$ alkyl), CN, amino, alkylamino, dialkylamino, fluoroalkyl, alkoxy, heteroaryl(C$_1$-C$_6$ alkyl), and heterocyclic(C$_1$-C$_6$ alkyl), wherein said alkyl, aryl, cycloalkyl, heterocyclic, or heteroaryl is further optionally substituted with one or more substituents selected from the group consisting of C$_1$-C$_6$ alkyl, halo, CN, hydroxy, methoxy, amino, C$_1$-C$_4$ alkyl amino, di(C$_1$-C$_4$ alkyl)amino, CF$_3$, —SO$_2$—(C$_1$-C$_6$ alkyl), and C$_3$-C$_6$ cycloalkyl;

R$_2$ is selected from the group consisting of hydrogen, deuterium, C$_1$-C$_6$ alkyl, C$_3$-C$_6$ cycloalkyl, halo, and cyano, where said alkyl may be substituted by one or more fluorine atoms;

R$_3$ is selected from the group consisting of hydrogen and deuterium;

R$_4$ is monocyclic or bicyclic aryl or monocyclic or bicyclic heteroaryl wherein said aryl or heteroaryl is optionally substituted with one or more substituents selected from the group consisting of C$_1$-C$_6$ alkyl, heterocycloalkyl, halo, CN, hydroxy, —CO$_2$H, C$_1$-C$_6$ alkoxy, amino, —N(C$_1$-C$_6$ alkyl)(CO)(C$_1$-C$_6$ alkyl), —NH(CO)(C$_1$-C$_6$ alkyl), —(CO)NH$_2$, —(CO)NH(C$_1$-C$_6$ alkyl), —(CO)N(C$_1$-C$_6$ alkyl)$_2$, —(C$_1$-C$_6$ alkyl)amino, —N(C$_1$-C$_6$ alkyl)$_2$, —SO$_2$—(C$_1$-C$_6$ alkyl), —(SO)NH$_2$, and C$_3$-C$_6$ cycloalkyl, where said alkyl, cycloalkyl, alkoxy, or heterocycloalkyl may be substituted by one or more C$_1$-C$_6$ alkyl, halo, CN, OH, alkoxy, amino, —CO$_2$H, —(CO)NH$_2$, —(CO)NH(C$_1$-C$_6$ alkyl), or —(CO)N(C$_1$-C$_6$ alkyl)$_2$, and where said alkyl may be further substituted by one or more fluorine atoms;

R$_5$ is selected from the group consisting of hydrogen, C$_1$-C$_6$ alkyl, C$_1$-C$_6$ alkoxy, and hydroxyl; j is 0, 1, 2, or 3; and, q is 0, 1 or 2.

The invention also provides a compound having the structure:

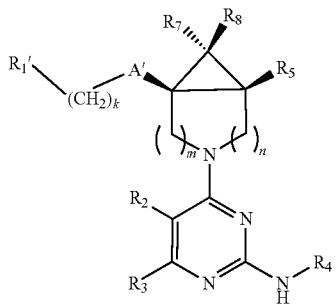

or a pharmaceutically acceptable salt thereof, wherein

A' is selected from the group consisting of a bond, C=O, —SO$_2$—, —(C=O)NR$_0$'—, —NR$_0$'(C=O)—, and —(CR$_a$'R$_b$')$_q$—, where R$_0$' is H or C$_1$-C$_4$ alkyl, and R$_a$' and R$_b$' are independently hydrogen, deuterium, C$_1$-C$_6$ alkyl, C$_3$-C$_6$ cycloalkyl, aryl, aryl(C$_1$-C$_6$ alkyl), heteroaryl, (C$_1$-C$_6$ alkyl)heteroaryl, heteroaryl(C$_1$-C$_6$ alkyl), and heterocyclic (C$_1$-C$_6$ alkyl);

R$_1$' is selected from the group consisting of hydrogen, deuterium, C$_1$-C$_4$ alkyl, C$_3$-C$_6$ cycloalkyl, aryl, heteroaryl, aryl(C$_1$-C$_6$ alkyl), CN, amino, alkylamino, dialkylamino, fluoroalkyl, alkoxy, heteroaryl(C$_1$-C$_6$ alkyl), and heterocyclic(C$_1$-C$_6$ alkyl), wherein said alkyl, aryl, cycloalkyl, heterocyclic, or heteroaryl is further optionally substituted with one or more substituents selected from the group consisting of C$_1$-C$_6$ alkyl, halo, CN, hydroxy, methoxy, amino, C$_1$-C$_4$ alkyl amino, di(C$_1$-C$_4$ alkyl)amino, CF$_3$, —SO$_2$—(C$_1$-C$_6$ alkyl), and C$_3$-C$_6$ cycloalkyl;

R$_2$ is selected from the group consisting of hydrogen, deuterium, C$_1$-C$_6$ alkyl, C$_3$-C$_6$ cycloalkyl, halo, and cyano, where said alkyl may be substituted by one or more fluorine atoms;

R$_3$ is selected from the group consisting of hydrogen and deuterium;

R$_4$ is monocyclic or bicyclic aryl or monocyclic or bicyclic heteroaryl wherein said aryl or heteroaryl is optionally substituted with one or more substituents selected from the group consisting of C$_1$-C$_6$ alkyl, heterocycloalkyl, halo, CN, hydroxy, —CO$_2$H, C$_1$-C$_6$ alkoxy, amino, —N(C$_1$-C$_6$ alkyl)(CO)(C$_1$-C$_6$ alkyl), —NH(CO)(C$_1$-C$_6$ alkyl), —(CO)NH$_2$, —(CO)NH(C$_1$-C$_6$ alkyl), —(CO)N(C$_1$-C$_6$ alkyl)$_2$, —(C$_1$-C$_6$ alkyl)amino, —N(C$_1$-C$_6$ alkyl)$_2$, —SO$_2$—(C$_1$-C$_6$ alkyl), —(SO)NH$_2$, and C$_3$-C$_6$ cycloalkyl, where said alkyl, cycloalkyl, alkoxy, or heterocycloalkyl may be substituted by one or more C$_1$-C$_6$ alkyl, halo, CN, OH, alkoxy, amino, —CO$_2$H, —(CO)NH$_2$, —(CO)NH(C$_1$-C$_6$ alkyl), or —(CO)N(C$_1$-C$_6$ alkyl)$_2$, and where said alkyl may be further substituted by one or more fluorine atoms;

R$_7$ and R$_8$ are independently hydrogen, C$_1$-C$_4$ alkyl, aryl, heteroaryl, (aryl)C$_1$-C$_6$ alkyl, (heteroaryl)C$_1$-C$_6$ alkyl, (heterocyclic)C$_1$-C$_6$ alkyl, (C$_1$-C$_6$ alkyl)aryl, (C$_1$-C$_6$ alkyl)heteroaryl, or (C$_1$-C$_6$ alkyl)heterocyclic, wherein said alkyl is further optionally substituted with one or more substituents selected from the group consisting of halo, hydroxy, methoxy, amino, CF$_3$, and C$_3$-C$_6$ cycloalkyl;

k is 0, 1, 2, or 3; m and n are both 1; and, q is 0, 1 or 2.

In certain embodiments, the invention provides a compound selected from the group consisting of:

[(1S)-2,2-difluorocyclopropyl]{(1R,5S)-3-[2-({5-fluoro-6-[(3S)-3-hydroxypyrrolidin-1-yl]pyridin-3-yl}amino)pyrimidin-4-yl]-3,8-diazabicyclo[3.2.1]oct-8-yl}methanone;

(1R,5S)-N-ethyl-3-[2-(1,2-thiazol-4-ylamino)pyrimidin-4-yl]-3,8-diazabicyclo[3.2.1]octane-8-carboxamide;

4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

(1R,5S)-3-(2-{[5-chloro-6-(methylcarbamoyl)pyridin-3-yl]amino}pyrimidin-4-yl)-N-ethyl-3,8-diazabicyclo[3.2.1]octane-8-carboxamide;

cyclopropyl[(1R,5S)-3-(2-{[1-(2-hydroxyethyl)-1H-pyrazol-4-yl]amino}pyrimidin-4-yl)-3,8-diazabicyclo[3.2.1]oct-8-yl]methanone;

N-(1-methyl-1H-pyrazol-4-yl)-4-{(1R,5S)-8-[1-(methylsulfonyl)azetidin-3-yl]-3,8-diazabicyclo[3.2.1]oct-3-yl}pyrimidin-2-amine;

4-({4-[(1R,5S)-8-{[(1S)-2,2-difluorocyclopropyl]carbonyl}-3,8-diazabicyclo[3.2.1]oct-3-yl]pyrimidin-2-yl}amino)-N,6-dimethylpyridine-2-carboxamide;

5-({4-[(1R,5S)-8-{[(1R,2S)-2-fluorocyclopropyl]carbonyl}-3,8-diazabicyclo[3.2.1]oct-3-yl]pyrimidin-2-yl}amino)-N,3-dimethylpyridine-2-carboxamide;

cyclopropyl[(1R,5S)-3-{2-[(1-methyl-1H-pyrazol-4-yl)amino]pyrimidin-4-yl}-3,8-diazabicyclo[3.2.1]oct-8-yl]methanone;

3-{(1R,5S)-3-[2-(1H-pyrazol-4-ylamino)pyrimidin-4-yl]-3,8-diazabicyclo[3.2.1]oct-8-yl}butanenitrile;

5-({4-[(1R,5S)-8-(cyclopropylcarbonyl)-3,8-diazabicyclo[3.2.1]oct-3-yl]pyrimidin-2-yl}amino)-N-ethyl-3-methylpyridine-2-carboxamide;

3-[(1R,5S)-3-{2-[(1-methyl-1H-pyrazol-4-yl)amino]pyrimidin-4-yl}-3,8-diazabicyclo[3.2.1]oct-8-yl]butanenitrile;

5-({4-[(1R,5S)-8-(cyclopropylcarbonyl)-3,8-diazabicyclo[3.2.1]oct-3-yl]pyrimidin-2-yl}amino)-3-methylpyridine-2-carboxamide;

(1R,5S)-N-ethyl-3-(2-{[5-fluoro-6-(methylcarbamoyl)pyridin-3-yl]amino}pyrimidin-4-yl)-3,8-diazabicyclo[3.2.1]octane-8-carboxamide;

3-chloro-5-({4-[(1R,5S)-8-(cyclopropylcarbonyl)-3,8-diazabicyclo[3.2.1]oct-3-yl]pyrimidin-2-yl}amino)-N-methylpyridine-2-carboxamide;

(1R,5S)-3-{2-[(1-methyl-1H-pyrazol-4-yl)amino]pyrimidin-4-yl}-N-(propan-2-yl)-3,8-diazabicyclo[3.2.1]octane-8-carboxamide;

(3,3-difluorocyclobutyl)[(1R,5S)-3-{2-[(1-methyl-1H-pyrazol-4-yl)amino]pyrimidin-4-yl}-3,8-diazabicyclo[3.2.1]oct-8-yl]methanone;

1-({(1R,5S)-3-[2-(1H-pyrazol-4-ylamino)pyrimidin-4-yl]-3,8-diazabicyclo[3.2.1]oct-8-yl}methyl)cyclopropanecarbonitrile;

3-[(1R,5S)-3-{2-[(1-methyl-1H-pyrazol-4-yl)amino]pyrimidin-4-yl}-3,8-diazabicyclo[3.2.1]oct-8-yl]butanenitrile;

(1S,2R)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile;

(1R,2S)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile;

[(1R,2R)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

[(1R,2R)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone (1R,5S)-3-{2-[(1-methyl-1H-pyrazol-4-yl)amino]pyrimidin-4-yl}-3,8-diazabicyclo[3.2.1]octane-8-carboxamide;

(1R,5S)-3-{2-[(1-methyl-1H-pyrazol-4-yl)amino]pyrimidin-4-yl}-N-[5-(trifluoromethyl)pyridin-2-yl]-3,8-diazabicyclo[3.2.1]octane-8-carboxamide;

N,3-dimethyl-5-[(4-{(1R,5S)-8-[(3-methyloxetan-3-yl)methyl]-3,8-diazabicyclo[3.2.1]oct-3-yl}pyrimidin-2-yl)amino]pyridine-2-carboxamide;

{3-[(1R,5S)-3-{2-[(1-methyl-1H-pyrazol-4-yl)amino]pyrimidin-4-yl}-3,8-diazabicyclo[3.2.1]oct-8-yl]-1-(methylsulfonyl)azetidin-3-yl}acetonitrile;

4-({4-[8-(cyanoacetyl)-3,8-diazabicyclo[3.2.1]oct-3-yl]pyrimidin-2-yl}amino)-N-ethylbenzamide;

(1R,5S)-N-(cyanomethyl)-3-{2-[(1-methyl-1H-pyrazol-4-yl)amino]pyrimidin-4-yl}-3,8-diazabicyclo[3.2.1]octane-8-carboxamide;

5-({4-[(1R,5S)-8-{[(1S,2R)-2-fluorocyclopropyl]carbonyl}-3,8-diazabicyclo[3.2.1]oct-3-yl]pyrimidin-2-yl}amino)-N,3-dimethylpyridine-2-carboxamide;

5-({4-[(1R,5S)-8-(cis-3-cyanocyclobutyl)-3,8-diazabicyclo[3.2.1]oct-3-yl]pyrimidin-2-yl}amino)-N,3-dimethylpyridine-2-carboxamide;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoropyridine-2-carboxamide 5-({4-[(1R,5S)-8-{[(1R)-2,2-difluorocyclopropyl]methyl}-3,8-diazabicyclo[3.2.1]oct-3-yl]pyrimidin-2-yl}amino)-N,3-dimethylpyridine-2-carboxamide;

N,3-dimethyl-5-({4-[(1R,5S)-8-(1,2-oxazol-5-ylmethyl)-3,8-diazabicyclo[3.2.1]oct-3-yl]pyrimidin-2-yl}amino)pyridine-2-carboxamide;

2-[5-({4-[(1R,5S)-8-{[(1S)-2,2-difluorocyclopropyl]carbonyl}-3,8-diazabicyclo[3.2.1]oct-3-yl]pyrimidin-2-yl}amino)pyridin-2-yl]-2-methylpropanenitrile;

3-{(1R,5S)-3-[2-(1H-pyrazol-4-ylamino)pyrimidin-4-yl]-3,8-diazabicyclo[3.2.1]oct-8-yl}propanenitrile;

(1R,5S)-N-ethyl-3-[2-(1H-pyrazol-4-ylamino)pyrimidin-4-yl]-3,8-diazabicyclo[3.2.1]octane-8-carboxamide;

4-[(1R,5S)-8-{[(1S)-2,2-difluorocyclopropyl]methyl}-3,8-diazabicyclo[3.2.1]oct-3-yl]-N-(1-methyl-1H-pyrazol-4-yl)pyrimidin-2-amine;

[(1S)-2,2-difluorocyclopropyl][(1R,5S)-3-(2-{[5-fluoro-6-(2-hydroxyethyl)pyridin-3-yl]amino}pyrimidin-4-yl)-3,8-diazabicyclo[3.2.1]oct-8-yl]methanone;

[(1S)-2,2-difluorocyclopropyl][(1R,5S)-3-(2-{[5-fluoro-6-(3-hydroxyazetidin-1-yl)pyridin-3-yl]amino}pyrimidin-4-yl)-3,8-diazabicyclo[3.2.1]oct-8-yl]methanone;

[(1R,5S)-3-(2-{[5-chloro-6-(2-hydroxyethoxy)pyridin-3-yl]amino}pyrimidin-4-yl)-3,8-diazabicyclo[3.2.1]oct-8-yl][(1S)-2,2-difluorocyclopropyl]methanone;

{3-[(1R,5S)-3-{2-[(1-methyl-1H-pyrazol-4-yl)amino]pyrimidin-4-yl}-3,8-diazabicyclo[3.2.1]oct-8-yl]oxetan-3-yl}acetonitrile;

[(1R,5S)-3-(2-{[5-chloro-6-(2-hydroxyethyl)pyridin-3-yl]amino}pyrimidin-4-yl)-3,8-diazabicyclo[3.2.1]oct-8-yl][(1S)-2,2-difluorocyclopropyl]methanone;

2-[(1R,5S)-3-{2-[(1-methyl-1H-pyrazol-4-yl)amino]pyrimidin-4-yl}-3,8-diazabicyclo[3.2.1]oct-8-yl]pyridine-4-carbonitrile;

3-[(1R,5S)-3-{2-[(1-methyl-1H-pyrazol-4-yl)amino]pyrimidin-4-yl}-3,8-diazabicyclo[3.2.1]oct-8-yl]cyclobutanecarbonitrile;

2-[(1R,5S)-3-{2-[(1-methyl-1H-pyrazol-4-yl)amino]pyrimidin-4-yl}-3,8-diazabicyclo[3.2.1]oct-8-yl]-1,3-oxazole-5-carbonitrile;

(1R,5S)-N-(2-cyanoethyl)-3-{2-[(1-methyl-1H-pyrazol-4-yl)amino]pyrimidin-4-yl}-3,8-diazabicyclo[3.2.1]octane-8-carboxamide;

N-(1-methyl-1H-pyrazol-4-yl)-4-[(1R,5S)-8-(1,2-oxazol-4-ylmethyl)-3,8-diazabicyclo[3.2.1]oct-3-yl]pyrimidin-2-amine;

4-({4-[(1R,5S)-8-{[(1S)-2,2-difluorocyclopropyl]carbonyl}-3,8-diazabicyclo[3.2.1]oct-3-yl]pyrimidin-2-yl}amino)-6-(hydroxymethyl)-N-methylpyridine-2-carboxamide;

(1-fluorocyclopropyl)[(1R,5S)-3-{2-[(1-methyl-1H-pyrazol-4-yl)amino]pyrimidin-4-yl}-3,8-diazabicyclo[3.2.1]oct-8-yl]methanone;

N-(1-methyl-1H-pyrazol-4-yl)-4-[(1R,5S)-8-(1,3-thiazol-2-ylmethyl)-3,8-diazabicyclo[3.2.1]oct-3-yl]pyrimidin-2-amine;

cyclopropyl{(1R,5S)-3-[2-(1,2-thiazol-4-ylamino)pyrimidin-4-yl]-3,8-diazabicyclo[3.2.1]oct-8-yl}methanone;

[(1S)-2,2-difluorocyclopropyl]{(1R,5S)-3-[2-({5-fluoro-6-[(3R)-3-hydroxypyrrolidin-1-yl]pyridin-3-yl}amino)pyrimidin-4-yl]-3,8-diazabicyclo[3.2.1]oct-8-yl}methanone;

5-({4-[(1R,5S)-8-{[(1S)-2,2-difluorocyclopropyl]methyl}-3,8-diazabicyclo[3.2.1]oct-3-yl]pyrimidin-2-yl}amino)-N,3-dimethylpyridine-2-carboxamide;

4-[(1R,5S)-8-{[(1R)-2,2-difluorocyclopropyl]methyl}-3,8-diazabicyclo[3.2.1]oct-3-yl]-N-(1-methyl-1H-pyrazol-4-yl)pyrimidin-2-amine;

6-({4-[(1R,5S)-8-(cyclopropylcarbonyl)-3,8-diazabicyclo[3.2.1]oct-3-yl]-5-fluoropyrimidin-2-yl}amino)imidazo[1,2-a]pyridine-2-carboxamide;

5-({4-[(1R,5S)-8-(cyclopropylcarbonyl)-3,8-diazabicyclo[3.2.1]oct-3-yl]-5-fluoropyrimidin-2-yl}amino)pyridine-2-sulfonamide;

5-({4-[(1R,5S)-8-(trans-3-cyanocyclobutyl)-3,8-diazabicyclo[3.2.1]oct-3-yl]pyrimidin-2-yl}amino)-N,3-dimethylpyridine-2-carboxamide;

1,2-oxazol-5-yl{(1R,5S)-3-[2-(1H-pyrazol-4-ylamino)pyrimidin-4-yl]-3,8-diazabicyclo[3.2.1]oct-8-yl}methanone;

N-(1-methyl-1H-pyrazol-4-yl)-4-[(1R,5S)-8-(methylsulfonyl)-3,8-diazabicyclo[3.2.1]oct-3-yl]pyrimidin-2-amine;

(1S,2S)-2-{[(1R,5S)-3-{2-[(1-methyl-1H-pyrazol-4-yl)amino]pyrimidin-4-yl}-3,8-diazabicyclo[3.2.1]oct-8-yl]methyl}cyclopropanecarbonitrile;

3-({4-[(1R,5S)-8-(cyclopropylcarbonyl)-3,8-diazabicyclo[3.2.1]oct-3-yl]-5-fluoropyrimidin-2-yl}amino)-N-propyl-1H-pyrazole-5-carboxamide;

(1S,2S)-2-{[(1R,5S)-3-{2-[(1-methyl-1H-pyrazol-4-yl)amino]pyrimidin-4-yl}-3,8-diazabicyclo[3.2.1]oct-8-yl]methyl}cyclopropanecarbonitrile;

cyclopropyl{(1R,5S)-3-[5-fluoro-2-(pyridazin-4-ylamino)pyrimidin-4-yl]-3,8-diazabicyclo[3.2.1]oct-8-yl}methanone;

4-({4-[6-(2,2-difluoropropanoyl)-3,6-diazabicyclo[3.1.1]hept-3-yl]-5-fluoropyrimidin-2-yl}amino)-N-ethyl-2-methylbenzamide;

(1S,2S)-2-cyano-N-[(1S,5R,6R)-3-(2-{[6-(2-hydroxyethoxy)pyridin-3-yl]amino}-5-methylpyrimidin-4-yl)-6-methyl-3-azabicyclo[3.1.0]hex-1-yl]cyclopropanecarboxamide;

N-[(1 S,5R)-3-(5-chloro-2-{[1-(2-hydroxyethyl)-1H-pyrazol-4-yl]amino}pyrimidin-4-yl)-3-azabicyclo[3.1.0]hex-1-yl]cyclopropanecarboxamide;

(1S)-2,2-difluoro-N-[(1S,5R,6R)-3-(5-fluoro-2-{[1-(oxetan-3-yl)-1H-pyrazol-4-yl]amino}pyrimidin-4-yl)-6-methyl-3-azabicyclo[3.1.0]hex-1-yl]cyclopropanecarboxamide;

(1S)-2,2-difluoro-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

N-{(1S,5R,6R)-3-[5-fluoro-2-({6-[(2S)-1-hydroxypropan-2-yl]pyridin-3-yl}amino)pyrimidin-4-yl]-6-methyl-3-azabicyclo[3.1.0]hex-1-yl}cyclopropanecarboxamide;

5-[(4-{(1S,5R,6R)-1-[(cyclopropylcarbonyl)amino]-6-methyl-3-azabicyclo[3.1.0]hex-3-yl}-5-fluoropyrimidin-2-yl)amino]-N,3-dimethylpyridine-2-carboxamide;

N-{(1S,5R,6R)-3-[2-({5-chloro-6-[(1R)-1-hydroxyethyl]pyridin-3-yl}amino)-5-fluoropyrimidin-4-yl]-6-methyl-3-azabicyclo[3.1.0]hex-1-yl}cyclopropanecarboxamide;

(1R)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

5-[(4-{(1R,5S,6S)-1-[(cyclopropylcarbonyl)amino]-6-methyl-3-azabicyclo[3.1.0]hex-3-yl}-5-fluoropyrimidin-2-yl)amino]-N,3-dimethylpyridine-2-carboxamide;

N-[(1R,5S)-3-(5-chloro-2-{[1-(2-hydroxyethyl)-1H-pyrazol-4-yl]amino}pyrimidin-4-yl)-3-azabicyclo[3.1.0]hex-1-yl]cyclopropanecarboxamide; and, (1S)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

or, a pharmaceutically acceptable salt thereof.

In certain other embodiments, the invention provides a compound selected from the group consisting of:

N-ethyl-4-({5-fluoro-4-[6-(2-fluoro-2-methylpropanoyl)-3,6-diazabicyclo[3.1.1]hept-3-yl]pyrimidin-2-yl}amino)-2-methylbenzamide;

N-ethyl-2-methyl-4-({4-[6-(trifluoroacetyl)-3,6-diazabicyclo[3.1.1]hept-3-yl]pyrimidin-2-yl}amino)benzamide; and, 4-({4-[6-(2,2-difluoropropanoyl)-3,6-diazabicyclo[3.1.1]hept-3-yl]pyrimidin-2-yl}amino)-N-ethylbenzamide;

or, a pharmaceutically acceptable salt thereof.

In yet other embodiments, the invention provides a compound selected from the group consisting of:

4-({4-[8-(cyclopropylcarbonyl)-3,8-diazabicyclo[3.2.1]oct-3-yl]-5-fluoropyrimidin-2-yl}amino)-N-ethylbenzamide;

N-ethyl-4-({5-fluoro-4-[8-(trifluoroacetyl)-3,8-diazabicyclo[3.2.1]oct-3-yl]pyrimidin-2-yl}amino)-2-methylbenzamide;

(1R,5S)-3-(2-{[5-methyl-6-(methylcarbamoyl)pyridin-3-yl]amino}pyrimidin-4-yl)-N-(2,2,2-trifluoroethyl)-3,8-diazabicyclo[3.2.1]octane-8-carboxamide;

(1R,5S)-N-(cyanomethyl)-3-(2-{[5-methyl-6-(methylcarbamoyl)pyridin-3-yl]amino}pyrimidin-4-yl)-3,8-diazabicyclo[3.2.1]octane-8-carboxamide;

5-({4-[(1R,5S)-8-{[(1S)-2,2-difluorocyclopropyl]carbonyl}-3,8-diazabicyclo[3.2.1]oct-3-yl]pyrimidin-2-yl}amino)-N,3-dimethylpyridine-2-carboxamide;

tert-butyl 3-(2-{[4-(ethylcarbamoyl)-3-methylphenyl]amino}-5-fluoropyrimidin-4-yl)-3,8-diazabicyclo[3.2.1]octane-8-carboxylate;

5-({4-[(1R,5S)-8-{[(1R,2R)-2-cyanocyclopropyl]carbonyl}-3,8-diazabicyclo[3.2.1]oct-3-yl]pyrimidin-2-yl}amino)-N,3-dimethylpyridine-2-carboxamide;

3-chloro-5-({4-[(1R,5S)-8-{[(1S)-2,2-difluorocyclopropyl]carbonyl}-3,8-diazabicyclo[3.2.1]oct-3-yl]pyrimidin-2-yl}amino)-N-methylpyridine-2-carboxamide;

N-(1-methyl-1H-pyrazol-4-yl)-4-[(1R,5S)-8-(1,2-thiazol-5-ylmethyl)-3,8-diazabicyclo[3.2.1]oct-3-yl]pyrimidin-2-amine;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-methylpyridine-2-carboxamide;

[(1S)-2,2-difluorocyclopropyl]{(1R,5S)-3-[2-({6-[(2S)-1-hydroxypropan-2-yl]pyridin-3-yl}amino)pyrimidin-4-yl]-3,8-diazabicyclo[3.2.1]oct-8-yl}methanone;

3-chloro-5-({4-[(1R,5S)-8-{[(1R,2R)-2-cyanocyclopropyl]carbonyl}-3,8-diazabicyclo[3.2.1]oct-3-yl]pyrimidin-2-yl}amino)-N-methylpyridine-2-carboxamide;

[(1S)-2,2-difluorocyclopropyl][(1R,5S)-3-(2-{[5-fluoro-6-(hydroxymethyl)pyridin-3-yl]amino}pyrimidin-4-yl)-3,8-diazabicyclo[3.2.1]oct-8-yl]methanone;

5-[(4-{(1R,5S)-8-[(2,2-difluorocyclopropyl)carbonyl]-3,8-diazabicyclo[3.2.1]oct-3-yl}pyrimidin-2-yl)amino]-3-methylpyridine-2-carboxamide;

5-({4-[(1R,5S)-8-(cyclopropylcarbonyl)-3,8-diazabicyclo[3.2.1]oct-3-yl]pyrimidin-2-yl}amino)-N,3-dimethylpyridine-2-carboxamide;

(1R,5S)-N-ethyl-3-(2-{[5-methyl-6-(methylcarbamoyl)pyridin-3-yl]amino}pyrimidin-4-yl)-3,8-diazabicyclo[3.2.1]octane-8-carboxamide;

[(1S)-2,2-difluorocyclopropyl]{(1R,5S)-3-[2-({6-[(2R)-1-hydroxypropan-2-yl]pyridin-3-yl}amino)pyrimidin-4-yl]-3,8-diazabicyclo[3.2.1]oct-8-yl}methanone;

N-(1-methyl-1H-pyrazol-4-yl)-4-[(1R,5S)-8-(1,2-oxazol-5-ylmethyl)-3,8-diazabicyclo[3.2.1]oct-3-yl]pyrimidin-2-amine;

cyclopropyl{(1R,5S)-3-[2-(1H-pyrazol-4-ylamino)pyrimidin-4-yl]-3,8-diazabicyclo[3.2.1]oct-8-yl}methanone;

5-({4-[(1R,5S)-8-{[(1R,2R)-2-cyanocyclopropyl]carbonyl}-3,8-diazabicyclo[3.2.1]oct-3-yl]pyrimidin-2-yl}amino)-3-fluoro-N-methylpyridine-2-carboxamide;

[(1R)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone; and, 5-({4-[(1R,5S)-8-{[(1R)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

or, a pharmaceutically acceptable salt thereof.

In other embodiments, the invention provides a compound selected from the group consisting of:

(1R)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

N-{(1S,5R,6R)-3-[5-fluoro-2-({6-[(2R)-1-hydroxypropan-2-yl]pyridin-3-yl}amino)pyrimidin-4-yl]-6-methyl-3-azabicyclo[3.1.0]hex-1-yl}cyclopropanecarboxamide;

N-[(1S,5R,6R)-3-(2-{[5-chloro-6-(hydroxymethyl)pyridin-3-yl]amino}-5-fluoropyrimidin-4-yl)-6-methyl-3-azabicyclo[3.1.0]hex-1-yl]cyclopropanecarboxamide; and, N-[(1S,5R,6R)-3-(5-fluoro-2-{[6-(2-hydroxyethyl)pyridin-3-yl]amino}pyrimidin-4-yl)-6-methyl-3-azabicyclo[3.1.0]hex-1-yl]cyclopropanecarboxamide;

or, a pharmaceutically acceptable salt thereof.

In one embodiment, the invention provides a compound which is [(1S)-2,2-difluorocyclo-propyl]{(1R,5S)-3-[2-(1H-pyrazol-4-ylamino)pyrimidin-4-yl]-3,8-diazabicyclo[3.2.1]oct-8-yl}methanone; or, a pharmaceutically acceptable salt thereof.

In another embodiment, the invention provides a compound which is [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone; or, a pharmaceutically acceptable salt thereof.

In yet another embodiment, the invention provides a compound which is 5-({4-[(1R,5S)-8-{[(1S) 2,2-difluorocyclopropyl]carbonyl}-3,8-diazabicyclo[3.2.1]oct-3-yl]pyrimidin-2-yl}amino)-3-fluoro-N-methylpyridine-2-carboxamide; or, a pharmaceutically acceptable salt thereof.

In another embodiment, the invention provides a compound which is (1R,5S)-N-ethyl-3-{2-[(1-methyl-1H-pyrazol-4-yl)amino]pyrimidin-4-yl}-3,8-diazabicyclo[3.2.1]octane-8-carboxamide; or, a pharmaceutically acceptable salt thereof.

In one embodiment, the invention provides a compound which is [(1R)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone; or, a pharmaceutically acceptable salt thereof.

In another embodiment, the invention provides a compound which is (1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide, or, a pharmaceutically acceptable salt thereof.

In a certain other embodiment, the invention provides a compound which is (1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide or, a pharmaceutically acceptable salt thereof.

In one embodiment, the invention provides a compound which is (1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide; or, a pharmaceutically acceptable salt thereof.

In another embodiment, the invention provides a compound which is (1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; or, a pharmaceutically acceptable salt thereof.

In a certain other embodiment, the invention provides a compound which is 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine; or, a pharmaceutically acceptable salt thereof.

The invention further provides a pharmaceutical or a veterinary composition comprising a compound of formula I, or a pharmaceutically acceptable salt thereof, and a pharmaceutically acceptable carrier.

The invention also provides a method for treating or preventing a disorder or condition selected from inflammation, autoimmune disease, neuroinflammation, arthritis, rheumatoid arthritis, spondyloarthropathies, systemic lupus erythematous, lupus nephritis, arthritis, osteoarthritis, gouty arthritis, pain, fever, pulmonary sarcoisosis, silicosis, cardiovascular disease, atherosclerosis, myocardial infarction, thrombosis, congestive heart failure and cardiac reperfusion injury, cardiomyopathy, stroke, ischaemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, alopecia, Alzheimer's disease, skin flushing, eczema, psoriasis, atopic dermatitis and sunburn, comprising administering to the subject a therapeutically effective amount of a compound of formula I, or a pharmaceutically acceptable salt thereof, or a pharmaceutically acceptable solvate of said compound or salt.

In certain embodiments, the invention provides the method above wherein the compound is selected from the group consisting of:

4-({4-[8-(cyclopropylcarbonyl)-3,8-diazabicyclo[3.2.1]oct-3-yl]-5-fluoropyrimidin-2-yl}amino)-N-ethylbenzamide;

N-ethyl-4-({5-fluoro-4-[8-(trifluoroacetyl)-3,8-diazabicyclo[3.2.1]oct-3-yl]pyrimidin-2-yl}amino)-2-methylbenzamide;

(1R,5S)-3-(2-{[5-methyl-6-(methylcarbamoyl)pyridin-3-yl]amino}pyrimidin-4-yl)-N-(2,2,2-trifluoroethyl)-3,8-diazabicyclo[3.2.1]octane-8-carboxamide;

(1R,5S)-N-(cyanomethyl)-3-(2-{[5-methyl-6-(methylcarbamoyl)pyridin-3-yl]amino}pyrimidin-4-yl)-3,8-diazabicyclo[3.2.1]octane-8-carboxamide;

5-({4-[(1R,5S)-8-{[(1S)-2,2-difluorocyclopropyl]carbonyl}-3,8-diazabicyclo[3.2.1]oct-3-yl]pyrimidin-2-yl}amino)-N,3-dimethylpyridine-2-carboxamide;

tert-butyl 3-(2-{[4-(ethylcarbamoyl)-3-methylphenyl]amino}-5-fluoropyrimidin-4-yl)-3,8-diazabicyclo[3.2.1]octane-8-carboxylate;

5-({4-[(1R,5S)-8-{[(1R,2R)-2-cyanocyclopropyl]carbonyl}-3,8-diazabicyclo[3.2.1]oct-3-yl]pyrimidin-2-yl}amino)-N,3-dimethylpyridine-2-carboxamide;

3-chloro-5-({4-[(1R,5S)-8-{[(1S)-2,2-difluorocyclopropyl]carbonyl}-3,8-diazabicyclo[3.2.1]oct-3-yl]pyrimidin-2-yl}amino)-N-methylpyridine-2-carboxamide;

N-(1-methyl-1H-pyrazol-4-yl)-4-[(1R,5S)-8-(1,2-thiazol-5-ylmethyl)-3,8-diazabicyclo[3.2.1]oct-3-yl]pyrimidin-2-amine;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-methylpyridine-2-carboxamide;

[(1S)-2,2-difluorocyclopropyl]{(1R,5S)-3-[2-({6-[(2S)-1-hydroxypropan-2-yl]pyridin-3-yl}amino)pyrimidin-4-yl]-3,8-diazabicyclo[3.2.1]oct-8-yl}methanone;

3-chloro-5-({4-[(1R,5S)-8-{[(1R,2R)-2-cyanocyclopropyl]carbonyl}-3,8-diazabicyclo[3.2.1]oct-3-yl]pyrimidin-2-yl}amino)-N-methylpyridine-2-carboxamide;

[(1S)-2,2-difluorocyclopropyl][(1R,5S)-3-(2-{[5-fluoro-6-(hydroxymethyl)pyridin-3-yl]amino}pyrimidin-4-yl)-3,8-diazabicyclo[3.2.1]oct-8-yl]methanone;

5-[(4-{(1R,5S)-8-[(2,2-difluorocyclopropyl)carbonyl]-3,8-diazabicyclo[3.2.1]oct-3-yl}pyrimidin-2-yl)amino]-3-methylpyridine-2-carboxamide;

5-({4-[(1R,5S)-8-(cyclopropylcarbonyl)-3,8-diazabicyclo[3.2.1]oct-3-yl]pyrimidin-2-yl}amino)-N,3-dimethylpyridine-2-carboxamide;

(1R,5S)-N-ethyl-3-(2-{[5-methyl-6-(methylcarbamoyl)pyridin-3-yl]amino}pyrimidin-4-yl)-3,8-diazabicyclo[3.2.1]octane-8-carboxamide;

[(1S)-2,2-difluorocyclopropyl]{(1R,5S)-3-[2-({6-[(2R)-1-hydroxypropan-2-yl]pyridin-3-yl}amino)pyrimidin-4-yl]-3,8-diazabicyclo[3.2.1]oct-8-yl}methanone;

N-(1-methyl-1H-pyrazol-4-yl)-4-[(1R,5S)-8-(1,2-oxazol-5-ylmethyl)-3,8-diazabicyclo[3.2.1]oct-3-yl]pyrimidin-2-amine;

cyclopropyl{(1R,5S)-3-[2-(1H-pyrazol-4-ylamino)pyrimidin-4-yl]-3,8-diazabicyclo[3.2.1]oct-8-yl}methanone;

5-({4-[(1R,5S)-8-{[(1R,2R)-2-cyanocyclopropyl]carbonyl}-3,8-diazabicyclo[3.2.1]oct-3-yl]pyrimidin-2-yl}amino)-3-fluoro-N-methylpyridine-2-carboxamide;

[(1R)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

5-({4-[(1R,5S)-8-{[(1R)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

N-ethyl-4-({5-fluoro-4-[6-(2-fluoro-2-methylpropanoyl)-3,6-diazabicyclo[3.1.1]hept-3-yl]pyrimidin-2-yl}amino)-2-methylbenzamide;

(1R)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

N-ethyl-2-methyl-4-({4-[6-(trifluoroacetyl)-3,6-diazabicyclo[3.1.1]hept-3-yl]pyrimidin-2-yl}amino)benzamide;

4-({4-[6-(2,2-difluoropropanoyl)-3,6-diazabicyclo[3.1.1]hept-3-yl]pyrimidin-2-yl}amino)-N-ethylbenzamide;

4-({4-[6-(cyclopropylcarbonyl)-3,6-diazabicyclo[3.1.1]hept-3-yl]pyrimidin-2-yl}amino)-N-ethyl-2-methylbenzamide;

N-{(1S,5R,6R)-3-[5-fluoro-2-({6-[(2R)-1-hydroxypropan-2-yl]pyridin-3-yl}amino)pyrimidin-4-yl]-6-methyl-3-azabicyclo[3.1.0]hex-1-yl}cyclopropanecarboxamide;

N-[(1S,5R,6R)-3-(2-{[5-chloro-6-(hydroxymethyl)pyridin-3-yl]amino}-5-fluoropyrimidin-4-yl)-6-methyl-3-azabicyclo[3.1.0]hex-1-yl]cyclopropanecarboxamide; and, N-[(1S,5R,6R)-3-(5-fluoro-2-{[6-(2-hydroxyethyl)pyridin-3-yl]amino}pyrimidin-4-yl)-6-methyl-3-azabicyclo[3.1.0]hex-1-yl]cyclopropanecarboxamide;

or, a pharmaceutically acceptable salt thereof.

In certain other embodiments, the invention provides a method for treating or preventing psoriasis, vitiligo, alopecia, or atopic dermatitis by administering to a mammal in need a therapeutically effective amount of a compound selected from the group consisting of:

[(1S)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

(1R,5S)-N-ethyl-3-{2-[(1-methyl-1H-pyrazol-4-yl)amino]pyrimidin-4-yl}-3,8-diazabicyclo[3.2.1]octane-8-carboxamide;

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

(1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; and, 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

or, a pharmaceutically acceptable salt thereof.

In other embodiments, the invention provides a method for treating or preventing systemic lupus erythematosus or lupus nephritis by administering to a mammal in need a therapeutically effective amount of a compound selected from the group consisting of:

[(1S)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

(1R,5S)-N-ethyl-3-{2-[(1-methyl-1H-pyrazol-4-yl)amino]pyrimidin-4-yl}-3,8-diazabicyclo[3.2.1]octane-8-carboxamide;

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

(1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; and, 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

or, a pharmaceutically acceptable salt thereof.

In other embodiments, the invention provides a method for treating or preventing primary biliary cirrhosis, autoimmune hepatitis, primary sclerosing cholangitis by administering to a mammal in need a therapeutically effective amount of a compound selected from the group consisting of:

[(1S)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

(1R,5S)-N-ethyl-3-{2-[(1-methyl-1H-pyrazol-4-yl)amino]pyrimidin-4-yl}-3,8-diazabicyclo[3.2.1]octane-8-carboxamide;

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

(1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; and, 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

or, a pharmaceutically acceptable salt thereof.

In certain other embodiments, the invention provides a method for treating or preventing inflammatory bowel disease, Crohn's disease, or ulcerative colitis by administering to a mammal in need a therapeutically effective amount of a compound selected from the group consisting of:

[(1S)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

(1R,5S)-N-ethyl-3-{2-[(1-methyl-1H-pyrazol-4-yl)amino]pyrimidin-4-yl}-3,8-diazabicyclo[3.2.1]octane-8-carboxamide;

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

(1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; and, 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

or, a pharmaceutically acceptable salt thereof.

In other embodiments, the invention provides a method for treating or preventing multiple sclerosis by administering to a mammal in need a therapeutically effective amount of a compound selected from the group consisting of:

[(1S)-2,2-difluorocyclopropyl]{(1R,5S)-3-[2-(1H-pyrazol-4-ylamino)pyrimidin-4-yl]-3,8-diazabicyclo[3.2.1]oct-8-yl}methanone;

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide;

(1R,5S)-N-ethyl-3-{2-[(1-methyl-1H-pyrazol-4-yl)amino]pyrimidin-4-yl}-3,8-diazabicyclo[3.2.1]octane-8-carboxamide;

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

(1R,2R)-2-cyano-N-[(1 S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

(1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropanecarbonitrile; and, 4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

or, a pharmaceutically acceptable salt thereof.

The invention further provides a method of treating or preventing a disorder or condition selected from acute myeloid leukemia, T cell acute lymphoblastic leukemia, multiple myeloma, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, PD, ALS, frontotemporal lobe dementia, and with neuropsychiatric disorders including schizophrenia, bipolar disorder, depression, treatment resistant depression, PTSD, anxiety, and auto-antibodies mediated encephalopathies, comprising the step of administering to a subject an effective amount of a composition comprising a compound of formula I, or a pharmaceutically acceptable salt thereof, or a pharmaceutically acceptable solvate of said compound or salt.

The invention also provides a method of treating a disease or condition for which a JAK inhibitor is indicated, in a subject in need of such treatment, comprising administering to the subject a therapeutically effective amount of a compound of formula I, or a pharmaceutically acceptable salt thereof, or a pharmaceutically acceptable solvate of said compound or salt.

In certain embodiments, the therapeutically effective amount used in accord with the method is from 0.01 mg/kg of body weight/day to 100 mg/kg of body weight/day. In certain other embod-iments, the therapeutically effective amount used in accord with the method is wherein the therapeutically effective amount is from 0.1 mg/kg of body weight/day to 10 mg/kg of body weight/day.

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of formula I can exist as cis- and trans-achiral diastereomers.

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula I, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I can generally be prepared by conventional techniques known to those skilled in the art or by processes analogous to those described in the accompanying Examples and Preparations using an appropriate isotopically-labeled reagent in place of the non-labeled reagent previously employed.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002).

Pharmaceutically acceptable salts of compounds of formula I may be prepared, respectively, by one or more of three methods: (i) by reacting the compound of formula I with the desired acid or base; (ii) by removing an acid- or base-labile protecting group from a suitable precursor of the compound of formula I or by ring-opening a suitable cyclic precursor, for example, a lactone or lactam, using the desired acid or base; or (iii) by converting one salt of the compound of formula I to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in *Remington's Pharmaceutical Sciences*, Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Compounds of the present invention are directed to amino pyrimidinyl compounds useful as Janus Kinase inhibitors (JAK-i). They are useful as therapeutic agents in connection with the treating or preventing a disorder or condition selected from rheumatoid arthritis, myositis, vasculitis, pemphigus, Crohn's disease, ulcerative colitis, Alzheimer's disease, lupus, nephritis, psoriasis, atopic dermatitis, autoimmune thyroid disorders, multiple sclerosis, major depression disorder, allergy, asthma, Sjogren's disease, dry eye syndrome, organ transplant rejection, xeno transplantation, Type I diabetes and complications from diabetes, cancer, leukemia, T cell acute lymphoblastic leukemia, adult T cell leukemia activated B-cell like, diffuse large B cell lymphoma, inflammatory bowel disease, septic shock, cardiopulmonary dysfunction, chronic pulmonary obstructive disorder, acute respiratory disease, cachexia, and other indications where immunosuppression/immunomodulation would be desirable, comprising the step of administering to a subject an effective amount of a compound of the invention.

There are substantial needs for safe and efficacious agents to control disorders related to JAK, such as atopic dermatitis, both in human and animals. The market for treating atopic dermatitis in animals is currently dominated by corticosteroids, which cause distressing and undesirable side effects in animals, specifically in companion animals such as dogs. Antihistamines are also used, but are poorly effective. A canine formulation of cyclosporine (ATOPICA™) is currently being marketed for atopic dermatitis, but is expensive and has a slow onset of efficacy. In addition, there are GI toleration issues with ATOPICA™. Compounds of the present invention are JAK inhibitors with selective efficacy against JAK1. These compounds are expected to provide an alternative to steroid usage and provide resolution of chronic pruritus and inflammation that would either persist in atopic dermatitis or slowly regress following removal of allergen or causative agent, such as fleas in flea-allergic dermatitis.

The present invention also provides any of the uses, methods or compositions as defined above wherein the compound of formula I, or pharmaceutically acceptable salt thereof, or pharmaceutically acceptable solvate of said compound or salt, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I, or pharmaceutically acceptable salt thereof, or pharmaceutically acceptable solvate of said compound or salt, particularly in the treatment of respiratory disease, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an α2-adrenoceptor agonist, e.g., phenylephrine, methoxamine, oxymetazoline or methylnorephrine; a muscarinic M3 receptor antagonist, e.g. tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g. celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an intigrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Conditions in which selective targeting of the JAK pathway or modulation of the JAK kinases, particularly JAK1, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection. Conditions which can benefit from selective inhibition of JAK1 are discussed in greater detail below.

Accordingly, the compound of formula I or its pharmaceutically acceptable salts, and pharmaceutical compositions thereof can be used to treat a variety of conditions or diseases such as the following:

Arthritis, including rheumatoid arthritis, juvenile arthritis, and psoriatic arthritis;

Autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, allergies or conditions including Crohn's disease and/or ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, or platelet aggregation;

Skin diseases, conditions or disorders including atopic dermatitis, eczema, psoriasis, scleroderma, pruritus or other pruritic conditions, vitiligo, alopecia;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma;

Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation.

Chemical Synthesis

The following schemes and written descriptions provide general details regarding the preparation of the compounds of the invention.

The compounds of the invention may be prepared by any method known in the art for the preparation of compounds of analogous structure. In particular, the compounds of the invention can be prepared by the procedures described by reference to the schemes that follow, or by the specific methods described in the examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I).

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in *Protective Groups in Organic Synthesis* by Theodora W. Greene and Peter G. M. Wuts, 3rd edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of formula I can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention.

According to a first process, compounds of formula (IA) may be prepared from compounds of formulae (VI) and (V), as illustrated by Scheme 1.

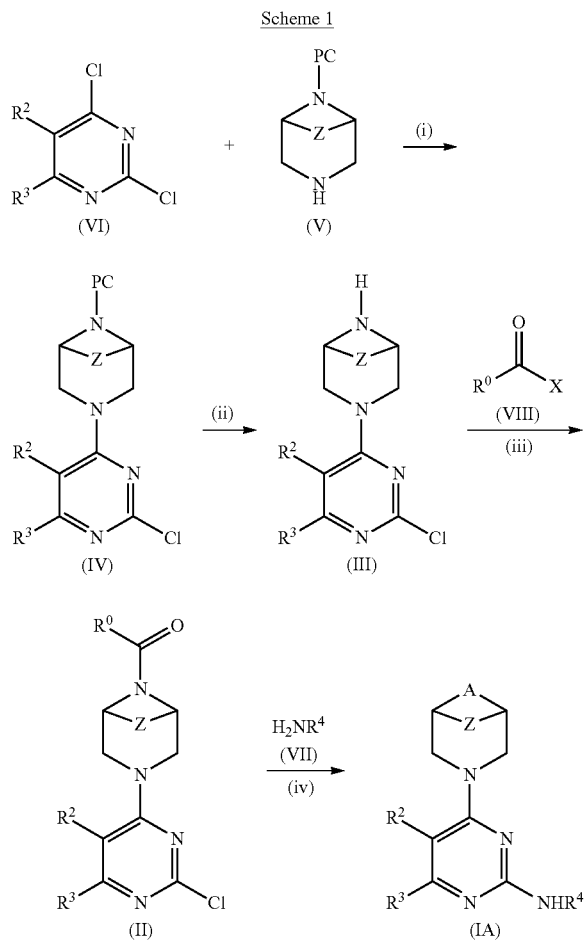

Wherein PG is tert-butoxycarbonyl; X is chloro, hydroxyl, a suitable leaving group or a suitable anhydride Z=$(CH_2)_n$; A is —N(C=O)$R^0$—;

Compounds of formulae (VI), (V), (VIII) and (VII) are commercially available or may be synthesized by those skilled in the art according to the literature or preparations described herein. Compounds of formula (IA) may be separated into the respective enantiomers via chiral separation of the racemate as required. Wherein $R^4$ contains a protecting group such as tert-butoxycarbonyl or tosyl, suitable deprotection conditions may be employed as necessary. Preferred conditions comprise 4M HCl in dioxane or 5N NaOH in dioxane.

Compounds of formula (IA) may be prepared from compounds of formula (II) according to process step (iv), a nucleophilic substitution reaction with compounds of formula (VII) under either Buchwald-Hartwig cross coupling conditions or mediated by acid and high temperatures. Typical Buchwald-Hartwig conditions comprise a suitable palladium catalyst with a suitable chelating phosphine ligand with an inorganic base in a suitable organic solvent at elevated temperatures either thermally or under microwave irradiation. Preferred conditions comprise tris(dibenzylideneacetone)dipalladium (0) and 2-dicyclohexylphosphino-2',4',6'-triisopropylbiphenyl or xantphos or RuPHOS palladium (II) phenethylamine chloride with sodium tert-butoxide or potassium phosphate or cesium carbonate in tert-amyl alcohol or DMSO at from 120-140° C. under microwave irradiation. Typical acidic conditions comprise a suitable inorganic acid in a suitable alcoholic solvent at elevated temperatures either thermally or under microwave irradiation. Preferred conditions comprise concentrated hydrochloric acid in iso-propanol at 140° C. under microwave irradiation.

Compounds of formula (II) may be prepared from compounds of formula (III) according to process step (iii), an amide bond formation reaction with compounds of formula (VIII), wherein X may be chloro, hydroxyl, a suitable leaving group or anhydride. Wherein compounds of formula (VIII) are acid chlorides, preferred conditions comprise triethylamine in DCM at room temperature. Wherein compounds of formula (VIII) are carboxylic acids, activation of the carboxylic acid using a suitable inorganic base and a suitable coupling agent is employed. Preferred conditions comprise DIPEA or triethylamine with HATU in DCM or DMF at room temperature. Wherein compounds of formula (VIII) are anhydrides, preferred conditions comprise stirring in DCM at room temperature. Wherein compounds of formula (VII) contain suitable leaving groups such as para-chlorophenoxy, preferred conditions comprise DIPEA in dioxane at reflux.

Compounds of formula (III) may be prepared from compounds of formula (IV) according to process step (ii) a deprotection reaction mediated by either an inorganic or organic acid in a suitable organic solvent. Preferred conditions comprise hydrochloric acid or THE in dioxane or DCM. Compounds of formula (IV) may be prepared from compounds of formulae (V) and (VI) according to process step (i), an aromatic nucleophilic substitution reaction in the presence of an inorganic base. Preferred conditions comprise triethylamine in methanol at from 0° C. to room temperature.

According to a second process, compounds of formula (IA) may be prepared from compounds of formula (IV) as illustrated by Scheme 2

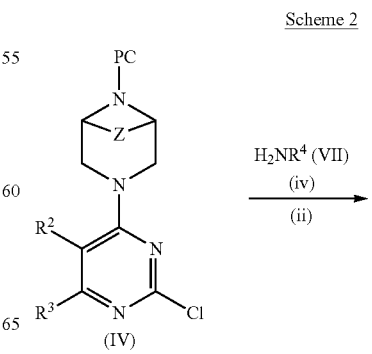

-continued

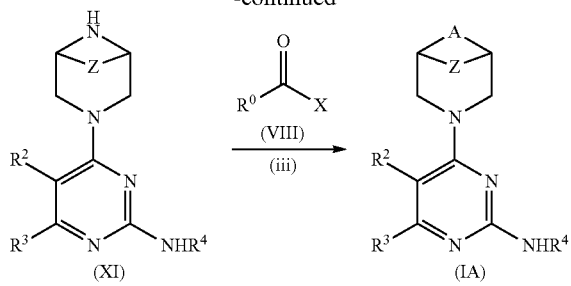

Wherein PG is tert-butoxycarbonyl; X is chloro, hydroxyl, a suitable leaving group or a suitable anhydride; $Z=(CH_2)_n$; A is $-N(C=O)R^0-$.

Compounds of formula (IV) may be prepared as described in Scheme 1.
Compounds of formulae (VIII) and (VII) are commercially available or may be synthesized by those skilled in the art according to the literature or preparations described herein. Compounds of formula (IA) may be prepared from compounds of formula (IV) by reversing the steps shown in Scheme 1. Compounds of formula (IA) may be prepared from compounds of formulae (XI) and (VIII) according to process step (iii), an amide bond formation reaction as described in Scheme 1.

Compounds of formula (XI) may be prepared from compounds of formula (IV) according to process steps (iv) and (ii), a nucleophilic substitution reaction with compounds of formula (VII) under either Buchwald-Hartwig cross coupling conditions or mediated by acid and high temperatures followed by a deprotection reaction mediated by either an inorganic or organic acid as described in Scheme 1. Alternatively the deprotection occurs in situ during process step (iv).

According to a third process, compounds of formula (IA) may be prepared from compounds of formula (XI) as illustrated by Scheme 3.

Scheme 3

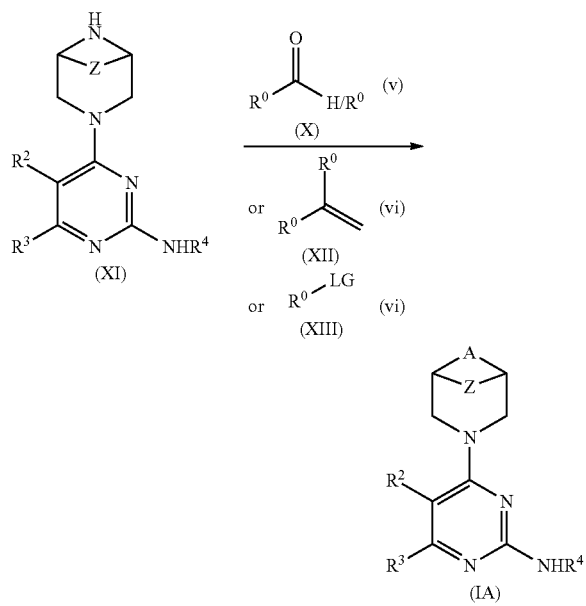

Wherein A is $NR^0$; $Z=(CH_2)_n$; LG is leaving group such as chloro, bromo, iodo, tosylate, mesylate.

Compounds of formula (XI) may be prepared as described in Scheme 1. Compounds of formula (X), (XII) and (XIII) are commercially available or may be synthesized by those skilled in the art according to the literature or preparations described herein. Compounds of formula (IA) may be prepared from compounds of formula (XI) according to either process step (v), a reductive amination reaction with aldehydes or ketones of formula (X) or process step (vi), a Michael addition reaction with conjugated alkenes of formula (XII) or process step (vii), an alkylation reaction with compounds of formula (XIII). Preferred conditions for the reductive amination comprise sodium triacetoxyborohydride or sodium cyanoborohydride in MeOH either with or without an inorganic base and an inorganic acid; such as triethylamine and acetic acid. Preferred conditions for the Michael addition comprise stirring compounds of formula (XI) with conjugated alkenes of formula (XII) in ethanol at from 0-140° C. either thermally or under microwave irradiation. Preferred conditions for the alkylation reaction comprise stirring compounds of formula (XI) with compounds of formula (XIII) that contain a suitable leaving group for alkylation with an inorganic base such as sodium carbonate with a catalyst such as tert-butylammonium iodide.

According to a fourth process, compounds of formula (IA) may be prepared from compounds of formula (XI) as illustrated by Scheme 4.

Scheme 4

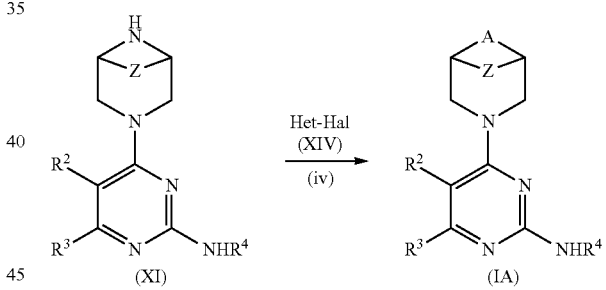

Wherein A is $NR^0$, $Z=(CH_2)_n$; wherein $R^0$ is heteroaryl; Hal is fluoro, chloro, bromo, iodo.

Compounds of formula (XI) may be prepared as described in Scheme 1. Compounds of formula (XIV) are commercially available or may be synthesized by those skilled in the art according to the literature or preparations described herein. Compounds of formula (IA) may be prepared from compounds of formula (XI) according to process step (iv) an a nucleophilic substitution reaction with compounds of formula (XIV) under either Buchwald-Hartwig cross coupling conditions as described in Scheme 1 or mediated by base and high temperatures. Preferred conditions mediated by base and high temperatures comprise triethylamine in isopropanol at 160° C. under microwave irradiation.

According to a fifth process, compounds of formula (IA) may be prepared from compounds of formula (XI) as illustrated by Scheme 5.

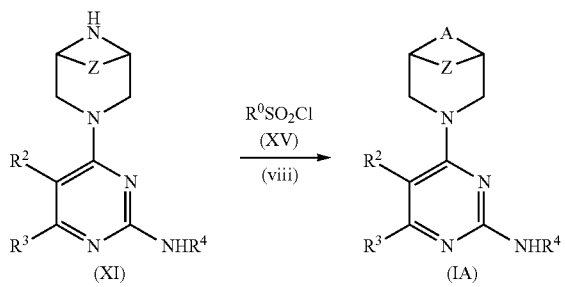

Wherein A is $NSO_2R^0$; $Z=(CH_2)_n$.

Compounds of formula (XI) may be prepared as described in Scheme 1. Compounds of formula (XV) are commercially available or may be synthesized by those skilled in the art according to the literature or preparations described herein. Compounds of formula (IA) may be prepared from compounds of formula (XI) according to process step (viii) a sulfonamide formation reaction with compounds of formula (XV). Preferred conditions comprise triethylamine in DCM at room temperature.

According to a sixth process, compounds of formula (IA) may be prepared from compounds of formula (XI) as illustrated by Scheme 6.

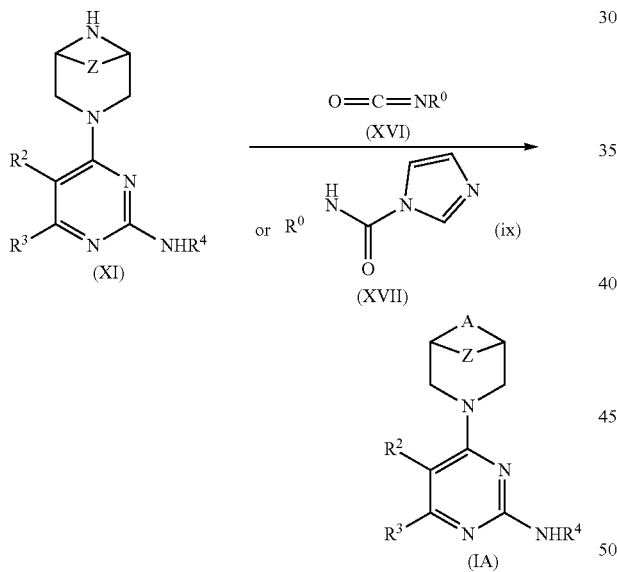

Wherein A is $-N(C=O)NHR^0-$; $Z=(CH_2)_n$.

Compounds of formula (XI) may be prepared as described in Scheme 1. Compounds of formula (XVI) and (XVII) are commercially available or may be synthesized by those skilled in the art according to the literature or preparations described herein.

Compounds of formula (IA) may be prepared from compounds of formula (XI) according to process step (ix), a urea formation reaction with isocyanates of formula (XVI) or imidazoureas of formula (XVII). Preferred conditions comprise triethylamine in DCM at temperatures from −50° C. to room temperature.

According to a seventh process, compounds of formula (IA) may also be interconverted to other compounds of formula (IA) as illustrated below in Scheme 7.

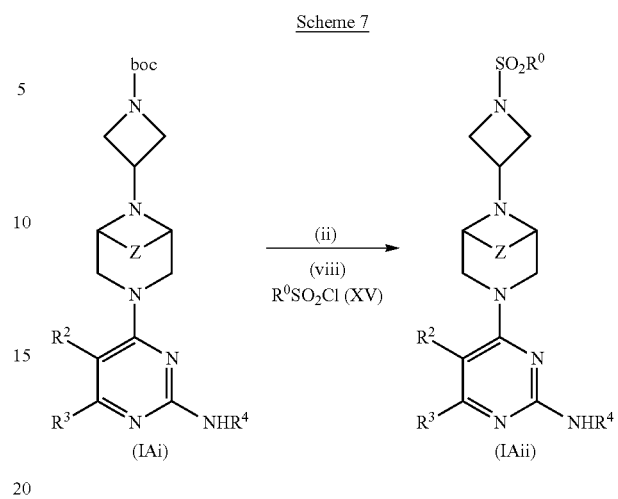

Wherein $Z=(CH_2)_n$.

Compounds of formula (IAi) may be prepared as for compounds of formula (IA) as described in Schemes 1-5. Compounds of formula (IAii) may be prepared from compounds of formula (IAi) according to process steps (ii) and (viii), a deprotection step followed by a sulfonamide formation reaction as described in Schemes 1 and 5. According to an eighth process, compounds of formula (IAiv) may also be interconverted to other compounds of formula (IAiii) as illustrated below in Scheme 8.

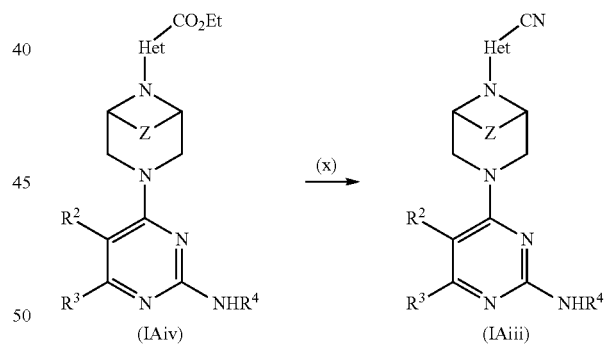

Wherein $Z=(CH_2)_n$.

Compounds of formula (IAiv) may be prepared as for compounds of formula (IA) as described in Schemes 1-5. Compounds of formula (IAiii) may be prepared from compounds of formula (IAiv) according to process step (x), a dehydration reaction via a primary carboxamide. Preferred conditions comprise 7M ammonia in methanol at elevated temperatures of 90° C. followed by dehydration with TFAA.

According to a ninth process, compounds of formula (IB) may be prepared from compounds of formula (XXIII) as illustrated by Scheme 9.

Scheme 9

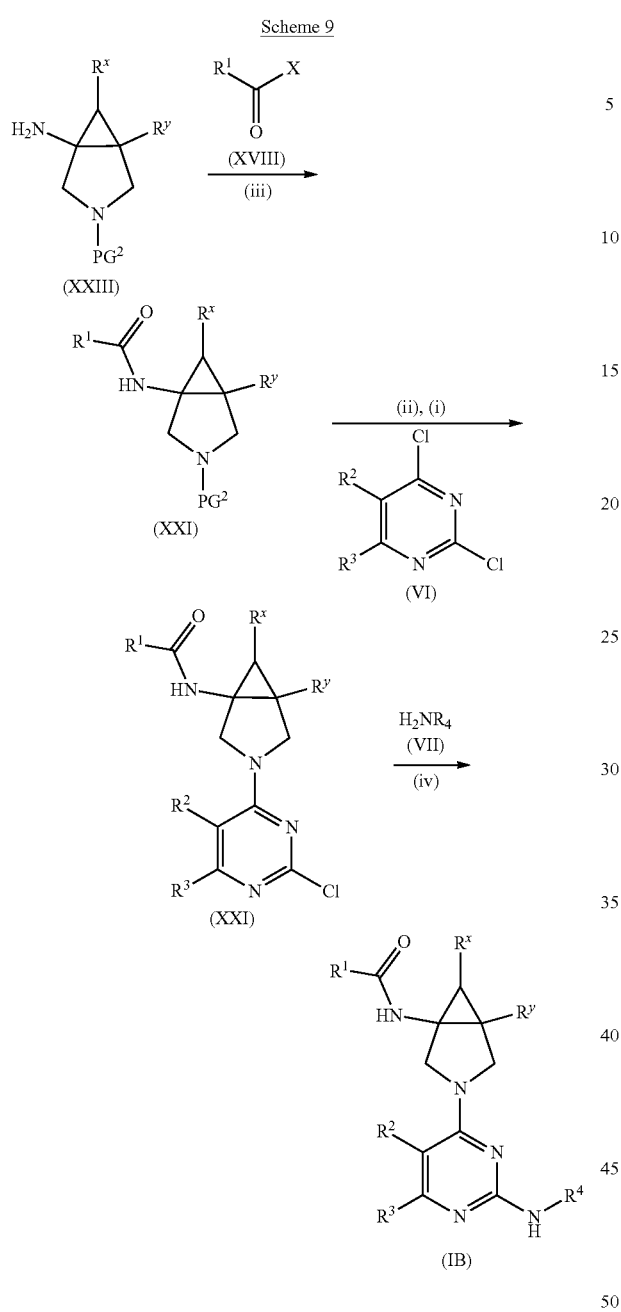

Scheme 1. Compounds of formula (XIX) may be prepared from compounds of formula (XXI) and (VI) according to process steps (ii) and (i), a deprotection reaction followed by an aromatic nucleophilic substitution reaction as described in Scheme 1. and as illustrated by Scheme 10. Compounds of formula (XIX) may be prepared from compounds of formula (XXIII) and (XVIII) according to process step (iii), an amide bond formation reaction as described in Scheme 1.

According to a tenth process, compounds of formula (IB) may be prepared from compounds of formula (XXIII) as illustrated by Scheme 10.

Scheme 10

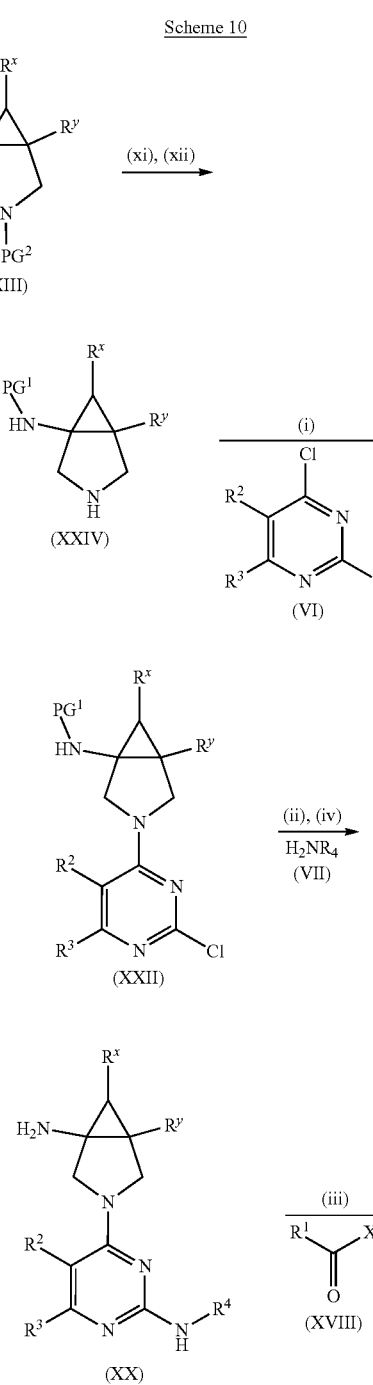

Wherein $R^x$ is H or Methyl, $R^y$ is H or $CH_2OH$, $PG^1$ is tert-butoxycarbonyl; $PG^2$ is benzyl; X is chloro, hydroxyl, a suitable leaving group or a suitable anhydride.

Compounds of formula (XXIII), (VI), (XVIII) and (VII) are commercially available or may be synthesized by those skilled in the art according to the literature or preparations described herein. Compounds of formula (IB) may be separated into the respective enantiomers via chiral separation of the racemate as required. Compounds of formula (IB) may be prepared from compounds of formula (XIX) and (VII) according to process step (iv) a nucleophilic substitution reaction with compounds of formula (VII) under either Buchwald-Hartwig cross coupling conditions or mediated by acid and high temperatures as described in Scheme 1.

Compounds of formula (IB) may also be prepared from compounds of formula (XX) and (XVIII) according to process step (iii) an acylation reaction as described in

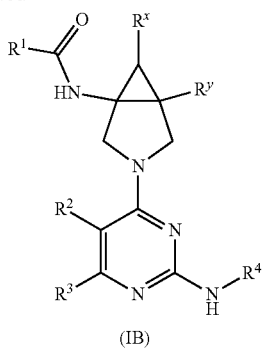

(IB)

Wherein R^x is H or Methyl, R^y is H or CH₂OH, PG¹ is tert-butoxycarbonyl; PG² is benzyl; X is chloro, hydroxyl, a suitable leaving group or a suitable anhydride. Compounds of formula (XX) may be prepared from compounds of formula (XXII) and (VII) according to process steps (ii) and (iv), a deprotection reaction and a nucleophilic substitution reaction with compounds of formula (VII) under either Buchwald-Hartwig cross coupling conditions or mediated by acid and high temperatures as described in Scheme 1. Deprotection may also occur during the process of reaction step (iv).

Compounds of formula (XXII) may be prepared from compounds of formula (XXIV) and (VI) according to process step (i) an aromatic nucleophilic substitution reaction as described in Scheme 1. Compounds of formula (XXIV) may be prepared from compounds of formula (XXIII) according to reaction steps (xi) and (xii), suitable deprotection and protection steps as necessary. Preferred protection conditions comprise di-tert-butyl dicarbonate with triethylamine at room temperature followed by deprotection of an orthogonal protecting group under hydrogenation over a metal catalyst. Preferred conditions comprise hydrogenation at 50 psi at room temperature over palladium hydroxide.

According to a eleventh process, Compounds of formula (IA) may be prepared from compounds of formulae (XXX) and (VIII), as illustrated by Scheme 11.

Scheme 11

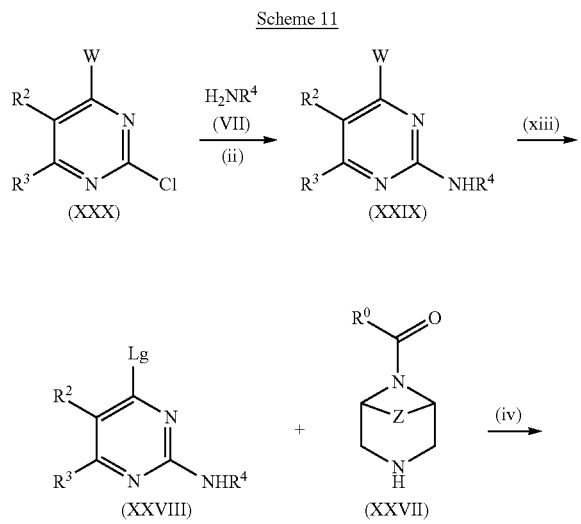

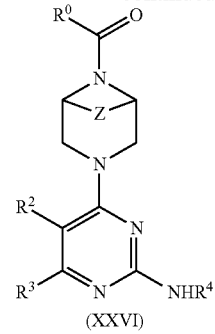

(XXVI)

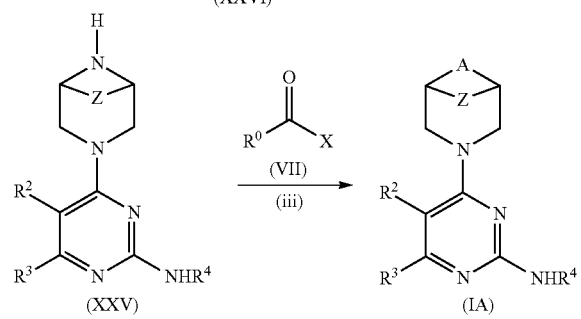

Wherein PG is tert-butoxycarbonyl; LG is a leaving group such as chloro, bromo, iodo, tosylate, mesylate; W is a hydroxyl or thiolether; X is chloro, hydroxyl, a suitable leaving group or a suitable anhydride; Z=(CH₂)$_h$; A is —N(C=O)R⁰—;

Compounds of formula (XXX), (XXVII), and (VII) are commercially available or may be synthesized by those skilled in the art according to the literature or preparations described herein, Compounds of formula (IA) may be prepared from compounds of formula (XXV) and (VII) according to process (iii), an amide bond formation reaction as described in Scheme 1.

Compounds of formula (XXV) can be prepared from compounds of formula (XXVIII) and (XXVII) according to process (iv), a nucleophilic substitution reaction as described in Scheme 1.

Compounds of formula (XXVIII) can be prepared from compounds of formula (XXIX) according to process (xiii), halogenation mediated by phosphoryl halides. Typical conditions comprise of reaction of a phoshoryl halide with or without additional solvent at room temperature or heated. Preferred conditions for conversion of an alcohol to halide comprise of phosphoryl chloride and heated to reflux.

Compound of formula (XXIX) can be prepared from compounds of formula (XXX) and (VII) according to process (ii), a nucleophilic substitution reaction as described in Scheme 1.

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

EXPERIMENTAL SECTION

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

$^1$H and $^{19}$F Nuclear magnetic resonance (NMR) spectra were in all cases consistent with the proposed structures. Characteristic chemical shifts (δ) are given in parts-per-million downfield from tetramethylsilane (for $^1$H-NMR) and upfield from trichlorofluoromethane (for $^{19}$F NMR) using conventional abbreviations for designation of major peaks: e.g., s, singlet; d, doublet; t, triplet; q, quartet; m, multiplet; br, broad. The following abbreviations have been used for common solvents: CDCl$_3$, deuterochloroform; d$_6$-DMSO, deuterodimethylsulfoxide; and CD$_3$OD, deuteromethanol. Where appropriate, tautomers may be recorded within the NMR data; and some exchangeable protons may not be visible. Mass spectra, MS (m/z), were recorded using either electrospray ionization (ESI) or atmospheric pressure chemical ionization (APCI). Where relevant and unless otherwise stated the m/z data provided are for isotopes $^{19}$F $^{35}$Cl, $^{79}$Br and $^{127}$I.

The nomenclature in this patent is written as described by IUPAC (International Union of Pure and Applied Chemistry and using ACD/Name Version 12 (Toronto, Canada) to generate names.

In the non-limiting Examples and Preparations that are set out later in the description, and in the aforementioned Schemes, the following abbreviations, definitions and analytical procedures may be referred to:
CDI is carbonyl di-imidazole;
DBU is diazabicyclo[5.4.0]undec-7-ene;
DCC is N,N'-dicyclohexylcarbodiimide;
DCM is dichloromethane; methylene chloride;
DEAD is diethylazodicarboxylate;
DIPEA/DIEA is N-ethyldiisopropylamine, N,N-diisopropylethylamine;
DMA is dimethylacetamide;
DMAP is dimethylaminopyridine;
DPPP is 1,3-bis(diphenylphosphino)propane;
EDCl•HCl is 1-(3-dimethylaminopropyl)-3-ethylcarbodiimide hydrochloride;
ee is enantiomeric excess;
HATU is 1-[Bis(dimethylamino)methylene]-1H-1,2,3-triazolo[4,5-b]pyridinium 3-oxid hexafluorophosphate;
HOBt is hydroxybenzotriazole;
LCMS is liquid chromatography mass spectrometry (Rt=retention time);
Pd$_2$(dba)$_3$ is trisdibenzylideneacetonedipalladium;
Pd(dppf)Cl2 is 1,1-bis(diphenylphosphino)ferrocene-palladium(II)dichloride;
RuPHOS is 2-Dicyclohexylphosphino-2',6'-diisopropoxybiphenyl;
TBDMS is tertbutyldimethylsilyl;
TLC is thin layer chromatography;
Xantphos/Xphos is 4,5-bis(diphenylphosphino)-9,9-dimethylxanthene.

GCMS Conditions
Column: 12 m×0.2 mm, HP-1 Methyl Siloxane, 0.33 µm film, 1.0 m/min column flow
Method: 7.6 min: Initial Oven Temp 105° C.; 0.1 min hold; 30° C./min ramp to 300° C. endpoint at 7.6 min or 7.6 min: Initial Oven Temp 60° C.; 0.1 min hold; 40° C./min ramp to 320° C. endpoint at 7.6 min or 5.1 min:
Initial Oven Temp 40° C.; 0.1 min hold; 30° C./min ramp to 150° C. endpoint at 5.1 min
GC Inlet Parameters: Front Inlet, Split 30:1, He, 8 psi pressure, 250° C. Injector, 33.9 ml/min total flow
MSD Tune: 230° C. Source Temp, 150° C. Quad Temp, 280° C. Aux2 Temp
Injection Volume: 1.0 µL
System Components: Agilent 5890 GC Oven with Agilent 5973 Mass Selective Detector LCMS Conditions
Acid: Waters Acquity HSS T3, 2.1 mm×50 mm, C18, 1.7 µm; Column Temperature 60° C.
Base: Waters Acquity UPLC BEH, 2.1 mm×50 mm, C18, 1.8 µm; Column Temperature 60° C.
Mobile Phase: A: 0.1% formic acid in water (v/v); Mobile phase B: 0.1% formic acid in acetonitrile (v/v).
Mobile Phase A: 0.1% ammonia in water (v/v); Mobile phase B: 0.1% ammonia in acetonitrile (v/v) Gradient Profiles:
1.5 min Run: Initial conditions: A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min $^1$H and $^{19}$F Nuclear magnetic resonance (NMR) spectra were in all cases consistent with the proposed structures. Characteristic chemical shifts (b) are given in parts-per-million downfield from tetramethylsilane (for $^1$H-NMR) and upfield from trichloro-fluoro-methane (for $^{19}$F NMR) using conventional abbreviations for designation of major peaks: e.g., s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol. Where appropriate, tautomers may be recorded within the NMR data; and some exchangeable protons may not be visible.

Mass spectra, MS (m/z), were recorded using either electrospray ionisation (ESI) or atmospheric pressure chemical ionisation (APCI). Where relevant and unless otherwise stated the m/z data provided are for isotopes $^{19}$F, $^{35}$Cl, $^{79}$Br and $^{127}$I. Where preparative TLC or silica gel chromatography has been used, one skilled in the art may choose any combination of solvents to purify the desired compound.

Purification Methods (PM)
The compounds of the Examples were purified according to one of the Purification Methods (PM) referred to below unless otherwise described:
Purification Method A: Preparative HPLC using [Agella venusil ASB C18 150×21.2 mm×5 µm, from 16% MeCN in water (0.225% formic acid) to 36% MeCN in water (0.225% formic acid)]
Purification Method B: Preparative HPLC using [Phenomenex Gemini C18 250×21.2 mm×8 um or 150 mm×25 mm×5 µm; from 16-55% MeCN in water (0.1% ammonia) to 36-60% MeCN in water (0.1% ammonia)]
Purification Method C: [YMC-Actus Triad C18 150×30 µm, from 24% MeCN in water (0.1% ammonia) to 44% MeCN in water (0.1% ammonia)]
Purification Method D: Preparative HPLC using [Phenomenex Gemini C18 250×21.2 mm×8 µm, from 25% MeCN in water (ammonia pH=10) to 45% MeCN in water (ammonia pH=10)] followed by chiral chromatography using AS 250× 25 mm I.D. 20 µM column, with supercritical $CO_2$: EtOH or IPA (0.05% aqueous ammonia) 70:30 at from 50-80 mL/min
Purification Method E: Preparative HPLC using [Phenomenex Gemini C18 250×21.2 mm×8 µm, from 25% MeCN in water (0.225% ammonia) to 45% MeCN in water (0.225% ammonia) followed by chiral chromatography using AD 250 mm×30 mm×20 µm column with mobile phase A: supercritical $CO_2$ and mobile phase B MeOH with 0.1% ammonia A:B 50:50 at 180 mL/min
Purification Method F: Silica gel column chromatography eluting with 100% DCM to 12% MeOH with 1% $NH_4OH$.
Purification Method G: Silica gel column chromatography eluting with 97:2:1 DCM:MeOH:$NH_3$ followed by preparative HPLC.
Purification Method H: Preparative HPLC using Column: Waters XBridge C18 19 mm×100 mm, 5µ; Mobile phase A: 0.03% ammonium hydroxide in water (v/v); Mobile phase B: 0.03% ammonium hydroxide in acetonitrile (v/v); from 5-20% B to 40-100% B at 25 mL/min flow rate.
Purification Method I: Preparative HPLC using Column: Waters Sunfire C18 19 mm×100 mm, 5µ; Mobile phase A: 0.05% TFA in water (v/v); Mobile phase B: 0.05% TFA in acetonitrile (v/v); from 20% B to 40% B at 6.75 minutes, then to 100% B at 7 minutes at 30 mL/min flow rate.

Specific Rotation

Specific rotations based on the equation $[\alpha]=(100\cdot\alpha)/(l\cdot c)$ and are reported as unitless numbers where the concentration c is in g/100 mL and the path length l is in decimeters. The units of the specific rotation, (deg·mL)/(g·dm), are implicit and are not included with the reported value.

Library Protocol 1

Preparative HPLC
Purification Method 1 (PM1): Phenomenex Gemini C18, 250×21.2 mm×8 µm; Acetonitrile-ammonium hydroxide; Flow rate 30 mL/min; Gradient time 8 mins.
Purification Method 2 (PM2): DIKMA Diamonsil C18 200 mm×20 mm×5 µm; MeCN-water (0.225% formic acid); Flow rate 35 mL/min; Gradient time 9 mins.
LCMS Method:
Column: XBridge C18 2.1 mm×50 mm×5 µm
Mobile Phase A: 0.05% ammonium hydroxide in water
Mobile phase B: 100% MeCN
Gradient: 5% B to 100% B at 3.40 minutes then back to 5% B at 4.21 minutes.
Flow rate: 0.8 mL/min The compounds of the Examples in the table below were prepared from ((1R,5S)-3-(2-chloro-5-fluoropyrimidin-4-yl)-3,8-diazabicyclo[3.2.1]octan-8-yl)(cyclopropyl)methanone (Preparation 27) and the appropriate amine according to Library Protocol 1.

| Ex | Name | SM/Data/HPLC Organic gradient |
|---|---|---|
| 1 | cyclopropyl{(1R,5S)-3-[5-fluoro-2-(pyridazin-4-ylamino)pyrimidin-4-yl]-3,8-diazabicyclo[3.2.1]oct-8-yl}methanone | Pyridazin-4-amine<br>Rt = 2.31 minutes<br>MS m/z 370 [M + H]$^+$<br>17-47% organic in PM 1. |
| 2 | 3-({4-[(1R,5S)-8-(cyclopropylcarbonyl)-3,8-diazabicyclo[3.2.1]oct-3-yl]-5-fluoropyrimidin-2-yl}amino)-N-propyl-1H-pyrazole-5-carboxamide | 5-amino-1H-pyrazole-3-carboxylic acid propylamide (Preparation 83).<br>Rt = 2.45 minutes<br>MS m/z 443 [M + H]$^+$<br>11-41% organic in PM 2. |
| 3 | 6-({4-[(1R,5S)-8-(cyclopropylcarbonyl)-3,8-diazabicyclo[3.2.1]oct-3-yl]-5-fluoropyrimidin-2-yl}amino)imidazo[1,2-a]pyridine-2-carboxamide | 7-amino-imidazo[1,2-a]pyridine-2-carboxylic acid amide(Preparation 86).<br>Rt = 2.22 minutes<br>MS m/z 451 [M + H]$^+$<br>10-40% organic in PM 2. |
| 4 | 5-({4-[(1R,5S)-8-(cyclopropylcarbonyl)-3,8-diazabicyclo[3.2.1]oct-3-yl]-5-fluoropyrimidin-2-yl}amino)pyridine-2-sulfonamide | 2-(methylsulfonyl)-pyridin-4-amine<br>Rt = 2.35 minutes<br>MS m/z 448 [M + H]$^+$<br>13-53% organic in PM 1. |

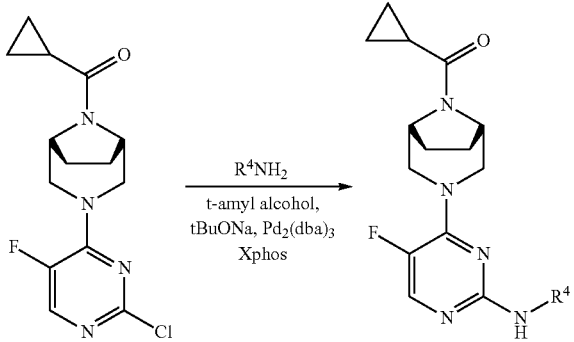

A 0.2M solution of ((1R,5S)-3-(2-chloro-5-fluoropyrimidin-4-yl)-3,8-diazabicyclo[3.2.1]octan-8-yl)(cyclopropyl) methanone (Preparation 27, 500 µl, 100 µmol) in tert-amyl alcohol was added to amines of formula ($R^4NH_2$) (150 µmol) followed by sodium tert-butoxide (200 µmol), $Pd_2$(dba)$_3$ (2 µmol) and XPhos (2 µmol) under nitrogen. The reactions were heated to 140° C. under microwave irradiation for 40 minutes. The reactions were cooled, concentrated in vacuo and purified using preparative HPLC.

Example 5

(1R,5S)-N-ethyl-3-[2-(1H-pyrazol-4-ylamino)pyrimidin-4-yl]-3,8-diazabicyclo[3.2.1]octane-8-carboxamide To a solution of (1R,5S)-3-(2-chloropyrimidin-4-yl)-N-ethyl-3,8-diazabicyclo[3.2.1]octane-8-carboxamide (Preparation 29, 184 mg, 0.624 mmol) and tert-butyl 4-amino-1H-pyrazole-1-carboxylate (PCT Publication No. WO2012022681, 126 mg, 0.686 mmol) in DMA (8 mL) was added $Cs_2CO_3$ (405.6 mg, 1.248 mmol), Pd(OAc)$_2$ (28 mg, 0.124 mmol) and xantphos (72 mg, 0.124 mmol). The reaction was purged with nitrogen for 3 minutes before heating to 120° C. under microwave irradiation for 1 hour. The reaction was concentrated in vacuo and purified by silica gel column chromatography eluting with 10% MeOH in DCM followed by preparative HPLC (Purification Method B) to afford the title compound (81 mg, 38%).
$^1$H NMR (400 MHz, DMSO-d$_6$): δ ppm 1.02 (t, 3H), 1.58 (d, 2H), 1.77 (d, 2H), 2.96-3.11 (m, 4H) 3.79-4.09 (m, 2H), 4.34 (br s, 2H), 6.07 (d, 1H), 6.67 (t, 1H), 7.49-7.94 (m, 3H), 8.82 (br s, 1H), 12.35 (br s, 1H). MS m/z 343 [M+H]+

Example 6

5-({4-[(1R,5S)-8-(cyclopropylcarbonyl)-3,8-diazabicyclo[3.2.1]oct-3-yl]pyrimidin-2-yl}amino)-N,3-dimethylpyridine-2-carboxamide To a solution of 5-((4-((1R,5S)-3,8-diazabicyclo[3.2.1]octan-3-yl)pyrimidin-2-yl)amino)-N,3-dimethylpicolinamide hydrochloride (Preparation 1, 77 mg, 0.220 mmol) and triethylamine (133 mg, 1.32 mmol) in DCM (10 mL) was added cyclopropanecarbonyl chloride (27 mg, 0.26 mmol) dropwise. The reaction was stirred at room temperature for 1 hour before concentrating in vacuo. The residue was purified using preparative HPLC to afford the title compound (48 mg, 52%).

$^1$H NMR (400 MHz, DMSO-$d_6$): δ ppm 0.60-0.85 (m, 4H), 1.53-2.07 (m, 5H), 2.56 (s, 3H), 2.75 (d, 3H), 2.95-3.04 (m, 1H), 3.04-3.15 (m, 1H), 3.96-4.26 (m, 2H), 4.55-4.67 (m, 1H), 4.73-4.85 (m, 1H), 6.28-6.37 (m, 1H), 7.99-8.11 (m, 2H), 8.39-8.47 (m, 1H), 8.74-8.81 (m, 1H), 9.52 (s, 1H). MS m/z 444 [M+Na]$^+$

Examples 7 and 8

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone and [(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone To a solution of (S)-2,2-difluorocyclopropane-1-carboxylic acid (Preparation 68, 318 mg, 2.61 mmol) in DCM (20 mL) was added 4-((1R,5S)-3,8-diazabicyclo[3.2.1]octan-3-yl)-N-(1-methyl-1H-pyrazol-4-yl)pyrimidin-2-amine hydrochloride (Preparation 19, 700 mg, 2.17 mmol), HATU (1.02 g, 2.61 mmol and DIPEA (0.76 mL, 4.34 mmol) and the reaction was stirred at room temperature for 18 hours. The reaction was diluted with DCM and saturated aqueous ammonium chloride solution. The organic layer was separated, washed with further ammonium chloride solution and concentrated in vacuo. The residue was purified using silica gel column chromatography eluting with 0-12% MeOH and 1% NH$_4$OH in DCM. The residue was dissolved in DCM and further washed with saturated aqueous ammonium chloride solution three times. The organic layer was collected, concentrated in vacuo and dried to afford the title compound (500 mg, 60%).

The title compound and its enantiomer may also be prepared according to the same method using racemic 2,2-difluorocyclopropane-1-carboxylic acid with additional chiral separation of the enantiomers after purification using the method below to afford:

Peak 1: Example 7

[(1S)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone $^1$H NMR (400 MHz, DMSO-$d_6$): δ ppm 1.58-2.06 (m, 6H), 2.82-3.27 (m, 3H), 3.80 (s, 3H), 4.14 (br s, 2H), 4.55-4.74 (m, 2H), 6.07-6.19 (m, 1H), 7.44 (s, 1H), 7.74 (br s, 1H), 7.93 (d, 1H), 8.90 (br s, 1H). MS m/z 390 [M+H]$^+$; [α]$_D^{20}$ 50.1 (c 1.27, EtOH)

Peak 2: Example 8

[(1R)-2,2-difluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone $^1$H NMR (400 MHz, DMSO-$d_6$): δ ppm 1.58-2.06 (m, 6H), 2.82-3.27 (m, 3H), 3.80 (s, 3H), 4.14 (br s, 2H), 4.55-4.74 (m, 2H), 6.07-6.19 (m, 1H), 7.44 (s, 1H), 7.74 (br s, 1H), 7.93 (d, 1H), 8.90 (br s, 1H). MS m/z 390 [M+H]$^+$; [α]$_D^{20}$ −51 (c 0.66, EtOH)

Example 7 may also be prepared according to the following method:

To a solution of (S)-2,2-difluorocyclopropane-1-carboxylic acid (Preparation 68, 18.1 g, 35.33 mmol), 4-((1R,5S)-3,8-diazabicyclo[3.2.1]octan-3-yl)-N-(1-methyl-1H-pyrazol-4-yl)pyrimidin-2-amine hydrochloride (Preparation 19, 11 g, 40 mmol) and DIPEA (41.7 mL, 246 mmol) in DMF (60 mL) was added T3P (102 mL, 176 mmol) and the reaction was stirred at room temperature for 1.5 hours. The reaction was quenched by the addition of saturated aqueous NaHCO$_3$ solution until pH 6 and concentrated in vacuo. The residue was dissolved in DCM and washed with saturated aqueous NaHCO$_3$ solution followed by water. The organic layer was collected, dried over sodium sulfate and concentrated in vacuo. The residue was purified using silica gel column chromatography eluting with 0-15% MeOH in DCM with 1% ammonia followed by chiral preparation using Chiral Tech OD-H 250 mm×21.2 mm, 5μ, using mobile phase A 75% CO$_2$ and mobile phase B 25% MeOH at a flow rate of 80 mL/min.

Example 9

4-({4-[8-(cyclopropylcarbonyl)-3,8-diazabicyclo[3.2.1]oct-3-yl]-5-fluoropyrimidin-2-yl}amino)-N-ethylbenzamide To a solution of 4-((4-((1R,5S)-3,8-diazabicyclo[3.2.1]octan-3-yl)-5-fluoropyrimidin-2-yl)amino)-N-ethylbenzamide hydrochloride (Preparation 24, 50 mg, 0.14 mmol) in DCM (5 mL) was added triethylamine (0.1 mL, 0.7 mmol), HATU (50 mg, 0.135 mmol) and cyclopropanecarboxylic acid (15 mg, 0.17 mmol). The reaction was stirred at room temperature for 18 hours before purification directly using silica gel column chromatography eluting with 0-10% MeOH in DCM to afford the title compound. $^1$H NMR (400 MHz, CDCl$_3$): δ ppm 0.78 (br s, 2H), 1.00 (d, 2H), 1.21 (t, 3H), 1.61-1.75 (m, 1H), 1.79 (d, 1H), 1.83-1.97 (m, 2H), 2.05 (d, 2H), 3.25 (dd, 2H) 3.36-3.53 (m, 2H), 4.16 (d, 1H), 4.28 (d, 1H), 4.52 (d, 1H), 4.74 (br s, 1H), 6.28 (t, 1H), 7.37 (s, 1H), 7.53 (d, 2H), 7.70 (d, 2H), 7.85 (d, 1H). MS m/z 439 [M+H]$^+$

Example 10

3-chloro-5-({4-[(1R,5S)-8-{[(1S)-2,2-difluorocyclopropyl]carbonyl}-3,8-diazabicyclo[3.2.1]oct-3-yl]pyrimidin-2-yl}amino)-N-methylpyridine-2-carboxamide The title compound was prepared according to the method described for Example 9 using 5-((4-((1R,5S)-3,8-diazabicyclo[3.2.1]octan-3-yl)pyrimidin-2-yl)amino)-3-chloro-N-methylpicolinamide hydrochloride (Preparation 5) and (S)-2,2-difluorocyclopropane-1-carboxylic acid (Preparation 68). The residue was purified by preparative HPLC followed by chiral chromatography as described below:

Preparative HPLC: DIKMA Diamonsil(2) C18 200×20 mm×5 μm

Mobile phase: from 10% MeCN in water (0.225% formic acid) to 60% MeCN in water (0.225% formic acid)

Preparative chiral chromatography: Chiralpak AD 250×30 mm I.D.10 μm

Mobile phase: Supercritical $CO_2$:MeOH (0.1% aqueous ammonia) 55:45;

Flow rate: 50 mL/min $^1$H NMR (400 MHz, DMSO-$d_6$): δ ppm 1.61-2.03 (m, 6H), 2.75 (d, 3H), 2.92-3.10 (m, 2H), 3.18-3.26 (m, 1H), 4.15 (br s, 2H), 4.58-4.76 (m, 2H), 6.40 (dd, 1H), 8.05-8.14 (m, 1H), 8.44 (d, 2H), 8.81 (dd, 1H), 9.77 (d, 1H). MS m/z 478 [M+H]$^+$ Examples 11 and 12

[(1S)-2,2-difluorocyclopropyl]{(1R,5S)-3-[2-({6-[(2R)-1-hydroxypropan-2-yl]pyridin-3-yl}amino)pyrimidin-4-yl]-3,8-diazabicyclo[3.2.1]oct-8-yl}methanone and (([(1S)-2,2-difluorocyclopropyl]{(1R,5S)-3-[2-({6-[(2S)-1-hydroxypropan-2-yl]pyridin-3-yl}amino)pyrimidin-4-yl]-3,8-diazabicyclo[3.2.1]oct-8-yl}methanone The title compounds were prepared according to the method described by Example 9 using racemic 2-(5-((4-((1R,5S)-3,8-diazabicyclo[3.2.1]octan-3-yl)pyrimidin-2-yl)amino)pyridin-2-yl)propan-1-ol hydrochloride (Preparation 2) and (S)-2,2-difluorocyclopropane-1-carboxylic acid (Preparation 68). The residue was purified using preparative HPLC followed by enantiomeric separation using chiral chromatography as described below:

Preparative HPLC: Kromasil Eternity XT C18 250×21.2×10 μm

Mobile phase: from 16% MeCN in water (Ammonia pH=10) to 36% MeCN in water (Ammonia pH=10);

Flow Rate: 30 mL/min

Preparative chiral chromatography: Chiralpak AD 250×30 mm I.D.10 μm

Mobile phase: Supercritical $CO_2$:IPA (aqueous ammonia) 55:45; Flow rate: 70 mL/min First eluting compound was arbitrarily assigned as: Example 11:

$^1$H NMR (400 MHz, DMSO-$d_6$): δ ppm 1.19 (d, 3H), 1.61-2.07 (m, 6H), 2.83-3.06 (m, 3H), 3.24 (br s, 2H), 3.43-3.53 (m, 1H), 3.62 (m, 1H), 4.18 (br s, 2H), 4.50-4.81 (m, 3H), 6.27 (m, 1H), 7.15 (d, 1H), 7.93-8.11 (m, 2H), 8.74 (br s, 1H), 9.19 (s, 1H). MS m/z 445 [M+H]$^+$ Second eluting compound was arbitrarily assigned as: Example 12

$^1$H NMR (400 MHz, DMSO-$d_6$): δ ppm 1.18 (d, 3H), 1.60-2.07 (m, 7H), 2.83-3.04 (m, 3H), 3.25 (dd, 1H), 3.44-3.52 (m, 1H), 3.57-3.66 (m, 1H), 4.13 (br s, 2H), 4.52-4.79 (m, 3H), 6.27 (dd, 1H), 7.15 (d, 1H), 7.93-8.09 (m, 2H), 8.74 (d, 1H), 9.19 (s, 1H). MS m/z 445 [M+H]$^+$ The following Examples were prepared according to the method described for Example 9 using the appropriate acid and amine as described. Purification details are as described or referred to below:

| Example No. | Structure/name | Starting Materials | Data |
| --- | --- | --- | --- |
| 13 | 4-({4-[(1R,5S)-8-(cyanoacetyl)-3,8-diazabicyclo[3.2.1]oct-3-yl]pyrimidin-2-yl}amino)-N-ethylbenzamide | Cyanoacetic acid and 4-((4-((1R,5S)-3,8-diazabicyclo[3.2.1]octan-3-yl)pyrimidin-2-yl)amino)-N-ethylbenzamide hydrochloride (Preparation 4). | Rt = 1.76 minutes MS m/z 420 [M + H]$^+$ Purification Method H. |
| 14 | 5-({4-[(1R,5S)-8-(cyclopropylcarbonyl)-3,8-diazabicyclo[3.2.1]oct-3-yl]pyrimidin-2-yl}amino)-N-ethyl-3-methylpyridine-2-carboxamide | Cyclopropanecarboxylic acid and 5-((4-((1R,5S)-3,8-diazabicyclo[3.2.1]octan-3-yl)pyrimidin-2-yl)amino)-N-ethyl-3-methylpicolinamide hydrochloride (Preparation 3). | $^1$H NMR (400 MHz, MeOH-$d_4$): δ ppm 0.87-0.97 (m, 4H), 1.26 (t, 3H), 1.77-2.15 (m, 5H), 2.65 (s, 3H), 3.40 (m, 2H), 3.45 (m, 2H), 4.07 (m, 1H), 4.56 (m, 1H), 4.85 (m, 2H), 6.69 (d, 1H), 7.87 (br s, 1H), 7.90 (d, 1H), 8.69 (br s, 1H). MS m/z 436 [M + H]$^+$ PM A. |
| 15 | 5-({4-[(1R,5S)-8-(cyclopropylcarbonyl)-3,8-diazabicyclo[3.2.1]oct-3-yl]pyrimidin-2-yl}amino)-3-methylpyridine-2-carboxamide | Cyclopropanecarboxylic acid and 5-((4-((1R,5S)-3,8-diazabicyclo[3.2.1]octan-3-yl)pyrimidin-2-yl)amino)-3-methylpicolinamide hydrochloride (Preparation 18). | $^1$H NMR (400 MHz, MeOH-$d_4$): δ ppm 0.86-0.98 (m, 4H), 1.78-2.13 (m, 5H), 2.62 (s, 3H), 3.11-3.35 (m, 3H), 4.41-4.49 (br s, 1H), 4.75-4.81 (m, 2H), 6.29-6.30 (m, 1H), 8.00-8.01 (m, 2H), 8.75-8.76 (m, 1H). MS m/z 408 [M + H]$^+$ PM B. |

-continued

| Example No. | Structure/name | Starting Materials | Data |
|---|---|---|---|
| 16 | cyclopropyl[(1R,5S)-3-(2-{[1-(2-hydroxyethyl)-1H-pyrazol-4-yl]amino}pyrimidin-4-yl)-3,8-diazabicyclo[3.2.1]oct-8-yl]methanone | Cyclopropanecarboxylic acid and 2-(4-((4-((1R,5S)-3,8-diazabicyclo-[3.2.1]octan-3-yl)pyrimidin-2-yl)amino)-1H-pyrazol-1-yl)ethan-1-ol hydrochloride (Preparation 20). | $^1$H NMR (400 MHz, MeOH-$d_4$): δ ppm 0.89-0.97 (m, 5H), 1.77-2.10 (m, 6H), 3.07-3.18 (m, 2H), 3.87 (t, 2H), 4.19 (t, 2H), 4.72-4.77 (m, 2H), 6.12 (d, 1H), 7.52 (s, 1H), 7.86-7.89 (m, 2H). MS m/z 384 [M + H]$^+$ PM C. |
| 17 | 1,2-oxazol-5-yl{(1R,5S)-3-[2-(1H-pyrazol-4-ylamino)pyrimidin-4-yl]-3,8-diazabicyclo[3.2.1]oct-8-yl}methanone | 4-((1R,5S)-3,8-diazabicyclo[3.2.1]octan-3-yl)-N-(1l2-pyrazol-4-yl)pyrimidin-2-amine hydrochloride (Preparation 22) and isoxazole-5-carboxylic acid. | $^1$H NMR (400 MHz, DMSO-$d_6$): δ ppm 1.56-2.39 (m, 4H), 2.96-3.22 (m, 2H), 4.01-4.37 (m, 2H), 4.61-4.96 (m, 2H), 6.04-6.20 (m, 1H), 7.10 (d, 1H), 7.42-7.84 (m, 2H), 7.87-8.04 (m, 1H), 8.77-8.82 (m, 1H), 8.83-8.94 (m, 1H), 12.19-12.48 (m, 1H), MS m/z 367 [M + H]$^+$ PM B. |
| 18 | [(1R,5S)-3-(2-{[5-chloro-6-(2-hydroxyethyl)pyridin-3-yl]amino}pyrimidin-4-yl)-3,8-diazabicyclo[3.2.1]oct-8-yl][(1S)-2,2-difluorocyclopropyl]methanone | 2-(5-((4-((1R,5S)-3,8-diazabicyclo[3.2.1]octan-3-yl)pyrimidin-2-yl)amino)-3-chloropyridin-2-yl)ethan-1-ol hydrochloride (Preparation 6) and (S)-2,2-difluorocyclopropane-1-carboxylic acid (Preparation 68). | $^1$H NMR (400 MHz, MeOH-$d_4$): δ ppm 1.75-2.07 (m, 6H), 3.00-3.07 (m, 1H), 3.11 (s, 2H), 3.81-3.95 (m, 2H), 4.09-4.41 (m, 2H), 4.58-4.83 (m, 4H), 6.23-6.34 (m, 1H), 7.92-8.06 (m, 1H), 8.24-8.35 (m, 1H), 8.61-8.72 (m, 1H). MS m/z 465 [M + H]$^+$ PM D. |
| 19 | [(1S)-2,2-difluoro-cyclopropyl][(1R,5S)-3-(2-{[5-fluoro-6-(2-hydroxyethyl)pyridin-3-yl]amino}pyrimidin-4-yl)-3,8-diazabicyclo[3.2.1]oct-8-yl]methanone | 2-(5-((4-((1R,5S)-3,8-diazabicyclo[3.2.1]octan-3-yl)pyrimidin-2-yl)amino)-3-fluoropyridin-2-yl)ethan-1-ol hydrochloride (Preparation 7) and (S)-2,2-difluorocyclopropane-1-carboxylic acid (Preparation 68). | $^1$H NMR (400 MHz, MeOH-$d_4$): δ ppm 1.58-2.07 (m, 1H), 2.81-2.89 (m, 1H), 2.90-3.26 (m, 2H), 3.62-3.73 (m, 1H), 3.98-4.32 (m, 1H), 4.53-4.78 (m, 2H), 6.25-6.37 (m, 1H), 8.00-8.15 (m, 2H), 8.54-8.67 (m, 1H), 9.46 (s, 1H). MS m/z 449 [M + H]$^+$ PM D. |
| 20 | [(1S)-2,2-difluoro-cyclopropyl]{(1R,5S)-3-[2-({5-fluoro-6-[(3S)-3-hydroxypyrrolidin-1-yl]pyridin-3-yl}amino)pyrimidin-4-yl]-3,8-diazabicyclo[3.2.1]oct-8-yl}methanone | (S)-1-(5-((4-((1R,5S)-3,8-diazabicyclo[3.2.1]octan-3-yl)pyrimidin-2-yl)amino)-3-fluoropyridin-2-yl)pyrrolidin-3-ol (Preparation 8) and (S)-2,2-difluorocyclo-propane-1-carboxylic acid (Preparation 68). | $^1$H NMR (400 MHz, DMSO-$d_6$): δ ppm 1.58-2.07 (m, 1H), 2.81-2.89 (m, 1H), 2.90-3.26 (m, 2H), 3.62-3.73 (m, 1H), 3.98-4.32 (m, 1H), 4.53-4.78 (m, 2H), 6.25-6.37 (m, 1H), 8.00-8.15 (m, 2H), 8.54-8.67 (m, 1H), 9.46 (s, 1H). MS m/z 490 [M + H]$^+$ PM B. |
| 21 | [(1S)-2,2-difluoro-cyclopropyl]{(1R,5S)-3-[2-({5-fluoro-6-[(3R)-3-hydroxypyrrolidin-1-yl]pyridin-3-yl}amino)pyrimidin-4-yl]-3,8-diazabicyclo[3.2.1]oct-8-yl}methanone | (R)-1-(5-((4-((1R,5S)-3,8-diazabicyclo[3.2.1]octan-3-yl)pyrimidin-2-yl)amino)-3-fluoropyridin-2-yl)pyrrolidin-3-ol (Preparation 9) and (S)-2,2-difluorocyclo-propane-1-carboxylic acid (Preparation 68). | $^1$H NMR (400 MHz, DMSO-$d_6$): δ ppm 1.59-2.06 (m, 8H), 2.82-3.03 (m, 2H), 3.10-3.29 (m, 2H), 3.48-3.67 (m, 3H), 4.00-4.37 (m, 3H), 4.59-4.74 (m, 2H), 4.85-4.94 (m, 1H), 6.16-6.27 (m, 1H), 7.78-7.89 (m, 1H), 7.95 (s, 1H), 8.11-8.22 (m, 1H), 8.90-9.03 (m, 1H). MS m/z 490 [M + H]$^+$ PM B. |

| Example No. | Structure/name | Starting Materials | Data |
|---|---|---|---|
| 22 | [(1S)-2,2-difluoro-cyclopropyl][(1R,5S)-3-(2-{[5-fluoro-6-(3-hydroxyazetidin-1-yl)pyridin-3-yl]amino}pyrimidin-4-yl)-3,8-diazabicyclo[3.2.1]oct-8-yl]methanone | 1-(5-((4-((1R,5S)-3,8-diazabicyclo[3.2.1]octan-3-yl)pyrimidin-2-yl)amino)-3-fluoropyridin-2-yl)azetidin-3-ol (Preparation 10) and (S)-2,2-difluorocyclo-propane-1-carboxylic acid (Preparation 68). | $^1$H NMR (400 MHz, DMSO-d$_6$): δ ppm 1.70-2.20 (m, 6H), 2.91-3.25 (m, 3H), 3.81-3.93 (m, 2H), 4.08-4.24 (m, 1H), 4.24-4.38 (m, 3H), 4.53-4.79 (m, 5H), 6.14-6.26 (m, 1H), 7.64-7.77 (m, 1H), 7.86-7.97 (m, 1H), 8.08-8.19 (m, 1H). MS m/z 476 [M + H]$^+$ PM D. |
| 23 | [(1R,5S)-3-(2-{[5-chloro-6-(2-hydroxyethoxy)pyridin-3-yl]amino}pyrimidin-4-yl)-3,8-diazabicyclo[3.2.1]oct-8-yl][(1S)-2,2-difluorocyclopropyl]methanone | 2-((5-((4-((1R,5S)-3,8-diazabicyclo[3.2.1]octan-3-yl)pyrimidin-2-yl)amino)-3-chloropyridin-2-yl)oxy)eth-an-1-ol hydrochloride (Preparation 11) and (S)-2,2-difluorocyclopropane-1-carboxylic acid (Preparation 68). | $^1$H NMR (400 MHz, DMSO-d$_6$): δ ppm 1.61-2.02 (m, 6H), 2.87-3.14 (m, 2H), 3.21-3.29 (m, 1H), 3.67-3.77 (m, 1H), 3.87-4.27 (m, 2H), 4.27-4.32 (m, 2H), 4.55-4.73 (m, 2H), 4.79-4.88 (m, 1H), 6.21-6.32 (m, 1H), 7.94-8.05 (m, 1H), 8.22-8.41 (m, 2H), 9.12-9.24 (m, 1H). MS m/z 481 [M + H]$^+$ PM B. |
| 24 | (1R,2R)-2-{[(1R,5S)-3-{2-[(1-ethyl-1H-pyrazol-4-yl)amino]pyrimidin-4-yl}-3,8-diazabicyclo[3.2.1]oct-8-yl]carbonyl}cyclopropane carbonitrile | (1R,2R)-2-cyanocyclo-propane-1-carboxylic acid (Preparation 72) and 4-((1R,5S)-3,8-diazabicyclo-[3.2.1]octan-3-yl)-N-(1-ethyl-1H-pyrazol-4-yl)pyrimidin-2-amine hydrochloride (Preparation 23). | $^1$H NMR (400 MHz, DMSO-d$_6$): δ ppm 1.33 (t, 3H), 1.42 (m, 1H), 1.63-1.81 (m, 3H), 1.80-2.10 (m, 2H), 2.88-3.15 (m, 4H), 4.07 (m, 2H), 4.04-4.09 (m, 2H), 4.60 (s, 1H), 4.85 (s, 1H), 6.11 (m, 1H), 7.45 (s, 1H), 7.75 (s, 1H), 7.92 (d, 1H), 8.86 (s, 1H). MS m/z 393 [M + H]$^+$ PM B (RT = 8.31 min). |
| 25 | [(1S)-2,2-difluorocyclopropyl][(1R,5S)-3-(2-{[5-fluoro-6-(hydroxymethyl)pyridin-3-yl]amino}pyrimidin-4-yl)-3,8-diazabicyclo[3.2.1]oct-8-yl]methanone | (5-((4-((1R,5S)-3,8-diazabicyclo[3.2.1]octan-3-yl)pyr-imidin-2-yl)amino)-3-fluoro-pyridin-2-yl)methanol hydrochloride (Preparation 12) and (S)-2,2-difluorocyclopropane-1-carboxylic acid (Preparation 68). | $^1$H NMR (400 MHz, DMSO-d$_6$): δ ppm 1.57-2.08 (m, 7H), 2.95 (d, 1H), 3.03 (d, 1H), 4.15 (br s, 2H), 4.50 (s, 2H), 4.59-4.76 (m, 2H), 5.15 (br s, 1H), 6.34 (m, 1H), 8.06 (d, 1H), 8.12 (d, 1H), 8.62 (d, 1H), 9.56 (br s, 1H). MS m/z 435 [M + H]$^+$ PM B. |
| 26 | 2-[5-({4-[(1R,5S)-8-{[(1S)-2,2-difluorocyclopropyl]carbonyl}-3,8-diazabicyclo[3.2.1]oct-3-yl]pyrimidin-2-yl}amino)pyridin-2-yl]-2-methylpropanenitrile | 2-(5-((4-((1R,5S)-3,8-diazabicyclo[3.2.1]octan-3-yl)pyrimidin-2-yl)amino)-pyridin-2-yl)-2-methylprop-anenitrile hydrochloride (Preparation 13) and (S)-2,2-difluorocyclopropane-1-carboxylic acid (Preparation 68). | $^1$H NMR (400 MHz, DMSO-d$_6$): δ ppm 1.67-1.884 (m, 11H), 2.92-2.95 (m, 2H), 3.20-3.28 (m, 2H), 4.20 (m, 2H), 4.65 (m, 2H), 6.29-6.32 (m, 1H), 7.47-7.50 (m, 1H), 8.01-8.03 (m, 1H), 8.24-8.26 (m, 1H), 8.81 (br s, 1H), 9.41 (s, 1H). MS m/z 454 [M + H]$^+$ PM B. |

-continued

| Example No. | Structure/name | Starting Materials | Data |
|---|---|---|---|
| 27 | 5-({4-[(1R,5S)-8-{[(1R,2R)-2-cyanocyclopropyl]carbonyl}-3,8-diazabicyclo[3.2.1]oct-3-yl]pyrimidin-2-yl}amino)-3-fluoro-N-methylpyridine-2-carboxamide | 5-((4-((1R,5S)-3,8-diazabicyclo[3.2.1]octan-3-yl)pyrimidin-2-yl)amino)-3-fluoro-N-methylpic-olinamide hydrochloride (Preparation 14) and (1R,2R)-2-cyanocyclo-propane-1-carboxylic acid (Preparation 72). | $^1$H NMR (400 MHz, DMSO-d$_6$): δ ppm 1.35 (m, 2H), 1.65 (m, 1H), 1.75 (m, 2H), 2.09 (m, 2H), 2.76 (m, 3H), 2.94-3.08 (m, 3H), 4.15 (m, 2H), 4.61 (m, 1H), 4.88 (m, 1H), 6.40-6.43 (m, 1H), 8.08-8.10 (m, 1H), 8.28 (m, 1H), 8.43-8.44 (m, 1H), 8.69 (s, 1H), 9.89 (s, 1H). MS m/z 452 [M + H]$^+$ PM B. |
| 28 | 5-({4-[(1R,5S)-8-{[(1R)-2,2-difluorocyclopropyl]carbonyl}-3,8-diazabicyclo[3.2.1]oct-3-yl]pyrimidin-2-yl}amino)-3-fluoro-N-methylpyridine-2-carboxamide | Racemic 2,2-difluoro-cyclopropane-1-carboxylic acid and 5-((4-((1R,5S)-3,8-diazabicyclo[3.2.1]octan-3-yl)pyrimidin-2-yl)amino)-3-fluoro-N-methyl-picolinamide hydrochloride (Preparation 14) with separation of the enantiomers as described above in PM E. | $^1$H NMR (400 MHz, DMSO-d$_6$): δ ppm 1.60-2.00 (m, 6H), 2.75-2.76 (m, 3H), 2.95-3.05 (m, 2H), 3.25 (m, 1H), 4.20 (m, 2H), 4.65 (m, 2H), 6.40 (m, 1H), 8.09-8.11 (m, 1H), 8.20-8.30 (m, 1H), 8.40 (m, 1H), 8.69 (s, 1H), 9.89 (s, 1H). SFC Rt = 5.05 minutes |
| 29 | 5-({4-[(1R,5S)-8-{[(1S)-2,2-difluorocyclopropyl]carbonyl}-3,8-diazabicyclo[3.2.1]oct-3-yl]pyrimidin-2-yl}amino)-3-fluoro-N-methylpyridine-2-carboxamide | Racemic 2,2-difluoro-cyclopropane-1-carboxylic acid and 5-((4-((1R,5S)-3,8-diazabicyclo[3.2.1]octan-3-yl)pyrimidin-2-yl)amino)-3-fluoro-N-methylpicol-inamide hydrochloride (Preparation 14) with separation of the enantiomers as described above in PM E. | $^1$H NMR (400 MHz, DMSO-d$_6$): δ ppm 1.60-2.05 (m, 6H), 2.75-2.76 (m, 3H), 2.95-2.98 (m, 2H), 3.19 (m, 1H), 4.20 (m, 2H), 4.63-4.73 (m, 1H), 6.39-6.43 (m, 1H), 8.09-8.11 (m, 1H), 8.24-8.27 (m, 1H), 8.43 (m, 1H), 8.69 (s, 1H), 9.89 (s, 1H). MS m/z 462 [M + H]$^+$ SFC Rt = 5.51 minutes |
| 30 | 3-chloro-5-({4-[(1R,5S)-8-(cyclopropylcarbonyl)-3,8-diazabicyclo[3.2.1]oct-3-yl]pyrimidin-2-yl}amino)-N-methylpyridine-2-carboxamide | 5-((4-((1R,5S)-3,8-diazabicyclo[3.2.1]octan-3-yl)pyrimidin-2-yl)amino)-3-chloro-N-methylpicol-inamide hydrochloride (Preparation 5) and cyclopropanecarboxylic acid. | $^1$H NMR (400 MHz, DMSO-d$_6$): δ ppm 0.78 (d, 4H), 1.57-1.89 (m, 3H), 2.03 (br s, 2H), 2.76 (d, 3H), 3.00-3.16 (m, 2H), 4.05 (s, 2H), 4.62 (br s, 1H), 4.79 (br s, 1H), 6.39 (d, 1H), 8.08 (d, 1H), 8.45 (s, 2H), 8.82 (d, 1H), 9.77 (s, 1H). MS m/z 442 [M + H]$^+$ PM B. |
| 31 | 3-chloro-5-({4-[(1R,5S)-8-{[(1R,2R)-2-cyanocyclopropyl]carbonyl}-3,8-diazabicyclo[3.2.1]oct-3-yl]pyrimidin-2-yl}amino)-N-methylpyridine-2-carboxamide | 5-((4-((1R,5S)-3,8-diazabicyclo[3.2.1]octan-3-yl)pyrimidin-2-yl)amino)-3-chloro-N-methylpicol-inamide hydrochloride (Preparation 5) and (1R,2R)-2-cyanocyclopropane-1-carboxylic acid (Preparation 72). | $^1$H NMR (400 MHz, DMSO-d$_6$): δ ppm 1.21 (t, 1H), 1.30-1.47 (m, 2H), 1.64 (d, 1H), 1.68-1.88 (m, 2H), 1.90-2.14 (m, 2H), 2.73 (d, 3H), 2.84-2.96 (m, 1H), 2.97-3.22 (m, 2H), 4.12 (br s, 2H), 4.60 (d, 1H), 4.87 (br s, 1H), 6.39 (t, 1H), 8.07 (dd, 1H), 8.43 (br s, 2H), 8.80 (d, 1H), 9.77 (s, 1H). MS m/z 467 [M + H]$^+$ PM B. |

-continued

| Example No. | Structure/name | Starting Materials | Data |
|---|---|---|---|
| 32 | 5-({4-[(1R,5S)-8-{[(1R,2R)-2-cyanocyclopropyl]carbonyl}-3,8-diazabicyclo[3.2.1]oct-3-yl]pyrimidin-2-yl}amino)-N,3-dimethylpyridine-2-carboxamide | 5-((4-((1R,5S)-3,8-diazabicyclo[3.2.1]octan-3-yl)pyrimidin-2-yl)amino)-N,3-dimethylpicolinamide hydrochloride (Preparation 1) and (1R,2R)-2-cyanocyclo-propane-1-carboxylic acid (Preparation 72). | $^1$H NMR (400 MHz, DMSO-d$_6$): δ ppm 1.29-1.51 (m, 2H), 1.55-2.16 (m, 5H), 2.56 (s, 3H), 2.75 (d, 3H), 2.89-3.12 (m, 3H), 4.13 (br s, 2H), 4.61 (d, 1H), 4.89 (br s, 1H), 6.35 (t, 1H), 8.02-8.10 (m, 2H), 8.45 (d, 1H), 8.77 (s, 1H), 9.56 (s, 1H). MS m/z 447 [M + H]$^+$ PM B. |
| 33 | 5-((4-((1R,5S)-8-((S)-2,2-difluorocyclopropane-1-carbonyl)-3,8-diazabicyclo[3.2.1]octan-3-yl)pyrimidin-2-yl)amino)-N,3-dimethylpicolinamide | 5-((4-((1R,5S)-3,8-diazabicyclo[3.2.1]octan-3-yl)pyrimidin-2-yl)amino)-N,3-dimethylpicolinamide hydrochloride (Preparation 1) and racemic 2,2-difluorocyclopropane-1-carboxylic acid with separation of the isomers using PM D Peak 2 arbitrarily assign as title compound. | $^1$H NMR (400 MHz, DMSO-d$_6$): δ ppm 1.67-1.88 (m, 6H), 2.57 (d, 3H), 2.76 (d, 3H), 2.95-3.06 (m, 2H), 3.21-3.24 (m, 1H), 4.64-4.72 (m, 2H), 6.32-6.36 (m, 1H), 8.064 (d, 2H), 8.43 (s, 1H), 8.77 (d, 1H), 9.54 (s, 1H). MS m/z 458 [M + H]$^+$ |
| 34 | 5-[(4-{(1R,5S)-8-[(2,2-difluorocyclopropyl)carbonyl]-3,8-diazabicyclo[3.2.1]oct-3-yl}pyrimidin-2-yl)amino]-3-methylpyridine-2-carboxamide | Racemic 2,2-difluoro-cyclopropane-1-carboxylic acid and 5-((4-((1R,5S)-3,8-diazabicyclo[3.2.1]octan-3-yl)pyrimidin-2-yl)amino)-3-methylpicolinamide hydrochloride (Preparation 26). | $^1$H NMR (400 MHz, DMSO-d$_6$): δ ppm 1.85-2.03 (m, 6H), 2.57 (s, 3H), 2.98 (d, 1 H), 3.07-3.28 (m, 3H), 4.08-4.36 (m, 2H), 4.62-4.75 (m, 2H), 6.34-6.38 (m, 1H), 7.20 (s, 1H), 7.84 (s, 1H), 8.07-8.10 (m, 2H), 8.74-8.78 (m, 1H), 9.54 (s, 1H). MS m/z 444 [M + H]$^+$ PM B. |
| 35 | 5-({4-[(1R,5S)-8-{[(1S)-2,2-difluorocyclopropyl]carbonyl}-3,8-diazabicyclo[3.2.1]oct-3-yl]pyrimidin-2-yl}amino)-3-methylpyridine-2-carboxamide | (S)-2,2-difluorocyclo-propane-1-carboxylic acid (Preparation 70) and 5-((4-((1R,5S)-3,8-diazabicyclo[3.2.1]octan-3-yl)pyrimidin-2-yl)amino)-3-methylpicolinamide hydrochloride (Preparation 26). | $^1$H NMR (400 MHz, DMSO-d$_6$): δ ppm 1.85-2.03 (m, 6H), 2.57 (s, 3H), 2.98 (d, 1 H), 3.07-3.28 (m, 3H), 4.08-4.36 (m, 2H), 4.62-4.75 (m, 2H), 6.34-6.38 (m, 1H), 7.20 (s, 1H), 7.84 (s, 1H), 8.07-8.10 (m, 2H), 8.74-8.78 (m, 1H), 9.54 (s, 1H). Rt = 0.55 minutes; MS m/z 444 [M + H]$^+$ PM F. |
| 36 | cyclopropyl[(1R,5S)-3-{2-[(1-methyl-1H-pyrazol-4-yl)amino]pyrimidin-4-yl}-3,8-diazabicyclo[3.2.1]oct-8-yl]methanone | 4-((1R,5S)-3,8-diazabicyclo[3.2.1]octan-3-yl)-N-(1-methyl-1H-pyrazol-4-yl)pyrimidin-2-amine hydrochloride (Preparation 26) and Cyclopropylcarboxylic acid. | $^1$H NMR (400 MHz, CDCl$_3$): δ ppm 0.78 (m, 4H), 0.90-1.00 (m, 2H), 1.60-2.05 (m, 4H), 3.10 (m, 1H), 3.80 (s, 1H), 3.90 (m, 1H), 4.10 (m, 1H), 4.50 (m, 1H), 4.80 (m, 1H), 5.80 (d, 1H), 7.20 (d, 1H), 7.40 (s, 1H), 7.60 (br s, 1H), 7.90 (m, 1H). Rt = 0.59 minutes MS m/z 354 [M + H]$^+$ PM F. |

| Example No. | Structure/name | Starting Materials | Data |
| --- | --- | --- | --- |
| 37 | (1S,2R)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile | 4-((1R,5S)-3,8-diazabicyclo[3.2.1]octan-3-yl)-N-(1-methyl-1H-pyrazol-4-yl)pyrimidin-2-amine hydrochloride (Preparation 19) and (1S,2R)-2-cyanocyclopropane-1-carboxylic acid (*J. Med. Chem.* (2013), 56 (11), 4521-4536). | $^1$H NMR (400 MHz, MeOH-d$_4$): δ ppm 1.40-1.50 (m, 1H), 1.70-2.20 (m, 6H), 2.60-2.70 (m, 1H), 3.10-3.30 (m, 2H), 3.35 (s, 3H), 4.10-4.40 (br m, 2H), 4.80 (m, 2H), 6.70 (m, 1H), 7.55 (s, 1H), 7.80 (s, 1H), 7.90 (m, 1H).<br>LCMS Rt = 0.50 minutes MS m/z 379 [M + H]$^+$ PM F. |
| 38 | (1R,2S)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile | 4-((1R,5S)-3,8-diazabicyclo[3.2.1]octan-3-yl)-N-(1-methyl-1H-pyrazol-4-yl)pyrimidin-2-amine hydrochloride (Preparation 19) and (1R,2S)-2-cyanocyclopropane-1-carboxylic acid (J. Med. Chem. (2013), 56 (11), 4521-4536). | $^1$H NMR (400 MHz, MeOH-d$_4$): δ ppm 1.40-1.50 (m, 1H), 1.70-2.20 (m, 6H), 2.60-2.70 (m, 1H), 3.10-3.30 (m, 2H), 3.35 (s, 3H), 4.10-4.40 (br m, 2H), 4.80 (m, 2H), 6.70 (m, 1H), 7.55 (s, 1H), 7.80 (s, 1H), 7.90 (m, 1H).<br>LCMS Rt = 0.49 minutes MS m/z 379 [M + H]$^+$ PM F. |
| 39 | (3,3-difluorocyclobutyl)[(1R,5S)-3-{2-[(1-methyl-1H-pyrazol-4-yl)amino]pyrimidin-4-yl}-3,8-diazabicyclo[3.2.1]oct-8-yl]methanone | 4-((1R,5S)-3,8-diazabicyclo[3.2.1]octan-3-yl)-N-(1-methyl-1H-pyrazol-4-yl)pyrimidin-2-amine hydrochloride (Preparation 19) and 3,3-difluoro-cyclobutanecarboxylic acid. | $^1$H NMR (400 MHz, CDCl$_3$): δ ppm 1.70-2.00 (m, 4H), 2.70-3.00 (m, 4H), 3.00-3.18 (m, 2H), 3.25-3.40 (m, 2H), 3.80 (s, 3H), 4.05-4.35 (br m, 2H), 4.40 (m, 1H), 4.75 (m, 1H), 6.10 (m, 1H), 7.50 (m, 1H), 7.75 (m, 1H), 7.90 (m, 1H).<br>LCMS Rt = 0.65 minutes MS m/z 404 [M + H]$^+$ PM F. |
| 40 | 4-({4-[(1R,5S)-8-{[(1S)-2,2-difluorocyclopropyl]carbonyl}-3,8-diazabicyclo[3.2.1]oct-3-yl]pyrimidin-2-yl}amino)-N,6-dimethylpyridine-2-carboxamide | 4-((4-((1R,5S)-3,8-diazabicyclo[3.2.1]octan-3-yl)pyrimidin-2-yl)amino)-N,6-dimethylpicolinamide (Preparation 16) and (S)-2,2-difluorocyclopropane-1-carboxylic acid (Preparation 68). | Rt = 2.43 minutes MS m/z 458 [M + H]$^+$ PM G. |
| 41 | 4-({4-[(1R,5S)-8-{[(1S)-2,2-difluorocyclopropyl]carbonyl}-3,8-diazabicyclo[3.2.1]oct-3-yl]pyrimidin-2-yl}amino)-6-(hydroxymethyl)-N-methylpyridine-2-carboxamide | 4-((4-((1R,5S)-3,8-diazabicyclo[3.2.1]octan-3-yl)pyrimidin-2-yl)amino)-6-(hydroxymethyl)-N-methylpicolinamide hydrochloride (Preparation 17) and (S)-2,2-difluorocyclopropane-1-carboxylic acid (Preparation 68). | Rt = 1.59 minutes MS m/z 474 [M + H]$^+$ PM G. |

Examples 42 and 43

[(1R,2R)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone and [(1S,2S)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone The title compounds were prepared according to the method described for Example 9 using 4-((1R,5S)-3,8-diazabicyclo[3.2.1]octan-3-yl)-N-(1-methyl-1H-pyrazol-4-yl)pyrimidin-2-amine hydrochloride (Preparation 19) and cis-racemic (1S,2S)-2-fluorocyclopropane-1-carboxylic acid (PCT Publication No. WO2005095322). The cis-racemic title compound was separated into its enantiomers using chiral chromatography as described below:

Column: IB 21 mm×250 mm×5 μm, Mobile phase A: CO$_2$; Mobile phase B: 0.2% Ammonium hydroxide in MeOH; 80:20 A/B; 15 minutes hold; flow rate 65 mL/min.

$^1$H NMR (400 MHz, MeOH-d$_4$): δ ppm 1.10-1.20 (m, 1H), 1.70-2.30 (m, 6H), 3.10-3.25 (m, 3H), 3.85 (s, 3H), 4.10-4.40 (br m, 2H), 4.75-5.00 (m, 2H), 6.15 (m, 1H), 7.55 (s, 1H), 7.80 (m, 1H), 7.90 (m, 1H). LCMS Rt=0.50 minutes; MS m/z 372 [M+H]+

Examples 44 and 45

5-({4-[(1R,5S)-8-{[(1R,2S)-2-fluorocyclopropyl]carbonyl}-3,8-diazabicyclo[3.2.1]oct-3-yl]perimidin-2-yl}amino)-N,3-dimethylpyridine-2-carboxamide and 5-({4-[(1R,5S)-8-{[(1S,2R)-2-fluorocyclopropyl]carbonyl}-3,8-diazabicclo[3.2.1]oct-3-yl]pyrimidin-2-yl}amino)-N,3-dimethylpyridine-2-carboxamide The title compounds were prepared according to the method described for Example 9 using 5-((4-((1R,5S)-3,8-diazabicyclo[3.2.1]octan-3-yl)pyrimidin-2-yl)amino)-N,3-dimethylpicolinamide hydrochloride (Preparation 1) and trans-racemic (1S,2S)-2-fluorocyclopropane-1-carboxylic acid (PCT Publication No. WO2005095322). The trans-racemic title compound was separated into its enantiomers using chiral chromatography as described below:
Column: Lux-cellulose-3; 250 mm×21.2 mm, 5μ; Mobile phase A: 75% $CO_2$, mobile phase B: MeOH, flow rate 80 mL/min.
First eluting isomer: Rt=6.06 minutes; Second eluting isomer: Rt=6.40 minutes
$^1$H NMR (400 MHz, MeOH-d$_4$): δ ppm 1.30-1.40 (m, 1H), 1.40-1.60 (m, 1H), 1.80-1.90 (m, 1H), 1.90-2.05 (m, 1H), 2.10-2.40 (m, 1H), 2.50-2.60 (m, 1H), 3.10-3.40 (m, 4H), 4.10-4.40 (br m, 2H), 4.70-5.00 (m, 2H), 6.30 (m, 1H), 8.00 (m, 2H), 8.80 (br s, 1H). MS m/z 440 [M+H]+

Example 46

(1-fluorocyclopropyl)[(1R,5S)-3-{2-[(1-methyl-1H-pyrazol-4-yl)amino]pyrimidin-4-yl}-3,8-diazabicyclo[3.2.1]oct-8-yl]methanone To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19,100 mg, 0.311 mmol) in dioxane (10 mL) was added DIEA (401 mg, 3.11 mmol) and racemic 4-chlorophenyl-1-fluorocyclopropane-1-carboxylate (Eur. Pat. Appl. 533013, 80 mg, 0.373 mmol). The reaction mixture was heated to reflux for 18 hours. The reaction was concentrated in vacuo and purified using preparative HPLC to afford the title compound as a yellow solid as the hemiformate salt (37 mg, 32%).
Preparative HPLC using Phenomenex Synergi C18 150 mm×30 mm×4 μm; from 5% MeCN in water (0.225% FA) to 25% MeCN in water (0.225% FA). $^1$H NMR (400 MHz, DMSO-d$_6$): δ ppm 1.27-1.32 (m, 4H), 1.69 (m, 2H), 1.90 (m, 2H), 3.04-3.07 (m, 2H), 3.18 (s, 3H), 4.13 (m, 2H), 4.72 (m, 2H), 6.11 (d, 1H), 7.42 (s, 1H), 7.92 (d, 1H), 8.87 (s, 1H). MS m/z 372 [M+H]+

Example 47

(1R,5S)-N-(2-cyanoethyl)-3-{2-[(1-methyl-1H-pyrazol-4-yl)amino]pyrimidin-4-yl}-3,8-diazabicyclo[3.2.1]octane-8-carboxamide To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 50 mg, 0.175 mmol) in DCM (10 mL) was added triethylamine (53 mg, 0.525 mmol) and N-(2-cyanoethyl)-1H-imidazole-1-carboxamide (Preparation 78, 0.35 mmol) and the reaction was stirred at room temperature for 3 hours. The reaction was concentrated in vacuo and purified using preparative HPLC (Purification Method B) to afford the title compound (31 mg, 47%). $^1$H NMR (400 MHz, DMSO-d$_6$): δ ppm 1.59-1.61 (m, 2H), 1.80-1.82 (m, 2H), 2.66 (t, 2H), 3.02 (m, 4H), 3.28-3.29 (m, 2H), 3.78 (s, 3H), 3.97 (br s, 2H), 4.36 (s, 2H), 6.10 (d, 1H), 7.14 (m, 1H), 7.43 (s, 1H), 7.72 (s, 1H), 7.90 (d, 1H), 8.84 (s, 1H). MS m/z 382 [M+H]+

Example 48

(1R,5S)-3-{2-[(1-methyl-1H-pyrazol-4-yl)amino]pyrimidin-4-yl}-N-[5-(trifluoromethyl)pyridin-2-yl]-3,8-diazabicyclo[3.2.1]octane-8-carboxamide The title compound was prepared according to the method described for Example 47 using phenyl[4-(trifluoromethyl)pyridine-2-yl]carbamate (PCT Publication No. WO2010006938) at 50° C. and purified using preparative HPLC (Purification Method B). $^1$H NMR (400 MHz, MeOH-d$_4$): δ ppm 1.80-1.83 (m, 2H), 2.02 (m, 2H), 3.20-3.23 (m, 2H), 3.85 (s, 3H), 4.17 (br m, 2H), 4.64 (m, 2H), 6.14 (d, 1H), 7.51 (s, 1H), 7.75 (s, 1H), 7.87 (d, 1H), 7.95-7.98 (m, 1H), 8.08 (d, 1H), 8.54 (s, 1H). MS m/z 474 [M+H]+

Example 49 cyclopropyl{(1R,5S)-3-[2-(1H-pyrazol-4-ylamino)pyrimidin-4-yl]-3,8-diazabicyclo[3.2.1]oct-8-yl}methanone To a solution of ((1R,5S)-3-(2-chloropyrimidin-4-yl)-3,8-diazabicyclo[3.2.1]octan-8-yl)(cyclo-propyl)methanone (Preparation 28, 100 mg, 0.342 mmol) and 1-H-pyrazol-4-amine (100 mg, 0.54 mmol) in iPrOH (5 mL) was added cHCl (2 drops) and the reaction was heated to 140° C. under microwave irradiation for 1 hour. The reaction was cooled, concentrated in vacuo and purified by silica gel column chromatography eluting with 5% MeOH in DCM followed by preparative HPLC (Purification Method B) to afford the title compound (34 mg, 29%).
$^1$H NMR (400 MHz, DMSO-d$_6$): δ ppm 0.77 (br s, 4H), 1.63 (br s, 1H), 1.74 (br s, 2H), 2.01 (d, 2H), 2.94-3.10 (m, 2H), 3.87-4.27 (m, 2H), 4.53-4.84 (m, 2H), 6.10 (d, 1H), 7.53 (br s, 1H), 7.78 (br s, 1H), 7.92 (d, 1H), 8.86 (br s, 1H), 12.36 (br s, 1H). MS m/z 340 [M+H]+

Example 50 and 51

((1R,5S)-3-(2-((1H-Pyrazol-4-yl)amino)pyrimidin-4-yl)-3,8-diazabicyclo[3.2.1]octan-8-yl)((R)-2,2-difluorocyclopropyl)methanone and ((1R,5S)-3-(2-((1H-Pyrazol-4-yl)amino)pyrimidin-4-yl)-3,8-diazabicyclo[3.2.1]octan-8-yl)((S)-2,2-difluorocyclopropyl)methanone The title compounds were prepared according to the method described for Example 49 using racemic ((1R,5S)-3-(2-chloropyrimidin-4-yl)-3,8-diazabicyclo[3.2.1]octan-8-yl)(2,2-difluorocyclopropyl)-methanone (Preparation 30) and tert-butyl 4-amino-1H-pyrazole-1-carboxylate. The enantiomers were purified using preparative HPLC (Purification Method B) followed by separation using chiral chromatography: Chiral preparative HPLC: Column AD 250

Example 50: ((1R,5S)-3-(2-((1H-pyrazol-4-yl)amino)pyrimidin-4-yl)-3,8-diazabi-cyclo[3.2.1]octan-8-yl)((R)-2,2-difluorocyclopropyl)methanone (25 mg, 11%)

$^1$H NMR (400 MHz, DMSO-$d_6$): δ ppm 1.60-2.04 (m, 5H), 2.84-2.96 (m, 1H), 2.96-3.17 (m, 1H), 3.18-3.32 (m, 2H), 3.97-4.40 (m, 2H), 4.54-4.76 (m, 2H), 6.05-6.22 (m, 1H), 7.43-7.86 (m, 2H), 7.89-8.01 (m, 1H), 8.84-9.05 (m, 1H), 12.32-12.51 (m, 1H). MS m/z 376 [M+H]$^+$ Example 51: ((1R,5S)-3-(2-((1H-pyrazol-4-yl)amino)pyrimidin-4-yl)-3,8-diazabicyclo[3.2.1]octan-8-yl)((S)-2,2-difluorocyclopropyl)methanone (23 mg, 10%)

$^1$H NMR (400 MHz, DMSO-$d_6$): δ ppm 1.59-2.05 (m, 5H), 2.86-2.95 (m, 1H), 2.96-3.16 (m, 1H), 3.16-3.32 (m, 2H), 3.93-4.40 (m, 2H), 4.54-4.77 (m, 2H), 6.04-6.21 (m, 1H), 7.41-7.86 (m, 2H), 7.87-8.00 (m, 1H), 8.79-9.00 (m, 1H), 12.27-12.43 (m, 1H). MS m/z 376 [M+H]$^+$ Example 51 may also be prepared according to the following method:

To a solution of (S)-2,2-difluorocyclopropane-1-carboxylic acid (Preparation 68, 28 mg, 0.227 mmol), 4-((1R,5S)-3,8-diazabicyclo[3.2.1]octan-3-yl)-N-(1H-pyrazol-4-yl)pyrimidin-2-amine hydrochloride (Preparation 22, 56 mg, 0.21 mmol) and DIPEA (0.22 mL, 1.24 mmol) in dichloromethane (3 mL) and DMF (1 mL) was added HATU (97 mg, 0.25 mmol) and the reaction was stirred at room temperature for 18 hours. The reaction was concentrated in vacuo. The residue was purified using silica gel column chromatography eluting with 0-20% MeOH in DCM to afford the title compound (26 mg, 34%).

Example 52 cyclopropyl{(1R,5S)-3-[2-(1,2-thiazol-4-ylamino)pyrimidin-4-yl]-3,8-diazabicyclo[3.2.1]oct-8-yl}methanone The title compound was prepared according to the method described for Example 49 using 4-isothiasolamine.

Preparative HPLC: Column: Phenomenex Gemini C18 250×21.2 mm×8 μm

Mobile phase: from 3% MeCN in water (0.225% formic acid) to 23% MeCN in water (0.225% formic acid);

Flow Rate: 30 mL/min. $^1$H NMR (400 MHz, DMSO-$d_6$): δ ppm 0.70-0.77 (m, 4H), 1.61-1.81 (m, 3H), 1.99-2.00 (m, 2H), 2.97-3.00 (m, 1H), 3.07-3.10 (m, 1H), 4.11 (s, 2H), 4.62 (s, 1H), 4.77 (s, 1H), 6.24 (d, 1H), 8.00 (d, 1H), 8.59 (s, 1H), 8.76 (s, 1H), 9.71 (s, 1H). MS m/z 357 [M+H]$^+$ Example 53

N,3-dimethyl-5-({4-[(1R,5S)-8-(1,2-oxazol-5-ylmethyl)-3,8-diazabicyclo[3.2.1]oct-3-yl]pyrimidin-2-yl}amino)pyridine-2-carboxamide To a solution of N-(2,2,2-trifluoroethyl)-1H-imidazole-1-carboxamide (Preparation 82) and 5-((4-((1R,5S)-3,8-diazabicyclo[3.2.1]octan-3-yl)pyrimidin-2-yl)amino)-N,3-dimethylpicolinamide hydrochloride (Preparation 1, 50 mg, 0.12 mmol) and 5-isoxazolecarboxaldehyde (32 mg, 0.33 mmol) in MeCN (1 mL) was added sodium triacetoxyborohydride (76 mg, 0.35 mmol) and the reaction was stirred at room temperature for 1.5 hours. The reaction was quenched by the addition of saturated aqueous NaHCO$_3$ solution and extracted into EtOAc three times. The organic layer was collected, dried over magnesium sulfate and concentrated in vacuo. The residue was purified by silica gel column chromatography eluting with 0-10% MeOH in DCM followed by trituration with diethylether to afford the title compound (30 mg, 59%). LCMS Rt=0.69 minutes; MS m/z 435 [M+H]$^+$ Example 54

N,3-dimethyl-5-[(4-{(1R,5S)-8-[(3-methyloxetan-3-yl)methyl]-3,8-diazabicclo[3.2.1]oct-3-yl}pyrimidin-2-yl)amino]pyridine-2-carboxamide The title compound may be prepared according to the method described for Example 53 using 3-methyloxetane-3-carbaldehyde with DIPEA in THF/DMSO. Purified using preparative HPLC.

Preparative HPLC: DIKMA Diamonsil(2) C18 200×20 mm×5 μm

Mobile phase: from 0-27% MeCN in water (0.225% FA); 35 mL/min flow rate. Rt=1.95 minutes; MS m/z 438 [M+H]$^+$ Example 55

N-(1-methyl-1H-pyrazol-4-yl)-4-[(1R,5S)-8-(1,2-thiazol-5-ylmethyl)-3,8-diazabicyclo[3.2.1]oct-3-yl]pyrimidin-2-amine To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 100 mg, 0.351 mmol) and 5-isothiazolecarboxaldehyde (55 mg, 0.49 mmol) in MeOH (10 mL) was added triethylamine (71 mg, 0.70 mmol) and acetic acid (3 drops). The solution was stirred at room temperature for 3 hours before the addition of sodium cyanoborohydride (44 mg, 0.702 mmol) at 0° C. The reaction was stirred at room temperature for 18 hours. The solution was concentrated in vacuo and purified by preparative HPLC (Purification Method B) to afford the title compound (26.2 mg, 20%). $^1$H NMR (400 MHz, DMSO-$d_6$): δ ppm 1.57 (d, 2H), 1.96 (br s, 2H), 3.06 (d, 2H), 3.77 (s, 9H), 6.06 (d, 1H), 7.28 (s, 1H), 7.42 (s, 1H), 7.74 (br s, 1H), 7.90 (d, 1H), 8.49 (d, 1H), 8.83 (br s, 1H). MS m/z 383 [M+H]$^+$ The following Examples were prepared according to the method described for Example 55 using 4-((1R,5S)-3,8-diazabicyclo[3.2.1]octan-3-yl)-N-(1-methyl-1H-pyrazol-4-yl)pyrimidin-2-amine hydrochloride (Preparation 19) and the appropriate aldehyde or ketone. Where necessary the imine formation was carried out at elevated temperatures of 95° C. in toluene with camphorsulfonic acid, or triethylamine and acetic acid were omitted. Purification methods are as described or referred to below:

column chromatography eluting with 0-10% MeOH (1% ammonia) in DCM followed by preparative HPLC (Purification Method H). Rt=1.18 minutes; MS m/z 419 [M+H]$^+$

| Example No. | Name | SM/Data |
|---|---|---|
| 56 | N-(1-methyl-1H-pyrazol-4-yl)-4-[(1R,5S)-8-(1,2-oxazol-5-ylmethyl)-3,8-diazabicyclo[3.2.1]oct-3-yl]pyrimidin-2-amine | 5-isoxazolecarboxaldehyde<br>$^1$H NMR (400 MHz, DMSO-d$_6$): δ ppm 1.54 (d, 2H), 1.91-2.03 (m, 2H), 3.03 (d, 2H), 3.66-4.05 (m, 7H), 6.05 (d, 1H), 6.47 (s, 1H), 7.41 (s, 1H), 7.72 (br s, 1H), 7.88 (d, 1H), 8.52 (d, 1H), 8.83 (br s, 1H).<br>MS m/z 337 [M + H]$^+$<br>PM B. |
| 57 | N-(1-methyl-1H-pyrazol-4-yl)-4-[(1R,5S)-8-(1,3-thiazol-2-ylmethyl)-3,8-diazabicyclo[3.2.1]oct-3-yl]pyrimidin-2-amine | 2-thiazolecarboxaldehyde<br>$^1$H NMR (400 MHz, DMSO-d$_6$): δ ppm 1.57 (d, 2H), 1.90-2.03 (m, 2H), 3.06 (d, 2H), 3.41 (br s, 2H), 3.76 (s, 3H), 3.84-4.15 (m, 4H), 6.06 (d, 1H), 7.41 (s, 1H), 7.64 (d, 1H), 7.74 (d, 2H), 7.89 (d, 1H), 8.83 (br s, 1H).<br>MS m/z 383 [M + H]$^+$<br>PM B. |
| 58 | N-(1-methyl-1H-pyrazol-4-yl)-4-[(1R,5S)-8-(1,2-oxazol-4-ylmethyl)-3,8-diazabicyclo[3.2.1]oct-3-yl]pyrimidin-2-amine | 4-isoxazolecarboxaldehyde<br>$^1$H NMR (400 MHz, DMSO-d$_6$): δ ppm 1.52 (d, 2H), 1.96 (d, 2H), 3.02 (d, 2H), 3.43-3.47 (m, 4H), 3.76 (s, 5H), 6.03 (d, 1H), 7.41 (s, 1H), 7.72 (br s, 1H), 7.87 (d, 1H), 8.02 (s, 1H), 8.31 (s, 1H), 8.78 (br s, 1H).<br>MS m/z 367 [M + H]$^+$<br>PM B. |
| 59 | Cis and trans 3-[(1R,5S)-3-{2-[(1-methyl-1H-pyrazol-4-yl)amino]pyrimidin-4-yl}-3,8-diazabicyclo[3.2.1]oct-8-yl]cyclobutanecarbonitrile | 3-oxo-cyclobutanecarbonitrile and isolated as the cis/trans mixture.<br>LCMS Rt = 0.63 minutes MS m/z 365 [M + H]$^+$<br>$^1$H NMR (400 MHz, MeOH-d$_4$): δ ppm 1.70 (m, 2H), 1.90 (m, 2H), 2.35 (m, 1H), 2.40 (m, 1H), 2.50 (m, 1H), 2.60 (m, 1H), 3.00 (m, 1H), 3.10-3.20 (m, 3H), 3.25-3.45 (m, 5H), 4.00-4.15 (br m, 2H), 6.10 (m, 1H), 7.55 (d, 1H), 7.80 (s, 1H), 7.90 (d, 1H). |

Example 60

N-(1-methyl-1H-pyrazol-4-yl)-4-{(1R,5S)-8-[1-(methylsulfonyl)azetidin-3-yl]-3,8-diazabicyclo[3.2.1]oct-3-yl}pyrimidin-2-amine To a solution of tert-butyl 3-((1R,5S)-3-(2-((1-methyl-1H-pyrazol-4-yl)amino)pyrimidin-4-yl)-3,8-diazabicyclo[3.2.1]octan-8-yl)azetidine-1-carboxylate (Preparation 135, 51 mg, 0.12 mmol) in DCM (1 mL) was added 4N HCl in dioxane (2 mL) and the reaction was stirred at room temperature for 2 hours. The reaction was concentrated in vacuo and dissolved in DCM (1 mL). DIPEA (61 µl, 0.348 mmol) followed by methanesulfonyl chloride (10 µl, 0.128 mmol) and the reaction was stirred at room temperature for 30 minutes. The reaction was quenched by the addition of water, concentrated in vacuo and purified using silica gel Examples 61 and 62

5-({4-[(1R,5S)-8-(cis-3-cyanocyclobutyl)-3,8-diazabicyclo[3.2.1]oct-3-yl]pyrimidin-2-yl}amino)-N,3-dimethylpyridine-2-carboxamide and 5-({4-[(1R,5S)-8-(trans-3-cyanocyclobutyl)-3,8-diazabicyclo[3.2.1]oct-3-yl]pyrimidin-2-yl}amino)-N,3-dimethylpyridine-2-carboxamide The title compounds were prepared using the method described for Example 55 using 3-oxo-cyclobutanecarbonitrile and 5-((4-((1R,5S)-3,8-diazabicyclo[3.2.1]octan-3-yl)pyrimidin-2-yl)amino)-N,3-dimethylpicolinamide hydrochloride (Preparation 1). The isomers were separated using chiral chromatography as described below:

Column: Lux Cellulose-4 250 mm×21.2 mm×5 µm; Mobile phase A: Heptanes; Mobile phase B: Ethanol; from 50:50 A:B to 100% B at 10 minutes then back to 50:50 A:B at 12.5 minutes. Flow rate: 27.0 mL/min. First eluting compound was arbitrarily assigned as Example 61: Rt=8.45 minutes, MS m/z 433 [M+H]+ Second eluting isomer was arbitrarily assigned as Example 62: Rt=9.35 minutes, MS m/z 433 [M+H]+

Examples 63 and 64

4-[(1R,5S)-8-{[(1R)-2,2-difluorocyclopropyl] methyl}-3,8-diazabicyclo[3.2.1]oct-3-yl]-N-(1-methyl-1H-pyrazol-4-yl)pyrimidin-2-amine and 4-[(1R,5S)-8-{[(1S)-2,2-difluorocyclopropyl] methyl}-3,8-diazabicyclo[3.2.1]oct-3-yl]-N-(1-methyl-1H-pyrazol-4-yl)pyrimidin-2-amine To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 32 mg, 11 mmol) and racemic (2,2-difluorocyclopropyl)methyl 4-methylbenzenesulfonate (PCT Publication No. WO20130908375, 30 mg, 12 mmol) in MeCN (3 mL) was added sodium carbonate (18 mg, 17 mmol) and tert-butylammonium iodide (6 mg, 17 mmol) and the reaction was stirred at 60° C. for 42 hours. The reaction was cooled and concentrated in vacuo. The residue was partitioned between DCM and saturated aqueous ammonium chloride solution. The organic layer was collected and purified using silica gel column chromatography eluting with 0-10% MeOH (1% ammonia) in DCM. The residue was dissolved in DCM and washed with ammonium chloride three times before concentrating in vacuo. The residue was then dissolved in EtOAc and washed with saturated aqueous NaHCO$_3$ solution, water, brine, and concentrated in vacuo to afford the racemic title compound that was separated into the two enantiomers using chiral chromatography as described below: Column: OJ-H 21 mm×250 mm×5μ, Mobile phase A: CO$_2$; Mobile phase B: MeOH (0.2% ammonium hydroxide) using 90% A and 10% B, Hold for 10 minutes, flow rate 75 mL/min.

$^1$H NMR (400 MHz, MeOH-d$_4$): δ ppm 1.20-1.30 (m, 1H), 1.50-2.05 (m, 6H), 2.50 (m, 1H), 2.75 (m, 1H), 3.15-3.20 (m, 3H), 3.50 (m, 1H), 3.90 (s, 3H), 4.00 (m, 2H), 6.10 (m, 1H), 7.50 (d, 1H), 7.78 (s, 1H), 7.85 (d, 1H). LCMS Rt=0.71 minutes; MS m/z 376 [M+H]+

Examples 65 and 66

4-[(1R,5S)-8-{[(1S)-2,2-difluorocyclopropyl] methyl}-3,8-diazabicclo[3.2.1]oct-3-yl]-N-(1H-pyrazol-4-yl)pyrimidin-2-amine and 4-[(1R,5S)-8-{ [(1R)-2,2-difluorocyclopropyl]methyl}-3,8-diazabicyclo[3.2.1]oct-3-yl]-N-(1H-pyrazol-4-yl) pyrimidin-2-amine The title compounds were prepared according to the method described for Examples 63 and 64 using racemic (2,2-difluorocyclopropyl)methyl 4-methylbenzenesulfonate (PCT Publication No. WO20130908375) and 4-((1R,5S)-3,8-diazabicyclo[3.2.1]octan-3-yl)-N-(1-tosyl-1H-pyrazol-4-yl)pyrimidin-2-amine (Preparation 15). The residue was dissolved in DCM (1 mL) and treated with 4N HCl in dioxane (1 mL) and stirred at room temperature for 18 hours. MeOH (1 mL) was added and the reaction continued for a further 18 hours. The reaction was concentrated in vacuo, eluted through a carbonate cartridge and separated into enantiomers using chiral chromatography as described below:

Column: AD-H 21 mm×250 mm×5μ, Mobile phase A: CO$_2$; Mobile phase B: MeOH (0.2% ammonium hydroxide) using 75% A and 25% B, Hold for 8 minutes, flow rate 75 mL/min.

First eluting isomer: Rt=5.74 minutes, Example 66; Second eluting isomer: Rt=6.44 minutes, Example 67

Examples 67 and 68

5-({4-[(1R,5S)-8-{[(1S)-2,2-difluorocyclopropyl] methyl}-3,8-diazabicyclo[3.2.1]oct-3-yl]pyrimidin-2-yl}amino)-N,3-dimethylpyridine-2-carboxamide and 5-({4-[(1R,5S)-8-{[(1R)-2,2-difluorocyclopropyl]methyl}-3,8-diazabicyclo[3.2.1]oct-3-yl]pyrimidin-2-yl}amino)-N,3-dimethylpyridine-2-carboxamide The title compounds were prepared according to the method described for Examples 63 and 64 using 5-((4-((1R,5S)-3,8-diazabicyclo[3.2.1]octan-3-yl)pyrimidin-2-yl)amino)-N,3-dimethylpicolinamide hydrochloride (Preparation 1).

The racemate was separated into two enantiomers using chiral chromatography as described below: Column: Chiral Tech OJ-H; 500 mm×21.2 mm, 5μ; Mobile phase A 70% CO$_2$, 30% MeOH (0.2% ammonia), flow rate 80 mL/min.

First eluting compound was arbitrarily assigned as Example 67: Rt=6.09 minutes, MS m/z 444 [M+H]+ Second eluting compound was arbitrarily assigned as Example 68: Rt=6.21 minutes, MS m/z 444 [M+H]+

Examples 69 and 70

(1S,2S)-2-{[(1R,5S)-3-{2-[(1-methyl-1H-pyrazol-4-yl)amino]pyrimidin-4-yl}-3,8-diazabicyclo[3.2.1] oct-8-yl]methyl}cyclopropanecarbonitrile and (1S, 2S)-2-{[(1R,5S)-3-{2-[(1-methyl-1H-pyrazol-4-yl) amino]pyrimidin-4-yl}-3,8-diazabicyclo[3.2.1]oct-8-yl]methyl}cyclopropanecarbonitrile The title compounds were prepared according to the method described for Examples 63 and 64 using (2-cyanocyclopropyl)methyl 4-methylbenzenesulfonate (Acta Pharmaceutica Suecica (1972), 9 (5), 491-498). The residue was separated into the two enantiomers using chiral chromatography as described below: Column: OD-H 21 mm×250 mm×5μ, Mobile phase A: CO$_2$; Mobile phase B: EtOH (0.2% ammonium hydroxide) using 70% A and 30% B, Hold for 7 minutes, flow rate 75 mL/min.

$^1$H NMR (400 MHz, MeOH-d$_4$): δ ppm 1.05-1.10 (m, 1H), 1.30 (m, 1H), 1.50-1.55 (m, 1H), 1.70 (m, 3H), 2.00 (m, 2H), 3.15-3.40 (m, 4H), 3.50 (m, 1H), 3.80 (s, 3H), 4.00 (br m, 2H), 4.80 (m, 1H), 6.10 (m, 1H), 7.55 (d, 1H), 7.75 (s, 1H), 7.90 (m, 1H). MS m/z 365 [M+H]+

Example 71

1-({(1R,5S)-3-[2-(1H-pyrazol-4-ylamino)pyrimidin-4-yl]-3,8-diazabicyclo[3.2.1]oct-8-yl}methyl)cyclopropanecarbonitrile The title compound was prepared according to the method described for Example 55 using 4-((1R,5S)-3,8-diazabicyclo [3.2.1]octan-3-yl)-N-(1-tosyl-1H-pyrazol-4-yl)pyrimidin-2-amine (Preparation 15) and 1-formylcyclopropane-1-carbonitrile (PCT Publication No. WO2009005675). The residue (5 mg, 0.011 mmol) was dissolved in MeOH (0.5 mL) and 5N NaOH (aq) (220 µl) was added with stirring for 1 hour. The reaction was concentrated in vacuo, azeotroped with DCM and purified using preparative HPLC (Purification Method H). Rt=1.06 minutes; MS m/z 351 [M+H]$^+$

Example 72

N-ethyl-4-({5-fluoro-4-[8-(trifluoroacetyl)-3,8-diazabicyclo[3.2.1]oct-3-yl]pyrimidin-2-yl}amino)-2-methylbenzamide To a solution of 4-((4-((1R,5S)-3,8-diazabicyclo[3.2.1]octan-3-yl)-5-fluoropyrimidin-2-yl)amino)-N-ethyl-2-methylbenzamide hydrochloride (Preparation 25, 30 mg, 0.08 mmol) in DCM (5 mL) was added TFAA (5 drops) and the reaction stirred at room temperature for 18 hours. The reaction was purified directly by silica gel column chromatography eluting with 0-10% MeOH in DCM followed by preparative HPLC (Purification Method I). Rt=2.22 minutes; MS m/z 481 [M+H]$^+$

Example 73 tert tert-butyl 3-(2-{[4-(ethylcarbamoyl)-3-methylphenyl]amino}-5-fluoropyrimidin-4-yl)-3,8-diazabicyclo[3.2.1]octane-8-carboxylate The title compound was prepared according to the method described for Preparation 24 Step 1 using 4-amino-N-ethyl-2-methyl-benzamide (PCT Publication No. WO2006109846). $^1$H NMR (400 MHz, DMSO-d$_6$): δ ppm 1.13 (t, 3H), 1.44-1.49 (m, 9H), 1.74 (d, 2H), 1.89 (br s, 2H), 2.35 (s, 3H), 3.18-3.28 (m, 4H), 4.16 (d, 2H), 4.26 (br s, 2H), 7.29 (d, 1H), 7.51-7.55 (m, 1H), 7.56 (s, 1H), 8.03-8.09 (m, 2H), 9.30 (s, 1H).

Example 74

(1R,5S)-N-ethyl-3-[2-(1,2-thiazol-4-ylamino)pyrimidin-4-yl]-3,8-diazabicyclo[3.2.1]octane-8-carboxamide To a solution of N-(4-((1R,5S)-3,8-diazabicyclo[3.2.1]octan-3-yl)pyrimidin-2-yl)isothiazol-4-amine hydrochloride (Preparation 21, 100 mg, 0.27 mmol) in DCM (10 mL) was added triethylamine (84 mg, 0.83 mmol) and the solution was cooled to 0° C. Isocyanatoethane (21.7 mg, 0.306 mmol) was added and the reaction was stirred at room temperature for 18 hours. The reaction was concentrated in vacuo and purified directly by Preparative HPLC (Purification Method B) to afford the title compound (29 mg, 29%). Preparative HPLC: Column: Phenomenex Gemini C18 250× 21.2 mm×24 µm Mobile phase: from 29% MeCN in water (Ammonia pH=10) to 39% MeCN in water (Ammonia pH=10); Flow Rate: 30 mL/min. $^1$H NMR (400 MHz, DMSO-d$_6$): δ ppm 1.021 (t, 3H), 1.58-1.59 (m, 2H), 1.77 (m, 2H), 3.01-3.08 (m, 4H), 3.96 (m, 2H), 4.35 (s, 2H), 6.23 (d, 1H), 6.67-6.69 (m, 1H), 7.98 (d, 1H), 8.59 (s, 1H), 8.75 (s, 1H), 9.68 (s, 1H). MS m/z 382 [M+Na]$^+$

Example 75

(1R,5S)-3-(2-{[5-chloro-6-(methylcarbamoyl)pyridin-3-yl]amino}pyrimidin-4-yl)-N-ethyl-3,8-diazabicyclo[3.2.1]octane-8-carboxamide The title compound was prepared according to the method described for Example 74 using 5-((4-((1R,5S)-3,8-diazabicyclo[3.2.1]octan-3-yl)pyrimidin-2-yl)amino)-3-chloro-N-methylpicolinamide hydrochloride (Preparation 5) and isocyanatoethane. The residue was purified using preparative HPLC as described below: Preparative HPLC: DIKMA Diamonsil(2) C18 200×20 mm×5 µm Mobile phase: from 10% MeCN in water (0.225% formic acid) to 30% MeCN in water (0.225% formic acid). $^1$H NMR (400 MHz, DMSO-d$_6$): δ ppm 1.02 (t, 3H), 1.53-1.63 (m, 2H), 1.74-1.84 (m, 2H), 2.75 (d, 3H), 3.03-3.12 (m, 4H), 3.96 (br s, 2H), 4.37 (br s, 2H), 6.36 (d, 1H), 6.72 (t, 1H), 8.05 (d, 1H), 8.45 (d, 2H), 8.80 (d, 1H), 9.74 (s, 1H). MS m/z 445 [M+H]$^+$

Example 76

(1R,5S)-3-{2-[(1-methyl-1H-pyrazol-4-yl)amino]pyrimidin-4-yl}-3,8-diazabicyclo[3.2.1]octane-8-carboxamide To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 30 mg, 0.09 mmol) and sodium isocyanate (14 mg, 0.21 mmol) in DCM (0.3 mL) was added acetic acid (11 µl, 0.186 mmol) and the reaction was stirred at room temperature for 18 hours. The reaction was concentrated in vacuo and purified by reverse phase silica gel column chromatography eluting with 5-50% MeCN in 0.1% aqueous ammonia followed by trituration with MeOH and diethylether to afford the title compound (26 mg, 85%).

$^1$H NMR (400 MHz, MeOH-d$_4$): δ ppm 1.70 (m, 2H), 1.90 (m, 2H), 3.10 (m, 2H), 3.90 (s, 3H), 4.00-4.15 (br m, 2H), 4.40 (m, 2H), 6.10 (m, 1H), 7.50 (s, 1H), 7.75 (s, 1H), 7.85 (m, 1H).

LCMS Rt=0.50 minutes; MS m/z 329 [M+H]$^+$

Example 77

N-(1-methyl-1H-pyrazol-4-yl)-4-[(1R,5S)-8-(methylsulfonyl)-3,8-diazabicyclo[3.2.1]oct-3-yl]pyrimidin-2-amine To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 100 mg, 0.31 mmol) in DCM (30 mL) at 10° C. was added triethylamine (350 mg, 3.46 mmol) followed by MsCl (280 mg, 2.44 mmol). The reaction was stirred at room temperature for 1 hour. The reaction was washed with water (10 mL) and the organic layer was concentrated in vacuo and purified using preparative HPLC (Purification Method B) to afford the title compound (70 mg, 62%). $^1$H NMR (400 MHz, DMSO-d$_6$): δ ppm 1.55-1.70 (m, 2H), 1.85-2.01 (m, 2H), 3.04 (s, 5H), 3.78 (s, 3H), 3.95-4.21 (m, 2H), 4.23-4.36 (m, 2H), 6.02-6.17 (m, 1H), 7.41 (s, 1H), 7.65-7.80 (m, 1H), 7.85-7.97 (m, 1H), 8.79-8.95 (m, 1H). MS m/z 364 [M+H]$^+$

Example 78

2-[(1R,5S)-3-{2-[(1-methyl-1H-pyrazol-4-yl)amino]pyrimidin-4-yl}-3,8-diazabicyclo[3.2.1]oct-8-yl]-1,3-oxazole-5-carbonitrile A solution of ethyl 2-((1R,5S)-3-(2-((1-methyl-1H-pyrazol-4-yl)amino)pyrimidin-4-yl)-3,8-diazabicyclo[3.2.1]octan-8-yl)oxazole-5-carboxylate (Preparation 136, 200 mg, 0.47 mmol) in 7M NH$_3$/MeOH (50 mL) was heated to 90°

C. in a sealed vessel for 18 hours. The reaction was concentrated in vacuo and dissolved in DCM (20 mL). Triethylamine (6 mL) followed by TFAA (3 mL) was added and the reaction was stirred at room temperature for 18 hours. The solution was washed with saturated aqueous NaHCO$_3$ solution, and concentrated in vacuo. The residue was purified by Preparative HPLC (Purification Method B) to afford the title compound (46 mg, 26%).

$^1$H NMR (400 MHz, DMSO-d$_6$): δ ppm 1.73 (d, 2H), 1.97-2.01 (m, 2H), 3.16 (d, 2H), 3.79 (s, 3H), 4.04-4.24 (m, 2H), 4.55 (br s, 2H), 6.14 (d, 1H), 7.42 (s, 1H), 7.75 (br s, 1H), 7.92 (d, 1H), 8.04 (s, 1H), 8.98 (br s, 1H). MS m/z 378 [M+H]$^+$ PM B HATU Example 79

3-{(1R,5S)-3-[2-(1H-pyrazol-4-ylamino)pyrimidin-4-yl]-3,8-diazabicyclo[3.2.1]oct-8-yl}propanenitrile To a solution of 4-((1R,5S)-3,8-diazabicyclo[3.2.1]octan-3-yl)-N-(1l2-pyrazol-4-yl)pyrimidin-2-amine hydrochloride (Preparation 22, 83 mg, 0.308 mmol) and triethylamine (622 mg, 6.16 mmol) in EtOH (10 mL) at 0° C. was added acrylonitrile (270 mg, 5.09 mmol) dropwise. The reaction was stirred at room temperature for 18 hours before concentrating in vacuo. The residue was purified by preparative HPLC (Purification Method B) to afford the title compound as a white solid (45 mg, 44%).

$^1$H NMR (400 MHz, DMSO-d$_6$): δ ppm 1.43-1.57 (m, 2H), 1.75-1.91 (m, 2H), 2.56-2.71 (m, 4H), 2.92-3.05 (m, 2H), 3.37-3.43 (m, 3H), 3.64-4.06 (m, 1H), 6.03 (d, 1H), 7.41-7.61 (m, 1H), 7.64-7.79 (m, 1H), 7.87 (d, 1H), 8.72-8.87 (m, 1H), 12.33 (br s, 1H). MS m/z 325 [M+H]$^+$ Examples 80 and 81

3-[(1R,5S)-3-{2-[(1-methyl-1H-pyrazol-4-yl)amino]pyrimidin-4-yl}-3,8-diazabicyclo[3.2.1]oct-8-yl]butanenitrile and 3-[(1R,5S)-3-{2-[(1-methyl-1H-pyrazol-4-yl)amino]pyrimidin-4-yl}-3,8-diazabicyclo[3.2.1]oct-8-yl]butanenitrile The title compound was prepared according to the method described for Example 80 using 4-((1R,5S)-3,8-diazabicyclo[3.2.1]octan-3-yl)-N-(1-methyl-1H-pyrazol-4-yl)pyrimidin-2-amine hydrochloride (Preparation 19) and E/Z-but-2-enenitrile at 100° C. in a sealed vessel. The residue was purified using silica gel column chromatography eluting with 5% MeCN in 0.1% aqueous ammonia to 40% MeCN in 0.1% aqueous ammonia followed by chiral separation using a Chiraltech OJ-H 250 mm×10 mm×5 µm column; with mobile phase A: 70% CO$_2$ and mobile phase B: 30% EtOH with 0.2% ammonia; flow rate 15 mL/min.

First eluting compound was arbitrarily assigned as Example 80: Peak 1 Rt=6.69 minutes; LCMS Rt=0.63 minutes MS m/z 353 [M+H]$^+$ Second eluting compound was arbitrarily assigned as Example 81: Peak 2 Rt=6.95 minutes and is Example 81; LCMS Rt=0.63 minutes; MS m/z 353 [M+H]$^+$ Example 82

3-{(1R,5S)-3-[2-(1H-pyrazol-4-ylamino)pyrimidin-4-yl]-3,8-diazabicyclo[3.2.1]oct-8-yl}butanenitrile The title compound was prepared according to the method described for Example 79 using 4-((1R,5S)-3,8-diazabicyclo[3.2.1]octan-3-yl)-N-(1l2-pyrazol-4-yl)pyrimidin-2-amine hydrochloride (Preparation 22) and E/Z-but-2-enenitrile at 140° C. under microwave irradiation for 8 hours. The residue was purified using reverse phase silica gel column chromatography eluting with from 5-75% MeCN (0.1% ammonia) in water.

$^1$H NMR (400 MHz, DMSO-d$_6$): δ ppm 0.50 (d, 3H), 0.90 (m, 2H), 1.00-1.20 (m, 2H), 2.10 (m, 1H), 2.30-2.40 (m, 2H), 2.80 (m, 2H), 3.00-3.40 (br m, 2H), 4.00 (m, 2H), 5.25 (m, 1H), 6.90 (m, 2H), 7.05 (m, 1H).

LCMS Rt=0.59 minutes; MS m/z 339 [M+H]$^+$

Example 83

{3-[(1R,5S)-3-{2-[(1-methyl-1H-pyrazol-4-yl)amino]pyrimidin-4-yl}-3,8-diazabicyclo[3.2.1]oct-8-yl]-1-(methylsulfonyl)azetidin-3-yl}acetonitrile The title compound was prepared according to the method described for Example 77 using 2-(3-((1R,5S)-3-(2-((1-methyl-1H-pyrazol-4-yl)amino)pyrimidin-4-yl)-3,8-diazabicyclo[3.2.1]octan-8-yl)azetidin-3-yl)acetonitrile hydrochloride (Example 84) and DIPEA. The residue was purified using silica gel column chromatography eluting with 10% MeOH (with 1% ammonia) in DCM.

$^1$H NMR (400 MHz, MeOH-d$_4$): δ ppm 1.75-1.90 (m, 4H), 3.05 (s, 3H), 3.20 (m, 2H), 3.30 (m, 2H), 3.40 (s, 3H), 3.80 (m, 2H), 3.85 (m, 2H), 4.00-4.20 (m, 4H), 6.10 (m, 1H), 7.55 (d, 1H), 7.78 (s, 1H), 7.90 (d, 1H).

LCMS Rt=0.52 minutes; MS m/z 458 [M+H]$^+$

Example 84

{3-[(1R,5S)-3-{2-[(1-methyl-1H-pyrazol-4-yl)amino]pyrimidin-4-yl}-3,8-diazabicyclo[3.2.1]oct-8-yl]oxetan-3-yl}acetonitrile The title compound was prepared according to the method described for Preparation 135 using 2-(3-oxetanylidene)acetonitrile at 85° C. for 5 days. The reaction was cooled and purified using Preparative HPLC (Purification Method H). LCMS Rt=1.50 minutes; MS m/z 381 [M+H]$^+$ Example 85

((1R,5S)-N-(cyanomethyl)-3-{2-[(1-methyl-1H-pyrazol-4-yl)amino]pyrimidin-4-yl}-3,8-diazabicyclo[3.2.1]octane-8-carboxamide To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 26 mg, 0.08 mmol) and N-(cyanomethyl)carbamoylimidazole (Preparation 79, 14 mg, 0.09 mmol) in EtOH (0.8 mL) was added triethylamine (110 µl, 0.082 mmol) in a sealed vessel and the reaction was heated to 60° C. for 2 hours. Further N-(cyanomethyl)carbamoylimidazole (2 mg, 0.01 mmol) was added and the reaction continued heating for 2 hours before concentrating in vacuo. The residue was dissolved in DCM (10 mL) and washed with brine, dried over magnesium sulfate and concentrated in vacuo. The residue was purified using silica gel column chromatography eluting with 0-10% MeOH in DCM to afford the title compound as a white solid (21 mg, 70%). $^1$H NMR (400 MHz, MeOH-d$_4$): δ ppm 1.78 (m, 2H), 2.00 (m, 2H), 3.15 (m, 4H), 3.88 (d, 3H), 4.00-4.15 (m, 2H), 4.43 (m, 2H), 6.10 (m, 1H), 7.55 (m, 1H), 7.75 (m, 1H), 7.90 (m, 1H). MS m/z 368 [M+H]$^+$

Example 86

(1R,5S)-N-ethyl-3-{2-[(1-methyl-1H-pyrazol-4-yl) amino]pyrimidin-4-yl}-3,8-diazabicyclo[3.2.1]octane-8-carboxamide The title compound was prepared according to Example 85 using N-ethyl-1H-imidazole-1-carboxamide (Preparation 80, 24 mg, 0.17 mmol) and 4-((1R,5S)-3,8-diazabicyclo [3.2.1]octan-3-yl)-N-(1-methyl-1H-pyrazol-4-yl)pyrimidin-2-amine hydrochloride (Preparation 19, 50 mg, 0.16 mmol). The residue was purified using silica gel column chromatography eluting with 0-10% MeOH in DCM to afford the title compound as a white solid (41 mg, 74%). $^1$H NMR (400 MHz, DMSO-d$_6$): δ ppm 1.00 (m, 3H), 1.55 (m, 2H), 1.75 (m, 2H), 3.10 (m, 3H), 3.18 (m, 3H) 3.80 (s, 3H), 4.00 (m, 1H), 4.10 (m, 1H), 4.40 (m, 2H), 6.10 (m, 1H), 6.67 (t, 1H), 7.45 (s, 1H), 7.73 (br s, 1H), 7.91 (d, 1H), 8.82 (s, 1H). LCMS Rt=0.58 minutes; MS m/z 357 [M+H]$^+$

Example 87

(1R,5S)-N-ethyl-3-(2-{[5-fluoro-6-(methylcarbamoyl)pyridin-3-yl]amino}pyrimidin-4-yl)-3,8-diazabicyclo[3.2.1]octane-8-carboxamide The title compound was prepared according to Example 85 using N-ethyl-1H-imidazole-1-carboxamide (Preparation 80) and 5-((4-((1R,5S)-3,8-diazabicyclo[3.2.1]octan-3-yl) pyrimidin-2-yl)amino)-3-fluoro-N-methylpicolinamide hydrochloride (Preparation 14) without triethylamine as base. $^1$H NMR (400 MHz, DMSO-d$_6$): δ ppm 1.04 (t, 3H), 1.60 (q, 2H), 1.81 (d, 2H), 2.78 (d, 3H), 2.93-3.14 (m, 4H), 3.18 (d, 2H), 4.39 (br s, 2H), 6.39 (d, 1H), 6.71 (t, 1H), 8.07 (d, 1H), 8.27 (d, 1H), 8.42 (d, 1H), 8.71 (s, 1H), 9.85 (s, 1H). MS m/z 429 [M+H]$^+$

Example 88

(1R,5S)-3-{2-[(1-methyl-1H-pyrazol-4-yl)amino] pyrimidin-4-yl}-N-(propan-2-yl)-3,8-diazabicyclo [3.2.1]octane-8-carboxamide The title compound was prepared according to the method described for Example 85 using N-isopropyl-1H-imidazole-1-carboxamide (Preparation 81) and 4-((1R,5S)-3,8-diazabicyclo[3.2.1]octan-3-yl)-N-(1-methyl-1H-pyrazol-4-yl)pyrimidin-2-amine hydrochloride (Preparation 19). Following chromatography the residue was dissolved in DCM, precipitated by the addition of diethylether and filtered. LCMS Rt=0.61 minutes; MS m/z 371 [M+H]$^+$

Example 89

(1R,5S)-3-(2-{[5-methyl-6-(methylcarbamoyl)pyridin-3-yl]amino}pyrimidin-4-yl)-N-(2,2,2-trifluoroethyl)-3,8-diazabicyclo[3.2.1]octane-8-carboxamide The title compound was prepared according to the method described for Example 85 using 5-((4-((1R,5S)-3,8-diazabicyclo[3.2.1]octan-3-yl)pyrimidin-2-yl)amino)-N,3-dimethylpicolinamide hydrochloride (Preparation 1). The residue was purified using silica gel column chromatography eluting with 0-20% MeOH (1% ammonia) in DCM. $^1$H NMR (400 MHz, MeOH-d$_4$): δ ppm 1.80 (m, 2H), 2.00 (m, 2H), 2.60 (s, 3H), 2.95 (s, 3H), 3.40 (m, 2H), 3.90-4.00 (m, 2H), 4.15 (br m, 2H), 4.50 (m, 2H), 6.30 (m, 1H), 8.00 (m, 2H), 8.75 (m, 1H). LCMS Rt=0.56 minutes; MS m/z 479 [M+H]$^+$

Example 90

(1R,5S)-N-(cyanomethyl)-3-(2-{[5-methyl-6-(methylcarbamoyl)pyridin-3-yl]amino}pyrimidin-4-yl)-3, 8-diazabicyclo[3.2.1]octane-8-carboxamide The title compound was prepared according to the method described for Example 85 using 5-((4-((1R,5S)-3,8-diazabicyclo[3.2.1]octan-3-yl)pyrimidin-2-yl)amino)-N,3-dimethylpicolinamide hydrochloride (Preparation 1) and N-(cyanomethyl)-1H-imidazole-1-carboxamide (Preparation 78). The residue was purified using silica gel column chromatography eluting with 0-20% MeOH (1% ammonia) in DCM. $^1$H NMR (400 MHz, MeOH-d$_4$): δ ppm 1.80 (m, 2H), 2.00 (m, 2H), 2.65 (s, 3H), 2.95 (s, 3H), 3.20 (m, 2H), 4.20 (m, 4H), 4.50 (m, 2H), 6.30 (m, 1H), 8.00 (m, 2H), 8.70 (s, 1H). LCMS Rt=0.50 min; MS m/z 436 [M+H]$^+$

Example 91

(1R,5S)-N-ethyl-3-(2-{[5-methyl-6-(methylcarbamoyl)pyridin-3-yl]amino}pyrimidin-4-yl)-3,8-diazabicyclo[3.2.1]octane-8-carboxamide The title compound was prepared according to the method described for Example 85 using 5-((4-((1R,5S)-3,8-diazabicyclo[3.2.1]octan-3-yl)pyrimidin-2-yl)amino)-N,3-dimethylpicolinamide hydrochloride (Preparation 1) and N-ethyl-1H-imidazole-1-carboxamide (Preparation 79). Following chromatography the title compound was further purified using Preparative HPLC (Purification Method H). Rt=1.69 minutes; MS m/z 425 [M+H]$^+$

Example 92

2-[(1R,5S)-3-{2-[(1-methyl-1H-pyrazol-4-yl)amino] pyrimidin-4-yl}-3,8-diazabicyclo[3.2.1]oct-8-yl] pyridine-4-carbonitrile To a solution of 4-((1R,5S)-3,8-diazabicyclo[3.2.1]octan-3-yl)-N-(1-methyl-1H-pyrazol-4-yl)pyrimidin-2-amine hydrochloride (Preparation 19, 51 mg, 0.16 mmol) in iPrOH (1.5 mL) was added 4-cyano-2-chloropyridine (45 mg, 0.32 mmol) and triethylamine (100 µl, 0.68 mmol). The reaction was heated to 160° C. under microwave irradiation for 13 hours. The reaction was cooled, concentrated in vacuo and purified using reverse phase silica gel column chromatography eluting with 5-100% MeCN in 0.1% aqueous ammonia to afford the title compound. $^1$H NMR (400 MHz, CDCl$_3$): δ ppm 1.70 (m, 2H), 1.90 (m, 2H), 3.10 (m, 2H), 3.70 (s, 3H), 3.80-3.90 (br m, 2H), 4.50 (m, 2H), 5.75 (d, 1H), 6.50 (br s, 1H), 6.60-6.70 (m, 2H), 7.35 (s, 1H), 7.50 (s, 1H), 7.80 (d, 1H), 8.15 (m, 1H). LCMS Rt=0.74 minutes; MS m/z 388 [M+H]$^+$

Examples 93 and 94

(1S)-2,2-difluoro-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide and (1R)-2,2-difluoro-N-[(1S,5R,6R)-3-{5-fluoro-2-[(1-methyl-1H-pyrazol-4-yl)amino] pyrimidin-4-yl}-6-methyl-3-azabicclo[3.1.0]hex-1-yl]cyclopropanecarboxamide To a solution of (1S,5R,6R)-3-(5-fluoro-2-((1-methyl-1H-pyrazol-4-yl)amino)pyrimidin-4-yl)-6-methyl-3-azabicyclo

[3.1.0]hexan-1-amine hydrochloride (Preparation 90, 148 mg, 0.15 mmol) in DMA (1 mL) and DCM (1 mL) was added racemic 2,2-difluorocyclopropane-1-carboxylic acid (51 mg, 0.42 mmol), HATU (188 mg, 0.49 mmol) and DIPEA (279 µl, 0.54 mmol) and the reaction was stirred at room temperature for 18 hours. The reaction was concentrated in vacuo and partitioned between EtOAc and water. The organic layer was collected, dried and concentrated in vacuo. The residue was purified using silica gel column chromatography eluting with from DCM to 91:8:1 DCM:MeOH:ammonia to afford the racemic title compound. The racemate was separated using chiral chromatography using ChiralTech AD-H column (250 mm×21.2 mm×5 um); mobile phase A: 80% $CO_2$; mobile phase B: 20% MeOH with 0.2% ammonia. The residue for each enantiomer may be purified further by recrystallization from MeOH.

Peak 2 Rt=5.89 minutes Example 93:

$^1$H NMR (400 MHz, MeOH-d$_4$): δ ppm 1.05-1.10 (m, 3H), 1.36-1.43 (m, 1H), 1.73-1.82 (m, 1H), 1.86-1.90 (m, 1H), 1.98-2.06 (m, 1H), 2.45-2.53 (m, 1H), 3.75-3.83 (m, 2H), 3.86 (s, 3H), 4.10 (m, 2H), 7.50 (s, 1H), 7.76 (d, 1H), 7.80 (s, 1H).

LCMS Rt=0.57 minutes; MS m/z 408 [M+H]$^+$

Peak 1 Rt=3.90 minutes Example 94:

$^1$H NMR (400 MHz, MeOH-d$_4$): δ ppm 1.05-1.10 (m, 3H), 1.40 (m, 1H), 1.75 (m, 1H), 1.80 (m, 1H), 2.00 (m, 1H), 2.50 (m, 1H), 3.60-3.80 (m, 5H), 4.10 (m, 2H), 7.50 (s, 1H), 7.80 (m, 2H).

LCMS Rt=0.57 minutes; MS m/z 408 [M+H]$^+$; $[α]_D^{20}$=16.8 (c 1.095, MeOH)

Example 95

(1R,2R)-2-cyano-N-[(1S,5R,6R)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide The title compound was prepared according to the method described for Example 93 using (1R,2R)-2-cyanocyclopropane-1-carboxylate (Preparation 72).

$^1$H NMR (400 MHz, DMSO-d$_6$): δ ppm 0.90 (m, 3H), 1.25-1.35 (m, 4H), 1.45 (m, 1H), 1.80 (m, 1H), 2.00 (m, 1H), 2.20 (m, 1H), 3.60-3.80 (m, 3H), 3.90 (m, 2H), 7.40 (s, 1H), 7.70 (s, 1H), 7.90 (d, 1H), 9.00 (br s, 1H), 9.10 (s, 1H). MS m/z 397 [M+H]$^+$; $[α]_D^{20}$=−113.3 (c 0.965, EtOH)

The following Examples were prepared according to the method described for Example 93 using the appropriate acid and amine as described. Purification details are as described or referred to below: Purification Method A: Purified using preparative HPLC: Column: Diol, 250 mm×21.2 mm×5 µm; mobile phase A: heptanes; mobile phase B: ethanol; from 50% B to 100% B at 10 minutes then return to 50% B at 12 minutes; Flow rate 27 mL/min.

Analytical LCMS: Phenomenex Luna C18; 150 mm×3 mm×5 µm, mobile phase A: 0.1% formic acid in water, mobile phase B: 0.1% formic acid in acetonitrile from 5% B to 100% B at 10 minutes then return to 5% B at 12.5 minutes. Flow rate 0.75 mL/min.

Purification Method B: Silica gel column chromatography eluting with 97:2:1 DCM:MeOH:NH$_4$OH.

Purification Method C: Preparative HPLC using [Phenomenex Gemini C18 250×21.2 mm×8 µm or 150 mm×25 mm×5 µm; from 16-55% MeCN in water (0.1% ammonia) to 36-60% MeCN in water (0.1% ammonia)]

| Ex. No. | Structure/name | Starting Materials | Data |
|---|---|---|---|
| 96 | (1S)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide | (1R,5S,6S)-3-(5-fluoro-2-((1-methyl-1H-pyrazol-4-yl)amino)pyrimidin-4-yl)-6-methyl-3-azabicyclo[3.1.0]hexan-1-amine hydrochloride (Preparation 91) and (S)-2,2-difluoro-cyclopropane-1-carboxylic acid (Preparation 68). | LCMS Rt = 0.50 minutes MS m/z 408 [M + H]$^+$ $[α]_D^{20}$ = 0 (c 1.095, EtOH) $^1$H NMR (400 MHz, DMSO-d$_6$): δ ppm 0.90 (m, 5H), 1.30 (m, 1H), 1.70-2.00 (m, 3H), 2.40 (m, 1H), 3.60-3.80 (m, 5H), 7.40 (s, 1H), 7.70 (s, 1H), 7.90 (m, 1H), 8.90-9.00 (m, 2H). PM B. |
| 97 | (1R)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide | (1R,5S,6S)-3-(5-fluoro-2-((1-methyl-1H-pyrazol-4-yl)amino)pyrimidin-4-yl)-6-methyl-3-azabicyclo[3.1.0]hexan-1-amine hydrochloride (Preparation 91) and (R)-2,2-difluoro-cyclopropane-1-carboxylic acid (Preparation 69). | LCMS Rt = 0.50 minutes MS m/z 408 [M + H]$^+$ $[α]_D^{20}$ = −7.1 (c 1.095, EtOH) $^1$H NMR (400 MHz, DMSO-d$_6$): δ ppm 0.90 (m, 5H), 1.30 (m, 1H), 1.70-2.00 (m, 3H), 2.40 (m, 1H), 3.60-4.00 (m, 5H), 7.40 (s, 1H), 7.70 (s, 1H), 7.90 (m, 1H), 8.90-9.00 (m, 2H). PM B. |

| Ex. No. | Structure/name | Starting Materials | Data |
|---|---|---|---|
| 98 | (1S,2S)-2-cyano-N-[(1S,5R,6R)-3-(2-{[6-(2-hydroxyethoxy)pyridin-3-yl]amino}-5-methylpyrimidin-4-yl)-6-methyl-3-azabicyclo[3.1.0]hex-1-yl]cyclopropanecarboxamide | 2-((5-((4-((1S,5R,6R)-1-amino-6-methyl-3-azabicyclo[3.1.0]hexan-3-yl)-5-methylpyrimidin-2-yl)amino)pyridin-2-yl)oxy)ethan-1-ol (Preparation 92) and (1S,2S)-2-cyano-cyclopropane-1-carboxylic acid (Preparation 73). | Rt = 5.64 minutes MS m/z 450 [M + H]$^+$ PM A. |
| 99 | (1S)-2,2-difluoro-N-[(1S,5R,6R)-3-(5-fluoro-2-{[1-(oxetan-3-yl)-1H-pyrazol-4-yl]amino}pyrimidin-4-yl)-6-methyl-3-azabicyclo[3.1.0]hex-1-yl]cyclopropanecarboxamide | (1S,5R,6R)-3-(5-fluoro-2-((1-(oxetan-3-yl)-1H-pyrazol-4-yl)amino)pyrimidin-4-yl)-6-methyl-3-azabicyclo[3.1.0]hexan-1-amine (Preparation 93) and (S)-2,2-difluorocyclopropane-1-carboxylic acid (Preparation 68). | $^1$H NMR (400 MHz, MeOH-d$_4$): δ ppm 1.03 (d, 3H), 1.31-1.40 (m, 1H), 1.71-1.89 (m, 2H), 1.99 (dt, 1H), 2.41-2.53 (m, 1H), 3.73-3.85 (m, 2H), 4.08 (dd, 2H), 4.95-5.09 (m, 4H), 5.48 (m, 1H), 7.63 (s, 1H), 7.75 (d, 1H), 8.04 (s, 1H). MS m/z 450 [M + H]$^+$ PM C. |

Examples 100 and 101

5-[(4-{(1S5R,6R)-1-[(cyclopropylcarbonyl)amino]-6-methyl-3-azabicyclo[3.1.0.]hex-3-yl}-5-fluoropyrimidin-2-yl)aminol]-N,3-dimethylpyridine-2-carboxamide and 5-(4-{10R,5S6S)-1-[(cyclopropylcarbonyl)aminol-6-methyl-3-azabicyclo[3.1.0]hex-3-yl}-5-fluoropyrimidin-2-yl)amino]-N,3-dimethylpyridine-2-carboxamide The title compounds were prepared according to the method described for Example 5 using trans-racemic N-(3-(2-chloro-5-fluoropyrimidin-4-yl)-6-methyl-3-azabicyclo[3.1.0]hexan-1-yl)cyclopropane-carboxamide (Preparation 95) and 5-amino-N,3-dimethylpicolinamide (Preparation 38). The residue was purified and separated in enantiomers by chiral chromatography: Chiral column: Lux Cellulose-4, 250 mm×21.2 mm×5 μm, mobile phase A: supercritical CO$_2$, mobile phase B: Methanol, A:B 65:35; flow rate 80 mL/min. First eluting isomer: Example 100; Second eluting isomer: Example 101.
MS m/z 440 [M+H]$^+$ Example 102

N-[(1S,5R,6R)-3-(5-fluoro-2-{[6-(2-hydroxyethyl)pyridin-3-yl]amino}pyrimidin-4-yl)-6-methyl-3-azabicyclo[3.1.0]hex-1-yl]cyclopropanecarboxamide The title compound was prepared according to the method described for Example 5 using N-((1S,5R,6R)-3-(2-chloro-5-fluoropyrimidin-4-yl)-6-methyl-3-azabicyclo[3.1.0]hexan-1-yl)cyclopropanecarboxamide (Preparation 95) and 2-(5-aminopyridin-2-yl)ethan-1-ol (Preparation 116). The residue was purified by silica gel column chromatography eluting with 10% MeOH in DCM followed by preparative HPLC (Purification Method B). $^1$H NMR (400 MHz, DMSO-d$_6$): δ ppm 0.64-0.66 (m, 4H), 0.90 (d, 3H), 1.24-1.28 (m, 1H), 1.49 (m, 1H), 1.76-1.77 (m, 1H), 2.76-2.80 (m, 2H), 3.39 (s, 1H), 3.64-3.70 (m, 4H), 3.87-3.88 (m, 1H), 4.59-4.61 (m, 1H), 7.13 (d, 1H), 7.94 (d, 1H), 7.97 (d, 1H), 8.71 (s, 1H), 8.74 (s, 1H), 9.20 (s, 1H). MS m/z 413 [M−H]$^−$ Examples 103 and 104

N N-{(1S,5R,6R)-3-[5-fluoro-2-({6-[(2R)-1-hydroxpropan-2-yl]pridin-3-yl}amino)pyrimidin-4-yl]-6-methyl-3-azabicyclo[3.1.0]hex-1-yl}cyclopropanecarboxamide and N-{(1S,5R,6R)-3-[5-fluoro-2-({6-[(2S)-1-hydroxypropan-2-yl]pyridin-3-yl}amino)pyrimidin-4-yl]-6-methyl-3-azabicyclo[3.1.0]hex-1-yl}cyclopropanecarboxamide The title compounds were prepared according to the method described for Example 5 using N-((1S,5R,6R)-3-(2-chloro-5-fluoropyrimidin-4-yl)-6-methyl-3-azabicyclo[3.1.0]hexan-1-yl)cyclopropanecarboxamide (Preparation 95) and racemic-2-(5-aminopyridin-2-yl)propan-1-ol (Preparation 40). The residue was purified using silica gel column chromatography eluting with 10% MeOH in DCM followed by preparative HPLC (Preparation Method B). The racemate was separated into its enantiomers using chiral chromatography:

Chiral column: Chiralpak IC, 250 mm×30 mm×5 μm, mobile phase A: supercritical CO$_2$, mobile phase B: IPA (0.1% ammonia), A:B 60:40; flow rate 70 mL/min.

First eluting isomer was arbitrarily assigned as Example 103;

$^1$H NMR (400 MHz, MeOH-d$_4$): δ ppm 0.76-0.86 (m, 4H), 1.00-1.02 (m, 3H), 1.28-1.38 (m, 4H), 1.54 (m, 1H), 1.76-1.83 (m, 1H), 3.00-3.05 (m, 1H), 3.66-3.80 (m, 4H), 4.03-4.05 (m, 2H), 7.23-7.27 (d, 1H), 7.80-7.81 (d, 1H), 8.04-8.05 (d, 1H), 8.84 (s, 1H). MS m/z 449 [M+Na]$^+$, 99.2% ee.

Second eluting isomer was arbitrarily assigned as Example 104;

$^1$H NMR (400 MHz, MeOH-d$_4$): δ ppm $^1$H NMR (400 MHz, MeOH-d$_4$): δ ppm 0.76-0.86 (m, 4H), 1.00-1.02 (m, 3H), 1.28-1.38 (m, 4H), 1.54 (m, 1H), 1.76-1.83 (m, 1H), 3.00-3.05 (m, 1H), 3.66-3.80 (m, 4H), 4.03-4.05 (m, 2H), 7.23-7.27 (d, 1H), 7.80-7.81 (d, 1H), 8.04-8.05 (d, 1H), 8.84 (s, 1H).

MS m/z 449 [M+Na]$^+$, 94% ee.

Example 105

N-[(1S,5R,6R)-3-(2-{[5-chloro-6-(hydroxymethyl)pyridin-3-yl]amino}-5-fluoropyrimidin-4-yl)-6-methyl-3-azabicyclo[3.1.0]hex-1-yl]cyclopropanecarboxamide

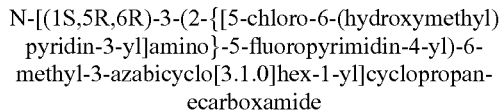

The title compound was prepared according to the method described for Example 5 using N-((1S,5R,6R)-3-(2-chloro-5-fluoropyrimidin-4-yl)-6-methyl-3-azabicyclo[3.1.0]hexan-1-yl)cyclopropanecarboxamide (Preparation 95) and (5-amino-3-chloropyridin-2-yl)methanol (Preparation 122). The residue was purified using silica gel column chromatography eluting with 30% petroleum ether in EtOAc followed by preparative HPLC (Purification Method B).

$^1$H NMR (400 MHz, MeOH-d$_4$): δ ppm 0.76-0.78 (m, 2H), 0.86 (m, 2H), 1.01-1.03 (m, 3H), 1.35-1.37 (m, 1H), 1.53 (m, 1H), 1.82 (m, 1H), 3.75-3.78 (m, 2H), 4.04 (m, 2H), 4.72 (s, 2H), 7.85 (m, 1H), 8.45 (s, 1H), 8.65 (s, 1H). MS m/z 433 [M+H]$^+$

Example 106

N-{(1S,5R,6R)-3-[2-({5-chloro-6-[(1R)-1-hydroxyethyl]pyridin-3-yl}amino)-5-fluoropyrimidin-4-yl]-6-methyl-3-azabicyclo[3.1.0]hex-1-yl}cyclopropanecarboxamide

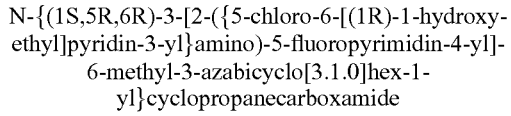

To a solution of tert-butyl ((1S,5R,6R)-3-(2-((5-chloro-6-((S)-1-hydroxyethyl)pyridin-3-yl)amino)-5-fluoropyrimidin-4-yl)-6-methyl-3-azabicyclo[3.1.0]hexan-1-yl)carbamate (Preparation 138 350 mg, 0.718 mmol) in MeOH (10 mL) was added 4M HCl in dioxane (10 mL, 4M) dropwise. The solution was stirred at room temperature for 1 hour before concentrating in vacuo. The residue (54 mg, 0.143 mmol) was dissolved in DMF (10 mL) and treated with triethylamine (86 mg, 0.85 mmol) cyclopropanecarboxylic acid (24 mg, 0.28 mmol) and HATU (86 mg, 0.23 mmol). The reaction was stirred at room temperature for 18 hours. The reaction was concentrated in vacuo and purified directly using preparative HPLC (Purification Method B) to afford the title compound (38 mg, 58%).

$^1$H NMR (400 MHz, DMSO-d$_6$): δ ppm 0.62-0.73 (m, 3H), 0.93 (s, 2H), 1.16-1.21 (m, 1H), 1.24-1.31 (m, 1H), 1.37 (d, 2H), 1.46-1.56 (m, 1H), 1.72-1.85 (m, 1H), 3.06-3.15 (m, 1H), 3.58-3.76 (m, 1H), 3.86-3.97 (m, 1H), 4.97-5.08 (m, 1H), 7.98-8.05 (m, 1H), 8.29-8.40 (m, 1H), 8.69-8.79 (m, 2H), 9.50-9.60 (m, 1H).

MS m/z 447 [M+H]$^+$

Examples 107 and 108

N-[(1S,5R)-3-(5-chloro-2-{[1-(2-hydroxyethyl)-1H-pyrazol-4-yl]amino}pyrimidin-4-yl)-3-azabicyclo[3.1.0]hex-1-yl]cyclopropanecarboxamide and
N-[(1R,5S)-3-(5-chloro-2-{[1-(2-hydroxyethyl)-1H-pyrazol-4-yl]amino}pyrimidin-4-yl)-3-azabicyclo[3.1.0]hex-1-yl]cyclopropanecarboxamide

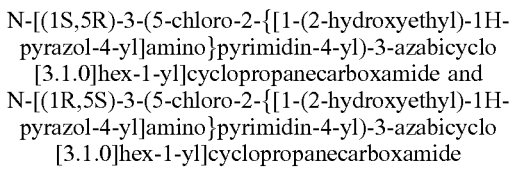

The racemic title compound was prepared according to the method described for Example 49 using racemic-N-(3-(2,5-dichloropyrimidin-4-yl)-3-azabicyclo[3.1.0]hexan-1-yl)cyclopropanecarboxamide (Preparation 98) and 4-amino-1H-pyrazole-1-ethanol.

The racemate was separated into its enantiomers using preparative chiral chromatography as described below:

Chiral column: Chiralpak Ad 250 mm×30 mm I.D. 20 μm; Mobile phase: supercritical C$_2$:EtOH (0.2% ammonia) 45:55; Flow rate: 80 mL/min First Eluting Isomer: Example 107

$^1$H NMR (400 MHz, MeOH-d$_4$): δ ppm 0.76-0.79 (m, 3H), 0.86-0.87 (m, 2H), 1.10 (m, 1H), 1.28 (m, 1H), 1.54 (m, 1H), 1.76 (m, 1H), 3.73 (m, 1H), 3.87 (m, 2H), 3.91-3.94 (m, 1H), 4.16 (m, 3H), 4.47-4.49 (m, 1H), 7.52 (s, 1H), 7.81 (s, 1H), 7.87 (s, 1H). MS m/z 404 [M+H]$^+$ Second Eluting Isomer: Example 108

$^1$H NMR (400 MHz, MeOH-d$_4$): δ ppm 0.76-0.79 (m, 3H), 0.86-0.87 (m, 2H), 1.10 (m, 1H), 1.28 (m, 1H), 1.54 (m, 1H), 1.76 (m, 1H), 3.73 (m, 1H), 3.87 (m, 2H), 3.91-3.94 (m, 1H), 4.16 (m, 3H), 4.47-4.49 (m, 1H), 7.52 (s, 1H), 7.81 (s, 1H), 7.87 (s, 1H). MS m/z 404 [M+H]$^+$

Example 109

(1S)-2,2-difluoro-N-[(1S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide

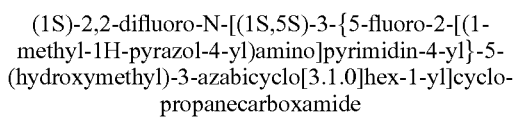

The title compound was prepared according to the method described for Example 49 using (S)-N-((1S,5S)-3-(2-chloro-5-fluoropyrimidin-4-yl)-5-(hydroxymethyl)-3-azabicyclo[3.1.0]hexan-1-yl)-2,2-difluorocyclopropane-1-carboxamide (Preparation 88) and 1-methyl-1H-pyrazol-4-ylamine at 85° C. The residue was purified using silica gel column chromatography eluting with 0-5% MeOH in DCM.

$^1$H NMR (400 MHz, MeOH-d$_4$): δ ppm 1.78-1.88 (m, 1H), 2.00-2.10 (m, 1H), 2.55-2.65 (m, 1H), 3.70 (m, 1H), 3.70 (m, 1H), 3.90 (s, 3H), 3.95-4.00 (m, 1H), 4.10-4.20 (m, 1H), 7.50 (s, 1H), 7.80 (s, 2H).

MS m/z 424 [M+H]$^+$

Example 110

(1R,2R)-2-cyano-N-[(1S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide

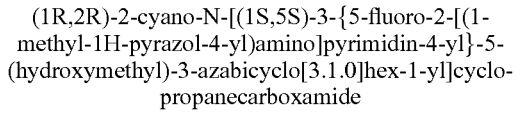

The title compound was prepared according to the method described by Example 109 using racemic-(1R,2R)-N-(3-(2-chloro-5-fluoropyrimidin-4-yl)-5-(hydroxymethyl)-3-azabicyclo[3.1.0]hexan-1-yl)-2-cyanocyclopropane-1-carboxamide (Preparation 89). The racemate was separated into its enantiomers using chiral chromatography as described below:

$^1$H NMR (400 MHz, DMSO-d$_6$): δ ppm 1.05 (d, 1H), 1.13 (m, 1H), 1.50 (m, 2H), 2.02 (m, 1H), 2.33 (m, 1H), 3.60-3.79 (m, 4H), 3.87 (s, 3H), 3.98 (m, 1H), 4.09 (m, 1H), 4.16 (m, 1H), 7.54 (s, 1H), 7.77-7.78 (m, 2H).

Column: Cellulose-3 21 mm×250 mm×5 μm; Mobile phase A: CO$_2$, Mobile phase B: MeOH; 90:10 A:B; hold for 10 minutes; 65 mL/min. Peak 2; Rt=7.08 minutes, MS m/z 413 [M+H]$^+$

Example 111

4-({4-[6-(2,2-difluoropropanoyl)-3,6-diazabicyclo[3.1.1]hept-3-yl]-5-fluoropyrimidin-2-yl}amino)-N-ethyl-2-methylbenzamide To a solution of 4-((4-(3,6-diazabicyclo[3.1.1]heptan-3-yl)-5-fluoropyrimidin-2-yl)amino)-N-ethyl-2-methylbenzamide (Preparation 126, 25 mg, 0.067 mmol) in DCM (5 mL) was added 2,2-difluoropropanoic acid (7 mg, 0.067 mmol), HATU (25 mg, 0.066 mmol) and triethylamine (0.03 mL, 0.2 mmol). The reaction was stirred at room temperature for 1 hour. The reaction was diluted with water, the organic phase collected through a phase separation cartridge and concentrated in vacuo. The residue was purified using preparative HPLC (Method 1, 5% B to 50% B in 8.5 min, to 100% B in 9 min, hold at 100% B to 10 min) to afford the title compound.
Preparative HPLC Conditions
Method 1: Waters Sunfire C18 19×500 mm, 5μ, Mobile Phase A: 0.05% TFA in water; Mobile Phase B: 0.05% TFA in Acetonitrile. Flow rate 25 mL/min.
Method 2: Waters Sunfire C18 19×500 mm, 5μ, Mobile Phase A: 0.05% Formic acid in water; Mobile Phase B: 0.05% Formic acid in Acetonitrile. Flow rate 25 mL/min.
LCMS QC Conditions:
Column: Waters Atlantis dC18 4.6×50 mm, 5μ
Modifier: TFA 0.05%
Gradient: 95% water:5% MeCN linear to 5% water:95% MeCN over 4 minutes, hold for 1 minute to 5 minutes. Flow rate: 2 mL/min
MS mode: ESI+; scan range 160-650 Da
$^1$H NMR (400 MHz, DMSO-$d_6$): δ ppm 1.15 (t, 3H), 1.77-1.88 (m, 4H), 2.37 (s, 3H), 2.86 (q, 1H), 3.23-3.30 (m, 2H), 4.02-4.09 (m, 2H), 4.09-4.19 (m, 2H), 4.65 (br s, 1H), 4.92 (br s, 1H), 7.31 (d, 1H), 7.60 (br s, 2H), 8.05-8.12 (m, 2H), 9.36 (s, 1H). LCMS Rt=1.96 minutes; MS m/z 463 [M+H]$^+$

Example 112

N-ethyl-4-({5-fluoro-4-[6-(2-fluoro-2-methylpropanoyl)-3,6-diazabicyclo[3.1.1]hept-3-yl]pyrimidin-2-yl}amino)-2-methylbenzamide The title compound was prepared, purified and analysed as described for Example 111 using 2-fluoro-2-methylpropanoic acid and 4-((4-(3,6-diazabicyclo[3.1.1]heptan-3-yl)-5-fluoropyrimidin-2-yl)amino)-N-ethyl-2-methylbenzamide (Preparation 126).
Prep. HPLC Method 1, 10% B to 50% B in 8.5 min, to 100% B in 9 min, hold at 100% B to 10 min.
$^1$H NMR (400 MHz, DMSO-$d_6$): δ ppm 1.13 (t, 3H), 1.38-1.49 (m, 3H), 1.52-1.61 (m, 3H), 1.74 (d, 1H), 2.35 (s, 3H), 2.77 (q, 1H), 3.20-3.28 (m, 2H), 3.94 (d, 1H), 4.02 (d, 1H), 4.06-4.13 (m, 1H), 4.17 (d, 1H), 4.52 (br s, 1H), 4.82 (br s, 1H), 7.28 (d, 1H), 7.54-7.63 (m, 2H), 8.05 (d, 2H), 9.31 (s, 1H).
LCMS Rt=1.95 minutes; MS m/z 459 [M+H]$^+$

Example 113

4-({4-[6-(cyclopropylcarbonyl)-3,6-diazabicyclo[3.1.1]hept-3-yl]pyrimidin-2-yl}amino)-N-ethyl-2-methylbenzamide The title compound was prepared, purified and analysed as described for Example 111 using cyclopropanecarboxylic acid and tert-butyl 3-(2-chloropyrimidin-4-yl)-3,6-diazabicyclo[3.1.1]heptanes-6-carboxylate hydrochloride (Preparation 128).
Preparative HPLC Method 2, 5% B to 100% B in 8.5 min, hold at 100% B to 10 min.
LCMS Rt=1.57 minutes; MS m/z 421 [M+H]$^+$

Example 114

4-({4-[6-(2,2-difluoropropanoyl)-3,6-diazabicyclo[3.1.1]hept-3-yl]pyrimidin-2-yl}amino)-N-ethylbenzamide The title compound was prepared, purified and analysed as described for Example 115 using 2,2-difluoropropanoic acid and 4-((4-3,6-diazabicyclo[3.1.1]heptan-3-yl)pyrimidin-2-yl)amino-N-ethylbenzamide hydrochloride (Preparation 127).
Prep. HPLC Method 1, 10% B to 60% B in 8.5 min, to 100% B in 9 min, hold at 100% B to 10 min.
$^1$H NMR (400 MHz, DMSO-$d_6$): δ ppm 1.17 (t, 3H), 1.76-1.88 (m, 4H), 2.87-2.95 (m, 1H), 3.28-3.37 (m, 2H), 3.84-4.14 (m, 4H), 4.70 (br s, 1H), 4.97 (br s, 1H), 6.51 (d, 1H), 7.75-7.83 (m, 2H), 7.91 (br s, 2H), 8.14 (d, 1H), 8.42 (br s, 1H), 10.48 (br s, 1H). LCMS Rt=1.93 minutes; MS m/z 431 [M+H]$^+$

Example 115

N-ethyl-2-methyl-4-({4-[6-(trifluoroacetyl)-3,6-diazabicyclo[3.1.1]hept-3-yl]pyrimidin-2-yl}amino)benzamide To a solution of 4-((4-(3,6-diazabicyclo[3.1.1]heptan-3-yl)pyrimidin-2-yl)amino)-N-ethyl-2-methylbenzamide hydrochloride (Preparation 128, 30 mg, 0.077 mmol) in DCM (5 mL) was added triethylamine (0.1 mL, 0.7 mmol) followed by TFAA (2 drops). The reaction was stirred at room temperature for 2 hours, concentrated in vacuo and purified and analysed using preparative HPLC (Method 2, 5% B to 100% B in 8.5 min, hold at 100% B to 10 min) as described for Example 111 to afford the title compound.
LCMS Rt=1.76 minutes; MS m/z 449 [M+H]$^+$

Example 116

N-ethyl-4-({5-fluoro-4-[6-(trifluoroacetyl)-3,6-diazabicyclo[3.1.1]hept-3-yl]pyrimidin-2-yl}amino)-2-methylbenzamide A solution of 1-(3-(2-chloro-5-fluoropyrimidin-4-yl)-3,6-diazabicyclo[3.1.1]heptan-6-yl)-2,2,2-trifluoroethan-1-one (Preparation 129, 100 mg, 0.31 mmol) and 4-amino-N-ethyl-2-methylbenzamide (PCT Publication No. WO2006109846) in isopropanol (3 mL) was treated with 1 drop of cHCl and heated to 140° C. for 40 minutes under microwave irradiation. The reaction was cooled, concentrated in vacuo and taken on directly to the next step.

Example 117

5-({4-[(1R,5S)-8-{[(1S)-2,2-Difluorocyclopropyl]carbonyl}-3,8-diazabicyclo[3.2.1]oct-3-yl]pyrimidin-2-yl}amino)-3-fluoropyridine-2-carboxamide To a solution of Preparation 144 (280 mg, 0.815 mmol) and Preparation 68 (129 mg, 1.06 mmol) in DMF (30 mL)

was added TEA (330 mg, 3.26 mmol) and HATU (372 mg, 0.979 mmol) at 0° C. The mixture was stirred at room temperature (10° C.) for 18 h. The solution was concentrated and purified by Preparative HPLC Preparative HPLC Conditions Phenomenex Synergi C18 150×30 mm, 4p, Mobile Phase A: acetonitrile; Mobile Phase B: water (adjusted to pH 10 with ammonia). Flow Rate: 35 mL/min. LCMS: (M+1=447.9, M+23=469.9) The racemate was separated using chiral chromatography using Chiralpal AS-H column (150 mm×4.6 mm×5 um); mobile phase A: 5% $CO_2$ to 40%; mobile phase B: MeOH with 0.05% DEA to provide the title compound (143 mg, 39%) at Rt=8.12 minutes. LCMS Rt=0.73 minutes, MS m/z 448.1 [M+H]

$^1$H NMR (400 MHz, DMSO-$d_6$): δ ppm 1.58-2.10 (m, 6H), 2.93-3.28 (m, 3H), 4.04-4.33 (m, 2H), 4.57-4.78 (m, 2H), 6.41 (dd, 1H), 7.37 (br. s., 1H), 7.80 (br. s., 1H), 8.10 (dd, 1H), 8.27 (m, 1H), 8.67 (d, 1H), 9.88 (s, 1H).

Preparation 1

5-((4-((1R,5S)-3,8-Diazabicyclo[3.2.1]octan-3-yl) pyrimidin-2-yl)amino)-N,3-dimethylpicolinamide hydrochloride Step 1

To tert-butyl (1R,5S)-3-(2-chloropyrimidin-4-yl)-3,8-diazabicyclo[3.2.1]octane-8-carboxylate (Preparation 34, 500 mg, 1.54 mmol) and 5-amino-N,3-dimethylpicolinamide (Preparation 38, 458 mg, 2.78 mmol) in DMA (20 mL) was added cesium carbonate (1 g, 3.08 mmol), xantphos (178 mg, 0.31 mmol) and palladium acetate (69 mg, 0.31 mmol). The reaction was purged with nitrogen for 1 minute before heating to 130° C. under microwave irradiation for 1 hour. The reaction was cooled, filtered and concentrated in vacuo. The residue was purified using silica gel column chromatography eluting with 50-80% EtOAc in petroleum ether.

Step 2

The resulting solid was dissolved in DCM (20 mL) and treated with 4M HCl in dioxane (20 mL) and the reaction was stirred at room temperature for 2 hours. The reaction was concentrated in vacuo to afford the title compound as the hydrochloride salt. $^1$H NMR (400 MHz, DMSO-$d_6$): bppm 1.67-1.83 (m, 2H), 1.90-2.06 (m, 2H), 2.58 (s, 3H), 2.78 (br s, 3H), 3.59-3.72 (m, 2H), 4.16-4.27 (m, 4H), 6.66-6.77 (n, 1H), 7.88 (br s, 1H), 8.17 (d, 1H), 8.46-8.60 (n, 1H), 8.66 (br s, 1H), 9.61-9.75 (n, 1H), 10.03-10.16 (n, 1H), 11.09 (br s, 1H).

MS m/z 354 [M+H][30]

The following preparations were prepared according to the method described by Preparation 1 using tert-butyl(1R, 5S)-3-(2-chloropyrimidin-4-yl)-3,8-diazabicyclo[3.2.1]octane-8-carboxylate (Preparation 34) and the appropriate amine as described below. The compounds were isolated as the hydrochloride salts unless otherwise specified.

Deprotection Method B: The Boc-protected intermediate was dissolved in DCM, treated with TFA and stirred at room temperature for 18 hours. The reaction was basified to pH=10 by the addition of triethylamine. The solution was concentrated in vacuo and purified by silica gel column chromatography eluting with 10% MeOH in EtOAc or 96:3:1 DCM:MeOH:NH$_3$.

Deprotection Method C: The Boc-protected intermediate was dissolved in DCM, treated with TFA and stirred at room temperature for 1.5 hours. The reaction was concentrated in vacuo, dissolved in MeOH and eluted through a carbonate cartridge to afford the free parent.

| Preparation number | Structure | Name | SM/Data |
|---|---|---|---|
| 2 | [structure] | Racemic 2-(5-((4-((1R,5S)-3,8-diazabicyclo[3.2.1]octan-3-yl)pyrimidin-2-yl)amino)-pyridin-2-yl)propan-1-ol hydrochloride | Racemic 2-(5-aminopyridin-2-yl)propan-1-ol (Preparation 40). Taken on directly to the next step. |
| 3 | [structure] | 5-((4-((1R,5S)-3,8-diazabicyclo[3.2.1]octan-3-yl)pyrimidin-2-yl)amino)-N-ethyl-3-methylpicolinamide hydrochloride | 5-amino-N-ethyl-3-methylpicolinamide (Preparation 42). Taken on directly to the next step. |

| Preparation number | Structure | Name | SM/Data |
|---|---|---|---|
| 4 | 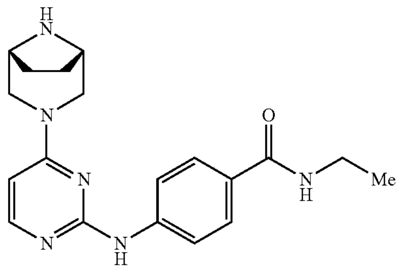 [SMILES: CCNC(=O)c1ccc(Nc2nccc(N3C[C@H]4CC[C@@H](C3)N4)n2)cc1] | 4-((4-((1R,5S)-3,8-diazabicyclo[3.2.1]octan-3-yl)pyrimidin-2-yl)amino)-N-ethylbenzamide hydrochloride | 4-amino-N-ethyl benzamide. Taken on directly to the next step. |
| 5 | 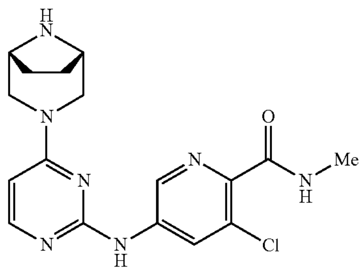 [SMILES: CNC(=O)c1ncc(Nc2nccc(N3C[C@H]4CC[C@@H](C3)N4)n2)cc1Cl] | 5-((4-((1R,5S)-3,8-diazabicyclo[3.2.1]octan-3-yl)pyrimidin-2-yl)amino)-3-chloro-N-methylpicolinamide hydrochloride | 5-amino-3-chloro-N-methylpicolinamide (Preparation 39).Taken on directly to the next step. |
| 6 | 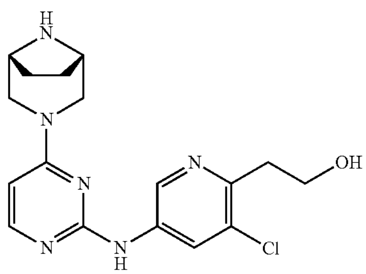 [SMILES: OCCc1ncc(Nc2nccc(N3C[C@H]4CC[C@@H](C3)N4)n2)cc1Cl] | 2-(5-((4-((1R,5S)-3,8-diazabicyclo[3.2.1]octan-3-yl)pyrimidin-2-yl)amino)-3-chloropyridin-2-yl)ethan-1-ol hydrochloride | 2-(5-amino-3-chloropyridin-2-yl)ethan-1-ol (Preparation 45). Taken on directly to the next step. |
| 7 | 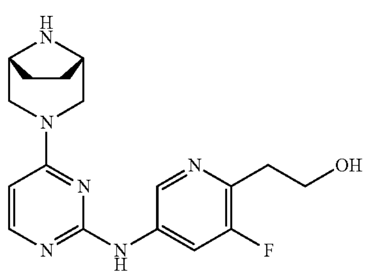 [SMILES: OCCc1ncc(Nc2nccc(N3C[C@H]4CC[C@@H](C3)N4)n2)cc1F] | 2-(5-((4-((1R,5S)-3,8-diazabicyclo[3.2.1]octan-3-yl)pyrimidin-2-yl)amino)-3-fluoropyridin-2-yl)ethan-1-ol hydrochloride | 2-(5-amino-3-fluoropyridin-2-yl)ethan-1-ol (Preparation 46). Taken on directly to the next step. |
| 8 | 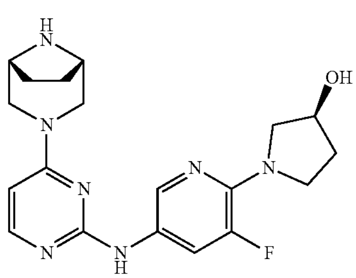 [SMILES: O[C@H]1CCN(c2ncc(Nc3nccc(N4C[C@H]5CC[C@@H](C4)N5)n3)cc2F)C1] | (S)-1-(5-((4-((1R,5S)-3,8-diazabicyclo[3.2.1]octan-3-yl)pyrimidin-2-yl)amino)-3-fluoropyridin-2-yl)pyrrolidin-3-ol hydrochloride | (S)-1-(5-amino-3-fluoropyridin-2-yl)pyrrolidin-3-ol (Preparation 47). Taken on directly to the next step. |

| Preparation number | Structure | Name | SM/Data |
|---|---|---|---|
| 9 | 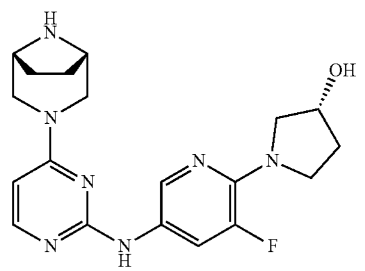 [SMILES: O[C@@H]1CCN(c2ncc(Nc3nccc(N4C[C@H]5CC[C@@H](C4)N5)n3)cc2F)C1] | (R)-1-(5-((4-((1R,5S)-3,8-diazabicyclo[3.2.1]octan-3-yl)pyrimidin-2-yl)amino)-3-fluoropyridin-2-yl)pyrrolidin-3-ol hydrochloride | (R)-1-(5-amino-3-fluoropyridin-2-yl)pyrrolidin-3-ol (Preparation 48). Taken on directly to the next step. |
| 10 | 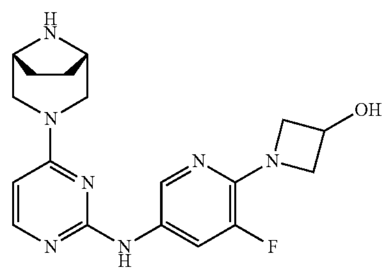 [SMILES: OC1CN(c2ncc(Nc3nccc(N4C[C@H]5CC[C@@H](C4)N5)n3)cc2F)C1] | 1-(5-((4-((1R,5S)-3,8-diazabicyclo[3.2.1]octan-3-yl)pyrimidin-2-yl)amino)-3-fluoropyridin-2-yl)azetidin-3-ol hydrochloride | 1-(5-amino-3-fluoropyridin-2-yl)azetidin-3-ol (Preparation 49). Taken on directly to the next step. |
| 11 | 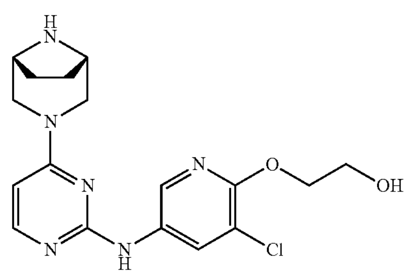 [SMILES: OCCOc1ncc(Nc2nccc(N3C[C@H]4CC[C@@H](C3)N4)n2)cc1Cl] | 2-((5-((4-((1R,5S)-3,8-diazabicyclo[3.2.1]octan-3-yl)pyrimidin-2-yl)amino)-3-chloropyridin-2-yl)oxy)ethan-1-ol hydrochloride | 2-((5-amino-3-chloropyridin-2-yl)oxy)ethan-1-ol (Preparation 50). Taken on directly to the next step. |
| 12 | 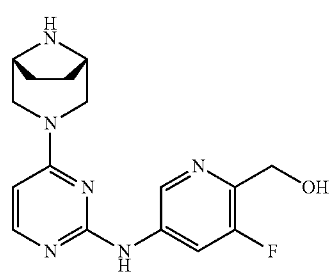 [SMILES: OCc1ncc(Nc2nccc(N3C[C@H]4CC[C@@H](C3)N4)n2)cc1F] | (5-((4-((1R,5S)-3,8-diazabicyclo[3.2.1]octan-3-yl)pyrimidin-2-yl)amino)-3-fluoropyridin-2-yl)methanol hydrochloride | 5-amino-3-fluoro-2-pyridine methanol (PCT Publication No. WO2013013815) Taken on directly to the next step. |
| 13 | 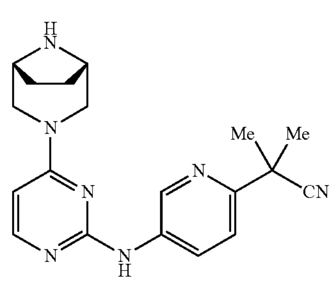 [SMILES: CC(C)(C#N)c1ccc(Nc2nccc(N3C[C@H]4CC[C@@H](C3)N4)n2)cn1] | 2-(5-((4-((1R,5S)-3,8-diazabicyclo[3.2.1]octan-3-yl)pyrimidin-2-yl)amino)pyridin-2-yl)-2-methylpropanenitrile | 2-)5-aminopyridin-2-yl)-2-methylpropanenitrile and using deprotection method B. |

| Preparation number | Structure | Name | SM/Data |
|---|---|---|---|
| 14 | 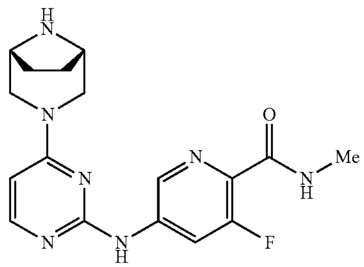 [SMILES: CNC(=O)c1ncc(Nc2nccc(N3C[C@H]4CC[C@@H](C3)N4)n2)cc1F] | 5-((4-((1R,5S)-3,8-diazabicyclo[3.2.1]octan-3-yl)pyrimidin-2-yl)amino)-3-fluoro-N-methylpicolinamide hydrochloride | 5-amino-3-fluoro-N-methylpicolinamide (Preparation 51). |
| 15 | 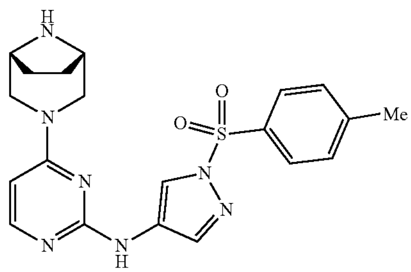 [SMILES: Cc1ccc(S(=O)(=O)n2cc(Nc3nccc(N4C[C@H]5CC[C@@H](C4)N5)n3)cn2)cc1] | 4-((1R,5S)-3,8-diazabicyclo[3.2.1]octan-3-yl)-N-(1-tosyl-1H-pyrazol-4-yl)pyrimidin-2-amine | 1-[(4-methylphenyl)sulfonyl]-1H-pyrazol-4-amine (PCT Publication No. WO2011106114). Deprotection method C. LCMS Rt = 0.73 minutes MS m/z 426 [M + H]$^+$ |
| 16 | 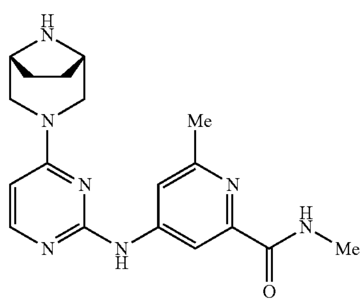 [SMILES: CNC(=O)c1cc(Nc2nccc(N3C[C@H]4CC[C@@H](C3)N4)n2)cc(C)n1] | 4-((4-((1R,5S)-3,8-diazabicyclo[3.2.1]octan-3-yl)pyrimidin-2-yl)amino)-N,6-dimethylpicolinamide | 4-amino-N,6-dimethylpicolinamide (Preparation 44). Deprotection method B. LCMS Rt = 0.39 minutes MS m/z 354 [M + H]$^+$ |
| 17 | 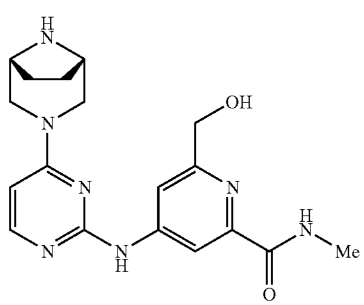 [SMILES: CNC(=O)c1cc(Nc2nccc(N3C[C@H]4CC[C@@H](C3)N4)n2)cc(CO)n1] | 4-((4-((1R,5S)-3,8-diazabicyclo[3.2.1]octan-3-yl)pyrimidin-2-yl)amino)-6-(hydroxymethyl)-N-methylpicolinamide hydrochloride | 4-amino-6-(hydroxymethyl)-N-methylpicolinamide hydrochloride (Preparation 125). Taken on directly to the next step. |

Preparation 18

5-((4-((1R,5S)-3,8-Diazabicyclo[3.2.1]octan-3-yl)pyrimidin-2-yl)amino)-3-methylpicolinamide hydrochloride The title compound was prepared according to the method described for Preparation 1 Step 1. Following the Buchwald step the intermediate was heated with ammonia in methanol to 90° C. in a sealed vessel. The reaction was cooled and concentrated in vacuo before deprotection with HCl as described.

Preparation 19

4-((1R,5S)-3,8-Diazabicyclo[3.2.1]octan-3-yl)-N-(1-methyl-1H-pyrazol-4-yl)pyrimidin-2-amine hydrochloride A solution of tert-butyl (1R,5S)-3-(2-chloropyrimidin-4-yl)-3,8-diazabicyclo[3.2.1]octane-8-carboxylate (Preparation 34, 2.25 g, 6.93 mmol) and 1-methyl-1H-pyrazol-4-ylamine hydrochloride (1.02 g, 7.62 mmol) in iPrOH (30 mL) was heated to 140° C. under microwave irradiation for 1 hour. The reaction was concentrated in vacuo to afford the title compound as the hydrochloride salt (2.2 g, 99%). $^1$H NMR (400 MHz, MeOH-d₄): δ ppm 1.97-2.02 (m, 2H), 2.19-2.20 (m, 2H), 3.48-3.51 (m, 1H), 3.72-3.78 (m, 1H), 3.98 (s, 3H), 4.20-4.31 (m, 3H), 6.67 (d, 1H), 7.81 (s, 1H), 7.86 (m, 2H). MS m/z 286 [M+H]$^+$ Preparation 20

2-(4-((4-((1R,5S)-3,8-Diazabicyclo[3.2.1]octan-3-yl)pyrimidin-2-yl)amino)-1H-pyrazol-1-yl)ethan-1-ol hydrochloride To a solution of tert-butyl (1R,5S)-3-(2-chloropyrimidin-4-yl)-3,8-diazabicyclo[3.2.1]octane-8-carboxylate (Preparation 34, 200 mg, 0.617 mmol) and 4-amino-1H-pyrazole-1-ethanol (134 mg, 0.74 mmol) in iPrOH (10 mL) was added 3 drops of concentrated HCl at room temperature. The reaction was heated to 140° C. under microwave irradiation for 40 minutes. The reaction was concentrated in vacuo to afford the title compound and taken on directly to the next step as the hydrochloride salt.

The following preparations were prepared according to the method described by Preparation 20 using tert-butyl (1R,5S)-3-(2-chloropyrimidin-4-yl)-3,8-diazabicyclo[3.2.1]octane-8-carboxylate (Preparation 34) and the appropriate amine as described below. The compounds were isolated as the hydrochloride salts.

Preparation 24

4-((4-((1R,5S)-3,8-Diazabicyclo[3.2.1]octan-3-yl)-5-fluoropyrimidin-2-yl)amino)-N-ethylbenzamide hydrochloride Step 1

To a solution of tert-butyl (1R,5S)-3-(2-chloro-5-fluoropyrimidin-4-yl)-3,8-diazabicyclo[3.2.1]octane-8-carboxylate (Preparation 35, 0.5 g, 1.5 mmol) in dioxane (5 mL) was added 4-amino-N-ethyl benzamide (0.26 g, 1.6 mmol), RuPHOS palladium (II) phenethylamine chloride (0.1 g, 0.1 mmol) and sodium tert-butoxide (0.15 g, 1.5 mmol). The reaction was heated to 120° C. under microwave irradiation for 25 minutes. The reaction was cooled and eluted through a solid phase extraction cartridge. The filtrate was purified using silica gel column chromatography eluting with 0-20% MeOH in DCM to afford boc-protected intermediate (0.65 g, 95%).

$^1$H NMR (400 MHz, DMSO-d₆): δ ppm 1.07 (t, 3H), 1.37-1.41 (m, 9H), 1.67 (d, 2H), 1.78-1.86 (m, 2H), 3.13-3.18 (m, 2H), 3.18-3.26 (m, 2H), 4.07-4.13 (m, 2H), 4.20 (br s, 2H), 7.65-7.69 (m, 2H), 7.69-7.74 (m, 2H), 8.02 (d, 1H), 8.19 (t, 1H), 9.43 (s, 1H).

| Preparation number | Structure | Name | SM/Data |
|---|---|---|---|
| 21 | 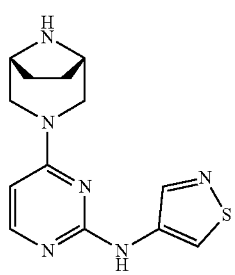 [SMILES: c1cc(N2C[C@H]3CC[C@@H](C2)N3)nc(Nc2cnsc2)n1] | N-(4-((1R,5S)-3,8-diazabicyclo[3.2.1]octan-3-yl)pyrimidin-2-yl)isothiazol-4-amine hydrochloride | MS m/z 289 [M + H]$^+$ 4-isothiazolamine |
| 22 | 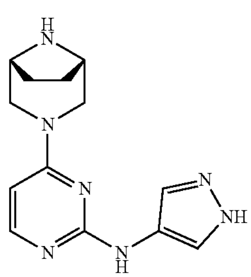 [SMILES: c1cc(N2C[C@H]3CC[C@@H](C2)N3)nc(Nc2cn[nH]c2)n1] | 4-((1R,5S)-3,8-diazabicyclo[3.2.1]octan-3-yl)-N-(1H-pyrazol-4-yl)pyrimidin-2-amine hydrochloride | tert-butyl 4-amino-1H-pyrazole-1-carboxylate (PCT Publication No. WO2012022681). |
| 23 | 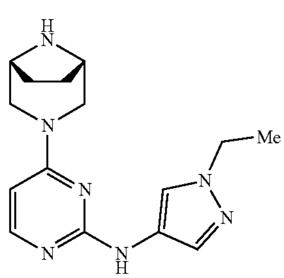 [SMILES: CCn1cc(Nc2nccc(N3C[C@H]4CC[C@@H](C3)N4)n2)cn1] | 4-((1R,5S)-3,8-diazabicyclo[3.2.1]octan-3-yl)-N-(1-ethyl-1H-pyrazol-4-yl)pyrimidin-2-amine hydrochloride | MS m/z 300 [M + H]$^+$ 1-ethyl-1H-pyrazol-4-amine |

Step 2

The intermediate was dissolved in DCM (5 mL) and MeOH (2 mL) and treated with 4M HCl in dioxane. The reaction was stirred at room temperature for 18 hours before concentrating in vacuo to afford the title compound as the hydrochloride salt.

Preparation 25

4-((4-((1R,5S)-3,8-Diazabicclo[3.2.1]octan-3-yl)-5-fluoropyrimidin-2-yl)amino)-N-ethyl-2-methylbenzamide hydrochloride tert-Butyl (1R,5S)-3-(2-((4-(ethylcarbamoyl)-3-methylphenyl)amino)-5-fluoropyrimidin-4-yl)-3,8-diaza-bicyclo[3.2.1]octane-8-carboxylate (Example 74) was dissolved in DCM (5 mL) and MeOH (2 mL) and treated with 4M HCl in dioxane. The reaction was stirred at room temperature for 18 hours before concentrating in vacuo to afford the title compound as the hydrochloride salt.

Preparation 26

5-((4-((1R,5S)-3,8-Diazabicyclo[3.2.1]octan-3-yl)pyrimidin-2-yl)amino)-3-methylpicolinamide hydrochloride A solution of tert-butyl (1R,5S)-3-(2-((6-(ethoxycarbonyl)-5-methylpyridin-3-yl)amino)pyrimidin-4-yl)-3,8-diazabicyclo[3.2.1]octane-8-carboxylate (Preparation 33, 100 mg, 0.214 mmol) in NH$_3$/MeOH (15 mL) was heated to 90° C. in a sealed vessel for 18 hours. The solution was concentrated in vacuo and the residue was treated with 4M HCl/dioxane (20 mL) and stirred at room temperature for 2 hours. solution was concentrated in vacuo to afford the title compound as the hydrochloride salt.

Preparation 27

((1R,5S)-3-(2-Chloro-5-fluoropyrimidin-4-yl)-3,8-diazabicyclo[3.2.1]octan-8-yl)(cyclopropyl)methanone To a suspension of (1R,5S)-3-(2-chloro-5-fluoropyrimidin-4-yl)-3,8-diazabicyclo[3.2.1]octane (Preparation 31, 4 g, 11.7 mmol), cyclopropanecarboxylic acid (2 g, 23.4 mmol) and triethylamine (3.5 g, 35.1 mmol) in DMF (40 mL) was added HATU (5.33 g, 14 mmol) at room temperature. After the addition, the reaction was stirred at room temperature for 30 minutes. The reaction was concentrated in vacuo and purified by silica gel column chromatography eluting with 20% petroleum ether in EtOAc to afford the title compound (2.5 g, 70%). $^1$H NMR (400 MHz, CDCl$_3$): δ ppm 0.80-0.86 (m, 2H), 1.01-1.05 (m, 2H), 1.66-2.09 (m, 5H), 3.29-3.34 (m, 2H), 4.23-4.26 (m, 1H), 4.37-4.40 (m, 1H), 4.53-4.52 (m, 1H), 4.77-4.78 (m, 1H), 7.94-7.95 (m, 1H). MS m/z 311 [M+H]$^+$ Preparation 28

((1R,5S)-3-(2-Chloropyrimidin-4-yl)-3,8-diazabicyclo[3.2.1]octan-8-yl)(cyclopropyl)methanone To a solution of (1R,5S)-3-(2-chloropyrimidin-4-yl)-3,8-diazabicyclo[3.2.1]octane (Preparation 32, 3.5 g, 15.57 mmol) in DCM (20 mL) was added triethylamine (7.86 g, 78 mmol) and cyclopropanecarbonyl chloride (3.26 g, 31 mmol) at room temperature. The reaction was stirred at room temperature for 1 hour. The reaction was washed with saturated aqueous NaHCO$_3$ solution (100 mL). The organic layer was collected, dried, concentrated in vacuo and purified by silica gel column chromatography eluting with 10% MeOH in to afford the title compound (2.5 g, 55%).
MS m/z 293 [M+H]$^+$ Preparation 29

(1R,5S)-3-(2-Chloropyrimidin-4-yl)-N-ethyl-3,8-diazabicyclo[3.2.1]octane-8-carboxamide To a solution of (1R,5S)-3-(2-chloropyrimidin-4-yl)-3,8-diazabicyclo[3.2.1]octane_(Preparation 32, 170 mg, 0.6173 mmol) in DCM (20 mL) was added triethylamine (125 mg, 1.23 mmol) followed by isocyanatoethane (175.4 mg, 2.47 mmol) at 0° C. The reaction was stirred at room temperature for 1 hour before concentrating in vacuo and purifying with silica gel column chromatography eluting with 20% petroleum ether in EtOAc to afford the title compound (184 mg, 100%). MS m/z 296 [M+H]$^+$ Preparation 30

Racemic ((1R,5S)-3-(2-Chloropyrimidin-4-yl)-3,8-diazabicyclo[3.2.1]octan-8-yl)(2,2-difluorocyclopropyl)methanone The title compound was prepared according to the method described for Preparation 27 using racemic 2,2-difluorocyclopropane-1-carboxylic acid. MS m/z 329 [M+H]$^+$ Preparation 31

(1R,5S)-3-(2-Chloro-5-fluoropyrimidin-4-yl)-3,8-diazabicyclo[3.2.1]octane

The title compound was prepared according to the method described for Preparation 25 using tert-butyl (1R,5S)-3-(2-chloro-5-fluoropyrimidin-4-yl)-3,8-diazabicyclo[3.2.1]octane-8-carboxylate (Preparation 35).

Preparation 32

(1R,5S)-3-(2-Chloropyrimidin-4-yl)-3,8-diazabicyclo[3.2.1]octane

The title compound was prepared according to the method described for Preparation 125 using tert-butyl (1R,5S)-3-(2-chloropyrimidin-4-yl)-3,8-diazabicyclo[3.2.1]octane-8-carboxylate (Preparation 34) in dioxane.

Preparation 33 tert-Butyl (1R,5S)-3-(2-((6-(ethoxycarbonyl)-5-methylpyridin-3-yl)amino)pyrimidin-4-yl)-3,8-diazabicyclo[3.2.1]octane-8-carboxylate The title compound was prepared according to the method described for Preparation 1 Step 1 using tert-butyl (1R,5S)-3-(2-chloropyrimidin-4-yl)-3,8-diazabicyclo[3.2.1]octane- 8-carboxylate (Preparation 34) and ethyl-5-amino-3-methylpicolinate (Preparation 41). MS m/z 469 [M+H]$^+$ Preparation 34 tert-Butyl (1R,5S)-3-(2-chloropyrimidin-4-yl)-3,8-diazabicyclo[3.2.1]octane-8-carboxylate To a solution of tert-butyl (1R,5S)-3,8-diazabicyclo[3.2.1]octane-8-carboxylate (Preparation 36, 11 g, 52 mmol) in MeOH (500 mL) was added 2,4-dichloropyrimidine (8.4 g, 57 mmol) and TEA (6.7 g, 66 mmol) at 0° C. The reaction was stirred at room temperature for 18 hours before concentrating in vacuo. The residue was purified by silica gel column chromatography eluting with 20% EtOAc in petroleum ether to afford the title compound as a white solid (12 g, 71%).

$^1$H NMR (400 MHz, CDCl$_3$): δ ppm 1.48 (s, 9H), 1.63-1.74 (m, 2H), 1.97 (br s, 2H), 3.18 (br s, 2H), 3.38-3.74 (m, 1H), 4.36 (br s, 3H), 6.35 (d, 1H), 8.06 (d, 1H). MS m/z 325 [M+H]$^+$ Preparation 35 tert-Butyl (1R,5S)-3-(2-chloro-5-fluoropyrimidin-4-v)-3,8-diazabicyclo[3.2.1]octane-8-carboxylate The title compound was prepared according to the method described for Preparation 36 using 2,4-dichloro-5-fluoropyrimidine. The residue was purified by silica gel column chromatography eluting with 0-100% EtOAc in heptanes. $^1$H NMR (400 MHz, DMSO-d$_6$): δ ppm 1.38 (s, 9H), 1.62 (d, 2H,) 1.76-1.84 (m, 2H), 3.16 (d, 2H), 4.08 (d, 2H), 4.15-4.22 (m, 2H), 8.17 (d, 1H).

Preparation 36 tert-Butyl (1R,5S)-3,8-diazabicclo[3.2.1]octane-8-carboxylate

A solution of tert-butyl (1R,5S)-3-benzyl-3,8-diazabicyclo[3.2.1]octane-8-carboxylate (Preparation 37, 19 g, 63 mmol) in methanol (500 mL) was hydrogenated over palladium on carbon (4 g) at 50 psi at room temperature for 18 hours. The reaction was filtered and the filtrate was concentrated in vacuo to afford the title compound as a white solid (13.2 g, 99%).

$^1$H NMR (400 MHz, MeOH-d$_4$): δ ppm 1.49 (s, 9H), 1.85-2.02 (m, 4H), 2.65 (d, 2H), 2.90 (d, 2H), 4.08 (br s, 2H).

Preparation 37 tert-Butyl (1R,5S)-3-benzyl-3,8-diazabicyclo[3.2.1]octane-8-carboxylate

A solution of (1R,5S)-3-benzyl-3,8-diazabicyclo[3.2.1]octane (20 g, 99 mmol), ditertbutyldicarboxylate (21 g, 97 mmol) and triethylamine (10 g, 99 mmol) in DCM (500 mL) was stirred at room temperature for 18 hours. The reaction was concentrated in vacuo and purified by silica gel column chromatography eluting with 1% EtOAc in petroleum ether to afford the title compound (19 g, 64%).

Preparation 38

5-Amino-N,3-dimethylpicolinamide

Ethyl 5-amino-3-methylpicolinate (Preparation 41, 500 mg, 2.78 mmol) was dissolved in ethanolic methylamine (30%, 50 mL) and the solution was heated to 100° C. in a sealed vessel for 18 hours. The reaction was cooled, concentrated in vacuo and used directly in the next reaction.

Preparation 39

5-Amino-3-chloro-N-methylpicolinamide

The title compound was prepared according to the method described for Preparation 38 using 5-amino-3-chloro-2-pyridinecarboxylic acid methyl ester.

Preparation 40

Racemic 2-(5-Sminopyridin-2-yl)propan-1-ol

To a solution of LiAlH$_4$ (1.16 g, 30.7 mmol) in THF (15 mL) cooled to 0° C. was added racemic methyl 2-(5-aminopyridin-2-yl)propanoate (Preparation 43, 850 mg, 4.72 mmol). The reaction was stirred at room temperature for 2 hours before quenching with Na$_2$SO$_4$.10H$_2$O. The reaction was filtered and the filtrate was concentrated in vacuo to afford the title compound (0.72 g, 100%).

$^1$H NMR (400 MHz, CDCl$_3$): δ ppm 1.28 (d, 3H), 2.94-3.01 (m, 1H), 3.62 (br s, 1H), 3.78 (m, 1H), 3.85-3.93 (m, 1H), 6.99 (d, 2H), 8.00 (m, 1H).

Preparation 41

Ethyl 5-amino-3-methylpicolinate

A solution of ethyl 3-methyl-5-nitropicolinate (Preparation 53, 28 g, 133 mmol) in ethanol (600 mL) was degassed with argon for 15 minutes. 10% palladium on carbon (12 g) was added and the reaction was hydrogenated under an atmosphere of hydrogen at room temperature for 18 hours. The reaction was filtered through a pad of celite and washed with ethanol. The filtrate was concentrated in vacuo and the residue purified by silica gel column chromatography eluting with 0-2% methanol in DCM followed by trituration in hexane to afford the title compound (22 g, 92%).

$^1$H NMR (400 MHz, CDCl$_3$): δ ppm 1.39 (t, 3H), 3.99 (br s, 2H), 4.38 (q, 2H), 6.76 (d, 1H), 7.98 (d, 1H).

The following preparations were prepared according to the method described by Preparation 41 using the appropriate nitro intermediate as described. The purification method was as described or referred to below:

Purification Method 1 (PM1): Silica gel column chromatography eluting with 25% petroleum ether in EtOAc.

| Preparation number | Structure | Name | SM/Data |
|---|---|---|---|
| 42 | [structure: 5-amino-N-ethyl-3-methylpicolinamide] | 5-amino-N-ethyl-3-methylpicolinamide | N-ethyl-3-methyl-5-nitropicolinamide (Preparation 52). PM1.<br>$^1$H NMR (400 MHz, CDCl$_3$): δ ppm 1.07 (t, 3H), 2.50 (s, 3H), 3.21 (m, 2H), 5.76 (br s, 2H), 6.71 (d, 1H), 7.75 (d, 1H), 8.24 (t, 1H).<br>MS m/z 180 [M + H]$^+$ |
| 43 | [structure: Racemic methyl 2-(5-aminopyridin-2-yl)propanoate] | Racemic methyl 2-(5-aminopyridin-2-yl)propanoate | Racemic methyl 2-(5-nitropyridin-2-yl)propanoate (Preparation 54) in methanol. Taken on directly to the next step. |
| 44 | [structure: 4-amino-N,6-dimethylpicolinamide] | 4-amino-N,6-dimethylpicolinamide | N,6-dimethyl-4-nitropicolinamide (Preparation 56).<br>$^1$H NMR (400 MHz, MeOH-d$_4$): δ ppm 2.35 (s, 3H), 2.90 (s, 3H), 6.50 (d, 1H), 7.05 (d, 1H). |

Preparation 45

2-(5-Amino-3-chloropyridin-2-yl)ethan-1-ol

To a solution of methyl 2-(3-chloro-5-nitropyridin-2-yl) acetate (Preparation 58, 4.6 g, 20 mmol) in EtOH/H$_2$O (50 mL/20 mL) was added ammonium chloride (20 g, 374 mmol) and Fe (8 g, 143 mmol). The reaction was stirred at room temperature for 3 hours before filtering and concentrating in vacuo. The residue was purified using silica gel column chromatography, dissolved in THF (50 mL) and added dropwise to a solution of LiAlH$_4$ (2.3 g, 55 mmol) in THF (50 mL) at 0° C. The reaction was stirred at room temperature for 3 hours before quenching with Na$_2$SO$_4$.10H$_2$O at 0° C. The mixture was filtered and the filtrate was concentrated in vacuo to afford the title compound as a yellow solid (1.3 g, 46%). MS m/z 173 [M+H]$^+$

Preparation 46

2-(5-Amino-3-fluoropyridin-2-yl)ethan-1-ol

The title compound was prepared according to the method described for Preparation 45, 57 and 58 using 2-chloro-3-fluoro-5-nitropyridine. MS m/z 157 [M+H]$^+$

Preparation 47

(S)-1-(5-Amino-3-fluoropyridin-2-yl)pyrrolidin-3-ol

To a solution of (S)-1-(3-fluoro-5-nitropyridin-2-yl)pyrrolidin-3-ol (Preparation 59, 250 mg, 1.10 mmol) in EtOH/H$_2$O (5 mL/2 mL) was added ammonium chloride (233 mg, 4.40 mmol) and Fe (123 mg, 2.20 mmol). The reaction was stirred at 80° C. for 30 minutes before filtering and concentrating in vacuo. The residue was purified using silica gel column chromatography eluting with 10-100% EtOAc in petroleum ether to afford the title compound (80 mg, 36%).

The following preparations were prepared according to the method described by Preparation 47 using the appropriate nitro intermediate as described. The purification method was as described or referred to below:

| Preparation number | Structure | Name | SM/Data |
|---|---|---|---|
| 48 | [structure: (R)-1-(5-amino-3-fluoropyridin-2-yl)pyrrolidin-3-ol with OH] | (R)-1-(5-amino-3-fluoropyridin-2-yl)pyrrolidin-3-ol | (R)-1-(3-fluoro-5-nitropyridin-2-yl)pyrrolidin-3-ol (Preparation 60). Taken on directly to the next step. |

| Preparation number | Structure | Name | SM/Data |
|---|---|---|---|
| 49 | 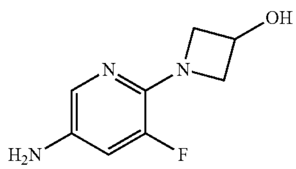 [SMILES: O=[N+]([O-])c1cnc(N2CC(O)C2)c(F)c1] | 1-(5-amino-3-fluoropyridin-2-yl)azetidin-3-ol | 1-(3-fluoro-5-nitropyridin-2-yl)azetidin-3-ol (Preparation 61). Taken on directly to the next step. |
| 50 | 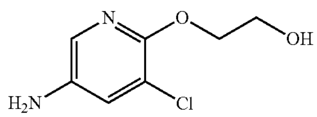 [SMILES: O=[N+]([O-])c1cnc(OCCO)c(Cl)c1] | 2-((5-amino-3-chloropyridin-2-yl)oxy)ethan-1-ol | 2-((3-chloro-5-nitropyridin-2-yl)oxy)ethan-1-ol (Preparation 62). Taken on directly to the next step. |

Preparation 51

5-Amino-3-fluoro-N-methylpicolinamide

To a solution of 5-((di-[tert-butoxycarbonyl])amino)-3-fluoropicolinic acid (Preparation 65, 750 mg, 2.11 mmol) in DMF (20 mL) was added triethylamine (3.2 g, 31.65 mmol), HATU (1.2 g, 3.17 mmol) and MeNH$_2$.HCl (1.5 g, 22.4 mmol) at 0° C. The reaction was stirred at room temperature for 18 hours then concentrated in vacuo. The residue was purified by silica gel column chromatography eluting with 33% petroleum ether in EtOAc and dissolving in MeOH (20 mL). To the solution was added 4M HCl in MeOH (30 mL) and the reaction was stirred at room temperature for 18 hours before concentrating in vacuo. The residue was dissolved in MeOH (20 mL) and adjusted to pH 10 by adding 1M aqueous NaHCO$_3$ solution. The mixture was concentrated in vacuo and added to 10:1 DCM:MeOH (100 mL) and stirred at room temperature for 30 minutes. The mixture was filtered and the filtrate was concentrated in vacuo to afford the title compound as a yellow solid (480 mg, 80%).
$^1$H NMR (400 MHz, DMSO-d$_6$): δ ppm 2.70-2.71 (d, 3H), 6.25 (s, 2H), 6.67-6.71 (dd, 1H), 7.75 (s, 1H), 8.20 (s, 1H).

Preparation 52

N-Ethyl-3-methyl-5-nitropicolinamide

The title compound was prepared according to the method described for Preparation 41 using ethyl 3-methyl-5-nitropicolinate (Preparation 53) and ethylamine at 70° C.
$^1$H NMR (400 MHz, CDCl$_3$): δ ppm 1.28 (t, 3H), 2.87 (s, 3H), 3.49 (q, 2H), 7.97 (br s, 1H), 8.37 (d, 1H), 9.17 (d, 1H).

Preparation 53

Ethyl 3-methyl-5-nitropicolinate

Sulfuric acid (150 mL) was added slowly to ethanol (600 mL) slowly at 0° C. To this solution was added 2-cyano-3-methyl-5-nitropyridine (15 g, 92 mmol) portion-wise and the reaction heated to reflux for 65 hours. The reaction was cooled, poured into ice-water and extracted into EtOAc. The organic layer was collected and the aqueous further washed with EtOAc. The organic extracts were combined, washed with brine, dried over sodium sulfate and concentrated in vacuo. The residue was purified using silica gel column chromatography eluting with 0-30% DCM in hexanes to afford the title compound (8.5 g, 44%). $^1$H NMR (400 MHz, CDCl$_3$): δ ppm 1.44 (t, 3H), 2.67 (s, 3H), 4.50 (q, 2H), 8.39 (d, 1H), 9.29 (d, 1H).

Preparation 54

Racemic Methyl 2-(5-nitropyridin-2-yl)propanoate

A solution of racemic 1-(tert-butyl) 3-methyl 2-methyl-2-(5-nitropyridin-2-yl)malonate (Preparation 55, 1.6 g, 5.15 mmol) and TFA (15 mL) in DCM (50 mL) was stirred at room temperature for 18 hours. The reaction was concentrated in vacuo and treated with triethylamine before purifying directly by silica gel column chromatography eluting with 25% EtOAc in petroleum ether to afford the title compound (0.99 g, 91%). $^1$H NMR (400 MHz, CDCl$_3$): δ ppm 1.61 (d, 3H), 3.72 (s, 3H), 4.10-4.30 (m, 1H), 7.51 (d, 1H), 8.46 (dd, 1H), 9.38 (d, 1H).

Preparation 55

Racemic 1-(tert-Butyl) 3-methyl 2-methyl-2-(5-nitropyridin-2-yl)malonate

To a solution of 1-(tert-butyl) 3-methyl 2-(5-nitropyridin-2-yl)malonate (PCT Publication No. WO 2007042299, 1.9 g, 6.41 mmol) in DMF (50 mL) was added cesium carbonate (4.18 g, 13 mmol) at 0° C. The reaction was stirred at room temperature for 10 minutes before the addition of MeI (3.64 g, 25.7 mmol) and stirring at room temperature for 3 hours. The reaction was added water (40 mL) at 10° C. and then extracted with EtOAc three times (3×50 mL). The organic layers were combined, concentrated in vacuo and purified by silica gel column chromatography eluting with 25% EtOAc in pentane to afford the title compound (1.6 g, 80%). $^1$H NMR (400 MHz, CDCl$_3$): δ ppm 1.47 (s, 9H), 1.89 (s, 3H), 3.80 (s, 3H), 7.71 (d, 1H), 8.47 (m, 1H), 9.35 (d, 1H).

Preparation 56

N,6-Dimethyl-4-nitropicolinamide

To a solution of 6-methyl-4-nitro-2-pyridinecarboxylic acid (2 g, 10 mmol) in THF (50 mL) was added HOBt (1.77 g, 13.1 mmol), EDCl.HCl (2.30 g, 12 mmol), DIPEA (1.90 mL, 10.9 mmol) and methylamine (5.46 mL, 10.9 mmol). The reaction was stirred at room temperature for 15 minutes followed by reflux for 30 minutes. The reaction was poured into saturated aqueous NaHCO$_3$ solution and extracted into EtOAc. The organic layer was collected dried over sodium sulfate and concentrated in vacuo. The residue was purified using silica gel column chromatography to afford the title compound.

Preparation 57

Methyl 2-(3-chloro-5-nitropyridin-2-yl)acetate

To a solution of 1-(tert-butyl) 3-methyl 2-(3-chloro-5-nitropyridin-2-yl)maonate (Preparation 58, 6.6 g, 20 mmol) in DCM (100 mL) was added TFA (100 mL) and the reaction was stirred at room temperature for 20 hours. The reaction was concentrated in vacuo to afford the title compound as the trifluoroacetate salt (6.8 g, 100%).

Preparation 58

1-(tert-Butyl) 3-methyl 2-(3-chloro-5-nitropyridin-2-yl)malonate

To a solution of NaH (6 g, 150 mmol) in DMF (30 mL) was added tert-butylmethylmalonate (5 g, 28.7 mmol) slowly. The mixture was stirred at room temperature for 30 minutes before the addition of 2,3-dichloro-5-nitropyridine (5 g, 26 mmol) dropwise. The reaction was stirred at room temperature for 2 hours. The reaction was concentrated in vacuo and purified by silica gel column chromatography to get afford the title compound (6.6 g, 77%) as red oil.

Preparation 59

(S)-1-(3-Fluoro-5-nitropyridin-2-yl)pyrrolidin-3-ol

To a mixture of NaH (227 mg, 5.68 mmol, 60%) in DME (30 mL) was added (S)-pyrrolidin-3-ol (494 mg, 5.68 mmol) and the reaction was stirred at room temperature for 1 hour. A solution of 2-chloro-4-fluoro-5-nitropyridine (250 mg, 1.42 mmol) in DME (10 mL) was added at 10° C. and stirred at room temperature for 1 hour. The reaction was quenched with water (30 mL) and extracted with EtOAc (100 mL×2). The organic layers were combined, concentrated in vacuo and purified by silica gel column chromatography eluting with 0-50% EtOAc in petroleum ether to afford the title compound (250 mg, 77%) as yellow solid.

The following preparations were prepared according to the method described by Preparation 59 using the appropriate fluoropyridine as described.

| Preparation number | Structure | Name | SM/Data |
| --- | --- | --- | --- |
| 60 | 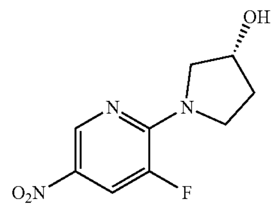 | (R)-1-(3-fluoro-5-nitropyridin-2-yl)pyrrolidin-3-ol | (R)-pyrrolidin-3-ol. $^1$H NMR (400 MHz, DMSO-d$_6$): δ ppm 1.82-2.05 (m, 2H), 3.58-3.92 (m, 4H), 4.34-4.44 (m, 1H), 5.09 (d, 1H), 8.16 (dd, 1H), 8.84 (dd, 1H). |
| 61 | 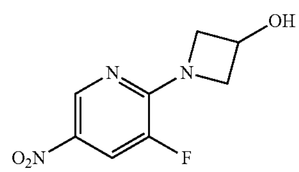 | 1-(3-fluoro-5-nitropyridin-2-yl)azetidin-3-ol | Azetidinol. $^1$H NMR (400 MHz, DMSO-d$_6$): δ ppm 3.98-4.09 (m, 2H), 4.47-4.55 (m, 2H), 4.58-4.69 (m, 2H), 5.87 (d, 1H), 8.13-8.21 (m, 1H), 8.75-8.88 (m, 1H). |
| 62 | 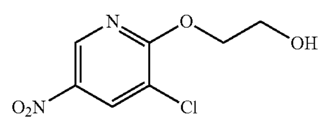 | 2-((3-chloro-5-nitropyridin-2-yl)oxy)ethan-1-ol | Ethane-1,2-diol. Taken on directly to the next step. |

Preparation 63

Methyl 4-((tert-butoxycarbonyl)amino)-6-(hydroxymethyl)picolinate

To a solution of dimethyl 4-((tert-butoxycarbonyl)amino)pyridine-2,6-dicarboxylate (Preparation 64, 300 mg, 0.967 mmol), in DCM (2 mL) and MeOH (1 mL) at 0° C. was added sodium borohydride (38 mg, 0.966 mmol). The reaction was stirred at this temperature for 30 minutes, further sodium borohydride (17 mg, 0.483 mmol) was added and the reaction stirred at room temperature for 18 hours. The reaction was quenched by the addition of 1:1 brine:water and extracted into EtOAc five times. The organic layers were combined, dried over sodium sulfate and concentrated in vacuo to afford the title compound as a white solid (232 mg, 85%). MS m/z 281 [M−H]$^-$ Preparation 64

Dimethyl 4-((tert-butoxycarbonyl)amino)pyridine-2,6-dicarboxylate

To a solution of dimethyl 4-bromopyridine-2,6-dicarboxylate (2.4 g, 8.76 mmol) in dioxane (30 mL) was added tert-butylcarbamate (1.13 g, 9.63 mmol), Pd$_2$(dba)$_3$ (246 mg, 0.263 mmol), xantphos (207 mg, 0.350 mmol) and cesium carbonate (5.7 g, 17.5 mmol). The reaction was degassed with argon and heated to 85° C. for 18 hours. The reaction was cooled, concentrated in vacuo and purified using silica gel column chromatography eluting with 20% EtOAc in heptanes to afford the title compound (1.2 g, 44%).

$^1$H NMR (400 MHz, CDCl$_3$): δ ppm 1.55 (s, 9H), 4.05 (s, 6H), 7.30 (d, 1H), 8.35 (d, 1H).

Preparation 65

5-((di-[tert-Butoxycarbonyl]amino)-3-fluoropicolinic acid

To a solution of ethyl 5-((di-[tert-butoxycarbonyl])amino)-3-fluoropicolinate (Preparation 66, 3.3 g, 8.59 mmol) in THF:water (46 mL, 15:8) was added LiOH (0.72 g, 17.12 mmol) at room temperature. The reaction was stirred at room temperature for 4 hours. The reaction was acidified to pH 3 by the addition of citric acid at 0° C. and extracted with ethyl acetate (50 mL×2). The combined organic layers were concentrated in vacuo to afford the title compound as a white solid (2.6 g, 86%).

MS m/z 357 [M+H]$^+$

Preparation 66

Ethyl 5-((di-[tert-butoxycarbonyl]amino)-3-fluoropicolinate

To a solution of di-[tert-butyl carbamate]-(6-bromo-5-fluoropyridin-3-yl) (Preparation 67, 3.7 g, 9.46 mmol) in ethanol (100 mL) was added Pd(OAc)$_2$ (1.6 g, 7.53 mmol), DPPP (3.12 g, 7.56 mmol) and triethylamine (5.4 g, 53.46 mmol). The reaction was heated to 60° C. under an atmosphere of carbon monoxide at 50 psi for 18 hours. The reaction was filtered and the filtrate was concentrated in vacuo. The residue was purified by silica gel column chromatography eluting with 10% EtOAc in petroleum ether to afford the title compound (3.3 g, 90%).

Preparation 67 di-[tert-Butyl carbamate]-(6-bromo-5-fluoropyridin-3-yl)

To a solution of 6-bromo-5-fluoro-3-pyridinamine (2.6 g, 13.6 mmol) in THF (100 mL) was added ditertbutyldicarbonate (8.81 g, 40.8 mmol), DIPEA (5.26 g, 40.8 mmol) and DMAP (83.2 mg, 0.68 mmol) at room temperature. The reaction was heated to reflux for 4 hours. The reaction was concentrated in vacuo and purified by silica gel column chromatography eluting with 10% EtOAc in petroleum ether to afford the title compound that was taken on directly to the next step (3.7 g, 56%).

Preparation 68

(S)-2,2-Difluorocyclopropane-1-carboxylic acid

To a solution of (S)-1-phenylethyl (S)-2,2-difluorocyclopropane-1-carboxylate (Preparation 70, 3.67 g, 16.2 mmol) in MeOH (48 mL) was added 1N NaOH (48 mL, 48 mmol) and the reaction was stirred at room temperature for 1.5 hours. The reaction was concentrated in vacuo, acidified to pH=5.8 using 12N HCl (aq) and extracted into nBuOH. The organic layer was collected and concentrated in vacuo to afford the title compound (1.5 g, 76%). $^1$H NMR (400 MHz, DMSO-d$_6$): δ ppm 1.90 (m, 2H), 2.65 (m, 1H).

Preparation 69

(R)-2,2-Difluorocyclopropane-1-carboxylic acid

The title compound was prepared according to the method described for Preparation 68 using (S)-1-phenylethyl(R)-2,2-difluorocyclopropane-1-carboxylate (Preparation 71).

Preparations 70 and 71

(S)-1-Phenylethyl(S)-2,2-difluorocyclopropane-1-carboxylate and (S)-1-phenylethyl(R)-2,2-difluorocyclopropane-1-carboxylate To a solution of 2,2-difluoro-cyclopropanecarboxylic acid (4.02 g, 33 mmol) in DCM (140 mL) was added DCC (8.16 g, 39 mmol) followed by DMAP (403 mg, 3.30 mmol) and the reaction was stirred for 10 minutes. (S)-1-phenylethan-1-ol (4.83 g, 39 mmol) was added and the reaction stirred at room temperature for 72 hours. The reaction was filtered, concentrated in vacuo and purified using silica gel column chromatography eluting with 0-5% EtOAc to afford the title compounds as a mixture of diastereomers. The diastereomers were separated using chromatography as described below: Kromasil Silica 10 um, 4.6×250 mm; run time 14 minutes; 1.0 mL/min; eluting with 3% MTBE in heptanes.

Peak 1: Rt=5.34 minutes; (S)-1-phenylethyl(S)-2,2-difluorocyclopropane-1-carboxylate (Preparation 70). $^1$H NMR (400 MHz, CDCl$_3$): δ ppm 1.61 (d, 3H), 1.74-1.79 (m, 1H), 2.06-2.12 (m, 1H), 2.45-2.53 (m, 1H), 5.95-6.00 (m, 1H), 7.33-7.42 (m, 5H).

Peak 2: Rt=6.22 minutes; (S)-1-phenylethyl(R)-2,2-difluorocyclopropane-1-carboxylate (Preparation 71). $^1$H NMR (400 MHz, CDCl$_3$): δ ppm 1.61 (d, 3H), 1.74-1.79 (m, 1H), 2.06-2.12 (m, 1H), 2.45-2.53 (m, 1H), 5.95-6.00 (m, 1H), 7.33-7.42 (m, 5H).

Preparation 72

(1R,2R)-2-Cyanocyclopropane-1-carboxylic acid

To a solution of benzyl (1R,2R)-2-cyanocyclopropane-1-carboxylate (Preparation 74, 100 mg, 0.5 mmol) in anhydrous THF (10 mL) was added wet Pd/C (10 mg). The reaction was degassed, then stirred at room temperature under a balloon of hydrogen for 1 hour. The reaction was filtered and the filtrate concentrated in vacuo to afford the title compound as a white solid that was used directly in the next step (56 mg, 100%).

Preparation 73

(1S,2S)-2-Cyanocyclopropane-1-carboxylic acid

The title compound was prepared according to the method described for Preparation 72 using benzyl (1S,2S)-2-cyanocyclopropane-1-carboxylate (Preparation 75).

Preparations 74 and 75

Benzyl(1R,2R)-2-Cyanocyclopropane-1-carboxylate and Benzyl(1S,2S)-2-Cyanocyclopropane-1-carboxylate To a solution of trans-racemic ethyl 2-cyanocyclopropane-1-carboxylate (Preparation 77, 24.7 g, 0.17 mol) in THF (400 mL) and water (200 mL) was added lithium hydroxide (14.9 g, 0.35 mol) and the reaction was stirred at room temperature for 2 hours. The reaction was diluted with water (20 mL) and extracted with DCM (2×30 mL). The aqueous layer was acidified to pH 2 with 1M HCl and extracted into EtOAc three times (3×400 mL). The combined organic layers were washed with brine, dried over sodium sulfate and concentrated in vacuo. The residue was recrystallized from ether to afford the carboxylic acid. To a portion of the acid (8 g, 0.072 mol) in DMF (150 mL) was added cesium carbonate (25.8 g, 0.35 mol) followed by benzyl bromide (13.6 g, 0.08 mol) and the reaction was stirred at room temperature for 18 hours. The reaction was diluted with water (300 mL) and extracted with EtOAc three times (3×400 mL). The combined organic layers were washed with brine, dried over sodium sulfate and concentrated in vacuo. The residue was purified by silica gel column chromatography eluting with 10-70% EtOAc in petroleum ether to afford the title compound as the trans-racemate (13.6 g, 94%).

The trans-racemate was separated by chiral chromatography as described below: Column: OD 300 mm×50 mm×10 µm.

Mobile phase: A: Supercritical $CO_2$, B: EtOH (0.1% $NH_3H_2O$), A:B=90:10; Flow rate: 180 mL/min Preparation 74: Benzyl (1S,2S)-2-cyanocyclopropane-1-carboxylate (5.80 g, 43%) Peak 1, Rt=3.61 minutes; $^1$H NMR (400 MHz, $CDCl_3$): δ ppm 1.50-1.56 (m, 2H), 1.96-1.99 (m, 1H), 2.29-2.32 (m, 1H), 5.16 (s, 2H), 7.35-7.41 (m, 5H).

Preparation 75: Benzyl (1R,2R)-2-cyanocyclopropane-1-carboxylate (5.82 g, 43%) Peak 2, Rt=3.87 minutes; $^1$H NMR (400 MHz, $CDCl_3$): δ ppm 1.50-1.56 (m, 2H), 1.96-1.98 (m, 1H), 2.30-2.32 (m, 1H), 5.16 (s, 2H), 7.35-7.41 (m, 5H).

Preparations 76 and 77 cis-racemic and trans-racemic Ethyl 2-cyanocyclopropane-1-carboxylate

Acrylonitrile (70 g, 1.32 mol) was stirred under reflux as ethyl diazoacetate (70 g, 0.614 mol) was added portion wise over period of 2.5 hours. After completion of the addition, the mixture was stirred at reflux for an additional 1.5 hours, before removing the excess acrylonitrile by distillation. The reaction was then heated to 125-130° C. and maintained there until nitrogen evolution ceased and the reaction was heated to 160-170° C. for 1 hour before cooling to room temperature under nitrogen. The reaction was distilled under vacuum and the product purified by silica gel column chromatography eluting with 10-50% EtOAc in petroleum ether afford trans-racemic ethyl 2-cyanocyclopropane-1-carboxylate as the first eluting compound (24 g, 28%) and cis-racemic ethyl 2-cyanocyclopropane-1-carboxylate as the second eluting compound (17 g, 20%).

Preparation 76

$^1$H NMR (400 MHz, $CDCl_3$): δ ppm 1.30 (m, 3H), 1.42 (m, 1H), 1.67 (m, 1H), 1.82 (m, 1H), 2.10 (m, 1H), 4.23 (m, 2H)

Preparation 77

$^1$H NMR (400 MHz, $CDCl_3$): δ ppm 1.28 (m, 3H), 1.42 (m, 1H), 1.66 (m, 1H), 1.82 (m, 1H), 2.10 (m, 1H), 4.23 (m, 2H); MS m/z 140 [M+H]$^+$ Preparation 78

N-(2-Cyanoethyl)-1H-imidazole-1-carboxamide

To a solution of CDI (250 mg, 1.56 mmol) and triethylamine (236 mg, 2.34 mmol) in anhydrous THF (15 mL) was added a solution of 2-cyanoethylamine (100 mg, 0.78 mmol) in anhydrous THF (5 mL) at 0° C. and the reaction was stirred at room temperature for 18 hours The reaction was concentrated in vacuo and purified by silica gel column chromatography eluting with EtOAc to afford the title compound as a colourless oil (44 mg, 34%). $^1$H NMR (400 MHz, $CDCl_3$): δ ppm 2.79 (t, 2H), 3.47 (q, 2H), 7.12 (s, 1H), 7.50 (s, 1H), 7.66 (br s, 1H), 8.39 (s, 1H).

Preparation 79

N-(Cyanomethyl)-1H-imidazole-1-carboxamide

To a solution of aminoacetonitrile bisulfate (436 mg, 2.75 mmol) and 1,1'-carbonyldiimidazole (500 mg, 3.0 mmol) in acetonitrile (3 mL) was added N,N-dimethylformamide (1 mL) and the reaction stirred at room temperature in a sealed vessel for 18 hours. The residue was concentrated in vacuo, taken up in DCM and filtered. The filtrate was purified using silica gel column chromatography eluting with 0-10% MeOH in DCM to afford the title compound.

$^1$H NMR (400 MHz, $CDCl_3$): δ ppm 3.50 (s, 2H), 7.18 (d, 1H), 7.30 (d, 1H), 7.75 (s, 1H).

Preparation 80

N-Ethyl-1H-imidazole-1-carboxamide

Ethylamine hydrochloride (1.78 g, 21 mmol) and CDI (4.20 g, 25 mmol) was stirred at room temperature in MeCN (20 mL) for 3 hours. The reaction was diluted with DCM, filtered and concentrated in vacuo. The residue was further diluted with DCM, filtered, and purified using silica gel column chromatography eluting with 0-10% MeOH in DCM to afford the title compound.

$^1$H NMR (400 MHz, $CDCl_3$): δ ppm 1.88 (t, 3H), 3.50 (m, 2H), 6.35 (br s, 1H), 7.10 (d, 1H), 7.40 (d, 1H), 8.20 (s, 1H).

Preparation 81

N-Isopropyl-1H-imidazole-1-carboxamide

The title compound was prepared according to the method described for Preparation 80 using isopropylamine hydrochloride with DMF (1 mL). The residue was suspended in EtOAc, filtered, the filtrate washed with brine, concentrated in vacuo and taken directly on to the next step.

$^1$H NMR (400 MHz, $CDCl_3$): δ ppm 1.20 (m, 6H), 4.10 (m, 1H), 6.95 (s, 1H), 7.50 (d, 1H), 7.80 (d, 1H), 7.80 (m, 1H), 8.20 (d, 1H).

Preparation 82

N-(2,2,2-Trifluoroethyl)-1H-imidazole-1-carboxamide

The title compound was prepared according to the method described for Preparation 80 using 2,2,2-trifluoroethan-1-amine hydrochloride with DMF. $^1$H NMR (400 MHz, $CDCl_3$): δ ppm 4.00 (m, 2H), 7.00 (d, 1H), 7.60 (d, 1H), 8.25 (s, 1H), 9.00 (br s, 1H).

Preparation 83

5-Amino-N-propyl-1H-pyrazole-3-carboxamide hydrochloride

A solution of 1-(tert-butyl) 3-ethyl 5-amino-1H-pyrazole-1,3-dicarboxylate (Preparation 84, 7.5 g, 29 mmol) in propylamine (40 mL) was heated to reflux for 48 hours. The reaction was cooled, concentrated in vacuo and dissolved in DCM (20 mL). 4N HCl in dioxane (20 mL) was added and the reaction stirred at room temperature for 2 hours. The resulting solid was filtered, washed with tert-butyl ether and dried. The solid was recrystallised from 2:1 EtOAc:IPA with decolourising charcoal to afford the title compound as the hydrochloride salt (5.1 g, 85%).

$^1$H NMR (400 MHz, MeOH-d$_4$): δ ppm 0.95 (t, 3H), 1.60 (m, 2H), 3.30 (m, 4H), 5.90 (br s, 1H).

Preparation 84

1-(tert-Butyl) 3-ethyl 5-amino-1H-pyrazole-1,3-dicarboxylate

To a solution of tert-butyl (Z)-2-(1-cyano-2-ethoxy-2-oxoethylidene)hydrazine-1-carboxylate (Preparation 85, 10.5 g, 41 mmol) in acetonitrile (150 mL) was added triethylamine (17.4 mL, 123 mmol) and the reaction was stirred at room temperature for 3 hours. The reaction was concentrated in vacuo and purified using silica gel column chromatography eluting with from 20-80% EtOAc in heptanes.

$^1$H NMR (400 MHz, CDCl$_3$): δ ppm 1.40 (t, 3H), 1.60 (s, 9H), 4.40 (q, 2H), 5.40 (br s, 2H), 5.95 (s, 1H).

Preparation 85 tert-Butyl (Z)-2-(1-cyano-2-ethoxy-2-oxoethylidene) hydrazine-1-carboxylate

To a solution of sodium ethylate (21% solution in EtOH, 51 mL, 137 mmol) in diethylether (30 mL) was added a solution of diethyl oxalate (20 g, 140 mmol) in diethylether (80 mL) dropwise over 15 minutes at 0° C. followed by stirring at this temperature for 1 hour. Acetonitrile (7.15 mL, 137 mmol) was added slowly and the reaction stirred at room temperature for 18 hours. The resulting precipitate was filtered, washed with 1:1 ether:ethanol and dried under vacuum. The solid (8.7 g, 53 mmol) was dissolved in ethanol (25 mL) and acetic acid (3.2 g, 53 mmol) and cooled to 0° C. tert-Butyl hydrazinecarboxylate (7.75 g, 59 mmol) was added and the reaction stirred at 0° C. for 1 hour followed by room temperature for 18 hours. The reaction was concentrated in vacuo and partitioned between EtOAc and saturated aqueous sodium carbonate solution. The organic layer was collected, dried over sodium sulfate and concentrated in vacuo to afford the title compound as an orange solid (10.5 g, 77%).

Preparation 86

6-Aminoimidazo[1,2-a]pyridine-2-carboxamide

To a solution of ethyl 6-aminoimidazo[1,2-a]pyridine-2-carboxylate (Preparation 87, 2 g, 0.0074 mol) in MeOH (30 mL) was added ammonia (3 g, 0.044 mol) and the reaction was heated to 100° C. in a sealed vessel for 24 hours. The reaction was cooled and concentrated in vacuo to afford the title compound (1.9 g, 90%).

Preparation 87

Ethyl 6-aminoimidazo[1,2-a]pyridine-2-carboxylate

To a solution of 2-amino-5-bromopyridine (5 g, 0.029 mol) in ethanol (180 mL) was added ethyl 3-bromo-2-oxopropanoate (5.64 g, 0.029 mol) and NaHCO$_3$ (4.86 g, 0.058 mol) and the reaction was heated to reflux for 18 hours. The reaction was cooled, concentrated in vacuo and partitioned between EtOAc and saturated aqueous sodium carbonate solution. The organic layer was collected, washed with brine, dried over magnesium sulfate and concentrated in vacuo. The residue was purified using silica gel column chromatpgraphy eluting with 30% EtOAc in petroleum ether to afford the title compound (4.2 g, 45%).

Preparation 88

(S)-N-((1S,5S)-3-(2-Chloro-5-fluoropyrimidin-4-yl)-5-(hydroxymethyl)-3-azabicyclo[3.1.0]hexan-1-yl)-2,2-difluorocyclopropane-1-carboxamide The title compound was prepared according to the method described for Preparation 27 using racemic-(5-amino-3-(2-chloro-5-fluoropyrimidin-4-yl)-3-azabicyclo[3.1.0]hexan-1-yl)methanol (Preparation 99) and (S)-2,2-difluorocyclopropane-1-carboxylic acid (Preparation 68) with DIPEA in DCM. The racemic residue was purified using silica gel column chromatography eluting with 50-100% EtOAc in heptanes. The second, more polar eluting isomer was collected as the title compound.

MS m/z 363 [M+H]$^+$

Preparation 89

Racemic-(1R,2R)-N-(3-(2-Chloro-5-fluoropyrimidin-4-yl)-5-(hydroxymethyl)-3-azabicyclo[3.1.0]hexan-1-yl)-2-cyanocyclopropane-1-carboxamide The racemic title compound was prepared according to the method described for Preparation 27 using racemic-(5-amino-3-(2-chloro-5-fluoropyrimidin-4-yl)-3-azabicyclo[3.1.0]hexan-1-yl)methanol (Preparation 99) and (1R,2R)-2-cyanocyclopropane-1-carboxylic acid (Preparation 72) with DIPEA in DCM. The residue was purified using silica gel column chromatography eluting with 50-100% EtOAc in heptanes. MS m/z 352 [M+H]$^+$

Preparation 90

(1S,5R,6R)-3-(5-Fluoro-2-((1-methyl-1H-pyrazol-4-yl)amino)pyrimidin-4-yl)-6-methyl-3-azabicyclo[3.1.0]hexan-1-amine hydrochloride To a solution of tert-butyl ((1S,5R,6R)-3-(2-chloro-5-fluoropyrimidin-4-yl)-6-methyl-3-azabicyclo-[3.1.0]hexan-1-yl)carbamate (Preparation 94, 1 g, 2.91 mmol) in isopropanol (10 mL) was added 1-methyl-1H-pyrazol-4-ylamine hydrochloride (506 mg, 3.79 mmol) and the reaction was heated to 140° C. under microwave irradiation for 1 hour. The resulting solid was filtered and dried to afford the title compound as the hydrochloride salt (991 mg, 86%). MS m/z 304 [M+H]+

The following preparations were prepared according to the method described by Preparation 90 or Preparation 1 using the appropriate halide and the appropriate amine as described below. The compounds were isolated as the hydrochloride salts unless otherwise specified.

Deprotection Method B: The Boc-protected intermediate was dissolved in DCM, treated with TFA and stirred at room temperature for 18 hours. The reaction was basified to pH=10 by the addition of triethylamine. The solution was concentrated in vacuo and purified by silica gel column chromatography eluting with 10% MeOH in DCM.

and purified directly using silica gel column chromatography eluting with 20% EtOAc in petroleum ether to afford the title compound as a white solid (2 g, 69%). $^1$H NMR (400 MHz, DMSO-$d_6$): δ ppm 0.98 (d, 3H), 1.39 (m, 1H), 1.45 (br s, 9H), 1.80 (m, 1H), 3.67-4.17 (m, 4H), 5.05 (m, 1H), 7.86 (d, 1H). MS m/z 343 [M+H]$^+$ Chiral Analytical Column: Chiralpak AD-3 150 mm×4.6 mm I.D., 3 μm; Retention Time: 3.83 minutes; 100% ee. Mobile phase: Methanol (0.05% Ethanolamine) in $CO_2$ from 5% to 40%, Flow rate: 2.5 mL/min

| Preparation number | Structure | Name | SM/Data |
|---|---|---|---|
| 91 | 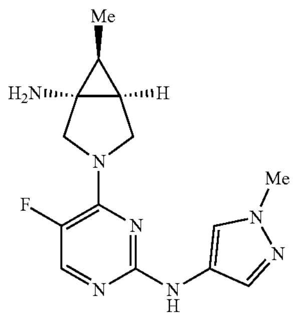 [SMILES: C[C@H]1[C@H]2CN(c3nc(Nc4cnn(C)c4)ncc3F)C[C@]21N] | (1R,5S,6S)-3-(5-fluoro-2-((1-methyl-1H-pyrazol-4-yl)amino)pyrimidin-4-yl)-6-methyl-3-azabicyclo[3.1.0]hexan-1-amine hydrochloride | tert-butyl ((1R,5S,6S)-3-(2-chloro-5-fluoropyrimidin-4-yl)-6-methyl-3-azabicyclo[3.1.0]hexan-1-yl)carbamate (Preparation 96) and 1-methyl-1H-pyrazol-4-ylamine hydrochloride. MS m/z 304 [M + H]$^+$ |
| 92 | 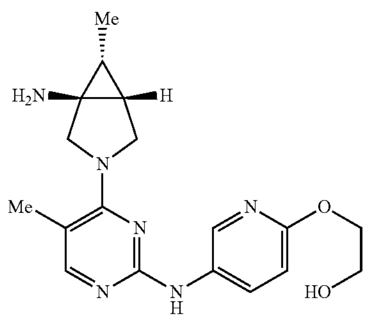 [SMILES: Cc1cnc(Nc2ccc(OCCO)nc2)nc1N1C[C@H]2[C@@H](C)[C@@]2(N)C1] | 2-((5-((4-((1S,5R,6R)-1-amino-6-methyl-3-azabicyclo[3.1.0]hexan-3-yl)-5-methylpyrimidin-2-yl)amino)pyridin-2-yl)oxy)ethan-1-ol | tert-butyl ((1S,5R,6R)-3-(2-chloro-5-methylpyrimidin-4-yl)-6-methyl-3-azabicyclo[3.1.0]hexan-1-yl)carbamate (Preparation 97) and 2-[(5-amino-2-pyridinyl)oxy]-ethanol. Taken on directly to the next step. |
| 93 | 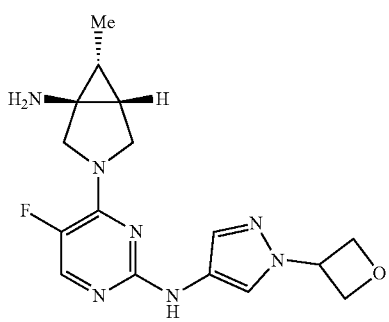 [SMILES: C[C@@H]1[C@@H]2CN(c3nc(Nc4cnn(C5COC5)c4)ncc3F)C[C@]12N] | (1S,5R,6R)-3-(5-fluoro-2-((1-(oxetan-3-yl)-1H-pyrazol-4-yl)amino)pyrimidin-4-yl)-6-methyl-3-azabicyclo[3.1.0]hexan-1-amine | tert-butyl ((1R,5S,6S)-3-(2-chloro-5-fluoropyrimidin-4-yl)-6-methyl-3-azabicyclo[3.1.0]hexan-1-yl)carbamate (Preparation 96) and 1-(oxetan-3-yl)-1H-pyrazol-4-amine (Preparation 123) with deprotection method B. |

Preparation 94 tert-Butyl ((1S,5R,6R)-3-(2-chloro-5-fluoropyrimidin-4-yl)-6-methyl-3-azabicyclo[3.1.0]hexan-1-yl) carbamate To a solution of tert-butyl ((1S,5R,6R)-6-methyl-3-azabicyclo[3.1.0]hexan-1-yl)carbamate (Preparation 101, 1.8 g, 8.50 mmol) and triethylamine (1.7 g, 16.8 mmol) in MeOH (100 mL) was added 2,4-dichloro-5-fluoropyrimidine (1.5 g, 9.03 mmol), and the reaction was stirred at room temperature for 18 hours. The reaction was concentrated in vacuo Preparation 95 and 95A N-((1S,5R,6R)-3-(2-Chloro-5-fluoropyrimidin-4-yl)-6-methyl-3-azabicclo[3.1.0]hexan-1-yl)cyclopropanecarboxamide and N-((1R,5S,6S)-3-(2-chloro-5-fluoropyrimidin-4-yl)-6-methyl-3-azabicyclo[3.1.0] hexan-1-yl)cyclopropanecarboxamide The title compounds were prepared as a trans-racemic mixture according to the method described by Preparation 94 using trans-racemic-6-methyl-3-azabicyclo[3.1.0]hexan-1-yl)cyclo-propanecarboxamide (Preparation 102). GCMS Rt=5.91 minutes MS m/z 310 [M]N-((1S,5R,6R)-3-(2-chloro-5-fluoropyrimidin-4-yl)-6-methyl-3-azabicyclo[3.1.0]hexan-1-yl)cyclopropanecarboxamide may also be prepared as the single enantiomer according to the methods described by Preparations 94 and 102 using N-((1S,5R,6R)-3-benzyl-6-methyl-3-azabicyclo[3.1.0]hexan-1-yl)cyclopropanecarboxamide (Preparation 107A).

Preparation 96 tert-Butyl ((1R,5S,6S)-3-(2-chloro-5-fluoropyrimidin-4-yl)-6-methyl-3-azabicyclo[3.1.0]hexan-1-yl)carbamate The title compound was prepared according to the methods described for Preparations 105, 101 and 94 using (1R,5S,6S)-3-benzyl-6-methyl-3-azabicyclo[3.1.0]hexan-1-amine (Preparation 110).

Preparation 97 tert-Butyl ((1S,5R,6R)-3-(2-chloro-5-methylpyrimidin-4-yl)-6-methyl-3-azabicyclo[3.1.0]hexan-1-yl)carbamate The title compound was prepared according to the method described for Preparation 94 using tert-butyl ((1S,5R,6R)-6-methyl-3-azabicyclo[3.1.0]hexan-1-yl)carbamate (Preparation 101) and 2,4-dichloro-5-methylpyrimidine. LCMS Rt=0.90 minutes; MS m/z 339 [M+H]$^+$ Preparation 98

Racemic-N-(3-(2,5-Dichloropyrimidin-4-yl)-3-azabicyclo[3.1.0]hexan-1-yl)cyclopropanecarboxamide The title compound was prepared according to the method described for Preparation 94 using racemic-N-(3-azabicyclo[3.1.0]hexan-1-yl)cyclopropanecarboxamide (Preparation 103) and 2,4,5-trichloropyrimidine. The residue was purified using silica gel column chromatography eluting with 10% MeOH in DCM.

Preparation 99

Racemic-(5-Amino-3-(2-chloro-5-fluoropyrimidin-4-yl)-3-azabicyclo[3.1.0]hexan-1-yl)methanol To a solution of racemic-tert-butyl (5-(((tert-butyldimethylsilyl)oxy)methyl)-3-(2-chloro-5-fluoropyrimidin-4-yl)-3-azabicyclo[3.1.0]hexan-1-yl)carbamate (Preparation 100, 1.25 g, 2.64 mmol) in DCM (25 mL) was added TFA (5 mL) and the reaction was stirred at 0° C. for 30 minutes followed by room temperature for 3 hours. The reaction was quenched with saturated aqueous NaHCO$_3$ solution, basified to pH=12 with solid NaOH and extracted into DCM. The organic layer was collected, dried over sodium sulfate and concentrated in vacuo. The residue was purified by silica gel column chromatography eluting with 0-5% MeOH in DCM to afford the title compound (200 mg, 30%).
LCMS Rt=0.49 minutes; MS m/z 261 [M$^{37}$Cl+H]$^+$ Preparation 100

Racemic-tert-Butyl (5-(((tert-butyldimethylsilyl)oxy)methyl)-3-(2-chloro-5-fluoropyrimidin-4-yl)-3-azabicyclo[3.1.0]hexan-1-yl)carbamate The title compound was prepared according to the method described for Preparation 94 using racemic-tert-butyl (5-(((tert-butyldimethylsilyl)oxy)methyl)-3-azabicyclo[3.1.0]hexan-1-yl)carbamate (Preparation 104) and 2,4-dichloro-5-fluoropyrimidine. MS m/z 473 [M+H]$^+$ Preparation 101 tert-Butyl ((1S,5R,6R)-6-methyl-3-azabicyclo[3.1.0]hexan-1-yl)carbamate

To a solution of tert-butyl ((1S,5R,6R)-3-benzyl-6-methyl-3-azabicyclo[3.1.0]hexan-1-yl)carbamate (Preparation 105, 3.4 g, 0.326 mmol) in MeOH (200 mL) was added Pd(OH)$_2$ (20%, 3 g) and the reaction was hydrogenated under 50 psi of hydrogen at room temperature for 2 days. The reaction was filtered and concentrated in vacuo to afford the title compound give (2.3 g, 100%).
The following preparations were prepared according to the method described by Preparation 101 or Preparation 1 using the appropriate benzyl protected intermediate as described below:

| Preparation number | Structure | Name | SM/Data |
|---|---|---|---|
| 102 | [structure] | N-((1S,5R,6R)-6-methyl-3-azabicyclo[3.1.0]hexan-1-yl)cyclopropanecarboxamide and N-((1R,5S,6S)-6-methyl-3-azabi-cyclo[3.1.0]hexan-1-yl)cyclopropanecarboxamide | GCMS Rt = 3.64 minutes MS m/z 181 [M] Trans-racemic 3-benzyl-6-methyl-3-azabi-cyclo[3.1.0]hexan-1-yl)cyclopropanecarboxamide (Preparation 107). Isolated as the trans-racemic mixture. |

-continued

| Preparation number | Structure | Name | SM/Data |
|---|---|---|---|
| 103 | (structure) | Racemic-N-(3-azabicyclo[3.1.0]hexan-1-yl)cyclopropanecarboxamide | Racemic-N-(3-benzyl-3-azabicyclo[3.1.0]hexan-1-yl)cyclopropanecarboxamide (Preparation 108) with Pd/C. Taken on directly to the next step. |
| 104 | (structure) BocNH, OTBDMS | Racemic-tert-butyl (5-(((tert-butyldimethylsilyl)oxy)methyl)-3-azabicyclo[3.1.0]hexan-1-yl)carbamate | Racemic-tert-butyl (3-benzyl-5-(((tert-butyldimethylsilyl)oxy)methyl)-3-azabicyclo[3.1.0]hexan-1-yl)carbamate (Preparation 106). Taken on directly to the next step. |

Preparation 105 tert-Butyl ((1S,5R,6R)-3-benzyl-6-methyl-3-azabicyclo[3.1.0]hexan-1-yl)carbamate To a solution of (1S,5R,6R)-3-benzyl-6-methyl-3-azabicyclo[3.1.0]hexan-1-amine (Preparation 109, 2.5 g, 0.0123 mol) and triethylamine (2.5 g, 0.0247 mmol) in DCM (50 mL) was added ditertbutyldicarbonate (2.6 g, 0.0130 mmol) and the reaction was stirred at room temperature for 18 hours. The reaction was filtered and the filtrate was purified directly by silica gel column chromatography eluting with 10% EtOAc in petroleum ether to afford the title compound as a yellow oil (3.4 g, 91%).

Preparation 106

Racemic-tert-Butyl (3-benzyl-5-(((tert-butyldimethylsilyl)oxy)methyl)-3-azabicclo[3.1.0]hexan-1-yl)carbamate The title compound was prepared according to the method described for Preparation 105 using racemic-3-benzyl-5-(((tert-butyldimethylsilyl)oxy)methyl)-3-azabicyclo[3.1.0]hexan-1-amine (Preparation 111) in TBME. MS m/z 433 [M+H]$^+$

Preparation 107

N-((1S,5R,6R)-3-Benzyl-6-methyl-3-azabicclo[3.1.0]hexan-1-yl)cyclopropanecarboxamide and N-((1R,5S,6S)-3-benzyl-6-methyl-3-azabicyclo[3.1.0]hexan-1-yl)cyclopropanecarboxamide To a solution of trans-racemic-3-benzyl-6-methyl-3-azabicyclo[3.1.0]hexan-1-amine (Preparations 109 and 110, 700 mg, 3.46 mmol) in DCM (15 mL) was added DIPEA (1.20 mL, 6.92 mmol) followed by cyclopropylcarbonyl chloride (362 mg, 3.46 mmol) and the reaction was stirred at room temperature for 2 hours. The reaction was concentrated in vacuo and purified directly using silica gel column chromatography eluting with 10-100% EtOAc in heptanes to afford the trans-racemic mixture of the title compounds (400 mg, 43%).
N-((1S,5R,6R)-3-benzyl-6-methyl-3-azabicyclo[3.1.0]hexan-1-yl)cyclopropanecarboxamide may also be prepared as the single enantiomer according to this preparation using (1S,5R,6R)-3-benzyl-6-methyl-3-azabicyclo[3.1.0]hexan-1-amine (Preparation 667C).

Preparation 108

Racemic-N-(3-Benzyl-3-azabicyclo[3.1.0]hexan-1-yl)cyclopropanecarboxamide

The title compound was prepared according to the method described by Preparation 107 using racemic-3-benzyl-3-azabicyclo[3.1.0]hexan-1-amine (Tetrahedron L., (2003), 44 (12), 2485-2487) and triethylamine with cyclopropylcarbonyl chloride. The residue was purified directly using silica gel column chromatography eluting with 10% MeOH in DCM.

Preparations 109 and 110

(1S,5R,6R)-3-Benzyl-6-methyl-3-azabicyclo[3.1.0] hexan-1-amine and (1R,5S,6S)-3-benzyl-6-methyl-3-azabicyclo[3.1.0]hexan-1-amine To a solution of (Z)-2-(benzyl(but-2-en-1-yl)amino)acetonitrile (Preparation 112, 64 g, 0.32 mol) in anhydrous THE (2 L) under nitrogen was added Ti(O$^i$Pr)$_4$ (300 g, 1.05 mol) followed by cyclohexylmagnesium chloride (2M solution in ether, 800 mL, 1.6 mol) dropwise at 20-30° C. over 1.5 hours. The reaction was then stirred at room temperature for 2 hours. The reaction was quenched by the addition of 10% aqueous NaOH (1 L) and stirred for 1 hour before filtering and concentrating in vacuo. The residue was dissolved in DCM (6 L), washed with water (2 L), dried over sodium sulfate and concentrated in vauco. The residue was purified using silica gel column chromatography eluting with 10% MeOH in DCM to afford the trans-racemic mixture of the title compounds (827 g, 36%).
$^1$H NMR (400 MHz, CDCl$_3$): δ ppm 1.07-1.08 (m, 1H), 1.18-1.21 (m, 1H), 1.25-1.28 (d, 3H), 2.54-2.56 (d, 1H), 2.76-2.81 (m, 2H), 3.05-3.07 (d, 1H), 3.55 (s, 2H), 7.21-7.31 (m, 5H). MS m/z 203 [M+H]$^+$ The trans-racemic compound may be separated into its enantiomers using chiral chromatography as described below:
Chiral column: IC 300 mm×50 mm×10 μm; Mobile phase: A: Supercritical CO$_2$, B: MeOH (with 0.1% aqueous ammonia), A:B=75:25 at 200 mL/min Chiral LCMS QC:
Chiralpak Pheno Lux Cellulose-2; 150 mm×4.6 mm I.D. 5 µm; mobile phase MeOH (0.05% ethanolamine) in $CO_2$ from 5-60%; flow rate 3 mL/min.

(1R,5S,6S)-3-Benzyl-6-methyl-3-azabicyclo[3.1.0]hexan-1-amine

First eluting isomer: Rt=6.78 minutes, 89.9% ee. $^1$H NMR (400 MHz, $CDCl_3$): δ ppm 1.08-1.11 (m, 1H), 1.16-1.22 (m, 1H), 1.26 (m, 3H) 2.54 (d, 1H), 2.70-2.84 (m, 2H), 3.05 (d, 1H), 3.59 (s, 2H), 7.23-7.30 (m, 5H).

(1S,5R,6R)-3-Benzyl-6-methyl-3-azabicyclo[3.1.0]hexan-1-amine

Second eluting isomer: Rt=6.10 minutes, 99.4% ee. $^1$H NMR (400 MHz, $CDCl_3$): δ ppm 1.05-1.13 (m, 1H), 1.20 (m, 1H), 1.26 (m, 3H), 2.53 (m, 1H), 2.71-2.84 (m, 2H), 3.05 (d, 1H), 3.58 (s, 2H), 7.25-7.30 (m, 5H).

Preparation 111

Racemic-3-Benzyl-5-(((tert-butyldimethylsilyl)oxy)methyl)-3-azabicyclo[3.1.0]hexan-1-amine The title compound was prepared according to the method described for Preparations 109 and 110 using 2-(benzyl(2-(((tert-butyldimethylsilyl)oxy)methyl)allyl)amino)acetonitrile (Preparation 114).

Preparation 112

(Z)-2-(Benzyl(but-2-en-1-yl)amino)acetonitrile

To a solution of 2-(benzyl(but-2-yn-1-yl)amino)acetonitrile (Preparation 113, 100 g, 0.5 mol) in MeOH (2000 mL) was added Lindlar catalyst (10 g) and the reaction was stirred at 30° C. under a balloon of hydrogen for 24 hours. The reaction was filtered and concentrated in vacuo to afford the title compound. $^1$H NMR (400 MHz, $CDCl_3$): δ ppm 1.72-1.74 (m, 3H), 3.26-3.27 (m, 2H), 3.45 (s, 2H), 3.69 (s, 2H), 5.45-5.48 (m, 1H), 5.73-5.77 (m, 1H), 7.29-7.39 (m, 5H).

Preparation 113

2-(Benzyl(but-2-yn-1-yl)amino)acetonitrile

To a solution of 2-(benzylamino)acetonitrile (Preparation 115, 666 g, 4.56 mol) in MeCN (11 L) was added 1-bromobut-2-yne (600 g, 4.51 mol) and potassium carbonate (1365 g, 14 mol) and the reaction was heated to 40° C. for 18 hours. The reaction was filtered, concentrated in vacuo and purified using silica gel column chromatography eluting with 3-10% EtOAc in petroleum ether to afford the title compound as a yellow oil (700 g, 77%). $^1$H NMR (400 MHz, $CDCl_3$): δ ppm 1.72-1.74 (m, 3H), 3.25-3.27 (d, 2H), 3.45 (s, 2H), 3.69 (s, 2H), 7.29-7.39 (m, 5H).

Preparation 114

2-(Benzyl(2-(((tert-butyldimethylsilyl)oxy)methyl)allyl)amino)acetonitrile

The title compound was prepared according to the method described by Preparation 113 using ((2-(bromomethyl)allyl)oxy)(tert-butyl)dimethylsilane and 2-(benzylamino)acetonitrile (Preparation 115) at 75° C. for 6 hours. $^1$H NMR (400 MHz, $CDCl_3$): b ppm 0.00 (s, 6H), 0.80 (s, 9H), 3.15 (s, 2H), 3.35 (s, 2H), 3.60 (s, 2H), 4.10 (s, 2H), 5.10 (m, 1H), 5.20 (m, 1H), 7.20-7.40 (m, 5H).

Preparation 115

2-(Benzylamino)acetonitrile

To a solution of benzylamine (1250 g, 11.68 mol) and DIPEA (2878 g, 22.31 mol) in acetonitrile (13 L) was added 2-bromoacetonitrile (1340 g, 11.17 mol) and the reaction was stirred at room temperature for 3 hours. The reaction was concentrated in vacuo and dissolved in DCM (2.5 L). The solution was washed with water (1.5 L×2), concentrated in vacuo and purified using silica gel column chromatography eluting with 10-30% EtOAc in petroleum ether (1600 g, 94%).
$^1$H NMR (400 MHz, $CDCl_3$): δ ppm 3.57 (s, 2H), 3.94 (s, 2H), 7.35-7.37 (m, 5H).

Preparation 116

2-(5-Aminopyridin-2-yl)ethan-1-ol

The title compound was prepared according to the method described for Preparation 40 using methyl 2-(5-aminopyridin-2-yl)acetate (PCT Publication No. WO2007042299).
$^1$H NMR (400 MHz, MeOH-$d_4$): δ ppm 2.80-2.85 (t, 2H), 3.80 (t, 2H), 7.05 (m, 2H), 7.90 (s, 1H).

Preparation 117

Racemic-1-(5-Amino-3-chloropyridin-2-yl)ethan-1-ol

To a suspension of racemic-tert-butyl (5-chloro-6-(1-hydroxyethyl)pyridin-3-yl)carbamate_(Preparation 118, 2.2 g, 8 mmol) in MeOH (50 mL) was added HCl/dioxane (4M, 30 mL) at 0° C. The reaction was stirred at room temperature for 18 hours before concentrating in vacuo to afford the title compound as the hydrochloride salt, which was taken on directly to the next step (2.2 g, 100%).

Preparation 118

Racemic-tert-Butyl (5-chloro-6-(1-hydroxyethyl)pyridin-3-yl)carbamate

To a suspension of di-tert-butyl (6-acetyl-5-chloropyridin-3-yl)carbamate (Preparation 119, 2.33 g, 6.7 mmol) in MeOH (50 mL) was added sodium borohydride (656 mg, 17.25 mmol) at 0° C. The reaction was stirred at room temperature for 3 hours before being quenched by the addition of water and extracted with EtOAc (3×50 mL). The combined organic layers were concentrated in vacuo to afford the title compound as a white solid (2 g, 85%). MS m/z 372 [M+H]$^+$ Preparation 119 tert-Butyl (6-acetyl-5-chloropyridin-3-yl)carbamate

To a suspension of di-tert-butyl (5-chloro-6-(methoxy(methyl)carbamoyl)pyridin-3-yl)carbamate (Preparation 120, 2.1 g, 6.7 mmol) in THF (150 mL) was added MeMgCl (2.2 mL, 3 mol/L) dropwise at −30° C. The reaction was stirred at room temperature for 3 hours before quenching with the addition of water. The reaction was extracted into EtOAc (3×50 mL) and concentrated in vacuo to afford the title compound as a white solid (2.3 g, 77%). MS m/z 271 [M+H]$^+$ Preparation 120

Di-tert-Butyl (5-chloro-6-(methoxy(methyl)carbamoyl)pyridin-3-yl)carbamate

To a solution of methyl 5-((di-tert-butoxycarbonyl) amino)-3-chloropicolinate (Preparation 121, 2 g, 5.18 mmol) in THF/H$_2$O (100 mL/50 mL) was added LiOH (435 mg, 10.36 mmol) at 0° C. and stirred at room temperature for 2 hours. The reaction was adjusted pH=2 with citric acid and extracted with EtOAc (3×100 mL). The combined organic layers were dried over sodium sulfate and concentrated in vacuo. The residue (1.35 g, 3.6 mmol) was dissolved in DCM (100 mL) and treated with N,O-dimethylhydroxylamine hydrochloride (423 mg, 4.3 mmol), triethylamine (1.1 g, 11 mmol) and HATU (1.65 g, 4.3 mmol) at 0° C. The reaction was stirred at room temperature for 3 hours. The reaction was concentrated in vacuo and purified directly using silica gel column chromatography eluting with 30% EtOAc in petroleum ether to afford the title compound (1.4 g, 94%). MS m/z 416 [M+H]$^+$ Preparation 121

Methyl 5-((di-tert-butoxycarbonyl)amino)-3-chloropicolinate

To a solution of methyl 5-amino-3-chloropicolinate (1.42 g, 7.63 mmol) and di-tert-butyldicarbonate (4.7 g, 18.8 mmol) in THF (150 mL) was added DIPEA (2.95 g, 22.87 mmol followed by DMAP (47 mg, 0.38 mmol). The reaction was heated to 70° C. for 3 hours. The reaction was concentrated in vacuo and purified by silica gel column chromatography eluting with 30% EtOAc in petroleum ether to afford the title compound (2.5 g, 85%). MS m/z 387 [M+H]$^+$ Preparation 122

(5-Amino-3-chloropyridin-2-yl)methanol

The title compound was prepared according to the method described for Preparation 40 using methyl 5-amino-3-chloropicolinate. The residue was purified using silica gel column chromatography eluting with 30% petroleum ether on EtOAc. $^1$H NMR (400 MHz, DMSO-d$_6$): δ ppm 4.42-4.44 (d, 2H), 4.88 (t, 1H), 5.57 (br s, 2H), 6.97 (s, 1H), 7.83 (s, 1H).

Preparation 123

1-(Oxetan-3-yl)-1H-pyrazol-4-amine

To a solution of 4-nitro-1-(oxetan-3-yl)-1H-pyrazole (Preparation 124, 119 mg, 0.70 mmol) in MeOH (20 mL) was added wet Pd/C (30 mg) and the reaction was hydrogenated under a balloon of hydrogen at room temperature for 2 hours. The reaction was filtered and the filtrate concentrated in vacuo to afford the title compound (100 mg, 100%).

Preparation 124

4-Nitro-1-(oxetan-3-yl)-1H-pyrazole

To a solution of 4-nitro-1H-pyrazole (0.3 g, 2.66 mmol) and 3-iodo-oxetane (1.47 g, 7.99 mmol) in DMF (13 mL) was added cesium carbonate (1.7 g, 5.23 mmol) and the reaction was heated to 100° C. for 18 hours. The reaction was concentrated in vacuo and purified by silica gel column chromatography eluting with EtOAc to afford the title compound (380 mg, 86%).
$^1$H NMR (400 MHz, MeOH-d$_4$): δ ppm 5.02 (br s, 4H), 5.61 (br s, 1H), 8.24 (br s, 1H), 8.68 (br s, 1H).

Preparation 125

4-Amino-6-(hydroxymethyl)-N-methylpicolinamide

Methyl 4-((tert-butoxycarbonyl)amino)-6-(hydroxymethyl)picoinate (Preparation 63, 220 mg, 0.78 mmol) in 2M methylamine in MeOH (4 mL) was heated to 60° C. for 18 hours. The reaction was cooled and the resulting solid filtered, dried, and dissolved in DCM (4 mL). To the solution was added MeOH (1 mL) followed by 4M HCl in dioxane (3 mL) and the reaction was stirred at room temperature for 4 hours. The resulting solid was filtered and dried to afford the title compound as the hydrochloride salt (75 mg, 40% over 2 steps). LCMS Rt=0.16 minutes; MS m/z 182 [M+H]$^+$ Preparation 126

4-((4-(3,6-Diazabicyclo[3.1.1]heptan-3-yl)-5-fluoropyrimidin-2-yl)amino)-N-ethyl-2-methylbenzamide To a solution of N-ethyl-4-((5-fluoro-4-(6-(2,2,2-trifluoroacetyl)-3,6-diazabicyclo[3.1.1]heptan-3-yl)pyrimidin-2-yl)amino)-2-methylbenzamide (Example 121, 100 mg, 0.21 mmol) in MeOH (5 mL) was added 1M NaOH (aq) (2 mL) and the reaction was stirred at 50° C. for 1 hour. The reaction was concentrated in vacuo and partitioned between DCM and water. The organic phase was collected through a phase separation cartridge and concentrated in vacuo to afford the title compound that was used directly in the next reaction.

Preparation 127

4-((4-(3,6-Diazabicyclo[3.1.1]heptan-3-yl)pyrimidin-2-yl)amino)-N-ethylbenzamide hydrochloride To a solution of 4-((4-chloropyrimidin-2-yl)amino)-N-ethylbenzamide (Preparation 132, 1.2 g, 4.3 mmol) and tert-butyl 3,6-diazabicyclo[3.1.1]heptanes-6-carboxylate (900 mg, 5 mmol) in THF (20 mL) was added triethylamine (2 mL, 10 mmol) and the reaction was heated to 50° C. for 18 hours. The reaction was cooled and purified directly using silica gel column chromatography eluting with 0-20% MeOH in DCM. The residue was dissolved in 1:1 MeOH: DCM (10 mL) and treated with 4M HCl in dioxane (5 mL).

The reaction was stirred at room temperature for 18 hours before concentrating in vacuo. The resulting solid was collected as the hydrochloride salt of the title compound (1.5 g, quant).
MS m/z 339 [M+H]+

Preparation 128

4-((4-(3,6-Diazabicyclo[3.1.1]heptan-3-yl)pyrimidin-2-yl)amino)-N-ethyl-2-methylbenzamide hydrochloride To a solution of tert-butyl 3-(2-chloropyrimidin-4-yl)-3,6-diazabicyclo[3.1.1]heptane-6-carboxylate (Preparation 131, 100 mg, 0.3 mmol) and 4-amino-N-ethyl-2-methylbenzamide (PCT Publication No. WO2006109846, 60 mg, 0.34 mmol) in dioxane (3 mL) was added sodium tert-butoxide (35 mg, 0.36 mmol) and RuPHOS (25 mg, 0.034 mmol). The reaction was heated to 140° C. under microwave irradiation for 25 minutes. The reaction was cooled, filtered and purified directly using silica gel column chromatography eluting with 0-20% MeOH in DCM. The residue was dissolved in DCM (5 mL) and treated with 4M HCl in dioxane with a few drops of MeOH to enable a solution. The reaction was stirred at room temperature for 18 hours and concentrated in vacuo to afford the title compound as the hydrochloride salt that was used directly in the next reaction.

Preparation 129

1-(3-(2-Chloro-5-fluoropyrimidin-4-yl)-3,6-diazabicyclo[3.1.1]heptan-6-yl)-2,2,2-trifluoroethan-1-one To a solution of tert-butyl 3-(2-chloro-5-fluoropyrimidin-4-yl)-3,6-diazabicyclo[3.1.1]heptane-6-carboxylate (Preparation 130, 200 mg, 0.61 mmol) in DCM (5 mL) was added 4M HCl in dioxane (4 mL) and the reaction was stirred at room temperature to ensure removal of the tert-butoxycarbonyl protecting group. The reaction was concentrated in vacuo, dissolved in DCM (5 mL), treated with TFAA (0.1 mL) and stirred at room temperature for 18 hours. The reaction was concentrated in vacuo and the residue partitioned between DCM and water. The organic layer was collected through a phase separation cartridge and concentrated in vacuo to afford the title compound that was taken directly on to the next step. MS m/z 325 [M+H]+

Preparation 130 tert-Butyl 3-(2-chloro-5-fluoropyrimidin-4-yl)-3,6-diazabicyclo[3.1.1]heptane-6-carboxylate To a solution of 5-fluoro-2,4-dichloropyrimidine (0.85 g, 5.1 mmol) in MeOH (15 mL) was added tert-butyl 3,6-diazabicyclo[3.1.1]heptanes-6-carboxylate (1 g, 5 mmol) followed by triethylamine (3 mL, 20 mmol) and the reaction was stirred at room temperature for 18 hours. The resulting precipitate was filtered, washed with MeOH and dried to afford the title compound as a white solid (1.46 g, 88%).
¹H NMR (400 MHz, DMSO-d₆): δ ppm 1.28 (s, 9H), 1.48 (d, 1H), 2.48-2.53 (m, 1H), 3.70 (br s, 2H), 4.03-4.19 (m, 4H), 8.88 (d, 1H). MS m/z 329 [M+H]+

Preparation 131 tert-butyl 3-(2-chloropyrimidin-4-yl)-3,6-diazabicyclo[3.1.1]heptane-6-carboxylate The title compound was prepared according to the method described for Preparation 130 using 2,4-dichloropyrimidine and tert-butyl 3,6-diazabicyclo[3.1.1]heptanes-6-carboxylate. The residue was purified using silica gel column chromatography eluting with 0-100% EtOAc in heptanes.
¹H NMR (400 MHz, DMSO-d₆): δ ppm 1.24 (s, 9H), 1.44 (d, 1H), 2.48-2.56 (m, 1H), 3.42 (m, 2H), 3.83 (br s, 1H), 3.92-4.04 (m, 1H), 4.15 (d, 2H), 6.70 (br d, 1H), 8.09 (d, 1H). MS m/z 311 [M+H]+

Preparation 132

4-((4-Chloropyrimidin-2-yl)amino)-N-ethylbenzamide

To a solution of 4-((4-chloropyrimidin-2-yl)amino)benzoic acid (Preparation 133, 1 g, 4 mmol) in DCM (20 mL) was added ethylamine (4.4 mL, 8.81 mmol) followed by HATU (1.71 g, 4.4 mmol) and triethylamine (1.23 mL, 8.81 mmol). The reaction was stirred at room temperature for 30 minutes before being poured into water. The organic layer was separated, dried over sodium sulfate and concentrated in vacuo. The residue was purified using silica gel column chromatography eluting with 0-100% EtOAc in heptanes to afford the title compound (1 g, 90%).
¹H NMR (400 MHz, DMSO-d₆): δ ppm 1.05 (t, 3H), 3.20-3.30 (m, 2H), 7.00 (m, 1H), 7.70 (m, 4H), 8.30 (t, 1H), 8.45 (s, 1H), 10.25 (br s, 1H). MS m/z 277 [M+H]+

Preparation 133

4-((4-Chloropyrimidin-2-yl)amino)benzoic acid

A mixture of 4-((4-hydroxypyrimidin-2-yl)amino)benzoic acid (Preparation 134, 5 g, 21.6 mmol) and POCl₃ was heated to reflux for 6 hours and then cooled to room temperature and concentrated in vacuo. The residue was poured into ice-water and the resulting solid was collected by filtration and dried to afford the title compound that was taken on directly to the next step.

Preparation 134

4-((4-Hydroxypyrimidin-2-yl)amino)benzoic acid

To a solution of 4-hydroxy-2-methylthiopyrimidine (5 g, 35.17 mmol) in diethylene glycol dimethyl ether (20 mL) was added 4-aminobenzoic acid (5.79 g, 42.2 mmol) and the reaction was heated to reflux for 18 hours. The reaction was cooled to room temperature and the resulting solid was filtered, washed with ether and dried to afford the title compound (6.5 g, 35.17 mmol). A sample was purified and analysed using preparative HPLC as described for Example 116 (Method 1, 5% B to 100% B in 9 min, hold at 100% B to 10 min) to obtain the following data. The remainder was taken directly on to the next step. LCMS Rt=1.37 minutes; MS m/z 232 [M+H]+

Preparation 135

2-(3-((1R,5S)-3-(2-((1-Methyl-1H-pyrazol-4-yl)amino)pyrimidin-4-yl)-3,8-diazabicyclo[3.2.1]octan-8-yl)azetidin-3-yl)acetonitrile hydrochloride To a solution of 1-Boc-3-(cyanomethylene)azetidine (PCT Publication No. WO2013043964, 60 mg, 0.308 mmol) and 4-((1R,5S)-3,8-diazabicyclo[3.2.1]octan-3-yl)-N-(1-methyl-1H-pyrazol-4-yl)pyrimidin-2-amine hydrochloride (Preparation 19, 83 mg, 0.257 mol) in MeCN (1 mL) and EtOH (1 mL) was added DBU (77 μl, 0.514 mmol) and the reaction was heated to 90° C. for 24 hours. Further 4-((1R,5S)-3,8-diazabicyclo[3.2.1]octan-3-yl)-N-(1-methyl-1H-pyrazol-4-yl)pyrimidin-2-amine hydrochloride (Preparation 19, 3 eq) was added and the reaction continued heating at 90° C. for 72 hours. The reaction was cooled, concentrated in vacuo and purified using silica gel column chromatography eluting with 0-10% MeOH (with 1% ammonia). The residue was dissolved in DCM (1 mL) and treated with 4M HCl in dioxane (1 mL). The reaction was stirred at room temperature for 1 hour before concentrating in vacuo to afford the title compound as the hydrochloride salt.

LCMS Rt=0.38 minutes; MS m/z 380 [M+H]$^+$

Preparation 136

Ethyl 2-((1R,5S)-3-(2-((1-methyl-1H-pyrazol-4-yl)amino)pyrimidin-4-yl)-3,8-diazabicyclo[3.2.1]octan-8-yl)oxazole-5-carboxylate A mixture of 4-((1R,5S)-3,8-diazabicyclo[3.2.1]octan-3-yl)-N-(1-methyl-1H-pyrazol-4-yl)pyrimidin-2-amine hydrochloride (Preparation 19, 300 mg, 0.614 mmol), ethyl-2-chloro-1,3-oxazole-5-carboxylate (300 mg, 1.71 mmol), potassium phosphate (163 mg, 0.613 mmol), X-phos (60 mg, 0.126 mmol) and Pd$_2$(dba)$_3$ (60 mg, 0.065 mmol) in DMSO (20 mL) was purged with nitrogen for 1 minutes. The reaction was heated to 130° C. for 30 minutes under microwave irradiation. The reaction was filtered, concentrated in vacuo and purified by silica gel column chromatography 0-20% MeOH in DCM to afford the title compound (200 mg, 76%). MS m/z 425 [M+H]$^+$ Preparation 137 and 138 tert-Butyl ((1S,5R,6R)-3-(2-((5-chloro-6-((R)-1-hydroxyethyl)pyridin-3-yl)amino)-5-fluoropyrimidin-4-yl)-6-methyl-3-azabicyclo[3.1.0]hexan-1-yl)carbamate and tert-Butyl ((1S,5R,6R)-3-(2-((5-chloro-6-((S)-1-hydroxyethyl)pyridin-3-yl)amino)-5-fluoropyrimidin-4-yl)-6-methyl-3-azabicyclo[3.1.0]hexan-1-yl)carbamate To a solution of racemic-1-(5-amino-3-chloropyridin-2-yl)ethan-1-ol (Preparation 117, 100 mg, 0.58 mmol), tert-butyl ((1S,5R,6R)-3-(2-chloro-5-fluoropyrimidin-4-yl)-6-methyl-3-azabicyclo[3.1.0]hexan-1-yl)carbamate (Preparation 94, 187 mg, 0.46 mmol) and Cs$_2$CO$_3$ (375 mg, 1.16 mmol) in DMA (5 mL) was added Pd(OAc)$_2$ (25 mg, 0.93 mmol) and xantphos (65 mg, 0.93 mmol) under nitrogen. The reaction was heated to 110° C. under microwave irradiation for 1 hour. The reaction was concentrated in vacuo and purified directly using silica gel column chromatography with 50% EtOAc in petroleum ether followed by preparative HPLC to afford the racemic title compound. The racemate was separated into its enantiomers by preparative chiral chromatography as described below:
Column: Chiralpak AS-3 150×4.6 mm I.D. 3 μm
Mobile phase: Ethanol (0.05% DEA) in CO$_2$ from 5% to 40%; Flow rate: 2.5 mL/min
First Eluting Enantiomer:
Example 137: tert-Butyl ((1S,5R,6R)-3-(2-((5-chloro-6-((R)-1-hydroxyethyl)pyridin-3-yl)amino)-5-fluoropyrimidin-4-yl)-6-methyl-3-azabicyclo[3.1.0]hexan-1-yl)carbamate. $^1$H NMR (400 MHz, DMSO-d$_6$): δ ppm 0.88-0.90 (m, 3H), 1.20-1.30 (m, 1H), 1.40 (m, 12H), 1.75 (m, 1H), 3.60 (m, 2H), 3.90 (m, 2H), 5.00 (m, 2H), 7.55 (br s, 1H), 8.00 (m, 1H), 8.35 (br s, 1H), 8.75 (br s, 1H), 9.55 (s, 1H). MS m/z 479 [M+H]$^+$; 100% ee.
Second Eluting Isomer:
Example 138: tert-Butyl ((1S,5R,6R)-3-(2-((5-chloro-6-((S)-1-hydroxyethyl)pyridin-3-yl)amino)-5-fluoropyrimidin-4-yl)-6-methyl-3-azabicyclo[3.1.0]hexan-1-yl)carbamate. $^1$H NMR (400 MHz, DMSO-d$_6$): δ ppm 0.88-0.90 (m, 3H), 1.20-1.30 (m, 1H), 1.35-1.39 (m, 12H), 1.75 (m, 1H), 3.60 (m, 2H), 3.90 (m, 2H), 5.00 (m, 2H), 7.55 (br s, 1H), 8.00 (m, 1H), 8.38 (br s, 1H), 8.71 (br s, 1H), 9.57 (s, 1H). MS m/z 479 [M+H]$^+$; 100% ee.

Preparation 139 tert-butyl (6-chloro-5-fluoropyridin-3-yl)carbamate

To a solution of 5-bromo-2-chloro-3-fluoropyridine (62.5 g, 297 mmol×4), Xantphos (38.4 g, 327.8 mmol×4), and Cs$_2$CO$_3$ (6.87 g, 11.9 mmol×4) in dioxane (2 L×4) was added Pd$_2$(dpa)$_3$ (10.8 g, 11.9 mmol×4). The mixture was heated to 85° C. overnight. The reactions were combined than filtered. The filtrate was purified by silica gel column chromatography eluting with 5% EtOAc in petroleum ether to afford the title compound (170 g, 58%). $^1$H NMR (400 MHz, CDCl$_3$): δ ppm 1.53 (s, 9H), 6.78 (br. s., 1H), 7.99 (d, 1H), 8.05 (d, 1H)

Preparation 140

Methyl 5-((tert-butoxycarbonyl)amino)-3-fluoropicolinate

To a solution of tert-butyl (6-chloro-5-fluoropyridin-3-yl)carbamate (Preparation 139, 43.3 g, 175.67 mmol×3), DPPP (14.46 g, 35.1 mmol×3), TEA (124.1 g, 1.228 mol×3) in MeOH (600 mL×3) was added Pd(OAc)$_2$ (7.88 g, 35.1 mmol×3). The mixture was stirred at 50 psi of CO at 60° C. for 36 hrs. The reaction mixtures were combined, filtered and the filtrated was concentrated under reduced pressure. The residue was purified by silica gel column chromatography eluting with 10% EtOAc in petroleum ether to afford the title compound (33.7 g, 71%). $^1$H NMR (400 MHz, CDCl$_3$): δ ppm 1.53 (s, 9H) 3.99 (s, 3H) 7.06 (br. s., 1H) 8.13 (d, 1H) 8.24 (s, 1H)

Preparation 141

6-chloro-5-fluoropyridin-3-amine hydrochloride

A mixture of methyl 5-((tert-butoxycarbonyl)amino)-3-fluoropicolinate (Preparation 140, 1.50 g, 5.55 mmol) in 1 N HCl/dioxane (70 mL, 4 M) was stirred at room temperature (10° C.) for 16 hours. The mixture was concentrated in vacuo to afford the title compound (1.1 g, 100%), which was used in the next step without further purification.

Preparation 142 tert-butyl-3-(2-((5-fluoro-6-(methoxycarbonyl)pyridin-3-yl)amino)pyrimidin-4-yl)-3,8-diazabicyclo[3.2.1]octane-8-carboxylate To a mixture of 6-chloro-5-fluoropyridin-3-amine hydrochloride (Preparation 141, 500 mg, 1.54 mmol), tert-butyl (1R,5S)-3-(2-chloropyrimidin-4-yl)-3,8-diazabicyclo[3.2.1]octane-8-carboxylate (Preparation 34, 314 mg, 1.85 mmol)

and $Cs_2CO_3$ (1000 mg, 3.08 mmol) in DMA (15 mL) was added Xantphos (178 mg, 0.308 mmol) and $Pd(OAc)_2$ (69.1 mg, 0.308 mmol) at room temperature (10° C.). The mixture was bubbled with $N_2$ for 3 min. The vial was sealed and then treated with microwave irradiation at 120° C. for 1 h. The mixture was concentrated and purified by column chromatography on silica gel 25% EtOAc in petroleum ether to 75% EtOAc in petroleum ether to give the title compound (296 mg, 42%). LCMS Rt=0.70 minutes; MS m/z 459 [M+H]

Preparation 143 tert-butyl-3-(2-((6-carbamoyl-5-fluoropyridin-3-yl) amino)pyrimidin-4-yl)-3,8-diazabicyclo[3.2.1]octane-8-carboxylate A solution of tert-butyl-3-(2-((5-fluoro-6-(methoxycarbonyl)pyridin-3-yl)amino)pyrimidin-4-yl)-3,8-diazabicyclo [3.2.1]octane-8-carboxylate (Preparation 142, 400 mg, 0.11 mmol) in $NH_3$/MeOH (80 mL, 4 M) was stirred at 100° C. in a 100 mL sealed tube for 8 h. The solution was concentrated in vacuo to afford the title compound (270 mg, 72%), which was used in the next step without further purification. LCMS Rt=0.67 minutes; MS m/z 444 [M+H]

Preparation 144

5-((4-(3,8-diazabicyclo[3.2.1]octan-3-yl)pyrimidin-2-yl)amino)-3-fluoropicolinamide hydrochloride To a mixture of Preparation 143 (250 mg, 0.564 mmol) in THF (10 mL) was added HCl/dioxane (20 mL, 4 M) at 0° C. The mixture was stirred at room temperature (10° C.) for 3 h. TLC (DCM:MeOH=10:1) showed some of the starting material was still remained. The solution was concentrated in vacuo to afford the title compound (300 mg, yield: 100%), which was taken to the next step directly.

Biological Evaluation

Compounds of the invention were evaluated by in vitro methods to determine their respective ability to inhibit the JAK kinases (TYK2, JAK1, JAK2, JAK3).

Assay Format

The human JAK inhibitory activity was determined by using a microfluidic assay to monitor phosphorylation of a synthetic peptide by the recombinant human kinase domain of each of the four members of the JAK family, JAK1, JAK2, JAK3 and TYK2. Reaction mixtures contained 1 M of a fluorescently labeled synthetic peptide, a concentration less than the apparent $K_m$, and 1 mM ATP. Each assay condition was optimized for enzyme concentration and room temperature incubation time to obtain a conversion rate of 20% to 30% phosphorylated peptide product. Reactions were terminated by the addition of stop buffer containing EDTA. Utilizing the LabChip 3000 mobility shift technology (Caliper Life Science), each assay reaction was sampled to determine the level of phosphorylation. This technology is separation-based, allowing direct detection of fluorescently labeled substrates and products. Separations are controlled by a combination of vacuum pressure and electric field strength optimized for each peptide substrate.

Assay Protocol

JAK Caliper Enzyme Assay at 1 mM ATP

Compounds were added to a 384-well plate. Reaction mixtures contained 10 mM HEPES, pH 7.4, 10 mM $MgCl_2$, 0.01% BSA, 0.0005% Tween 20, 1 mM ATP and 1 M peptide substrate. The JAK and TYK2 assays contained 1 M of the IRStide peptide (5FAM-KKSRGDYMTMQID) and the JAK2 and JAK3 assays contained 1 M of the JAKtide peptide (FITC-KGGEEEEYFELVKK). The assays were initiated by the addition of 20 nM JAK1, 1 nM JAK2, 1 nM JAK or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly overtime to ensure 20% to 30% phosphorylation. The assays were stopped with 15 μL of 180 mM HEPES, pH 7.4, 20 mM EDTA, and 0.2% Coating Reagent 3. The assay plates were placed on a Caliper Life Science LC3000 instrument, and each well was sampled using appropriate separation conditions to measure the unphosphorylated and phosphorylated peptide.

Data Analysis

The data was collected using the HTS Well Analyzer software from Caliper Life Sciences. The data output for data analysis is the percent product converted calculated on peak height (Equation 1).

$$\% \text{ product converted} = 100*((\text{product})/(\text{product}+\text{substrate}))$$ Equation 1:

The percent effect at each compound concentration was calculated based on the positive and negative control well contained within each assay plate (Equation 2). The positive control wells contained a saturating concentration of a control compound that produced a level of phosphorylation comparable to background (i.e., completely inhibited JAK1, JAK2, JAK3 or TYK2). The negative control wells contained DMSO alone (at the same concentration as the compound wells) that was used to set the baseline activity in the assay (i.e., uninhibited JAK1, JAK2, JAK3 or TYK2).

$$\% \text{ effect} = 100*((\text{sample well}-\text{negative control})/(\text{positive control}-\text{negative control}))$$ Equation 2:

The percent effect was plotted against the compound concentration compound. An unconstrained sigmoid curve was fitted using a 4 parameter logistic model and the compound concentration required for 50% inhibition ($IC_{50}$) was determined (Equation 3).

$$y = ((\text{max}-\text{min})/(1+((x/IC_{50})^s)))+\text{min}$$ Equation 3:

Where max is the maximum asymptote (complete inhibition), min is the minimum asymptote (no inhibition) and s is the slope factor. $IC_{50}$ values are reported in nM for each compound:

| Ex. No. | Structure | IC$_{50}$ (nM) | | | |
|---|---|---|---|---|---|
| | | TYK2 | JAK1 | JAK2 | JAK3 |
| 1 | 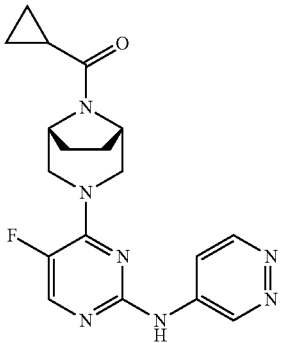 [SMILES: O=C(C1CC1)N1[C@@H]2CC[C@H]1CN(c1nc(Nc3ccnnc3)ncc1F)C2] | 1098 | 2730 | >10000 | >10000 |
| 2 | 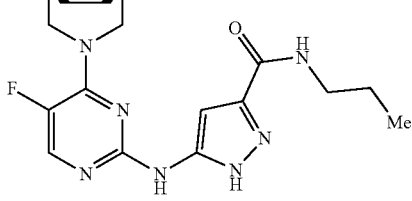 | 432 | 1547 | 4721 | >10000 |
| 3 | 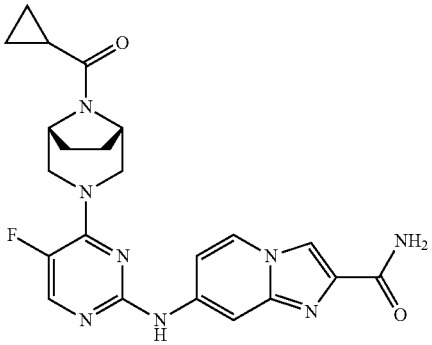 [SMILES: NC(=O)c1cn2ccc(Nc3ncc(F)c(N4C[C@H]5CC[C@@H](C4)N5C(=O)C4CC4)n3)cc2n1] | 128 | 215 | 1974 | >10000 |
| 4 | 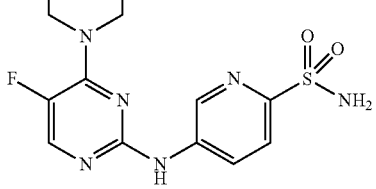 | 176 | 659 | 2885 | >10000 |

-continued
| Ex. No. | Structure | IC$_{50}$ (nM) | | | |
|---|---|---|---|---|---|
| | | TYK2 | JAK1 | JAK2 | JAK3 |
| 5 | 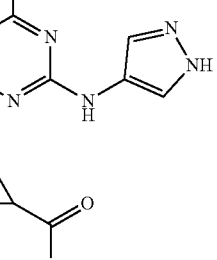 | 41 | 41 | 477 | >10000 |
| 6 | 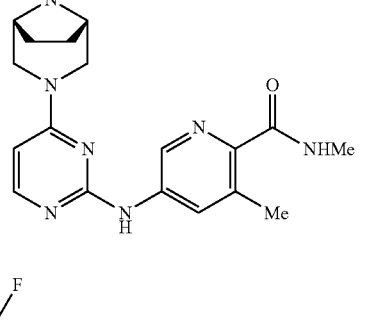 | 36 | 337 | 754 | >10000 |
| 7 | 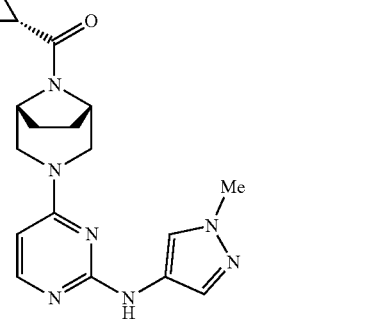 | 23 | 17 | 77 | 6494 |
| 8 | 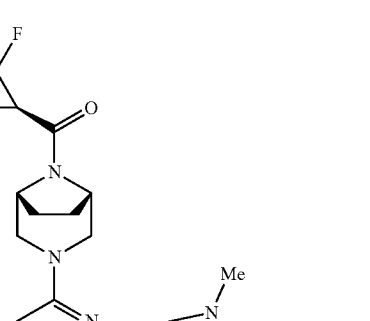 | 702 | 842 | 3148 | >10000 |

-continued
| Ex. No. | Structure | IC$_{50}$ (nM) | | | |
|---|---|---|---|---|---|
| | | TYK2 | JAK1 | JAK2 | JAK3 |
| 9 | 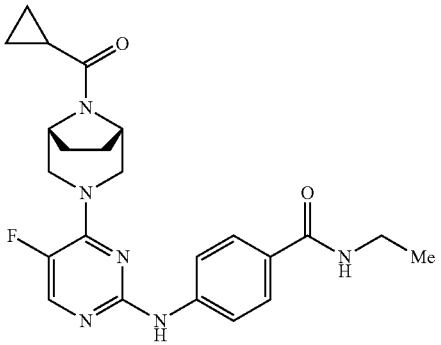 [SMILES: CCNC(=O)c1ccc(Nc2ncc(F)c(N3C[C@H]4CC[C@@H](C3)N4C(=O)C3CC3)n2)cc1] | 4 | 20 | 112 | 1661 |
| 10 | 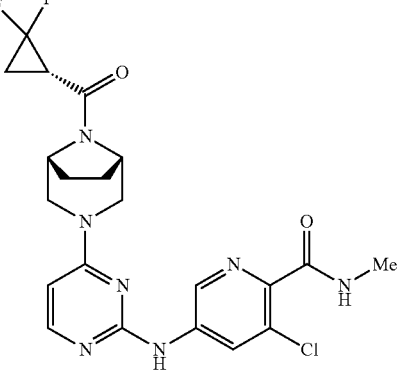 | 22 | 171 | 367 | >10000 |
| 11 | 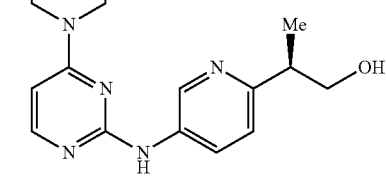 | 40 | 139 | 141 | >10000 |
| 12 | 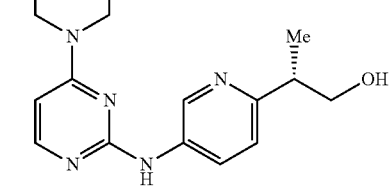 | 28 | 79 | 80 | >10000 |

-continued
| Ex. No. | Structure | IC₅₀ (nM) | | | |
|---|---|---|---|---|---|
| | | TYK2 | JAK1 | JAK2 | JAK3 |
| 13 | 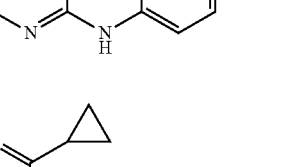 | 12 | 41 | 199 | >10000 |
| 14 | 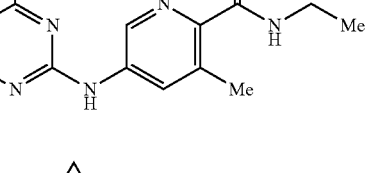 | 79 | 757 | 745 | >10000 |
| 15 | 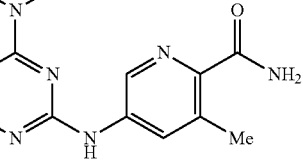 | 84 | 588 | 855 | >10000 |
| 16 | 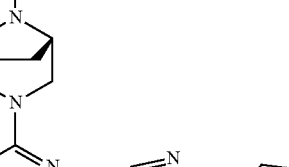 | 66 | 150 | 421 | >10000 |

-continued

| Ex. No. | Structure | IC$_{50}$ (nM) | | | |
|---|---|---|---|---|---|
| | | TYK2 | JAK1 | JAK2 | JAK3 |
| 17 | 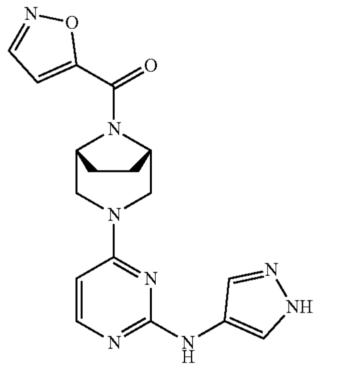 [SMILES: O=C(c1ccno1)N1[C@@H]2CC[C@H]1CN(c1ccnc(Nc3cn[nH]c3)n1)C2] | 242 | 684 | 3375 | >10000 |
| 18 | 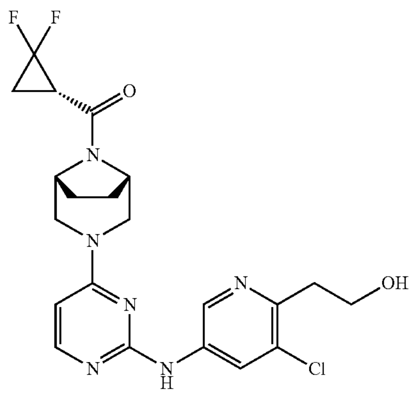 [SMILES: O=C([C@@H]1CC1(F)F)N1[C@@H]2CC[C@H]1CN(c1ccnc(Nc3cnc(CCO)c(Cl)c3)n1)C2] | 62 | 352 | 331 | >10000 |
| 19 | 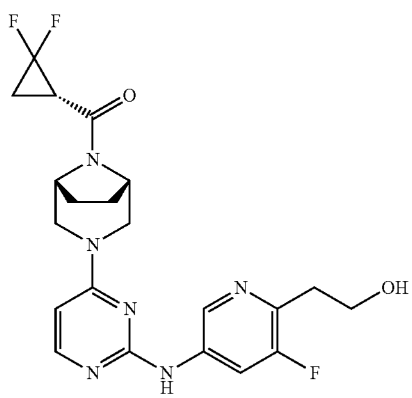 [SMILES: O=C([C@@H]1CC1(F)F)N1[C@@H]2CC[C@H]1CN(c1ccnc(Nc3cnc(CCO)c(F)c3)n1)C2] | 52 | 463 | 402 | >10000 |
| 20 | 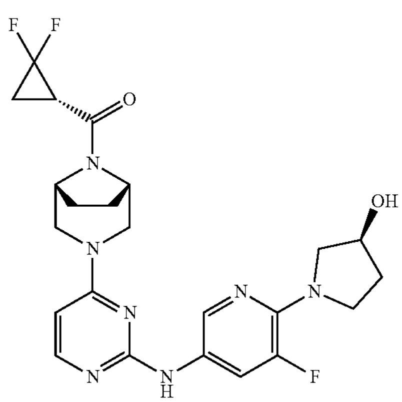 [SMILES: O=C([C@@H]1CC1(F)F)N1[C@@H]2CC[C@H]1CN(c1ccnc(Nc3cnc(N4CC[C@H](O)C4)c(F)c3)n1)C2] | 58 | 314 | 346 | >10000 |

-continued
| Ex. No. | Structure | IC₅₀ (nM) | | | |
|---|---|---|---|---|---|
| | | TYK2 | JAK1 | JAK2 | JAK3 |
| 21 | 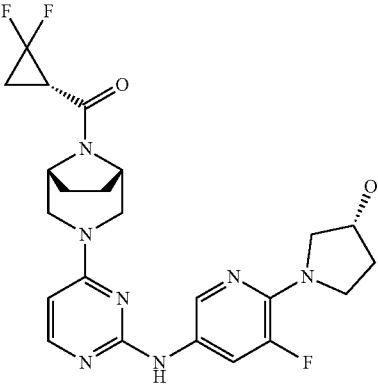 | 95 | 622 | 434 | >10000 |
| 22 | 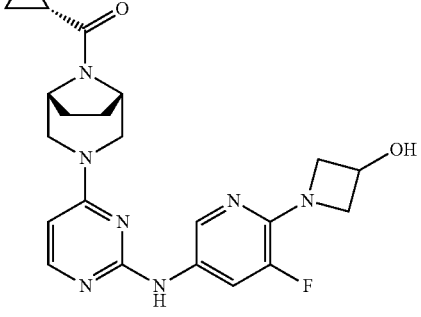 | 55 | 490 | 312 | >10000 |
| 23 | 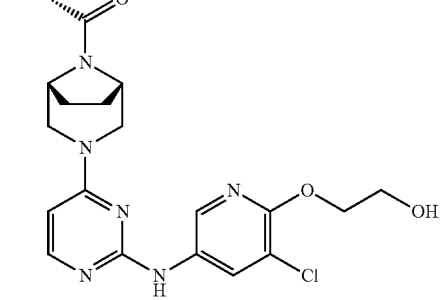 | 58 | 258 | 498 | >10000 |
| 24 | 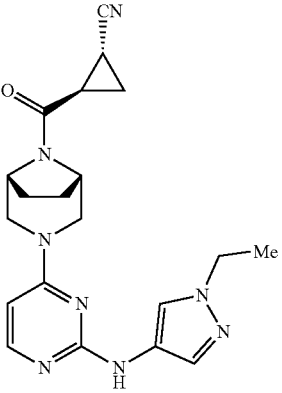 [SMILES: CCn1cc(Nc2nccc(N3C[C@H]4CC[C@@H](C3)N4C(=O)[C@@H]3C[C@H]3C#N)n2)cn1] | 32 | 13 | 67 | 4987 |

-continued
| Ex. No. | Structure | IC$_{50}$ (nM) | | | |
|---|---|---|---|---|---|
| | | TYK2 | JAK1 | JAK2 | JAK3 |
| 25 | 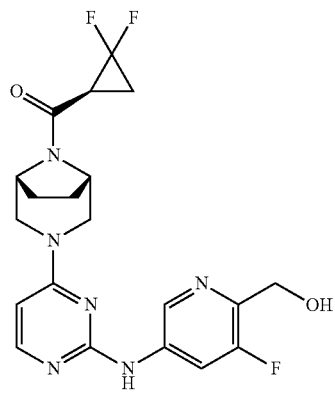 [SMILES: O=C([C@@H]1CC1(F)F)N1[C@@H]2CC[C@H]1CN(c1ccnc(Nc3cnc(CO)c(F)c3)n1)C2] | 34 | 317 | 468 | >10000 |
| 26 | 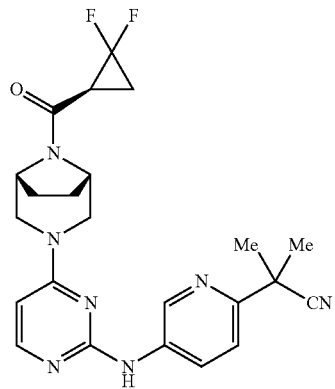 [SMILES: CC(C)(C#N)c1ccc(Nc2nccc(N3C[C@H]4CC[C@@H](C3)N4C(=O)[C@@H]3CC3(F)F)n2)cn1] | 25 | 60 | 192 | >10000 |
| 27 | 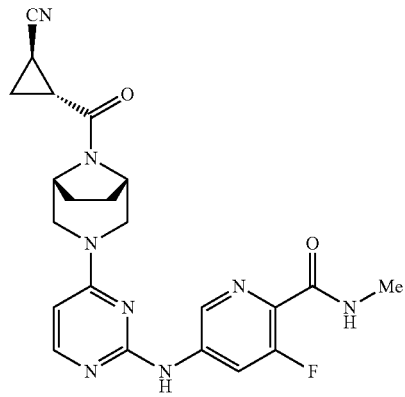 [SMILES: CNC(=O)c1ncc(Nc2nccc(N3C[C@H]4CC[C@@H](C3)N4C(=O)[C@@H]3C[C@H]3C#N)n2)cc1F] | 61 | 78 | 640 | >10000 |

-continued

| Ex. No. | Structure | IC$_{50}$ (nM) | | | |
|---|---|---|---|---|---|
| | | TYK2 | JAK1 | JAK2 | JAK3 |
| 28 | | 736 | 1371 | 8152 | >10000 |
| 29 | | 31 | 131 | 487 | >10000 |
| 30 | | 97 | 1156 | 2126 | >10000 |
| 31 | | 32 | 78 | 401 | >10000 |

-continued
| Ex. No. | Structure | IC$_{50}$ (nM) | | | |
|---|---|---|---|---|---|
| | | TYK2 | JAK1 | JAK2 | JAK3 |
| 32 | 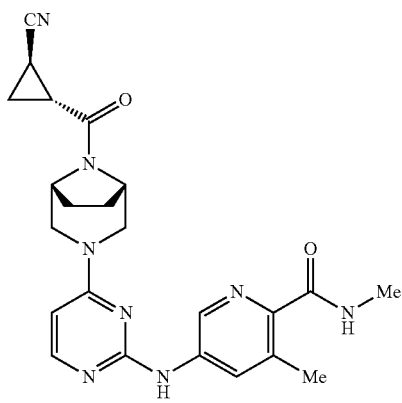 [SMILES: CNC(=O)c1ncc(Nc2nccc(N3C[C@H]4CC[C@@H](C3)N4C(=O)[C@@H]3C[C@H]3C#N)n2)cc1C] | 17 | 28 | 140 | >10000 |
| 33 | 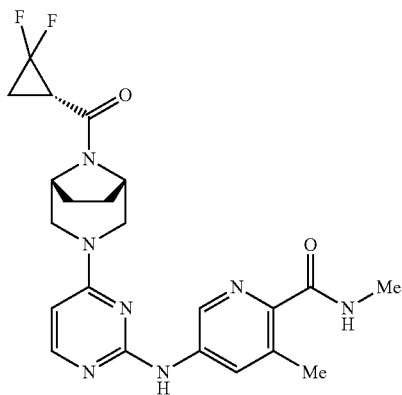 [SMILES: CNC(=O)c1ncc(Nc2nccc(N3C[C@H]4CC[C@@H](C3)N4C(=O)[C@@H]3CC3(F)F)n2)cc1C] | 15 | 62 | 116 | 9276 |
| 34 | 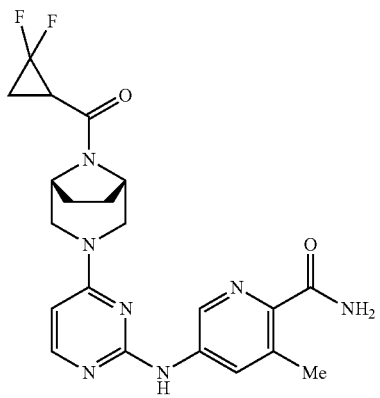 [SMILES: Cc1cc(Nc2nccc(N3C[C@H]4CC[C@@H](C3)N4C(=O)C3CC3(F)F)n2)cnc1C(N)=O] | 36 | 152 | 377 | >10000 |

| Ex. No. | Structure | IC$_{50}$ (nM) | | | |
|---|---|---|---|---|---|
| | | TYK2 | JAK1 | JAK2 | JAK3 |
| 35 | 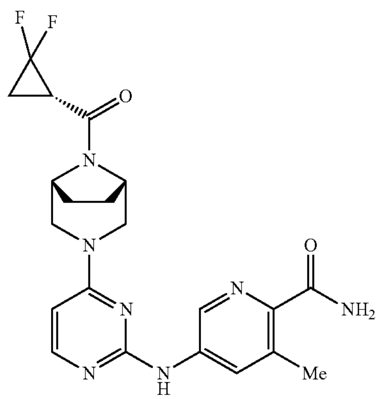 [SMILES: Cc1cc(Nc2nccc(N3C[C@H]4CC[C@@H](C3)N4C(=O)[C@@H]3CC3(F)F)n2)cnc1C(N)=O] | 23 | 170 | 337 | >10000 |
| 36 | 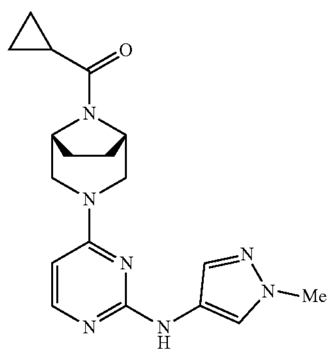 [SMILES: Cn1cc(Nc2nccc(N3C[C@H]4CC[C@@H](C3)N4C(=O)C3CC3)n2)cn1] | 76 | 199 | 684 | >10000 |
| 37 | 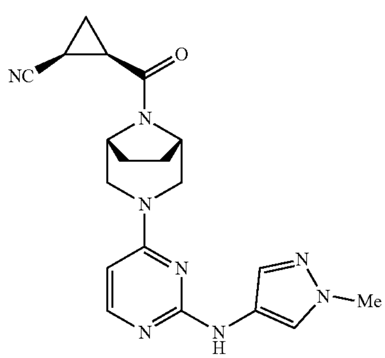 [SMILES: Cn1cc(Nc2nccc(N3C[C@H]4CC[C@@H](C3)N4C(=O)[C@@H]3C[C@@H]3C#N)n2)cn1] | 250 | 467 | 1398 | 8306 |
| 38 | 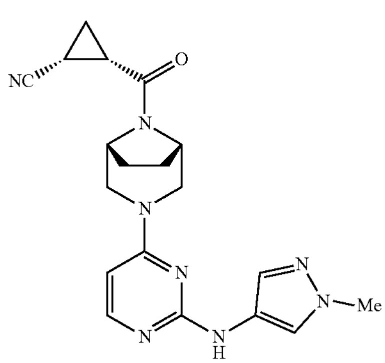 [SMILES: Cn1cc(Nc2nccc(N3C[C@H]4CC[C@@H](C3)N4C(=O)[C@H]3C[C@H]3C#N)n2)cn1] | 427 | 707 | 2328 | >10000 |

-continued
| Ex. No. | Structure | IC$_{50}$ (nM) | | | |
|---|---|---|---|---|---|
| | | TYK2 | JAK1 | JAK2 | JAK3 |
| 39 | 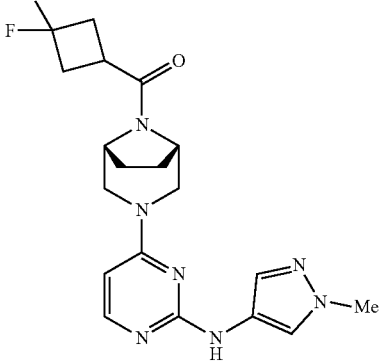 | 136 | 305 | 1171 | >10000 |
| 40 | 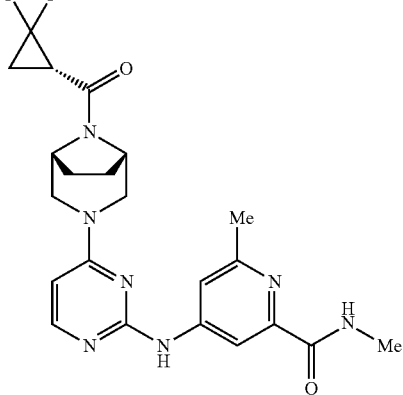 | 70 | 369 | 189 | >10000 |
| 41 | 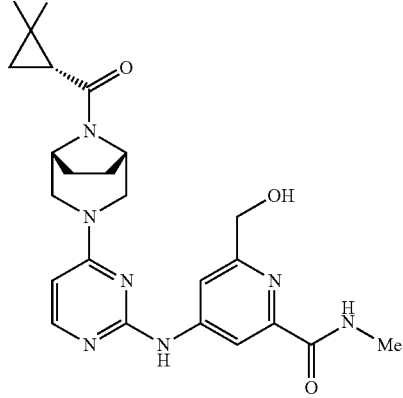 | 84 | 201 | 279 | >10000 |

-continued

| Ex. No. | Structure | IC$_{50}$ (nM) | | | |
|---|---|---|---|---|---|
| | | TYK2 | JAK1 | JAK2 | JAK3 |
| 42 | 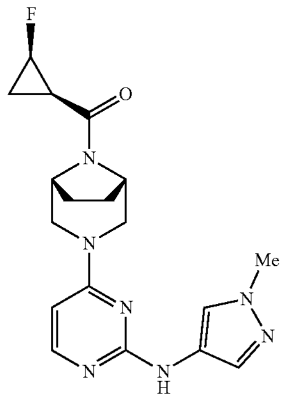 [SMILES: Cn1cc(Nc2nccc(N3C[C@H]4CC[C@@H](C3)N4C(=O)[C@H]3C[C@H]3F)n2)cn1] | 437 | 717 | 2459 | >10000 |
| 43 | 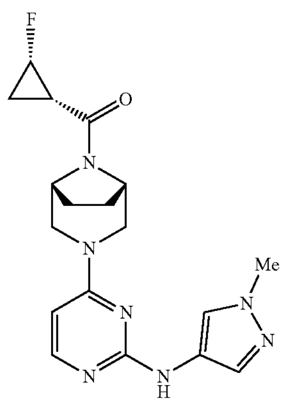 [SMILES: Cn1cc(Nc2nccc(N3C[C@H]4CC[C@@H](C3)N4C(=O)[C@@H]3C[C@@H]3F)n2)cn1] | 474 | 902 | 2842 | >10000 |
| 44 | 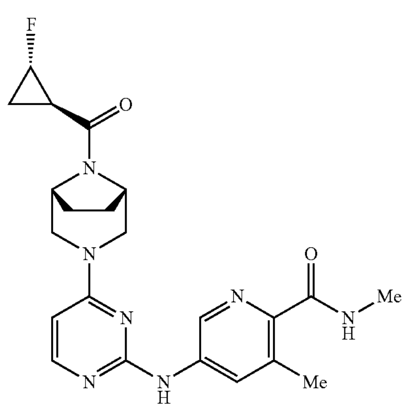 [SMILES: CNC(=O)c1ncc(Nc2nccc(N3C[C@H]4CC[C@@H](C3)N4C(=O)[C@H]3C[C@@H]3F)n2)cc1C] | 72 | 475 | 854 | >10000 |

-continued
| Ex. No. | Structure | IC₅₀ (nM) | | | |
|---|---|---|---|---|---|
| | | TYK2 | JAK1 | JAK2 | JAK3 |
| 45 | 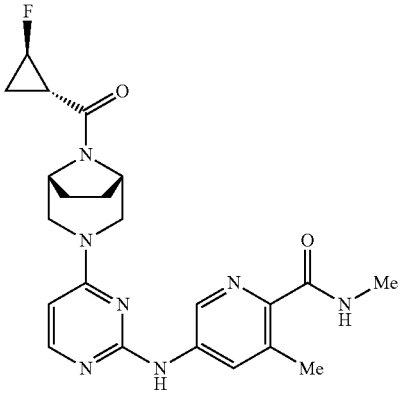 | 17 | 46 | 100 | 7402 |
| 46 | 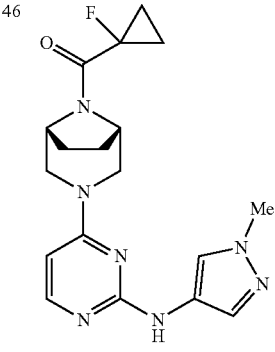 | 84 | 173 | 526 | 4158 |
| 47 | 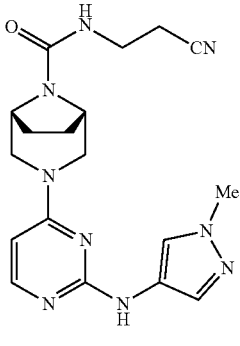 [SMILES: Cn1cc(Nc2nccc(N3C[C@H]4CC[C@@H](C3)N4C(=O)NCCC#N)n2)cn1] | 65 | 42 | 262 | >10000 |
| 48 | 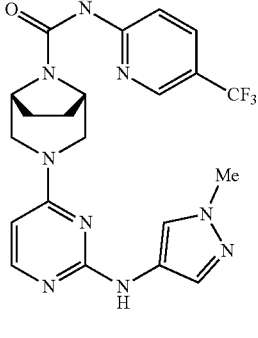 | 964 | 300 | 2508 | >10000 |

-continued

| Ex. No. | Structure | IC₅₀ (nM) | | | |
|---|---|---|---|---|---|
| | | TYK2 | JAK1 | JAK2 | JAK3 |
| 49 | 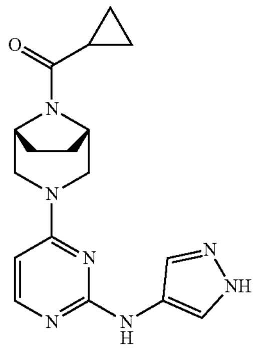 [SMILES: O=C(C1CC1)N1[C@@H]2CC[C@H]1CN(c1ccnc(Nc3cn[nH]c3)n1)C2] | 49 | 77 | 614 | >10000 |
| 50 | 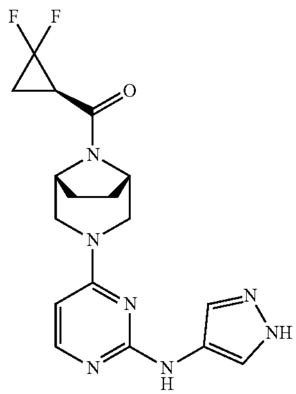 [SMILES: O=C([C@H]1CC1(F)F)N1[C@@H]2CC[C@H]1CN(c1ccnc(Nc3cn[nH]c3)n1)C2] | 436 | 478 | 3418 | >10000 |
| 51 | 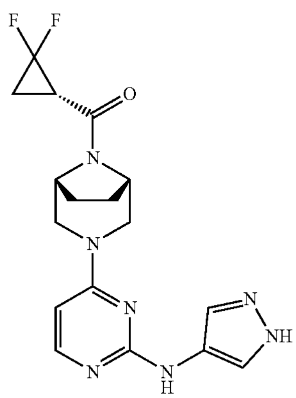 [SMILES: O=C([C@@H]1CC1(F)F)N1[C@@H]2CC[C@H]1CN(c1ccnc(Nc3cn[nH]c3)n1)C2] | 11 | 13 | 97 | 8611 |
| 52 | 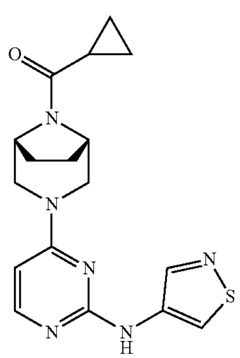 [SMILES: O=C(C1CC1)N1[C@@H]2CC[C@H]1CN(c1ccnc(Nc3cnsc3)n1)C2] | 93 | 172 | 1241 | >10000 |

-continued

| Ex. No. | Structure | IC₅₀ (nM) | | | |
|---|---|---|---|---|---|
| | | TYK2 | JAK1 | JAK2 | JAK3 |
| 53 | 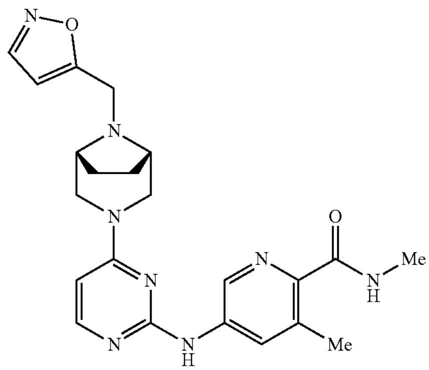 [SMILES: CNC(=O)c1ncc(Nc2nccc(N3C[C@H]4CC[C@@H](C3)N4Cc3ccno3)n2)cc1C] | 24 | 226 | 375 | >10000 |
| 54 | 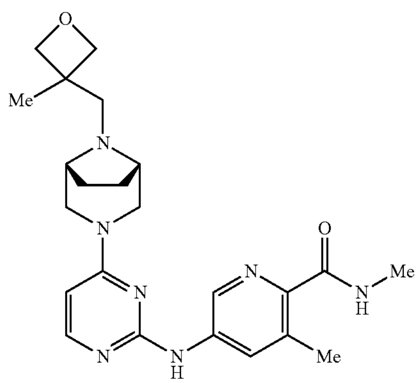 [SMILES: CNC(=O)c1ncc(Nc2nccc(N3C[C@H]4CC[C@@H](C3)N4CC3(C)COC3)n2)cc1C] | 8 | 19 | 29 | 4292 |
| 55 | 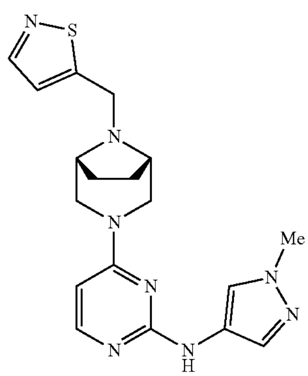 | 23 | 35 | 221 | 8615 |
| 56 | 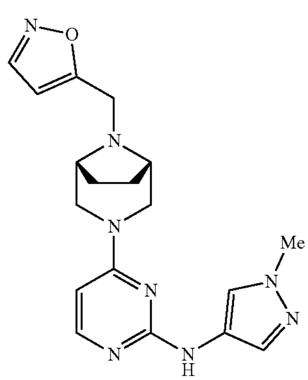 [SMILES: Cn1cc(Nc2nccc(N3C[C@H]4CC[C@@H](C3)N4Cc3ccno3)n2)cn1] | 41 | 110 | 394 | >10000 |

| Ex. No. | Structure | IC₅₀ (nM) | | | |
|---|---|---|---|---|---|
| | | TYK2 | JAK1 | JAK2 | JAK3 |
| 57 | 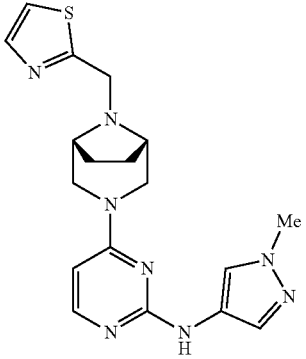 [SMILES: Cn1cc(Nc2nccc(N3C[C@H]4CC[C@@H](C3)N4Cc3nccs3)n2)cn1] | 89 | 294 | 1069 | >10000 |
| 58 | 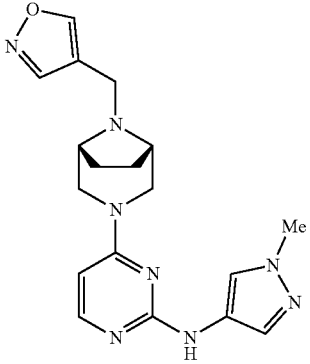 [SMILES: Cn1cc(Nc2nccc(N3C[C@H]4CC[C@@H](C3)N4Cc3cnoc3)n2)cn1] | 73 | 267 | 821 | >10000 |
| 59 | 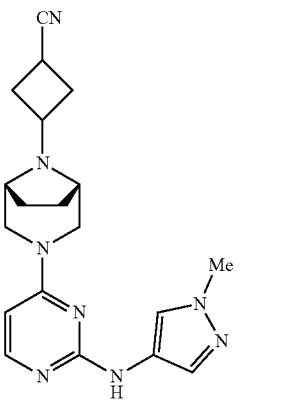 [SMILES: Cn1cc(Nc2nccc(N3C[C@H]4CC[C@@H](C3)N4C3CC(C#N)C3)n2)cn1] | 62 | 78 | 236 | 8798 |
| 60 | 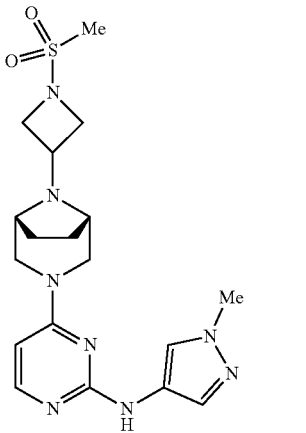 [SMILES: Cn1cc(Nc2nccc(N3C[C@H]4CC[C@@H](C3)N4C3CN(S(C)(=O)=O)C3)n2)cn1] | 70 | 36 | 159 | >10000 |

-continued

| Ex. No. | Structure | IC$_{50}$ (nM) | | | |
|---|---|---|---|---|---|
| | | TYK2 | JAK1 | JAK2 | JAK3 |
| 61 | 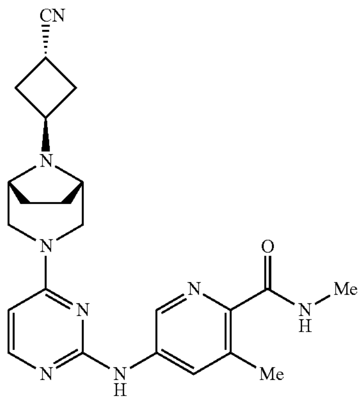 [SMILES: CNC(=O)c1ncc(Nc2nccc(N3C[C@H]4CC[C@@H](C3)N4[C@H]3C[C@H](C#N)C3)n2)cc1C] | 18 | 31 | 44 | 4083 |
| 62 | 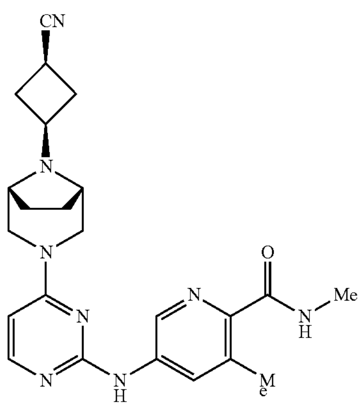 [SMILES: CNC(=O)c1ncc(Nc2nccc(N3C[C@H]4CC[C@@H](C3)N4[C@H]3C[C@@H](C#N)C3)n2)cc1C] | 224 | 1021 | 1387 | >10000 |
| 63 | 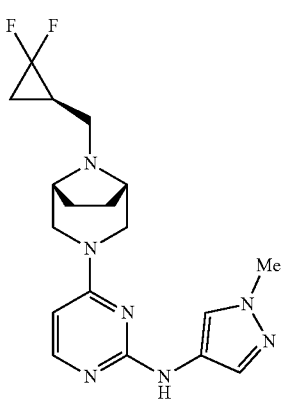 [SMILES: Cn1cc(Nc2nccc(N3C[C@H]4CC[C@@H](C3)N4C[C@H]3CC3(F)F)n2)cn1] | 125 | 303 | 856 | >10000 |

| Ex. No. | Structure | IC$_{50}$ (nM) | | | |
|---|---|---|---|---|---|
| | | TYK2 | JAK1 | JAK2 | JAK3 |
| 64 | 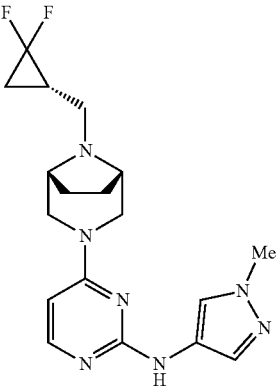 [SMILES: Cn1cc(Nc2nccc(N3C[C@H]4CC[C@@H](C3)N4C[C@@H]3CC3(F)F)n2)cn1] | 41 | 95 | 320 | >10000 |
| 65 | 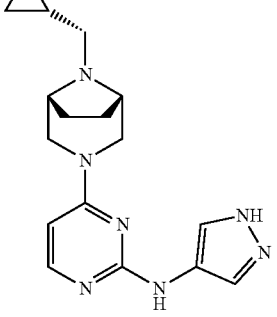 | 22 | 35 | 223 | >10000 |
| 66 | 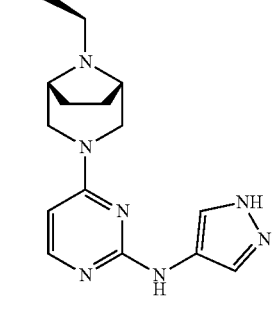 | 65 | 106 | 655 | >10000 |
| 67 | 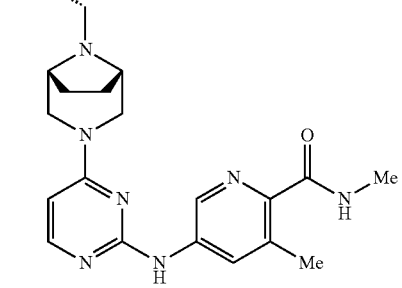 | 108 | 418 | 973 | >10000 |

-continued

| Ex. No. | Structure | IC₅₀ (nM) | | | |
|---|---|---|---|---|---|
| | | TYK2 | JAK1 | JAK2 | JAK3 |
| 68 | 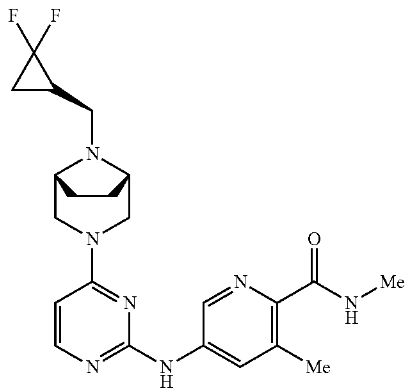 | 22 | 85 | 188 | >10000 |
| 69 | 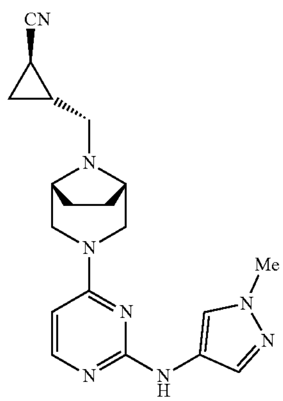 | 811 | 1098 | 5703 | >10000 |
| 70 | 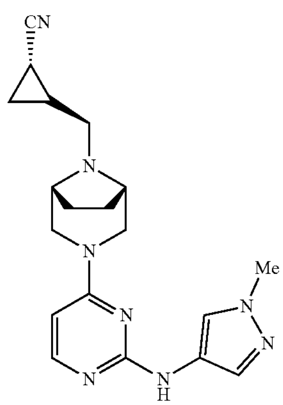 | 261 | 259 | 1541 | >10000 |
| 71 | 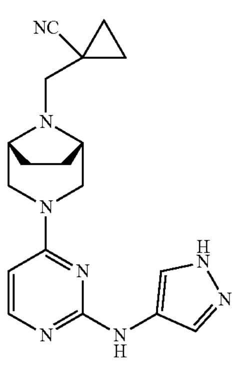 [SMILES: N#CC1(CN2[C@@H]3CC[C@H]2CN(c2ccnc(Nc4cn[nH]c4)n2)C3)CC1] | 152 | 153 | 453 | >10000 |

-continued
| Ex. No. | Structure | IC$_{50}$ (nM) | | | |
|---|---|---|---|---|---|
| | | TYK2 | JAK1 | JAK2 | JAK3 |
| 72 | 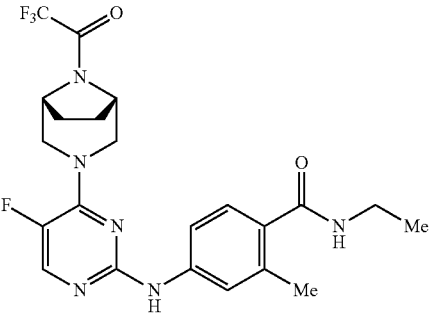 [SMILES: CCNC(=O)c1ccc(Nc2ncc(F)c(N3C[C@H]4CC[C@@H](C3)N4C(=O)C(F)(F)F)n2)cc1C] | 6 | 81 | 151 | 411 |
| 73 | 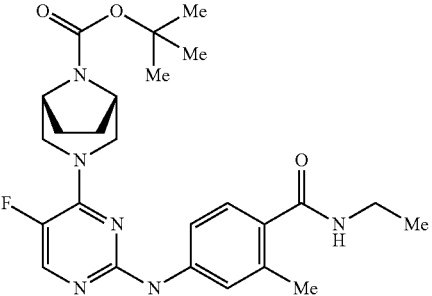 | 17 | 260 | 170 | 1771 |
| 74 | 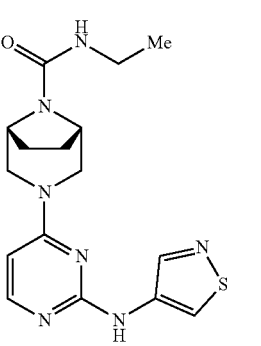 [SMILES: CCNC(=O)N1[C@@H]2CC[C@H]1CN(c1ccnc(Nc3cnsc3)n1)C2] | 65 | 67 | 691 | >10000 |
| 75 | 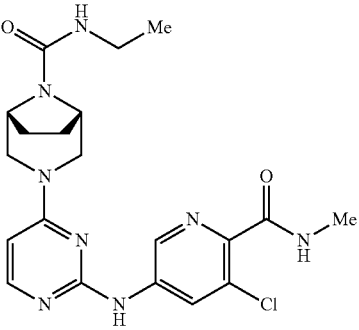 [SMILES: CCNC(=O)N1[C@@H]2CC[C@H]1CN(c1ccnc(Nc3cnc(C(=O)NC)c(Cl)c3)n1)C2] | 66 | 462 | 1289 | >10000 |

-continued

| Ex. No. | Structure | IC₅₀ (nM) | | | |
|---|---|---|---|---|---|
| | | TYK2 | JAK1 | JAK2 | JAK3 |
| 76 | 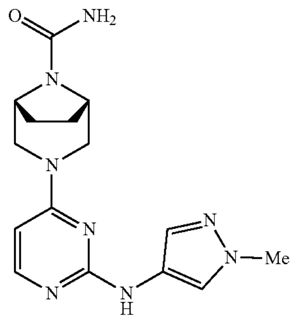 [SMILES: Cn1cc(Nc2nccc(N3C[C@H]4CC[C@@H](C3)N4C(N)=O)n2)cn1] | 662 | 537 | 1476 | >10000 |
| 77 | 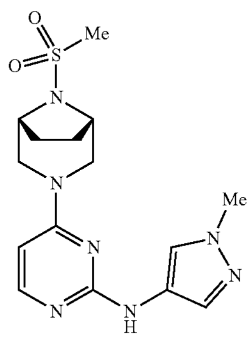 [SMILES: Cn1cc(Nc2nccc(N3C[C@H]4CC[C@@H](C3)N4S(C)(=O)=O)n2)cn1] | 256 | 380 | 653 | >10000 |
| 78 | 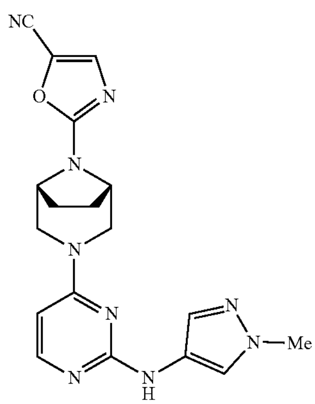 [SMILES: Cn1cc(Nc2nccc(N3C[C@H]4CC[C@@H](C3)N4c3ncc(C#N)o3)n2)cn1] | 63 | 68 | 461 | >10000 |
| 79 | 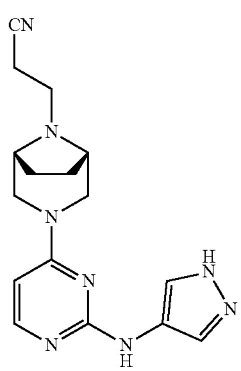 [SMILES: N#CCCN1[C@@H]2CC[C@H]1CN(c1ccnc(Nc3cn[nH]c3)n1)C2] | 34 | 38 | 406 | 8425 |

-continued

| Ex. No. | Structure | IC$_{50}$ (nM) | | | |
|---|---|---|---|---|---|
| | | TYK2 | JAK1 | JAK2 | JAK3 |
| 80 | 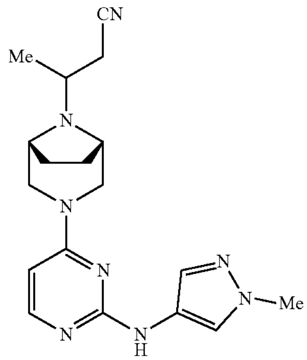 [SMILES: CC(CC#N)N1[C@@H]2CC[C@H]1CN(c1ccnc(Nc3cnn(C)c3)n1)C2] | 79 | 190 | 436 | >10000 |
| 81 | 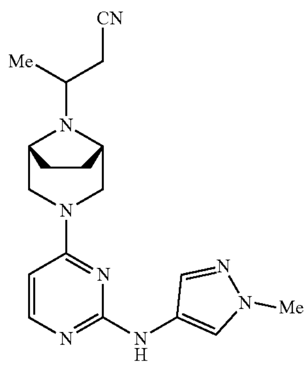 [SMILES: CC(CC#N)N1[C@@H]2CC[C@H]1CN(c1ccnc(Nc3cnn(C)c3)n1)C2] | 199 | 405 | 603 | >10000 |
| 82 | 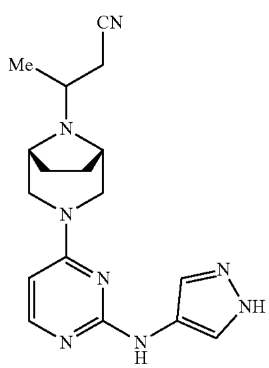 [SMILES: CC(CC#N)N1[C@@H]2CC[C@H]1CN(c1ccnc(Nc3cn[nH]c3)n1)C2] | 79 | 135 | 473 | >10000 |
| 83 | 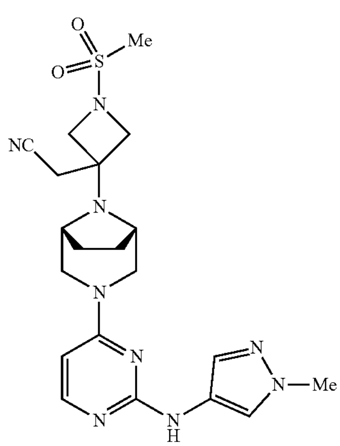 [SMILES: Cn1cc(Nc2nccc(N3C[C@H]4CC[C@@H](C3)N4C3(CC#N)CN(S(C)(=O)=O)C3)n2)cn1] | 11 | 7 | 21 | 1239 |

-continued

| Ex. No. | Structure | IC$_{50}$ (nM) | | | |
|---|---|---|---|---|---|
| | | TYK2 | JAK1 | JAK2 | JAK3 |
| 84 | 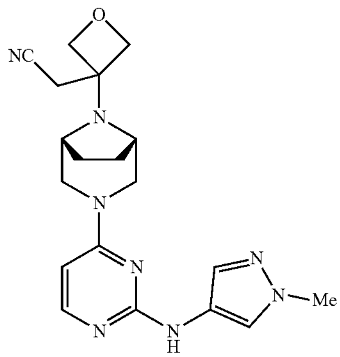 [SMILES: Cn1cc(Nc2nccc(N3C[C@H]4CC[C@@H](C3)N4C3(CC#N)COC3)n2)cn1] | 62 | 141 | 155 | >10000 |
| 85 | 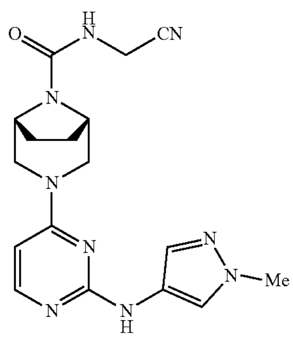 [SMILES: Cn1cc(Nc2nccc(N3C[C@H]4CC[C@@H](C3)N4C(=O)NCC#N)n2)cn1] | 16 | 13 | 67 | 2477 |
| 86 | 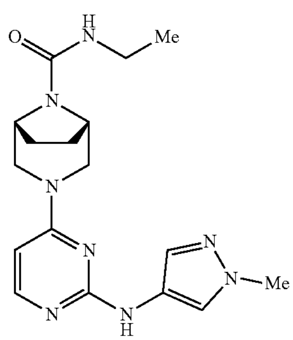 [SMILES: CCNC(=O)N1[C@@H]2CC[C@H]1CN(c1ccnc(Nc3cnn(C)c3)n1)C2] | 71 | 104 | 538 | >10000 |
| 87 | 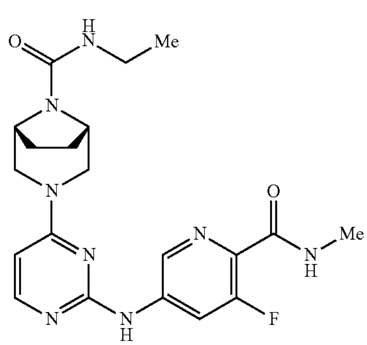 [SMILES: CCNC(=O)N1[C@@H]2CC[C@H]1CN(c1ccnc(Nc3cnc(C(=O)NC)c(F)c3)n1)C2] | 93 | 337 | 1787 | >10000 |

-continued

| Ex. No. | Structure | IC₅₀ (nM) | | | |
|---|---|---|---|---|---|
| | | TYK2 | JAK1 | JAK2 | JAK3 |
| 88 | 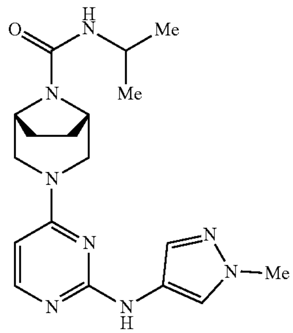 [SMILES: CC(C)NC(=O)N1[C@@H]2CC[C@H]1CN(c1ccnc(Nc3cnn(C)c3)n1)C2] | 110 | 165 | 894 | >10000 |
| 89 | 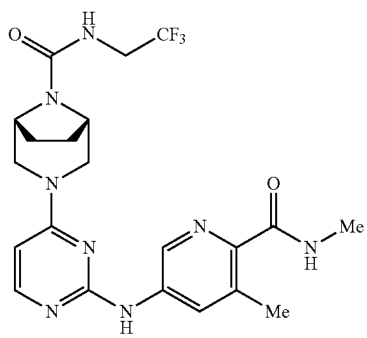 [SMILES: CNC(=O)c1ncc(Nc2nccc(N3C[C@H]4CC[C@@H](C3)N4C(=O)NCC(F)(F)F)n2)cc1C] | 9 | 10 | 65 | 4426 |
| 90 | 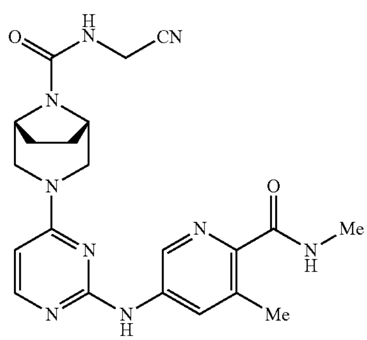 [SMILES: CNC(=O)c1ncc(Nc2nccc(N3C[C@H]4CC[C@@H](C3)N4C(=O)NCC#N)n2)cc1C] | 14 | 17 | 76 | 4168 |
| 91 | 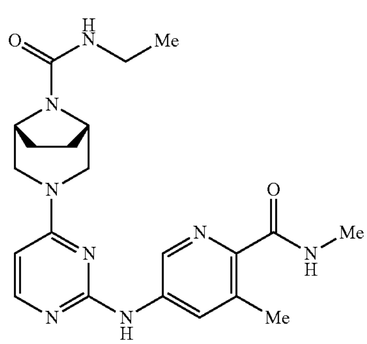 [SMILES: CCNC(=O)N1[C@@H]2CC[C@H]1CN(c1ccnc(Nc3cnc(C(=O)NC)c(C)c3)n1)C2] | 39 | 183 | 513 | >10000 |

| Ex. No. | Structure | IC$_{50}$ (nM) | | | |
|---|---|---|---|---|---|
| | | TYK2 | JAK1 | JAK2 | JAK3 |
| 92 | 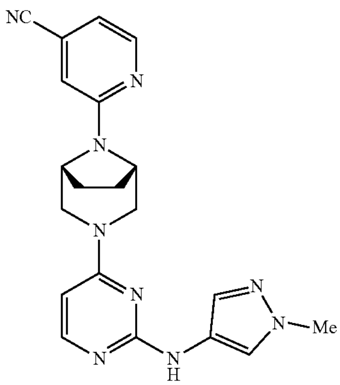 [SMILES: Cn1cc(Nc2nccc(N3C[C@H]4CC[C@@H](C3)N4c3cc(C#N)ccn3)n2)cn1] | 62 | 52 | 264 | 6564 |
| 93 | 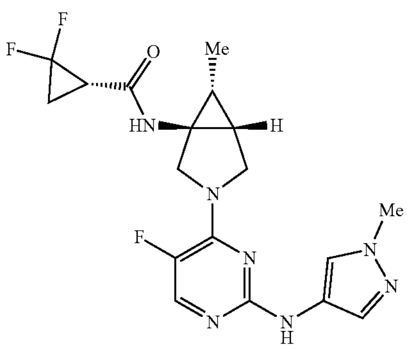 [SMILES: C[C@@H]1[C@@H]2CN(c3nc(Nc4cnn(C)c4)ncc3F)C[C@]12NC(=O)[C@@H]1CC1(F)F] | 28 | 41 | 652 | 4267 |
| 94 | 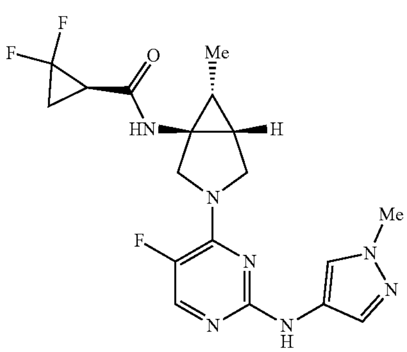 [SMILES: C[C@@H]1[C@@H]2CN(c3nc(Nc4cnn(C)c4)ncc3F)C[C@]12NC(=O)[C@H]1CC1(F)F] | 56 | 113 | 1132 | 4023 |
| 95 | 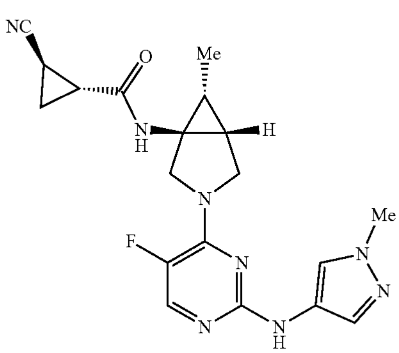 [SMILES: C[C@@H]1[C@@H]2CN(c3nc(Nc4cnn(C)c4)ncc3F)C[C@]12NC(=O)[C@@H]1C[C@H]1C#N] | 35 | 11 | 228 | 255 |

| Ex. No. | Structure | IC₅₀ (nM) | | | |
|---|---|---|---|---|---|
| | | TYK2 | JAK1 | JAK2 | JAK3 |
| 96 | 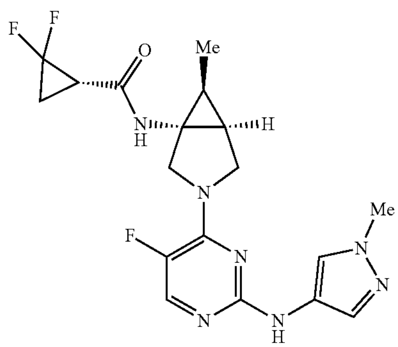 [SMILES: C[C@H]1[C@H]2CN(c3nc(Nc4cnn(C)c4)ncc3F)C[C@]21NC(=O)[C@@H]1CC1(F)F] | 924 | 684 | 2676 | >10000 |
| 97 | 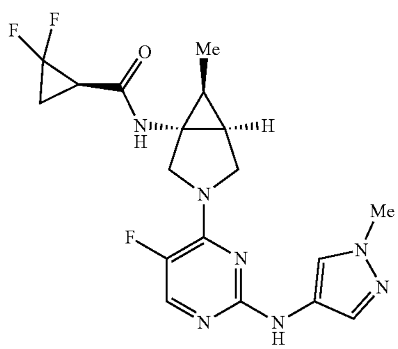 [SMILES: C[C@H]1[C@H]2CN(c3nc(Nc4cnn(C)c4)ncc3F)C[C@]21NC(=O)[C@H]1CC1(F)F] | 588 | 672 | 1883 | 9970 |
| 98 | 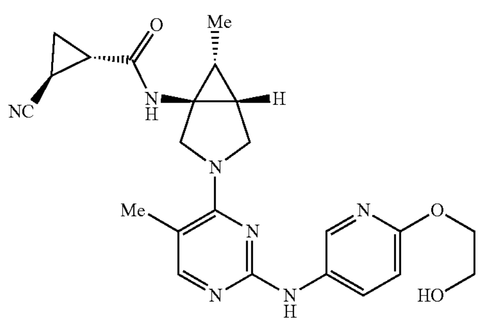 [SMILES: Cc1cnc(Nc2ccc(OCCO)nc2)nc1N1C[C@H]2[C@@H](C)[C@@]2(NC(=O)[C@H]2C[C@@H]2C#N)C1] | 19 | 13 | 147 | 2599 |
| 99 | 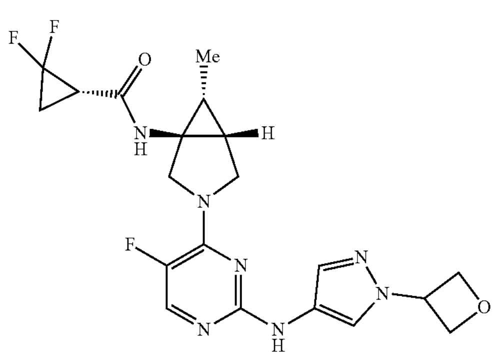 [SMILES: C[C@@H]1[C@@H]2CN(c3nc(Nc4cnn(C5COC5)c4)ncc3F)C[C@]12NC(=O)[C@@H]1CC1(F)F] | 26 | 65 | 391 | 4937 |

| Ex. No. | Structure | IC$_{50}$ (nM) | | | |
|---|---|---|---|---|---|
| | | TYK2 | JAK1 | JAK2 | JAK3 |
| 100 | 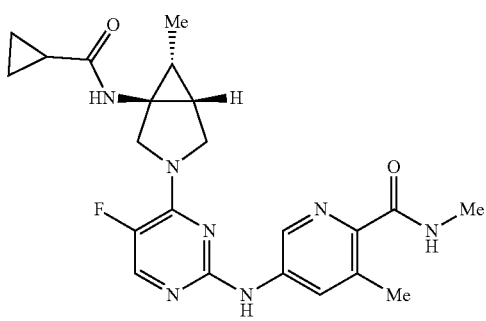 [SMILES: CNC(=O)c1ncc(Nc2ncc(F)c(N3C[C@H]4[C@@H](C)[C@@]4(NC(=O)C4CC4)C3)n2)cc1C] | 97 | 965 | 4253 | >10000 |
| 101 | 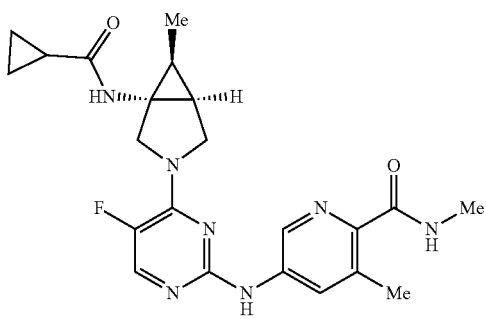 [SMILES: CNC(=O)c1ncc(Nc2ncc(F)c(N3C[C@@H]4[C@H](C)[C@]4(NC(=O)C4CC4)C3)n2)cc1C] | 663 | 1881 | 2908 | >10000 |
| 102 | 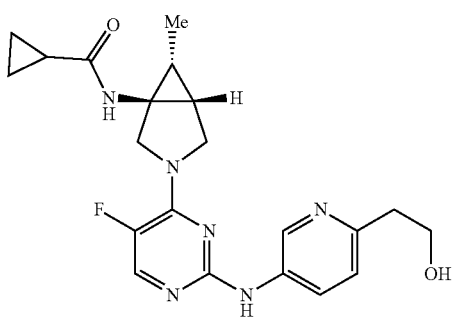 [SMILES: C[C@@H]1[C@@H]2CN(c3nc(Nc4ccc(CCO)nc4)ncc3F)C[C@]12NC(=O)C1CC1] | 252 | 2076 | 6872 | >10000 |
| 103 | 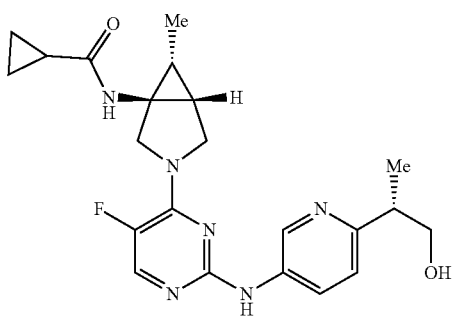 [SMILES: C[C@H](CO)c1ccc(Nc2ncc(F)c(N3C[C@H]4[C@@H](C)[C@@]4(NC(=O)C4CC4)C3)n2)cn1] | 150 | 1738 | 3465 | >10000 |

-continued

| Ex. No. | Structure | IC$_{50}$ (nM) | | | |
| --- | --- | --- | --- | --- | --- |
| | | TYK2 | JAK1 | JAK2 | JAK3 |
| 104 | 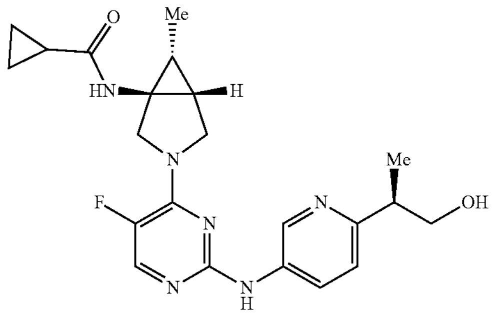 [SMILES: C[C@@H]1[C@@H]2CN(c3nc(Nc4ccc([C@@H](C)CO)nc4)ncc3F)C[C@]12NC(=O)C1CC1] | 86 | 1150 | 3127 | >10000 |
| 105 | 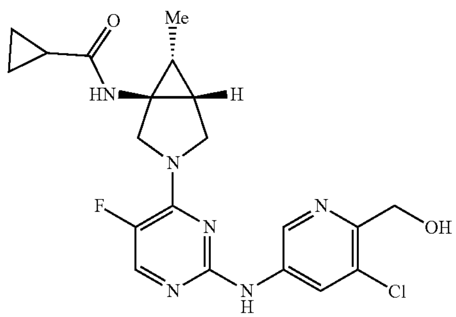 [SMILES: C[C@@H]1[C@@H]2CN(c3nc(Nc4cnc(CO)c(Cl)c4)ncc3F)C[C@]12NC(=O)C1CC1] | 152 | 1569 | 6100 | >10000 |
| 106 | 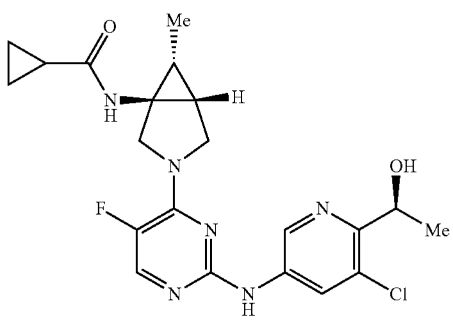 [SMILES: C[C@H](O)c1ncc(Nc2ncc(F)c(N3C[C@H]4[C@@H](C)[C@@]4(NC(=O)C4CC4)C3)n2)cc1Cl] | 229 | 2297 | 9412 | >10000 |
| 107 | 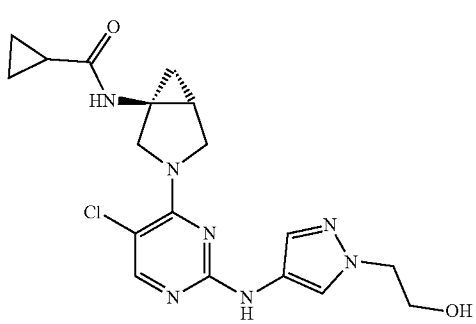 | 21 | 19 | 177 | 1883 |

-continued

| Ex. No. | Structure | IC$_{50}$ (nM) | | | |
|---|---|---|---|---|---|
| | | TYK2 | JAK1 | JAK2 | JAK3 |
| 108 | 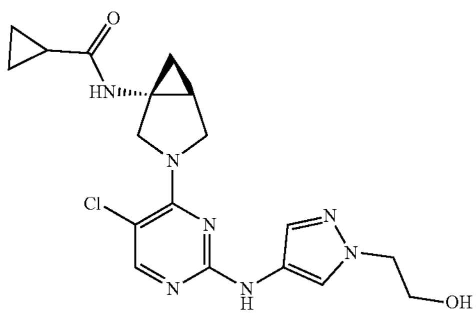 | 675 | 323 | 1491 | 3964 |
| 109 | 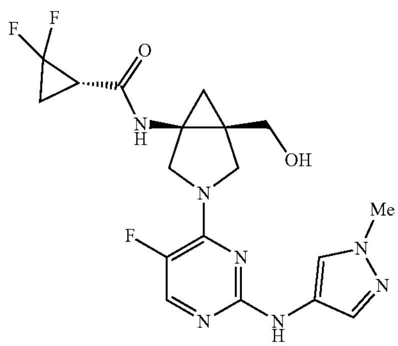 [SMILES: Cn1cc(Nc2ncc(F)c(N3C[C@@]4(CO)C[C@@]4(NC(=O)[C@@H]4CC4(F)F)C3)n2)cn1] | 51 | 211 | 2337 | >10000 |
| 110 | 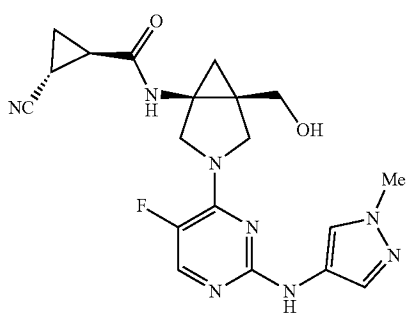 [SMILES: Cn1cc(Nc2ncc(F)c(N3C[C@@]4(CO)C[C@@]4(NC(=O)[C@@H]4C[C@H]4C#N)C3)n2)cn1] | 58 | 29 | 455 | 928 |
| 111 | 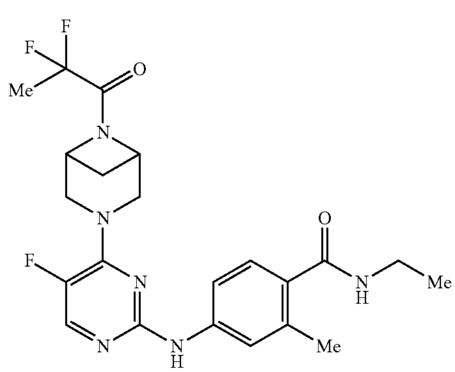 [SMILES: CCNC(=O)c1ccc(Nc2ncc(F)c(N3CC4CC(C3)N4C(=O)C(C)(F)F)n2)cc1C] | 56 | 1691 | 2214 | 4867 |

-continued

| Ex. No. | Structure | IC$_{50}$ (nM) | | | |
|---|---|---|---|---|---|
| | | TYK2 | JAK1 | JAK2 | JAK3 |
| 112 | 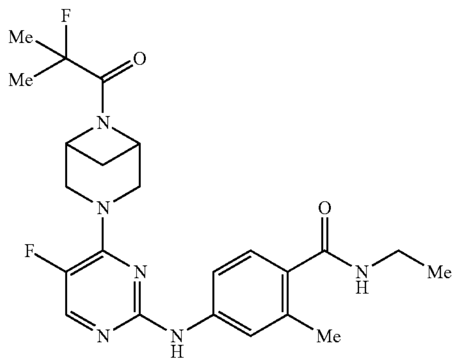 [SMILES: CCNC(=O)c1ccc(Nc2ncc(F)c(N3CC4CC(C3)N4C(=O)C(C)(C)F)n2)cc1C] | 21 | 4068 | 3037 | >10000 |
| 113 | 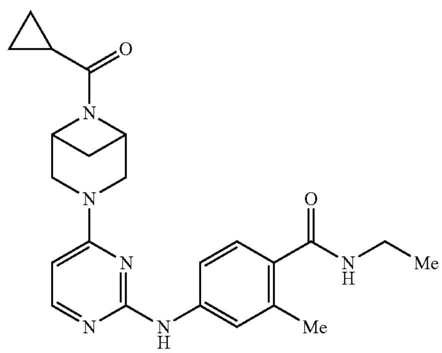 [SMILES: CCNC(=O)c1ccc(Nc2nccc(N3CC4CC(C3)N4C(=O)C3CC3)n2)cc1C] | 82 | 8584 | 7865 | >10000 |
| 114 | 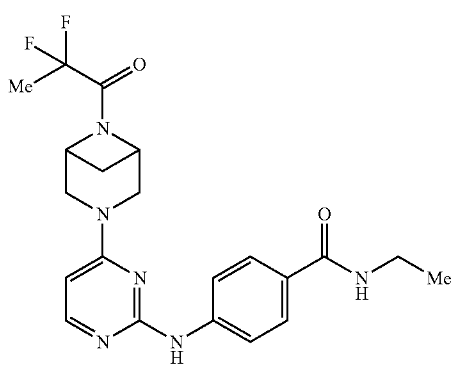 [SMILES: CCNC(=O)c1ccc(Nc2nccc(N3CC4CC(C3)N4C(=O)C(C)(F)F)n2)cc1] | 62 | 955 | 1855 | >10000 |
| 115 | 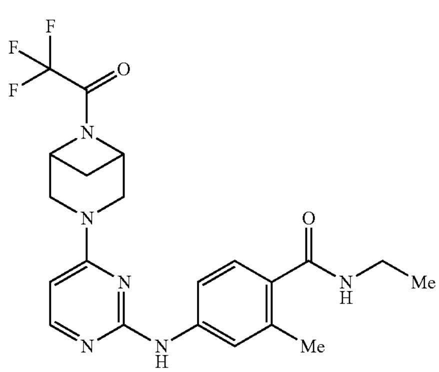 [SMILES: CCNC(=O)c1ccc(Nc2nccc(N3CC4CC(C3)N4C(=O)C(F)(F)F)n2)cc1C] | 64 | 3790 | 3309 | >10000 |

| Ex. No. | Structure | IC$_{50}$ (nM) | | | |
|---|---|---|---|---|---|
| | | TYK2 | JAK1 | JAK2 | JAK3 |
| 116 | 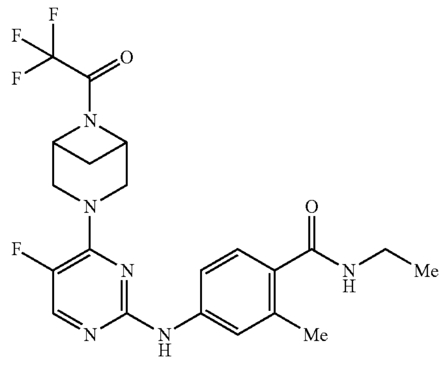 [SMILES: CCNC(=O)c1ccc(Nc2ncc(F)c(N3CC4CC(C3)N4C(=O)C(F)(F)F)n2)cc1C] | 20 | 1469 | 1911 | 9819 |
| 117 | 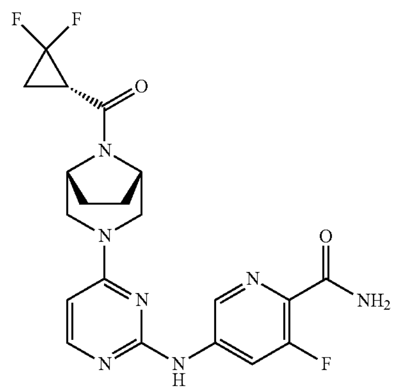 [SMILES: NC(=O)c1ncc(Nc2nccc(N3C[C@H]4CC[C@@H](C3)N4C(=O)[C@@H]3CC3(F)F)n2)cc1F] | 32 | 114 | 452 | >10000 |

2. Selected compounds were assessed for their ability to inhibit interferon alpha signalling in a human whole blood flow cytometry assay. Intereron alpha signals through TYK2 and JAK1.

Human Whole Blood INFα Induced STAT3 Phosphorylation Assay

Test articles were prepared as 30 mM stocks in DMSO. A 11-point 2.5 dilution series was created in DMSO with a top concentration of 5 mM. Further dilution was done by adding 4 μL of the above test article solutions into 96 μL of PBS with a top concentration of 200 μM. Human whole blood was collected from healthy donors via vein puncture into Vacutainer collection tubes containing sodium heparin (Catalog No. 366480; Becton Dickinson, Franklin Lakes, N.J.). Blood was warmed to 37° C. prior to use. Human whole blood was aliquoted (90 μL/well) in 96-well, deep-well, V-bottom plates and treated with compounds at 11 different concentrations (0.2% DMSO final) at 37° C. for 60 minutes. This was followed by a challenge with IFNα (5 μL/well; final, 5000 U/Ml) for 15 minutes. Samples were treated with warm 1× Lyse/Fix buffer (700 μL/well) to terminate activation and further incubated at 37° C. for 20 minutes to lyse red blood cells. Plates were centrifuged at 300×g for 5 minutes, supernatant was aspirated, and cells were washed with 800 μL per well of staining buffer. The washed cell pellets were resuspended with 350 μL per well of pre-chilled 90% methanol, and incubated on ice for 30 minutes. After the removal of 90% methanol, cells were washed once with staining buffer (800 μL/well). Cell pellets were resuspended in staining buffer containing anti-pSTAT3-AlexaFluor647 (1 to 150 dilution, 150 μL/well), and incubated at room temperature in the dark overnight.

Samples were transferred to 96-well U-bottom plates and flow cytometric analysis was performed on a FACSCalibur, FACSCanto or LSRFortessa equipped with a HTS plate loader (BD Biosciences). The lymphocyte population was gated for histogram analysis of pSTAT3. Background fluorescence was defined using unstimulated cells and a gate was placed at the foot of the peak to include ~0.5% gated population. The histogram statistical analysis was performed using CellQuest™ Pro version 5.2.1 (BD Biosciences), FACSDiva version 6.2 (BD Biosciences) or FlowJo version 7.6.1 (Ashland, Oreg.) software. Relative fluorescence unit (RFU), which measures the level of phospho STAT3, was calculated by multiplying the percent positive population and its mean fluorescence. Data from 11 compound concentrations (singlicate at each concentration) was normalized as a percentage of control based on the formula: % of Control=100×(A−B)/(C−B)

where A is the RFU from wells containing compound and cytokine, B is the RFU from wells without cytokine and compound (minimum fluorescence) and C is the RFU from wells containing only cytokine (maximum fluorescence). Inhibition curves and IC50 values were determined using the Prism version 5 software (GraphPad, La Jolla, Calif.).

| Example Number | HWB IFN alpha IC50 (nM) |
|---|---|
| 5 | 105 |
| 6 | 232 |
| 7 | 30 |
| 10 | 439 |
| 11 | 134 |
| 12 | 88 |
| 14 | 287 |
| 15 | 534 |
| 18 | 338 |
| 19 | 238 |
| 20 | 458 |
| 21 | 731 |
| 22 | 410 |
| 23 | 428 |
| 24 | 43 |
| 25 | 229 |
| 26 | 247 |
| 27 | 139 |
| 29 | 118 |
| 30 | 653 |
| 31 | 284 |
| 32 | 115 |
| 33 | 122 |
| 35 | 90 |
| 36 | 119 |
| 44 | 562 |
| 45 | 110 |
| 46 | 209 |
| 49 | 85 |
| 51 | 20 |
| 53 | 287 |
| 55 | 168 |
| 56 | 78 |
| 57 | 338 |
| 58 | 158 |
| 59 | 84 |
| 60 | 103 |
| 61 | 135 |
| 64 | 71 |
| 65 | 60 |
| 66 | 187 |
| 74 | 213 |
| 75 | 751 |
| 79 | 65 |
| 80 | 112 |
| 83 | 85 |
| 84 | 156 |
| 85 | 120 |
| 86 | 116 |
| 87 | 582 |
| 89 | 118 |
| 90 | 247 |
| 91 | 195 |
| 93 | 191 |
| 95 | 87 |
| 98 | 246 |
| 109 | 507 |
| 110 | 146 |
| 112 | 775 |
| 113 | 939 |
| 114 | 166 |
| 115 | 234 |

What is claimed is:

1. A compound having the structure:

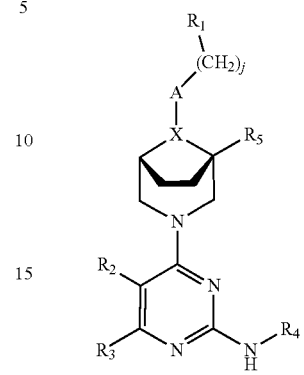

or a pharmaceutically acceptable salt thereof, wherein

X is N;

A is selected from the group consisting of a bond and C=O;

$R_1$ is $C_3$-$C_6$ cycloalkyl, wherein said cycloalkyl is further optionally substituted with one or more halo;

$R_2$ is hydrogen;

$R_3$ is hydrogen;

$R_4$ is monocyclic heteroaryl wherein said heteroaryl is optionally substituted with one or more $C_1$-$C_6$ alkyl; and, $R_5$ is hydrogen; and, j is 0 or 1.

2. The compound of claim 1, wherein A is C=O, or a pharmaceutically acceptable salt thereof.

3. The compound of claim 1, wherein j is 0, or a pharmaceutically acceptable salt thereof.

4. The compound of claim 1, wherein $R_4$ is monocyclic heteroaryl and said monocyclic heteroaryl is pyrazole, or a pharmaceutically acceptable salt thereof.

5. The compound of claim 4, wherein said monocyclic heteroaryl is pyrazole substituted by $C_1$-$C_6$ alkyl, or a pharmaceutically acceptable salt thereof.

6. A compound having the structure:

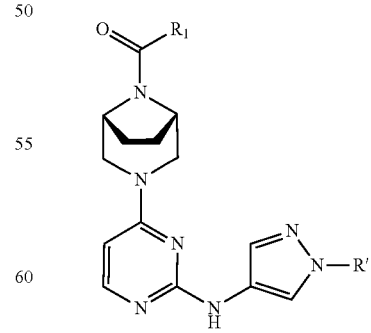

or a pharmaceutically acceptable salt thereof, wherein $R_1$ is $C_3$-$C_6$ cycloalkyl, further optionally substituted with one or more halo and wherein R' is $C_1$-$C_6$ alkyl.

7. The compound of claim 6 having the structure:
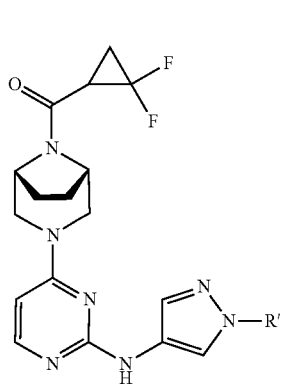
wherein R' is $C_1$-$C_6$ alkyl.
8. The compound of claim 6 having the structure:
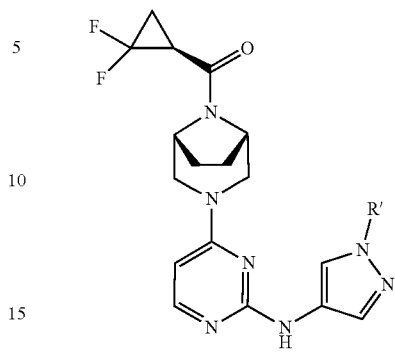
wherein R' is $C_1$-$C_6$ alkyl.
9. A pharmaceutical composition comprising a compound of any of claims 1 to 8, or a pharmaceutically acceptable salt thereof, and a pharmaceutically acceptable carrier.
* * * * *